US007820675B2

(12) United States Patent
Johansson et al.

(10) Patent No.: US 7,820,675 B2
(45) Date of Patent: Oct. 26, 2010

(54) BENZOFURAN COMPOUNDS

(75) Inventors: Gary Johansson, Uppsala (SE); Peter Brandt, Solna (SE); Björn M. Nilsson, Stockholm (SE)

(73) Assignee: Biovitrum AB, Stockholm (SE)

( * ) Notice: Subject to any disclaimer, the term of this patent is extended or adjusted under 35 U.S.C. 154(b) by 616 days.

(21) Appl. No.: 11/018,019

(22) Filed: Dec. 20, 2004

(65) Prior Publication Data
US 2006/0287291 A1 Dec. 21, 2006

Related U.S. Application Data

(60) Provisional application No. 60/549,652, filed on Mar. 3, 2004.

(30) Foreign Application Priority Data
Dec. 19, 2003 (SE) .................... 0303480-8

(51) Int. Cl.
*A61P 3/04* (2006.01)
*A61K 31/18* (2006.01)
*A61K 31/47* (2006.01)
*A61K 31/495* (2006.01)
*A61K 31/496* (2006.01)
*C07D 295/04* (2006.01)
*C07D 487/06* (2006.01)
*C07D 241/04* (2006.01)
*C07D 215/38* (2006.01)
*C07D 217/22* (2006.01)
*C07D 403/04* (2006.01)
*C07D 405/04* (2006.01)

(52) U.S. Cl. .................. 514/254.11; 514/414; 544/376; 548/453

(58) Field of Classification Search ............ 514/254.11, 514/414; 544/376; 548/453
See application file for complete search history.

(56) References Cited

U.S. PATENT DOCUMENTS

| 5,464,863 | A | * | 11/1995 | Nagamine et al. ............ 514/443 |
| 5,858,995 | A | * | 1/1999 | Kawai et al. ................. 514/100 |
| 6,191,141 | B1 | | 2/2001 | Edwards et al. |
| 2006/0074076 | A1* | | 4/2006 | Termin et al. ........... 514/217.03 |
| 2006/0293361 | A1 | | 12/2006 | Caldirola et al. |

FOREIGN PATENT DOCUMENTS

| EP | 0 701 819 | 3/1996 |
| EP | 0 815 861 | 1/1998 |
| WO | WO 98/27081 | 6/1998 |
| WO | WO 99/02502 | 1/1999 |
| WO | WO 99/37623 | 7/1999 |
| WO | WO 99/42465 A2 | 8/1999 |
| WO | WO 00/34242 | 6/2000 |
| WO | WO 01/32646 A2 | 5/2001 |
| WO | WO 02/098857 A1 | 12/2002 |
| WO | WO 02/100822 A1 | 12/2002 |
| WO | WO 03/013510 A1 | 2/2003 |
| WO | WO 03/072198 | 9/2003 |
| WO | WO 04/000828 A1 | 12/2003 |

OTHER PUBLICATIONS

Bentley et al., "5-$HT_6$ Antisense Oligonucleotide I.C.V. Affects Rat Performance in the Water Maze and Feeding", *Journal of Psychopharmacology*, 11(3):255 (1997).
Bentley et al., "Effect of the 5-HT6 Antagonist, Ro 4-6790 on Food Consumption in Rats Trained to a Fixed Feeding Regime", *British Journal of Pharmacology*, 126:66P (1999).
Isaac et al., "6-bicyclopiperazinyl-1-arylsulfonylindoles and 6-Bicyclopiperidinyl-1-arylsulfonylindoles Derivatives as Novel, Potent, and Selective 5-$HT_6$ Receptor Antagonists", *Bioorganic & Medicinal Chemistry Letters*, 10:1719-1721 (2000).
Pullagurla et al., "$N_1$-Benzenesulfonylgramine and $N_1$-Benzenesulfonylskatole: Novel 5-$HT_6$ Receptor Ligand Templates", *Bioorganic & Medicinal Chemistry Letters*, 13:3355-3359 (2003).
Ruat et al., "A Novel Rat Serotonin (5-$HT_6$) Receptor: Molecular Cloning, Localization and Stimulation of cAMP Accumulation", *Biochemical and Biophysical Research Communications*, 193(1):268-276 (1993).
Sebben et al., "5-$HT_6$ receptors positively coupled to adenylyl cyclase in striatal neurones in culture", *Neuro Report*, 5(18):2553-2557 (1994).
Slassi et al., "Recent progress in 5-$HT_6$ receptor antagonists for the treatment of CNS diseases", *Expert Opinion Therapeutic Patents*, 12(4):513-527 (2002).
Woolley et al., "A role for 5-$HT_6$ receptors in retention of spatial learning in the Morris water maze", *Neuropharmacology*, 41:210-219 (2001).

(Continued)

*Primary Examiner*—James O Wilson
*Assistant Examiner*—Brenda L. Coleman
(74) *Attorney, Agent, or Firm*—Fish & Richardson P.C.

(57) ABSTRACT

The present invention relates to compounds of formula (I):

Formula (I)

wherein
P, $R^3$, $W_1$, and $W_2$ are as described herein, to pharmaceutical compositions comprising the compounds, to processes for their preparation, as well as to the use of the compounds for the preparation of a medicament against 5-$HT_6$ receptor-related disorders.

35 Claims, No Drawings

OTHER PUBLICATIONS

Bentley et al., "Effect of the 5-HT$_6$ Antagonist, Ro 04-6790 on Food Consumption in Rats Trained to a Fixed Feeding Regime", *British Journal of Pharmacology*, 126 (1999): suppl.

Bourson et al., "Involvement of HT$_6$ Receptors in Nigro-Striatal Function in Rodents", *British Journal of Pharmacology*, 125:1562-1566 (1998).

Dawson et al., "Selective Enhancement of Glutamatergic Neurotransmission in the Frontal Cortex and Dorsal Hippocampus by antagonism of the 5-HT$_6$ Receptor", *Monitoring Molecules in Neuroscience*, pp. 318-319, Jun. 16-19, 2001.

Dawson et al., "The 5-HT$_6$ Receptor Antagonist SB-271046 Selectively Enhances Excitatory Neurotransmission in the Rat Frontal Cortex and Hippocampus", *Neuropsychopharmacology*, 25(5)P:662-668 (2001).

Dawson et al., "Potentiation of Amphetamine-Induced Changes in Dopamine and 5-HT by a 5-HT$_6$ Receptor Antagonist", *Brain Research Bulletin*, 59(6):513-521 (2003).

Foley et al., "The 5-HT$_6$ Receptor Antagonist SB-271045 Reverses Scopolamine-Disrupted Consolidation of a Passive Avoidance Task and Ameliorates Spatial Task Deficits in Aged Rats", *Neuropsychopharmacology*, 29:93-100 (2004).

Frantz et al., "5-HT$_6$ Receptor Antagonism Potentiates the Behavioral and Neurochemical Effects of Amphetamine but not Cocaine", *Neuropharmacology*, 42:170-180 (2002).

Lacroix et al., "5-HT$_6$ Receptor Antagonist SB-271046 Enhances Extracellular Levels of Monoamines in the Rat Medial Prefrontal Cortex", *Synapse*, 51:158-164 (2004).

Matsumoto et al., "Characterization of Endogenous Serotonin-Mediated Regulation of Dopamine Release in Rat Prefrontal Cortex", *European Journal of Pharmacology*, 383:39-48 (1999).

Meneses, Role of 5-HT$_6$ Receptors in Memory Formation, *Drug News & Perspectives*, 14(7):396-400 (2001).

Meneses, "Effects of the 5-HT$_6$ Receptor Antagonist Ro 4-6790 on Learning Consolidation", *Behavioural Brain Research*, 118:107-110 (2001).

Minabe et al., "Effect of the Acute and Chronic Administration of the Selective 5-HT$_6$ Receptor Antagonist SB-271046 on the Activity of Midbrain Dopamine Neurons in Rats: In Vivo Electrophysiological Study", *Synapse*, 52:20-28 (2004).

Otano et al., "Anxiogenic-Like Effects and Reduced Stereological Counting of Immunolabelled 5-Hydroxytryptamine$_6$ Receptos in Rat Nucleus Accumbens by Antisense Oligonucleotides", *Neuroscience*, 92(3):1001-1009 (1999).

Riemer et al., "Influence of the 5-HT$_6$ Receptor on Acetylcholine Release in the Cortex: Pharmacological Characterization of 4-(2-Bromo-6-pyrrolidine-1-ylpyridine-4-sulfonyl)phenylamine, a Potent and Selective 5-HT$_6$ Receptor Antagonist", *J. Med. Chem.*, 46:1273-1276 (2003).

Roberts et al., "The Distribution of 5-HT$_6$ Receptors in Rat Brain: An Autoradiographic Binding Study Using the Radiolabelled 5-HT$_6$ Receptor Antagonist [$^{125}$I]SB-258585", *Brain Research*, 934:49-57 (2002).

Rogers et al., "5-HT$_6$ Receptor Antagonists Enhance Retention of a Water Maze Task in the Rat", *Psychopharmacology*, 158:114-119 (2001).

Shirazi-Southall et al., "Effects of Typical and Atypical Antipsychotics and Receptor Selective Compounds on Acetylcholine Efflux in the Hippocampus of the Rat", *Neuropsychopharmacology*, 26(5):583-594 (2002).

Sleight et al., *Brit. J. Pharmacol.*, (1998) 124, 556-562.

Tsai et al., "Association Analysis of the 5-HT$_6$ Receptor Polymorphism C267T in Alzheimer's Disease", *Neuroscience Letters*, 276:138-139 (1999).

Wesolowska et al., "Anxiolytic-like and Antidepressant-like Effects Producted by the Selective 5-HT$_6$ Receptor Antagonist SB-258585 after Intrahippocampal Administration to Rats," *Behavioural Pharmacology* 18:439-446, (2007).

Wesokowska et al., "Effects of the brain-penetrant and Selective 5-HT$_6$ Receptor Antagonist SB-399885 in Animal Models of Anxiety and Depression," *NeuroPharmacology*, 52:1274-1283 (2007).

Woolley et al., "Reversal of a Cholinergic-Induced Deficit in a Rodent Model of Recognition Memory by the Selective 5-HT$_6$ Receptor Antagonist, Ro 04-6790", *Psychopharmacology*, 170:358-367 (2003).

Woolley et al., "5-HT$_6$ Receptors", *Current Drug Targets—CNS & Neurological Disorders*, 3:59-79 (2004).

* cited by examiner

BENZOFURAN COMPOUNDS

CROSS-REFERENCE TO RELATED APPLICATIONS

This application claims the benefit of U.S. Provisional Application No. 60/549,652, filed on Mar. 3, 2004 and Swedish Application No.: 0303480-8, filed on Dec. 19, 2003. The contents of both of these prior applications are incorporated herein by references in their entireties.

TECHNICAL FIELD

This invention relates generally to modulating serotonin 5-$HT_6$ receptor.

BACKGROUND

Obesity is a condition characterized by an increase in body fat content resulting in excess body weight above accepted norms. Obesity is among the important nutritional disorders in the western world and can represent a major health problem in industrialized countries. This disorder can lead to increased mortality due to increased incidences of diseases such as cardiovascular disease, digestive disease, respiratory disease, cancer and type 2 diabetes. Searching for compounds, which reduce body weight has been ongoing. One line of research has included activation of serotoninergic systems, either by direct activation of serotonin receptor subtypes or by inhibiting serotonin reuptake.

Serotonin (5-hydroxytryptamine or 5-HT), a transmitter of the peripheral and central nervous system, is believed to modulate a wide range of physiological and pathological functions, including anxiety, sleep regulation, aggression, feeding and depression. Multiple serotonin receptor subtypes have been identified and cloned. One of these, the 5-HT6 receptor, displays affinity for antidepressants such as clozapine and is believed to be positively coupled to adenylyl cyclase. The effect of 5-HT6 antagonist and 5-HT6 antisense oligonucleotides is believed to be involved in the reduction of food intake in rats. Compounds believed to have enhanced affinity and selectivity for the 5-HT6 receptor have also been identified.

SUMMARY

It has surprisingly been found that the compounds according to the present invention show affinity for the 5-$HT_6$ receptor as antagonists at nanomolar range. Compounds according to the present invention and their pharmaceutically acceptable salts have 5-$HT_6$ receptor antagonist, agonist and partial agonist activity and are believed to be of potential use in the treatment or prophylaxis of obesity and type 2 diabetes, to achieve reduction of body weight and of body weight gain, as well as in the treatment or prophylaxis of disorders of the central nervous system such as anxiety, depression, panic attacks, memory disorders, cognitive disorders, epilepsy, sleep disorders, migraine, anorexia, bulimia, binge eating disorders, obsessive compulsive disorders, psychoses, Alzheimer's disease, Parkinson's disease, Huntington's chorea and/or schizophrenia, panic attacks, Attention Deficit Hyperactive Disorder (ADHD), withdrawal from drug abuse, neurodegenerative diseases characterized by impaired neuronal growth, and pain. The reduction of body weight and of body weight gain (e.g. treating body-weight disorders) is achieved inter alia by reduction of food intake. As used herein, the term "body weight disorders" refers to the disorders caused by an imbalance between energy intake and energy expenditure, resulting in abnormal (e.g., excessive) body weight. Such body weight disorders include obesity.

In one aspect, this invention relates to compounds of the Formula (I):

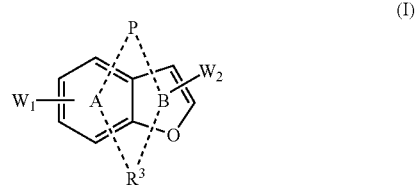

(I)

wherein:
P is selected from a substituent of Formula (II)-(VII):

(II)

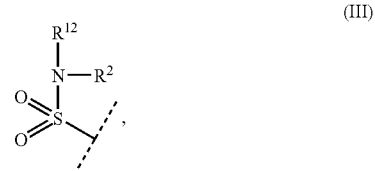

(III)

(IV)

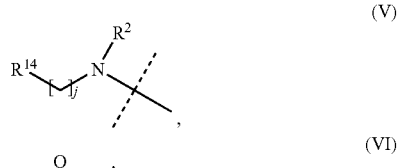

(V)

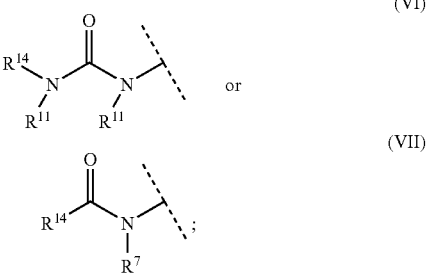

(VI)

or (VII)

wherein:
x, y and j are each independently selected from 0, 1, and 2;
wherein the dashed bonds denote that P and $R^3$, respectively, may be attached to either the A or B ring at any carbon atom that allows the substitution, provided that P and $R^3$ are not both simultaneously attached to ring B;
$R^1$ is selected from:
(a) $C_{1-6}$-alkyl,
(b) $C_{1-6}$-alkoxy-$C_{1-6}$-alkyl,
(c) $C_{3-6}$-alkenyl, (d) hydroxy-$C_{1-6}$-alkyl,
(e) halo-$C_{1-6}$-alkyl,
(f) aryl,
(g) arylcarbonylmethyl,
(h) aryl-$C_{3-6}$-alkenyl,
(i) aryl-$C_{1-6}$-alkyl,
(j) $C_{3-7}$-cycloalkyl,
(k) heteroaryl,
(l) 4-piperidinyl,
(m) N-substituted 4-piperidinyl, wherein the substituents are selected from $C_{1-6}$-alkyl and aryl-$C_{1-6}$-alkyl,
(o) heteroaryl-$C_{1-6}$-alkyl,
wherein any heteroaryl or aryl residue, alone or as part of another group may be substituted, independently, in one or more positions with a substituent selected from:
(a) hydrogen,
(b) halogen,
(c) $C_{1-6}$-alkyl,
(d) hydroxy,
(e) $C_{1-6}$-alkoxy,
(f) $C_{2-6}$-alkenyl,
(g) $C_{2-3}$-alkynyl,
(h) phenyl,
(i) phenoxy,
(j) benzyloxy,
(k) benzoyl,
(l) benzyl,
(m) —$OCF_3$,
(n) —CN,
(o) hydroxy-$C_{1-6}$-alkyl,
(p) $C_{1-6}$-alkoxy-$C_{1-6}$-alkyl,
(q) halo-$C_{1-6}$-alkyl,
(r) —$NR^9R^9$,
(s) —$NO_2$,
(t) —$CONR^9R^9$,
(u) —$NR^7COR^{10}$,
(v) —C(=O)$R^{10}$,
(x) $C_{1-6}$-alkoxycarbonyl,
(y) $C_{1-6}$-alkylthio,
(z) —$SCF_3$,
(aa) —CHF=$CH_2$,
(ab) methylsulfonyl, or
(ac) —COOH
with the proviso that when the substituent on the said aryl or heteroaryl residue is selected from phenyl, phenoxy, benzyloxy, benzoyl and benzyl, the phenyl ring thereof may be optionally substituted by one or more of halogen, $C_{1-4}$-alkyl, $C_{1-4}$-alkylthio, $C_{1-4}$-alkoxy, cyano, or trifluoromethyl;
$R^2$ is selected from:
(a) hydrogen,
(b) $C_{1-6}$-alkyl,
(c) $C_{1-6}$-alkoxy-$C_{2-6}$ alkyl,
(d) hydroxy-$C_{2-6}$-alkyl,
(e) —$(CH_2)_m$—$CH_2$—F, wherein m is 2-4,
(f) 3,3-trifluoropropyl, or
(g) $C_{1-4}$-alkylsulfonyl, provided that P is selected from a substituent of formula (V);
$W_1$ and $W_2$ are each independently selected from:
(a) hydrogen,
(b) halogen,
(c) $C_{1-6}$-alkyl,
(d) hydroxy,
(e) $C_{1-6}$-alkoxy,
(f) $C_{1-6}$-alkylthio,
(g) $C_{2-6}$-alkenyl,
(h) phenyl,
(i) phenoxy,
(j) benzyloxy,
(k) benzoyl,
(l) benzyl,
(m) —$OCF_3$,
(n) —CN,
(o) hydroxy-$C_{1-6}$-alkyl,
(p) $C_{1-6}$-alkoxy-$C_{1-6}$-alkyl,
(q) halo-$C_{1-6}$-alkyl,
(r) —$CONR^9R^9$,
(s) —C(=O)$R^{10}$,
(t) $C_{1-6}$-alkoxycarbonyl,
(u) —$SCF_3$, or
(v) —CHF=$CH_2$,
with the proviso that when $W_1$ and $W_2$ are selected from phenyl, phenoxy, benzoyl, benzyloxy and benzyl, the phenyl ring thereof may be optionally substituted by one or more of halogen, $C_{1-4}$-alkyl, $C_{1-4}$-alkoxy, cyano, or trifluoromethyl, and with the further proviso that, when $W_1$ and $W_2$ are not selected from methoxy, methyl and halogen, at least one of $W_1$ and $W_2$ is selected from hydrogen;

$R^3$ is H when P is a substituent of Formula (II) wherein $R^1$ is N-substituted 4-piperidinyl, or $R^3$ is a group selected from:

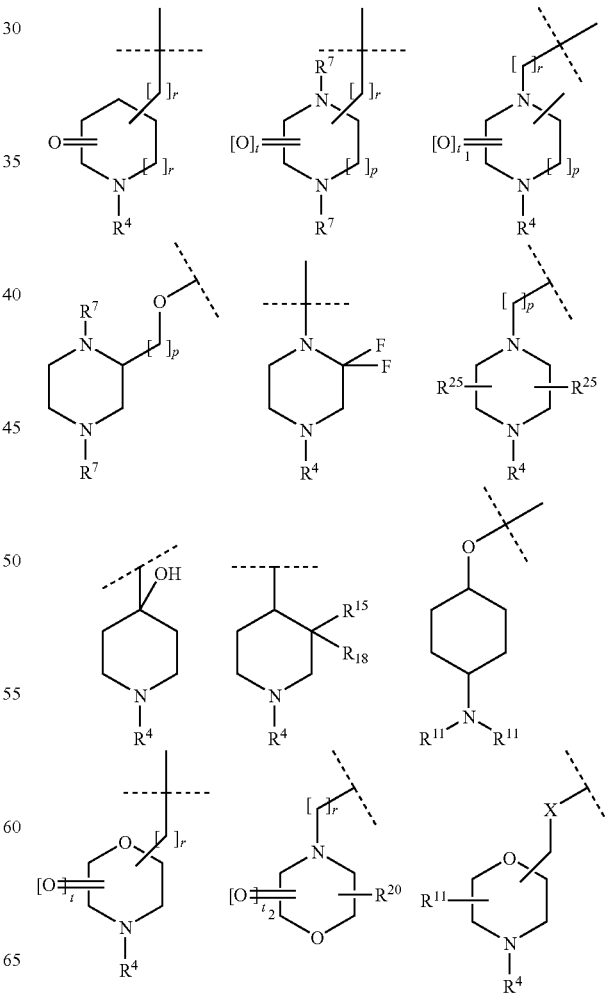

-continued
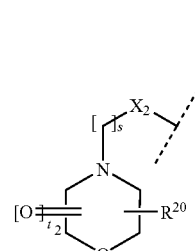 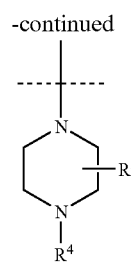 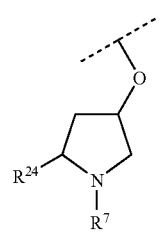 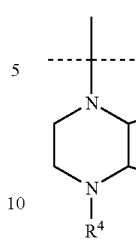 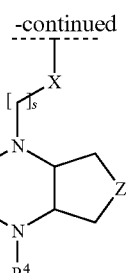 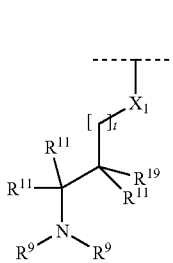
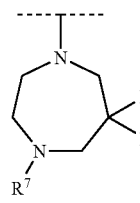 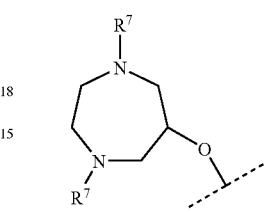 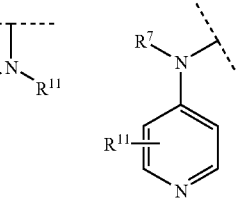
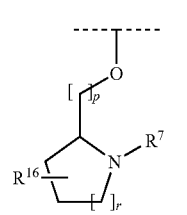 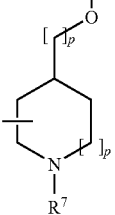 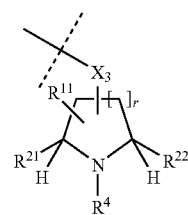 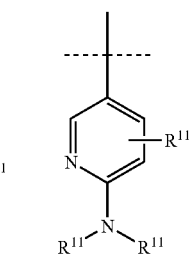
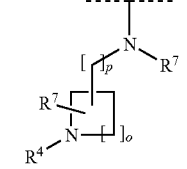 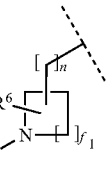 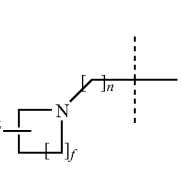 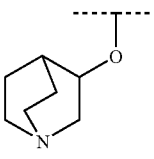 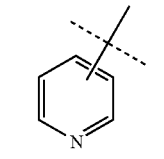
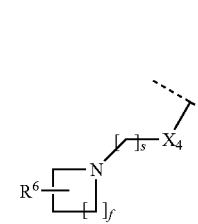 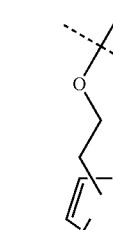 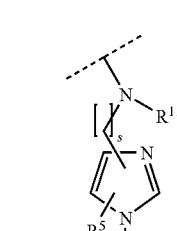 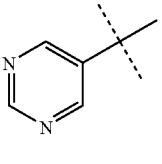
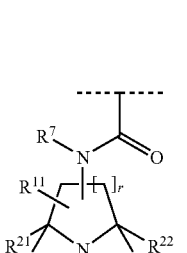 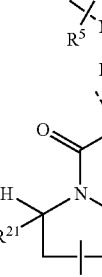 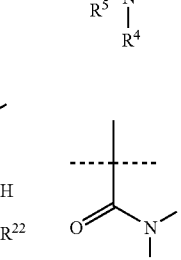 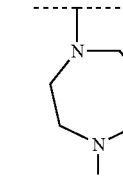 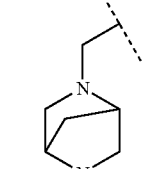
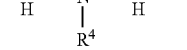   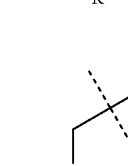 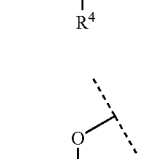
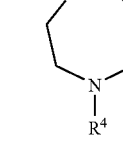 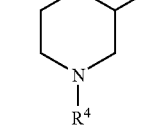

-continued

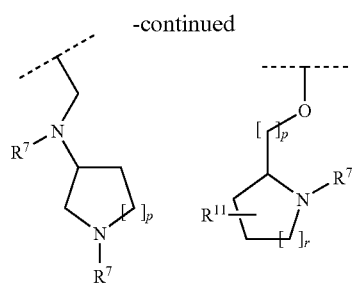

$R^3$ may also be a group selected from:

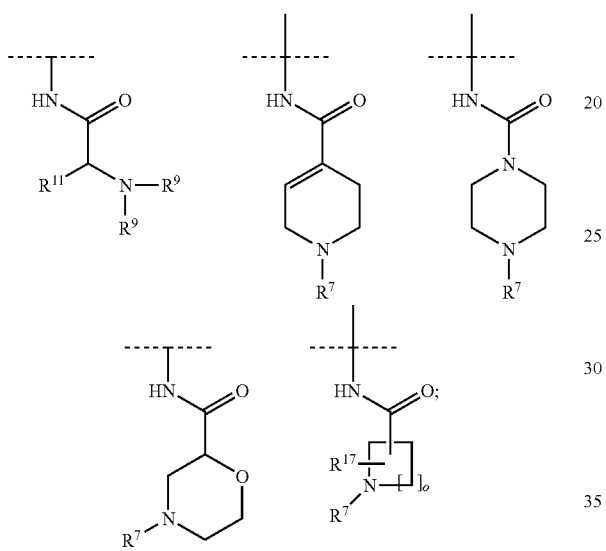

and further from a group selected from:
—O—(C═NH)NR$^{11}$R$^{11}$, or
—(CH$_2$)$_n$—O—NH(C═NH)—NR$^{11}$R$^{11}$;
wherein
n=0, 1, 2, or 3,
r is each independently 0, 1 or 2,
o=1, 2, or 3,
p is each independently 1 or 2,
s=2 or 3,
t=0 or 1,
t$_1$=1 or 2,
t$_2$=0 or 1,
f=1, 2, 3 or 4, and
f$_1$=1, 2 or 4;
with the proviso that when t$_1$ and p simultaneously are 1, r is not 0;
X is selected from O, NR$^7$ and S;
X$_1$ is selected from NR$^7$ and S;
X$_2$ is selected from O, NR$^7$ and S, provided that X$_2$ is selected from NR$^7$ and S when t$_2$=0;
X$_3$ is selected from NR$^7$ and S, provided that X$_3$ is selected from S when r=1;
X$_4$ is selected from O, NR$^7$ and S, provided that X$_4$ is selected from S and NR$^7$ when f is selected from 2, 3, and 4;
Q is selected from CH$_2$, SO$_2$ and oxygen, provided that when Q is SO$_2$ or oxygen, p is 1;
Z is selected from SO$_2$ and oxygen;
when P is a group selected from a substituent of Formula (V)-(VII), R$^3$ is additionally selected from the following groups:

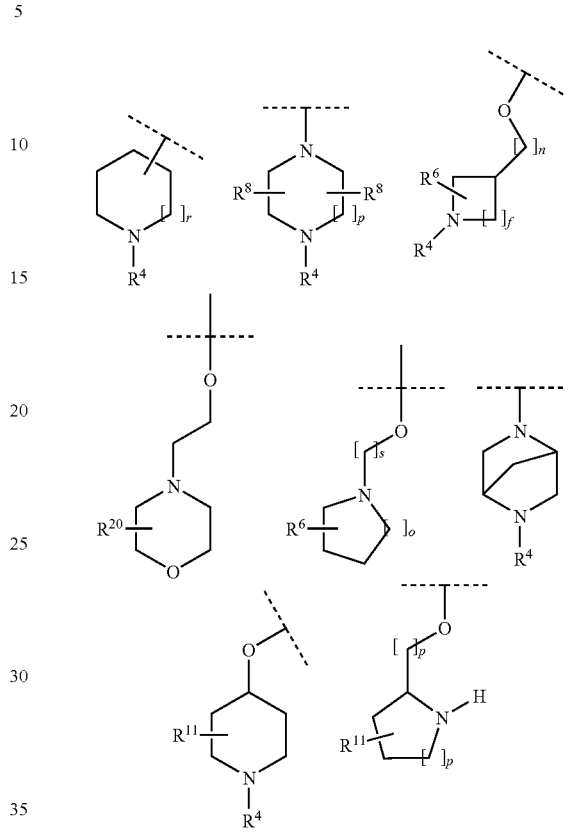

wherein:
n=0, 1, 2 or 3
r=0, 1 or 2,
o=1, 2, or 3,
p=1 or 2,
s=2 or 3, and
f=1, 2, 3 or 4;
R$^4$ is a group selected from:
(a) hydrogen,
(b) C$_{1-6}$-alkyl,
(c) 2-cyanoethyl,
(d) hydroxy-C$_{2-6}$-alkyl,
(e) C$_{3-6}$-alkenyl,
(f) C$_{3-6}$-alkynyl,
(g) C$_{3-7}$-cycloalkyl,
(h) C$_{3-7}$-cycloalkyl-C$_{1-4}$-alkyl,
(i) C$_{1-6}$-alkoxy-C$_{2-6}$-alkyl
(j) —C(═NH)—N—R$^{11}$R$^{11}$,
(k) —C(═O)—N—R$^{11}$R$^{11}$,
(l) —CH$_2$—CO—N—R$^{11}$R$^{11}$, or
(m) 3,3,3-trifluoropropyl;
R$^5$ is selected from:
(a) hydrogen,
(b) C$_{1-4}$-alkyl,
(c) hydroxy-C$_{1-4}$-alkyl,
(d) C$_{1-4}$-alkoxymethyl,
(e) halo-C$_{1-4}$-alkyl,
(f) —NR$^{11}$R$^{11}$,
(g) —CO—NR$^{11}$R$^{11}$, (h) hydroxy, provided that the said hydroxy group is not attached to a carbon atom adjacent to a ring nitrogen atom, or
(i) fluorine, provided that the said fluorine atom is not attached to a carbon atom adjacent to a ring nitrogen atom;

$R^6$ is selected from:
(a) hydrogen,
(b) $C_{1-4}$-alkyl,
(c) hydroxy-$C_{1-4}$-alkyl,
(d) $C_{1-4}$-alkoxy-$C_{1-4}$-alkyl,
(e) hydroxy, provided that the said hydroxy group is not attached to a carbon atom adjacent to a heterocyclic ring nitrogen atom, and further provided that the said heterocyclic ring is not substituted with oxo,
(f) fluorine, provided that the said fluorine atom is not attached to a carbon atom adjacent to a ring nitrogen atom, or
(g) halo-$C_{1-4}$-alkyl;

$R^7$ is each independently selected from:
(a) hydrogen, provided that $R^7$ is not hydrogen when present simultaneously with r and said r is 1 or 2,
(b) $C_{1-4}$-alkyl,
(c) hydroxy-$C_{2-4}$-alkyl, or
(d) methoxy-$C_{2-4}$-alkyl;

$R^8$ is each independently selected from:
(a) hydrogen, or
(b) $C_{1-4}$-alkyl, and
when both $R^8$ simultaneously are selected from $C_{1-4}$-alkyl, said $C_{1-4}$-alkyls may be attached to the same or different carbon atoms, or when two groups are present at the same carbon atom they may together form a cyclopropane ring;

$R^9$ is each independently selected from:
(a) hydrogen,
(b) $C_{1-6}$-alkyl
(c) $C_{3-7}$-cycloalkyl, or
wherein the two $R^9$ groups together with the nitrogen to which they are attached form a heterocyclic ring; and provided that when the two $R^9$ groups form a piperazine ring, the nitrogen of the said piperazine ring that allows the substitution is substituted with $C_{1-4}$-alkyl, and further provided that when the two $R^9$ groups form a piperidine ring, any ring carbon atom in the said piperidine ring may be optionally substituted with methyl;

$R^{10}$ is selected from:
(a) $C_{1-6}$-alkyl,
(c) aryl, or
(d) heteroaryl,
wherein heteroaryl or aryl may be substituted in one or more positions with substituents selected from halogen, $C_{1-4}$-alkyl, $C_{1-4}$-alkoxy, cyano, trifluoromethyl;

$R^{11}$ is each independently selected from:
(a) hydrogen,
(b) methyl, or
(c) ethyl, provided that $R^{11}$ is present in a group $R^4$ or $R^{26}$ selected from —$CH_2$—CO—N—$R^{11}R^{11}$;

$R^{12}$ is selected from:
(a) hydrogen,
(b) $C_{1-6}$-alkyl,
(c) aryl,
(d) aryl-$C_{1-6}$-alkyl,
(e) $C_{3-7}$-cycloalkyl,
(f) $C_{3-7}$-cycloalkyl-$C_{1-4}$-alkyl,
(g) heteroaryl, or
(h) heteroaryl-$C_{1-6}$-alkyl, wherein any heteroaryl or aryl residue, alone or as part of another group, is optionally substituted, independently, in one or more positions with substituents selected from:
(a) hydrogen,
(b) halogen,
(c) $C_{1-6}$-alkyl,
(d) hydroxy,
(e) $C_{1-6}$-alkoxy,
(f) $C_{2-6}$-alkenyl,
(g) $C_{2-6}$-alkynyl,
(h) phenyl,
(i) phenoxy,
(j) benzyloxy,
(k) benzoyl,
(l) benzyl,
(m) —$OCF_3$,
(n) —CN,
(o) hydroxy-$C_{1-6}$-alkyl,
(p) $C_{1-6}$-alkoxy-$C_{1-6}$-alkyl,
(q) halo-$C_{1-6}$-alkyl,
(r) —$NR^9R^9$,
(s) —$NO_2$,
(t) —$CONR^9R^9$,
(u) —$NR^7COR^{10}$,
(v) —C(=O)$R^{10}$,
(x) $C_{1-6}$-alkoxycarbonyl,
(y) $C_{1-6}$-alkylthio,
(z) —$SCF_3$,
(aa) —CHF=$CH_2$,
(ab) methylsulfonyl, or
(ac) —COOH;

with the proviso that when the substituent on the said aryl or heteroaryl residue is selected from phenyl, phenoxy, benzyloxy, benzoyl, and benzyl, the phenyl ring thereof may be optionally substituted by one or more of halogen, $C_{1-4}$-alkyl, $C_{1-4}$-alkoxy, cyano, or trifluoromethyl;

$R^{13}$ is selected from:
(a) $C_{1-6}$-alkyl,
(b) $C_{3-6}$-cycloalkyl,
(c) aryl,
(d) heteroaryl,
(e) aryl-$C_{1-2}$-alkyl, or
(f) heteroaryl-$C_{1-2}$-alkyl,
wherein any heteroaryl or aryl residue may be substituted in one or more positions with substituents selected from halogen, $C_{1-4}$-alkyl, $C_{1-4}$-alkoxy, cyano, trifluoromethyl, and acetyl;

$R^{14}$ is selected from:
(a) aryl,
(b) heteroaryl,
(c) aryl-$C_{1-3}$-alkyl, or
(d) heteroaryl-$C_{1-3}$-alkyl,
wherein any heteroaryl or aryl residue may be substituted in one or more positions with substituents selected from halogen, $C_{1-4}$-alkyl, $C_{1-4}$-alkoxy, cyano, and trifluoromethyl;

$R^{15}$ is selected from:
(a) fluorine, or
(b) hydroxy;

$R^{16}$ is selected from:
(a) hydrogen, provided that r=0,
(b) amino,
(c) dimethylamino,
(d) F, or
(e) OH;

$R^{17}$ is selected from:
(a) hydrogen,
(b) $C_{1-4}$-alkyl, (c) hydroxy, provided that the said hydroxy group is not attached to a carbon atom adjacent to a ring nitrogen atom;

$R^{18}$ is selected from:
(a) hydrogen, or
(b) fluorine;

$R^{19}$ is selected from:
(a) hydrogen,
(b) methyl,
(c) trifluoromethyl, or
(d) $C_{1-2}$-alkoxymethyl;

and provided that at least one of $R^{19}$ and $R^{11}$, when present simultaneously, is selected from a non-hydrogen substituent, and further provided that when $R^{19}$ is selected from trifluoromethyl or $C_{1-2}$-alkoxymethyl, each $R^{11}$ is selected from hydrogen;

$R^{20}$ is selected from:
(a) hydrogen,
(b) $C_{1-4}$-alkyl,
(c) hydroxy-$C_{1-4}$-alkyl,
(d) $C_{1-4}$-alkoxy-$C_{1-4}$-alkyl, or
(e) fluoromethyl;

with the proviso that when $t_2$ is 1, $R^{20}$ is H;

$R^{21}$ and $R^{22}$ are each independently selected from:
(a) hydrogen, or
(b) methyl, provided that, when present at the same time as $R^{11}$, at least two of $R^{11}$, $R^{21}$ and $R^{22}$ are selected from hydrogen;

$R^{23}$ is selected from:
(a) hydroxy-$C_{1-4}$-alkyl,
(b) $C_{1-4}$-alkoxymethyl,
(c) halo-$C_{1-4}$-alkyl, or
(d) —CO—NR$^{11}$R$^{11}$, provided that $R^4$ is not selected from —C(=NH)—N—R$^{11}$R$^{11}$, —C(=O)—N—R$^{11}$R$^{11}$, and —CH$_2$—CO—N—R$^{11}$R$^{11}$;

$R^{24}$ is selected from:
(a) hydroxymethyl,
(b) methoxymethyl, or
(c) fluoromethyl;

$R^{25}$ is each independently selected from
(a) hydrogen,
(b) $C_{1-4}$-alkyl,
(c) hydroxy-$C_{1-4}$-alkyl,
(d) $C_{1-4}$-alkoxy-$C_{1-4}$-alkyl, or
(e) fluoromethyl;

with the proviso that when both $R^{25}$ simultaneously are selected from $C_{1-4}$-alkyl, said $C_{1-4}$-alkyls may be attached to the same or different carbon atoms, and with the further proviso that when one $R^{25}$ is selected from hydroxy-$C_{1-4}$-alkyl, $C_{1-4}$-alkoxy-$C_{1-4}$-alkyl, and fluoromethyl, the other $R^{25}$ represents hydrogen; and $R^{26}$ is selected from
(a) 2-cyanoethyl,
(b) $C_{3-6}$-alkenyl,
(c) $C_{3-6}$-alkynyl,
(d) $C_{3-7}$-cycloalkyl,
(e) $C_{3-7}$-cycloalkyl-$C_{1-4}$-alkyl,
(f) —CH$_2$—CO—NR$^{11}$R$^{11}$, or
(g) 3,3,3-trifluoropropyl;

with the proviso that $R^2$ and $R^{12}$ in Formula (III) are not simultaneously selected from hydrogen; and with the further proviso that the said $R^2$ and $R^{12}$ together may for a heterocyclic ring selected from piperidine, pyrrolidine, morpholine, piperazine thiomorpholine, and provided that when $R^2$ and $R^{12}$ together form a piperazine ring, the distal piperazine nitrogen may be optionally substituted by $C_{1-4}$ alkyl or aryl, and wherein said aryl is substituted in one or more positions with substituents selected from halogen, $C_{1-4}$-alkyl, $C_{1-4}$-alkoxy, cyano, trifluoromethyl; or $R^2$ and $R^{12}$ together form a heteroaromatic ring of Formula (VIII):

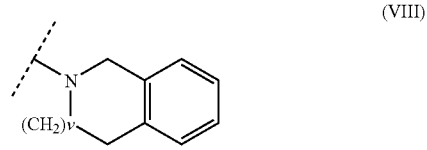

(VIII)

wherein v is 0, 1 or 2; and further provided that when $R^{15}$ is selected from hydroxy, $R^{18}$ is selected from hydrogen; and pharmaceutically acceptable salts, hydrates, solvates, geometrical isomers, tautomers, optical isomers, and prodrug forms thereof.

Preferred is a compound of the Formula (Ib):

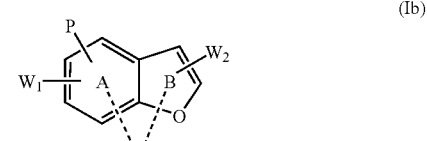

(Ib)

wherein:

P is selected from a substituent of Formula (II)-(VII):

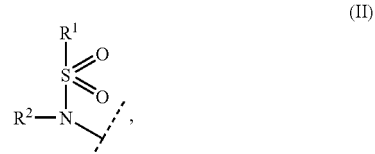

(II)

(III)

(IV)

(V)

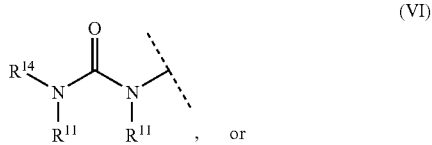

(VI)

, or

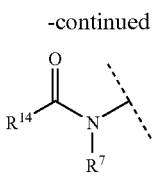

(VII)

wherein:
x, y and j are each independently selected from 0, 1, and 2
wherein the dashed bonds denote that $R^3$ may be attached to either the A or B ring at any carbon atom that allows the substitution;

$R^1$ is selected from:
(a) $C_{1-6}$-alkyl,
(b) $C_{1-6}$-alkoxy-$C_{2-6}$-alkyl,
(c) $C_{3-6}$-alkenyl,
(d) hydroxy-$C_{2-6}$-alkyl,
(e) halo-$C_{1-6}$-alkyl,
(f) aryl,
(g) arylcarbonylmethyl,
(h) aryl-$C_{3-6}$-alkenyl,
(i) aryl-$C_{1-6}$-alkyl,
(j) $C_{3-7}$-cycloalkyl,
(k) heteroaryl,
(o) heteroaryl-$C_{1-6}$-alkyl, wherein any heteroaryl or aryl residue, alone or as part of another group may be optionally substituted, independently, in one or more positions with a substituent selected from
(b) halogen,
(c) $C_{1-6}$-alkyl,
(d) hydroxy,
(e) $C_{1-6}$-alkoxy,
(f) $C_{2-6}$-alkenyl,
(g) $C_{2-3}$-alkynyl,
(h) phenyl,
(i) phenoxy,
(j) benzyloxy,
(k) benzoyl,
(l) benzyl,
(m) —$OCF_3$,
(n) —CN,
(o) hydroxy-$C_{1-6}$-alkyl,
(p) $C_{1-6}$-alkoxy-$C_{1-6}$-alkyl,
(q) halo-$C_{1-6}$-alkyl,
(r) —$NR^9R^9$,
(s) —$NO_2$,
(t) —$CONR^9R^9$,
(u) —$NR^7COR^{10}$,
(v) —$C(=O)R^{10}$,
(x) $C_{1-6}$-alkoxycarbonyl,
(y) $C_{1-6}$-alkylthio,
(z) —$SCF_3$,
(aa) —$CHF=CH_2$,
(ab) methylsulfonyl, or
(ac) —COOH, with the proviso that when the substituent on the said aryl or heteroaryl residue is selected from phenyl, phenoxy, benzyloxy, benzoyl and benzyl, the phenyl ring thereof may be optionally substituted by one or more of halogen, $C_{1-4}$-alkyl, $C_{1-4}$-alkylthio, $C_{1-4}$-alkoxy, cyano, or trifluoromethyl;

$R^2$ is selected from:
(a) hydrogen,
(b) $C_{1-6}$-alkyl,
(c) $C_{1-6}$-alkoxy-$C_{2-6}$ alkyl,
(d) hydroxy-$C_{2-6}$-alkyl, (e) —$(CH_2)_m$—$CH_2$—F, wherein m is 2-4, or
(g) $C_{1-4}$-alkylsulfonyl, provided that P is selected from a substituent of formula (V);

$W_1$ and $W_2$ are each independently selected from:
(a) hydrogen,
(b) halogen,
(c) $C_{1-6}$-alkyl,
(d) hydroxy,
(e) $C_{1-6}$-alkoxy,
(f) $C_{1-6}$-alkylthio,
(g) $C_{2-6}$-alkenyl,
(m) —$OCF_3$,
(n) —CN,
(o) hydroxy-$C_{1-6}$-alkyl,
(p) $C_{1-6}$-alkoxy-$C_{1-6}$-alkyl,
(q) halo-$C_{1-6}$-alkyl,
(r) —$CONR^9R^9$,
(s) —$C(=O)R^{10}$,
(t) $C_{1-6}$-alkoxycarbonyl,
(u) —$SCF_3$, or
(v) —$CHF=CH_2$, with the proviso that when $W_1$ and $W_2$ are not selected from hydroxy, methoxy, methyl and halogen, at least one of $W_1$ and $W_2$ is selected from hydrogen;

$R^3$ is a group selected from:

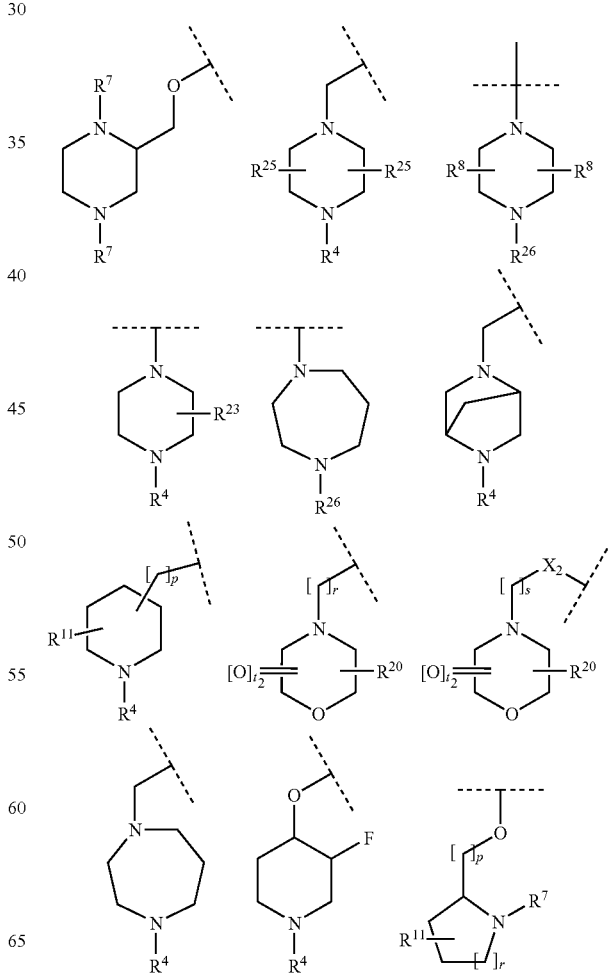

-continued

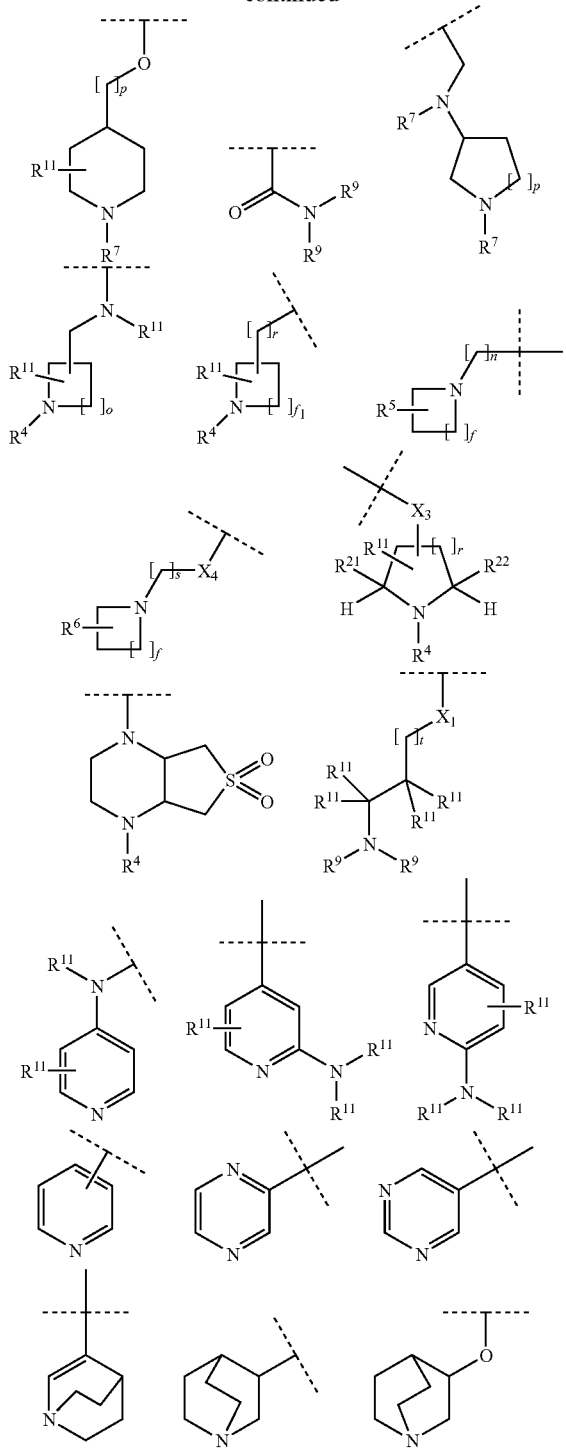

wherein
n=0, 1, 2 or 3,
r=0, 1 or 2,
o=1, 2 or 3,
p=1 or 2,
s=2 or 3,
t=0 or 1,
$t_2$=0 or 1, f=1, 2, 3 or 4, and
$f_1$=1, 2 or 4;
$X_1$ is selected from $NR^7$ and S;
$X_2$ is selected from O, $NR^7$ and S, provided that when $t_2$=0 and s=2 then $X_2$ is selected from $NR^7$ and S;
$X_3$ is selected from $NR^7$ and S, provided that $X_3$ is selected from S when r=1;
$X_4$ is selected from O, $NR^7$ and S, provided that $X_4$ is selected from S and $NR^7$ when f is selected from 2 and 3, and $R^6$ simultaneously is selected from hydrogen and $C_{1-4}$ alkyl;

when P is a group selected from a substituent of Formula (V)-(VII), $R^3$ is additionally selected from the following groups:

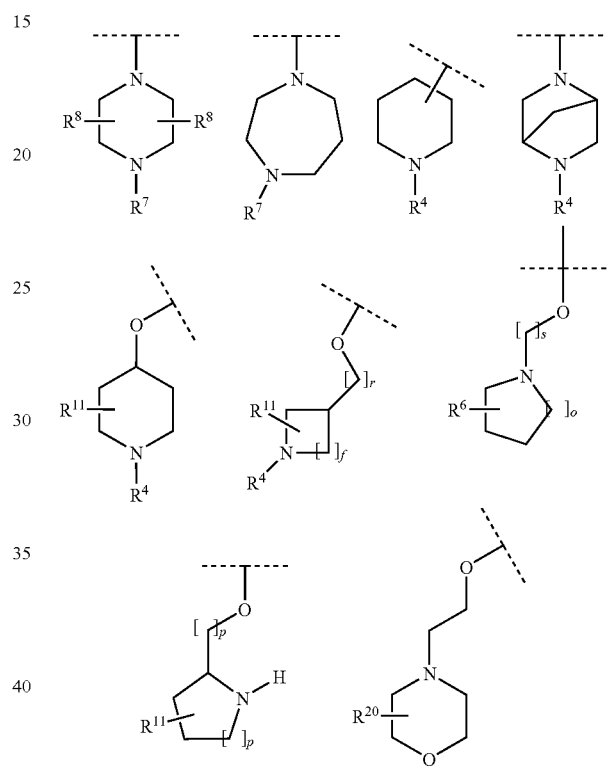

wherein:
r=0, 1 or 2,
o=1, 2 or 3,
p is each independently 1 or 2,
s=2 or 3, and
f=1, 2, 3 or 4;
$R^4$ is selected from:
(a) hydrogen,
(b) $C_{1-6}$-alkyl,
(c) 2-cyanoethyl,
(d) hydroxy-$C_{2-6}$-alkyl,
(e) $C_{3-6}$-alkenyl,
(f) $C_{3-6}$-alkynyl,
(g) $C_{3-7}$-cycloalkyl,
(h) $C_{3-7}$-cycloalkyl-$C_{1-4}$-alkyl,
(i) $C_{1-6}$-alkoxy-$C_{2-6}$-alkyl
(l) —$CH_2$—CO—N—$R^{11}R^{11}$, or
(m) 3,3,3-trifluoropropyl;
$R^5$ is selected from:
(a) hydrogen,
(b) $C_{1-4}$-alkyl,
(c) hydroxy-$C_{1-4}$-alkyl, (d) $C_{1-4}$-alkoxymethyl,
(e) halo-$C_{1-4}$-alkyl,
(f) —$NR^{11}R^{11}$,
(h) hydroxy, provided that the said hydroxy group is not attached to a carbon atom adjacent to a ring nitrogen atom, or
(i) fluorine, provided that the said fluorine atom is not attached to a carbon atom adjacent to a ring nitrogen atom;

$R^6$ is selected from:
(a) hydrogen,
(b) $C_{1-4}$-alkyl,
(c) hydroxy-$C_{1-4}$-alkyl,
(d) $C_{1-4}$-alkoxy-$C_{1-4}$-alkyl,
(e) hydroxy, provided that the said hydroxy group is not attached to a carbon atom adjacent to a heterocyclic ring nitrogen atom,
(f) fluorine, provided that the said fluorine atom is not attached to a carbon atom adjacent to a ring nitrogen atom, or
(g) halo-$C_{1-4}$-alkyl;

$R^7$ is each independently selected from:
(a) hydrogen, provided that $R^7$ is not hydrogen when present simultaneously with r and said r is 1 or 2,
(b) $C_{1-4}$-alkyl,
(c) hydroxy-$C_{2-4}$-alkyl, or
(d) methoxy-$C_{2-4}$-alkyl;

$R^8$ is each independently selected from:
(a) hydrogen, or
(b) $C_{1-4}$-alkyl, with the proviso that when both $R^8$ simultaneously are selected from $C_{1-4}$-alkyl, said $C_{1-4}$-alkyl may be attached to the same or different carbon atoms, or when two groups are present at the same carbon atom they may together form a cyclopropane ring;

$R^9$ is each independently selected from:
(a) hydrogen,
(b) $C_{1-6}$-alkyl
(c) $C_{3-7}$-cycloalkyl, or
the two $R^9$ groups together with the nitrogen to which they are attached form a heterocyclic ring; and provided that when the two $R^9$ groups form a piperazine ring, the nitrogen of the said piperazine ring that allows the substitution may be optionally substituted with $C_{1-4}$-alkyl; and further provided that when the two $R^9$ groups form a piperidine ring, any ring carbon atom in the said piperidine ring may be optionally substituted with methyl;

$R^{10}$ is selected from:
(a) $C_{1-6}$-alkyl,
(c) aryl, or
(d) heteroaryl,
wherein heteroaryl or aryl may be optionally substituted in one or more positions with substituents selected from halogen, $C_{1-4}$-alkyl, $C_{1-4}$-alkoxy, cyano, trifluoromethyl;

$R^{11}$ is each independently selected from:
(a) hydrogen,
(b) methyl, or
(c) ethyl, provided that $R^{11}$ is present in a group $R^4$ or $R^{26}$ selected from —$CH_2$—CO—N—$R^{11}R^{11}$;

$R^{12}$ is selected from:
(a) hydrogen,
(b) $C_{1-6}$-alkyl,
(c) aryl,
(d) aryl-$C_{1-6}$-alkyl,
(e) $C_{3-7}$-cycloalkyl,
(f) $C_{3-7}$-cycloalkyl-$C_{1-4}$-alkyl,
(g) heteroaryl, or
(h) heteroaryl-$C_{1-6}$-alkyl, wherein any heteroaryl or aryl residue, alone or as part of another group, may be optionally substituted, independently, in one or more positions with substituents selected from:
(b) halogen,
(c) $C_{1-6}$-alkyl,
(d) hydroxy,
(e) $C_{1-6}$-alkoxy,
(f) $C_{2-6}$-alkenyl,
(g) $C_{2-3}$-alkynyl,
(h) phenyl,
(i) phenoxy,
(j) benzyloxy,
(k) benzoyl,
(l) benzyl,
(m) —$OCF_3$,
(n) —CN,
(o) hydroxy-$C_{1-6}$-alkyl,
(p) $C_{1-6}$-alkoxy-$C_{1-6}$-alkyl,
(q) halo-$C_{1-6}$-alkyl,
(r) —$NR^9R^9$,
(s) —$NO_2$,
(t) —$CONR^9R^9$,
(u) —$NR^7COR^{10}$,
(v) —C(=O)$R^{10}$,
(x) $C_{1-6}$-alkoxycarbonyl,
(y) $C_{1-6}$-alkylthio,
(z) —$SCF_3$,
(aa) —CHF=$CH_2$,
(ab) methylsulfonyl, or
(ac) —COOH, with the proviso that when the substituent on the said aryl or heteroaryl residue is selected from phenyl, phenoxy, benzyloxy, benzoyl, and benzyl, the phenyl ring thereof may be optionally substituted by one or more of halogen, $C_{1-4}$-alkyl, $C_{1-4}$-alkoxy, cyano, or trifluoromethyl;

$R^{13}$ is selected from:
(a) $C_{1-6}$-alkyl,
(b) $C_{3-6}$-cycloalkyl,
(c) aryl,
(d) heteroaryl,
(e) aryl-$C_{1-2}$-alkyl, or
(f) heteroaryl-$C_{1-2}$-alkyl, wherein any heteroaryl or aryl residue may be optionally substituted in one or more positions with substituents selected from halogen, $C_{1-4}$-alkyl, $C_{1-4}$-alkoxy, cyano, trifluoromethyl, and acetyl;

$R^{14}$ is selected from:
(a) aryl,
(b) heteroaryl,
(c) aryl-$C_{1-3}$-alkyl, or
(d) heteroaryl-$C_{1-3}$-alkyl, wherein any heteroaryl or aryl residue may be substituted in one or more positions with substituents selected from halogen, $C_{1-4}$-alkyl, $C_{1-4}$-alkoxy, cyano, and trifluoromethyl;

$R^{20}$ is each independently selected from:
(a) hydrogen,
(b) methyl,
with the proviso that when $t_2$ is 1, $R^{20}$ is H;

$R^{21}$ and $R^{22}$ are each independently selected from:
(a) hydrogen, or
(b) methyl,
provided that, when present simultaneously with $R^{11}$, at least two of $R^{11}$, $R^{21}$ and
$R^{22}$ are selected from hydrogen;

$R^{23}$ is selected from:
(a) hydroxy-$C_{1-4}$-alkyl,
(b) $C_{1-4}$-alkoxymethyl, or
(c) halo-$C_{1-4}$-alkyl;

$R^{25}$ is each independently selected from:
(a) hydrogen,
(b) $C_{1-4}$-alkyl,
(c) hydroxy-$C_{1-4}$-alkyl,
(d) $C_{1-4}$-alkoxy-$C_{1-4}$-alkyl, or
e) fluoromethyl,
with the proviso that when both $R^{25}$ simultaneously are selected from $C_{1-4}$-alkyl, said $C_{1-4}$-alkyl may be attached to the same or different carbon atoms, and with the further proviso that when one $R^{25}$ is selected from hydroxy-$C_{1-4}$-alkyl, $C_{1-4}$-alkoxy-$C_{1-4}$-alkyl, and fluoromethyl, the other $R^{25}$ represents hydrogen;
$R^{26}$ is selected from:
(a) 2-cyanoethyl,
(b) $C_{3-6}$-alkenyl,
(c) $C_{3-6}$-alkynyl,
(d) $C_{3-7}$-cycloalkyl,
(e) $C_{3-7}$-cycloalkyl-$C_{1-4}$-alkyl,
(f) —$CH_2$—CO—$NR^{11}R^{11}$, or
(g) 3,3,3-trifluoropropyl;
with the proviso that $R^2$ and $R^{12}$ in Formula (III) are not simultaneously selected from hydrogen; and with the further proviso that the said $R^2$ and $R^{12}$ together may form a heterocyclic ring selected from piperidine, pyrrolidine, morpholine, piperazine thiomorpholine, and provided that when $R^2$ and $R^{12}$ together form a piperazine ring, the distal piperazine nitrogen may be optionally substituted by $C_{1-4}$ alkyl or aryl, and wherein said aryl may be optionally substituted in one or more positions with substituents selected from halogen, $C_{1-4}$-alkyl, $C_{1-4}$-alkoxy, cyano, trifluoromethyl; or $R^2$ and $R^{12}$ together form a heteroaromatic ring of Formula (VIII):

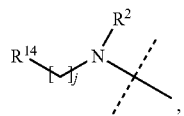
(VIII)

wherein v is 0 or 1.
It is further preferred that:
P is selected from a substituent of Formula (II)-(V)

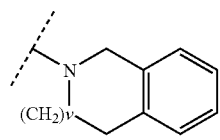
(II)

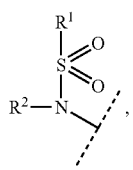
(III)

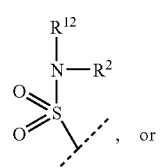
(IV)

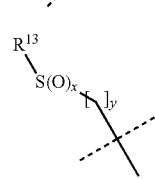
(V)

wherein x is 2, y is 0 and j is 1;
$R^1$ is selected from:
(f) aryl,
(i) aryl-$C_{1-3}$-alkyl,
(k) heteroaryl,
(o) heteroaryl-$C_{1-3}$-alkyl,
wherein any heteroaryl or aryl residue, alone or as part of another group may be optionally substituted, independently, in one or more positions with a substituent selected from:
(b) halogen,
(c) $C_{1-4}$-alkyl,
(d) hydroxy,
(e) $C_{1-4}$-alkoxy,
(m) —$OCF_3$,
(n) —CN,
(o) hydroxy-$C_{1-4}$-alkyl,
(p) $C_{1-2}$-alkoxy-$C_{1-2}$-alkyl,
(q) halo-$C_{1-3}$-alkyl,
(r) —$NR^9R^9$,
(t) —$CONR^9R^9$,
(u) —$NR^7COR^{10}$,
(v) —$C(=O)R^{10}$,
(x) $C_{1-3}$-alkoxycarbonyl,
(y) $C_{1-3}$-alkylthio, or
(ab) methylsulfonyl,
$R^2$ is selected from:
(a) hydrogen,
(b) $C_{1-4}$-alkyl,
$W_1$ and $W_2$ are each independently selected from:
(a) hydrogen,
(b) halogen,
(c) $C_{1-4}$-alkyl,
(d) hydroxy,
(e) $C_{1-4}$-alkoxy,
(f) $C_{1-4}$-alkylthio,
(m) —$OCF_3$,
(n) —CN,
(o) hydroxy-$C_{1-2}$-alkyl,
(p) $C_{1-2}$-alkoxy-$C_{1-2}$-alkyl,
(q) —$CF_3$,
(r) —$CONR^9R^9$,
(s) acetyl,
(t) $C_{1-4}$-alkoxycarbonyl, or
with the proviso that when $W_1$ and $W_2$ are not selected from hydroxy, methoxy, methyl and halogen, at least one of $W_1$ and $W_2$ is selected from hydrogen;

R³ is a group selected from:

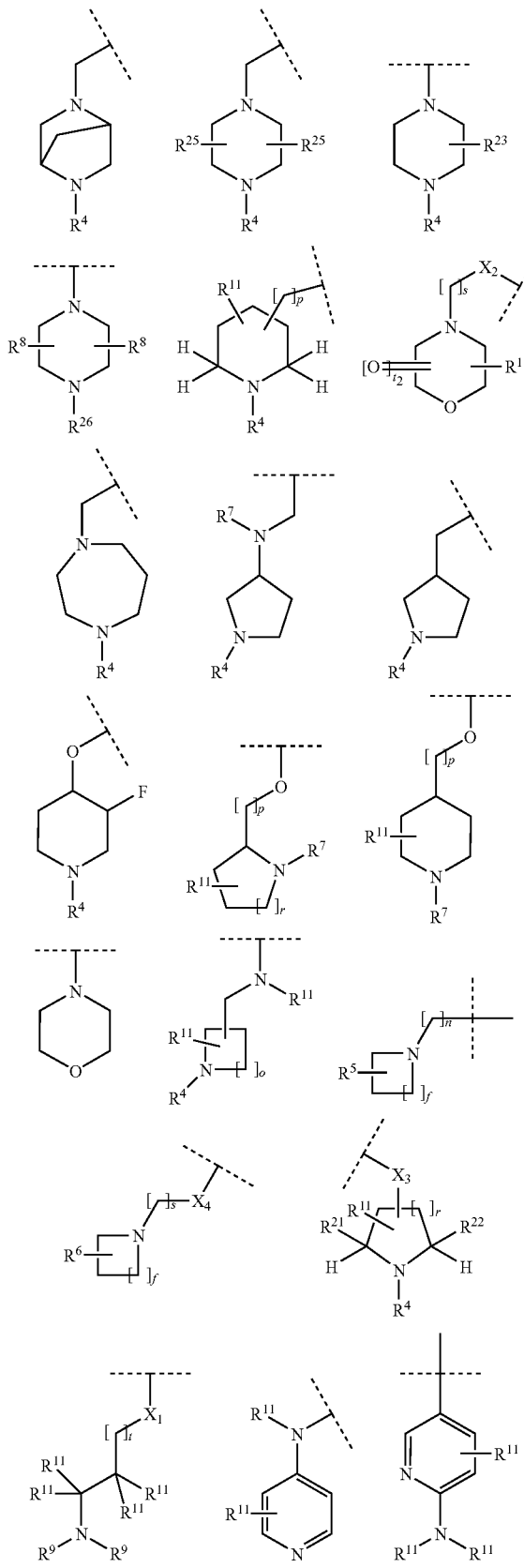

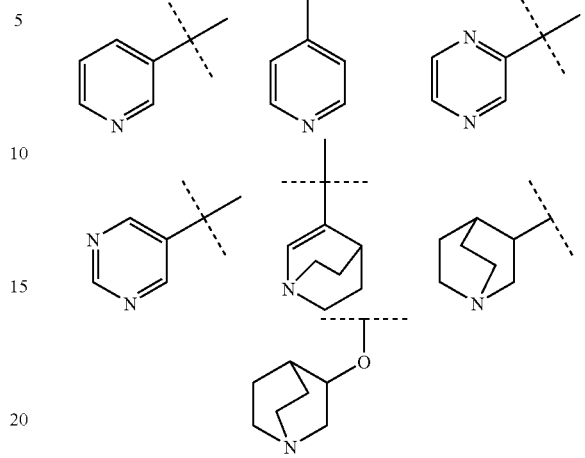

wherein:
n=0, 1, 2 or 3
r is 0, 1 or 2,
o=1, 2, or 3,
p is 1 or 2,
s=2 or 3,
t=0 or 1,
t₂=0 or 1, and
f=1, 2, 3 or 4;
X₁ is selected from NR⁷ and S;
X₂ is selected from O, NR⁷ and S, provided that X₂ is selected from NR⁷ and S when t=0 and s=2;
X₃ is selected from NR⁷ and S, provided that X₃ is selected from S when r=1;
X₄ is selected from O, NR⁷ and S, provided that X₄ is selected from S and NR⁷ when f is selected from 2 and 3, and R⁶ simultaneously is selected from hydrogen and C₁₋₄ alkyl; or;
when P is a group selected from formula (V) wherein j=1, R³ is additionally selected from the following group;

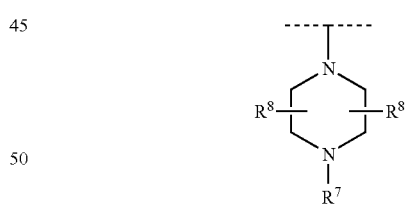

R⁴ is selected from:
(a) hydrogen,
(b) C₁₋₄-alkyl,
(d) hydroxy-C₂₋₄-alkyl,
(g) C₃₋₆-cycloalkyl,
(h) C₃₋₆-cycloalkyl-C₁₋₄-alkyl,
(i) C₁₋₄-alkoxy-C₂₋₄-alkyl
(m) 3,3,3-trifluoropropyl;
R⁵ is selected from:
(a) hydrogen,
(b) C₁₋₄-alkyl,
(c) hydroxy-C₁₋₄-alkyl,
(d) C₁₋₄-alkoxymethyl,
(e) halo-C₁₋₄-alkyl, (f) —NR$^{11}$R$^{11}$,
(g) hydroxy, provided that the said hydroxy group is not attached to a carbon atom adjacent to a ring nitrogen atom, or
(h) fluorine, provided that the said fluorine atom is not attached to a carbon atom adjacent to a ring nitrogen atom;

R$^6$ is selected from:
(a) hydrogen,
(b) C$_{1-4}$-alkyl,
(c) hydroxy-C$_{1-4}$-alkyl,
(d) C$_{1-4}$-alkoxy-C$_{1-4}$-alkyl,
(e) hydroxy, provided that the said hydroxy group is not attached to a carbon atom adjacent to a heterocyclic ring nitrogen atom,
(f) fluorine, provided that the said fluorine atom is not attached to a carbon atom adjacent to a ring nitrogen atom, or
(g) halo-C$_{1-4}$-alkyl;

R$^7$ is each independently selected from:
(a) hydrogen, provided that R$^7$ is not hydrogen when present simultaneously with r and said r is 1 or 2,
(b) C$_{1-4}$-alkyl,
(c) hydroxy-C$_{2-4}$-alkyl, or
(d) methoxy-C$_{2-4}$-alkyl;

R$^8$ is each independently selected from:
(a) hydrogen, or
(b) C$_{1-4}$-alkyl, with the proviso that when both R$^8$ simultaneously are selected from C$_{1-4}$-alkyl, said C$_{1-4}$-alkyl may be attached to the same or different carbon atoms, or when two groups are present at the same carbon atom they may together form a cyclopropane ring;

R$^9$ is each independently selected from:
(a) hydrogen,
(b) C$_{1-6}$-alkyl, or
the two R$^9$ groups together with the nitrogen to which they are attached form a heterocyclic ring; and provided that when the two R$^9$ groups form a piperazine ring, the nitrogen of the said piperazine ring that allows the substitution is optionally substituted with C$_{1-4}$-alkyl;

R$^{10}$ is selected from:
(a) C$_{1-6}$-alkyl,
(c) aryl, or
(d) heteroaryl,
wherein heteroaryl or aryl may be substituted in one or more positions with substituents selected from halogen, C$_{1-4}$-alkyl, C$_{1-4}$-alkoxy, cyano, trifluoromethyl;

R$^{11}$ is each independently selected from:
(a) hydrogen, or
(b) methyl,
(c) ethyl, provided that R$^{11}$ is present in a group R$^{26}$ selected from —CH$_2$—CO—NR$^{11}$R$^{11}$;

R$^{12}$ is selected from:
(a) hydrogen,
(c) aryl,
(d) aryl-C$_{1-3}$-alkyl,
(g) heteroaryl, or
(h) heteroaryl-C$_{1-3}$-alkyl,
wherein any heteroaryl or aryl residue, alone or as part of another group, may be optionally substituted, independently, in one or more positions with substituents selected from
(b) halogen,
(c) C$_{1-4}$-alkyl,
(d) hydroxy,
(e) C$_{1-4}$-alkoxy,
(m) —OCF$_3$,
(n) —CN,
(o) hydroxy-C$_{1-3}$-alkyl,
(p) C$_{1-3}$-alkoxy-C$_{1-3}$-alkyl,
(q) halo-C$_{1-4}$-alkyl,
(r) —NR$^9$R$^9$,
(t) —CONR$^9$R$^9$,
(u) —NR$^7$COR$^{10}$,
(v) —C(=O)R$^{10}$,
(x) C$_{1-3}$-alkylthio, or
(ab) methylsulfonyl;

R$^{13}$ is selected from:
(c) aryl,
(d) heteroaryl,
(e) aryl-C$_{1-2}$-alkyl, or
(f) heteroaryl-C$_{1-2}$-alkyl,
wherein any heteroaryl or aryl residue may be optionally substituted in one or more positions with substituents selected from halogen, C$_{1-4}$-alkyl, C$_{1-4}$-alkoxy, cyano, trifluoromethyl and acetyl;

R$^{14}$ is selected from:
(a) aryl,
(b) heteroaryl,
(c) aryl-C$_{1-3}$-alkyl, or
(d) heteroaryl-C$_{1-3}$-alkyl;
wherein any heteroaryl or aryl residue may be optionally substituted in one or more positions with substituents selected from halogen, C$_{1-4}$-alkyl, C$_{1-4}$-alkoxy, cyano, and trifluoromethyl;

R$^{20}$ is selected from:
(a) hydrogen, or
(b) methyl,
with the proviso that when t$_2$ is 1, R$^{20}$ is H;

R$^{21}$ and R$^{22}$ are each independently selected from:
(a) hydrogen, or
(b) methyl,
provided that, when present simultaneously with R$^{11}$, at least two of R$^{11}$, R$^{21}$ and R$^{22}$ are selected from hydrogen;

R$^{23}$ is selected from:
(a) hydroxy-C$_{1-4}$-alkyl,
(b) C$_{1-4}$-alkoxymethyl, or
(c) halo-C$_{1-4}$-alkyl;

R$^{25}$ is selected from:
(a) hydrogen,
(b) C$_{1-4}$-alkyl,
(c) hydroxy-C$_{1-4}$-alkyl,
(d) C$_{1-4}$-alkoxy-C$_{1-4}$-alkyl, or
(e) fluoromethyl;
with the proviso that when both R$^{25}$ simultaneously are selected from C$_{1-4}$-alkyl, said C$_{1-4}$-alkyl may be attached to the same or different carbon atoms, and with the further proviso that when one R$^{25}$ is selected from hydroxy-C$_{1-4}$-alkyl, C$_{1-4}$-alkoxy-C$_{1-4}$-alkyl, and fluoromethyl; the other R$^{25}$ represents hydrogen;

R$^{26}$ is selected from:
(e) C$_{3-7}$-cycloalkyl-C$_{1-4}$-alkyl,
(f) —CH$_2$—CO—NR$^{11}$R$^{11}$, or
(g) 3,3,3-trifluoropropyl;
with the proviso that R$^2$ and R$^{12}$ in Formula (III) are not simultaneously selected from hydrogen; and with the further proviso that the said R$^2$ and R$^{12}$ together may for a heterocyclic ring selected from piperidine, pyrrolidine, morpholine, piperazine thiomorpholine, and provided that when R$^2$ and R$^{12}$ together form a piperazine ring, the distal piperazine nitrogen may be optionally substituted by C$_{1-4}$ alkyl or aryl, and wherein said aryl may be optionally substituted in one or more positions with substituents selected from halogen, C$_{1-4}$-alkyl, C$_{1-4}$-alkoxy, cyano, trifluoromethyl; or R$^2$ and R$^{12}$ together form a heteroaromatic ring of Formula (VIII):

(VIII)

wherein v is 0 or 1.

A set of preferred compounds within this invention are those of the general Formula (XII):

(XII)

wherein $W_1$, $W_2$, P and $R^3$ are as defined for formula (Ib).

Further preferred compounds of Formula (XII) are compounds wherein

P is selected from a substituent of Formula (II)-(IV);

x is 2 and y is 0;

$R^1$ is selected from aryl and heteroaryl, wherein any heteroaryl or aryl residue may be optionally substituted, independently, in one or more positions with a substituent selected from halogen, $C_{1-4}$-alkyl, $C_{1-4}$-alkoxy and trifluoromethyl;

$R^2$ is selected from hydrogen;

$W_1$ and $W_2$ are hydrogen;

$R^3$ is a group selected from wherein
p=1 or 2,
$R^4$ is selected from:
  (a) hydrogen, or
  (b) $C_{1-4}$-alkyl;
$R^{11}$ is each independently selected from:
  (a) hydrogen, or
  (b) methyl,
  (c) ethyl, provided that $R^{11}$ is present in a group $R^{26}$ selected from —$CH_2$—CO—$NR^{11}R^{11}$;
$R^{12}$ and $R^{13}$ are each independently selected from aryl and heteroaryl,
wherein any heteroaryl or aryl residue may be optionally substituted, independently, in one or more positions with a substituent selected from halogen, $C_{1-4}$-alkyl, $C_{1-4}$-alkoxy, and $CF_3$;
$R^{25}$ is selected from:
  (a) hydrogen, or
  (b) $C_{1-4}$-alkyl;
$R^{26}$ is selected from:
  (e) $C_{3-7}$-cycloalkyl-$C_{1-4}$-alkyl,
  (f) —$CH_2$—CO—$NR^{11}R^{11}$, or
  (g) 3,3,3-trifluoropropyl.

In more preferred compounds of Formula (XII),

P is selected from a substituent of Formula (II)-(IV);

x is 2 and y is 0;

$R^1$, $R^{12}$ and $R^{13}$ are each independently selected from phenyl or substituted phenyl selected from 2-methoxy-5-methylphenyl, 2-methylphenyl, 4-methylphenyl, 4-fluorophenyl, 3,4-dimethoxyphenyl, 2-chlorophenyl, 2-trifluoromethylphenyl, 2,6-dichlorophenyl, 3-chloro-4-methylphenyl, 3-methylphenyl, 3,6-dichloro-2-methylphenyl, and 2-chloro-5-fluorophenyl; or heteroaryl or substituted heteroaryl selected from 2-thienyl, 5-chloro-2-thienyl, 5-chloro- and 1,3-dimethyl-1H-pyrazol-4-yl;

$R^2$ is selected from hydrogen;
$W_1$ and $W_2$ are hydrogen;
$R^3$ is a group selected from:

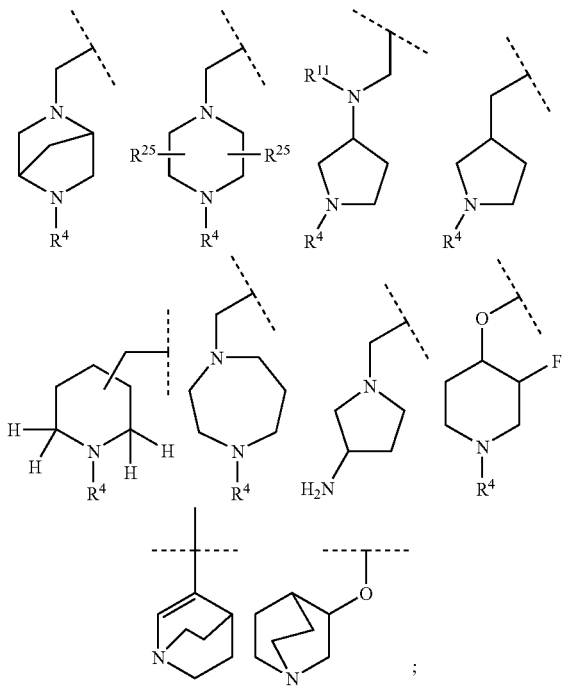

$R^4$ is each independently selected from:
(a) hydrogen, or
(b) methyl,
$R^{11}$ is each independently selected from:
(a) hydrogen, or
(b) methyl;
$R^{25}$ is each independently selected from:
(a) hydrogen, or
(b) methyl.

In some embodiments, $R^4$ can be hydrogen, methyl, or ethyl.

In some embodiments, $R^4$ or $R^{11}$ can be hydrogen.

A yet further set of preferred compounds within this invention are those of the general Formula (XIII):

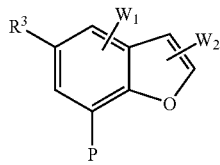

(XIII)

wherein $W_1$, $W_2$, P and $R^3$ are as defined for Formula (Ib).

Further preferred compounds of Formula (XIII) are compounds wherein:
P is selected from a substituent of Formula (II)-(IV);
x is 2 and y is 0;

$R^1$ is selected from aryl and heteroaryl, wherein any heteroaryl or aryl residue may be optionally substituted, independently, in one or more positions with a substituent selected from halogen, $C_{1-4}$-alkyl, trifluoromethoxy, and $C_{1-4}$-alkoxy;
$R^2$ is selected from hydrogen;
$W_1$ and $W_2$ are hydrogen;
$R^3$ is a group selected from:

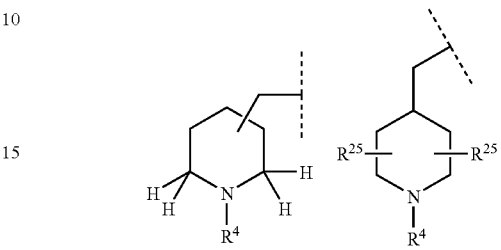

wherein:
$R^4$ is each independently selected from:
(a) hydrogen, or
(b) $C_{1-4}$-alkyl;
$R^{25}$ is each independently selected from:
(a) hydrogen, or
(b) $C_{1-4}$-alkyl, with the proviso that when both $R^{25}$ represent $C_{1-4}$-alkyl, said $C_{1-4}$-alkyl may be attached to the same or different carbon atoms;
$R^{12}$ and $R^{13}$ are each independently selected from aryl and heteroaryl, wherein any heteroaryl or aryl residue may be optionally substituted, independently, in one or more positions with a substituent selected from halogen, $C_{1-4}$-alkyl, trifluoromethyl, and $C_{1-4}$-alkoxy.

In more preferred compounds of Formula (XIII),
P is selected from a substituent of Formula (II);
$R^1$ is selected from 2-methoxy-5-methylphenyl;
$R^2$ is selected from hydrogen;
$W_1$ and $W_2$ are hydrogen;
$R^3$ is a group selected from:

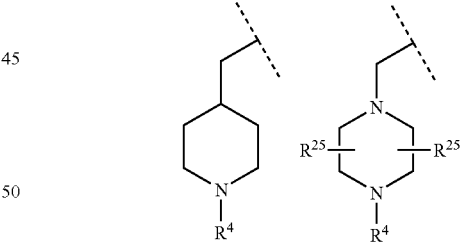

$R^4$ is each independently selected from
a) hydrogen, or
b) methyl;
$R^{25}$ is each independently selected from:
a) hydrogen, or
b) methyl.

Preferred compounds include:
N-(7-{Methyl[3-(methylamino)propyl]amino}-1-benzofuran-5-yl)benzenesulfonamide hydrochloride,
N-(7-Piperidin-1-yl-1-benzofuran-5-yl)benzenesulfonamide,
4-Fluoro-N-(7-piperidin-1-yl-1-benzofuran-5-yl)benzenesulfonamide, 3,4-Dimethoxy-N-(7-piperidin-1-yl-1-benzofuran-5-yl)benzenesulfonamide hydrochloride,
3,4-Dimethoxy-N-(7-pyrrolidin-1-yl-1-benzofuran-5-yl)benzenesulfonamide,
N-(7-Pyrrolidin-1-yl-1-benzofuran-5-yl)benzenesulfonamide,
4-Fluoro-N-(7-pyrrolidin-1-yl-1-benzofuran-5-yl)benzenesulfonamide hydrochloride,
4-Fluoro-N-(7-morpholin-4-yl-1-benzofuran-5-yl)benzenesulfonamide hydrochloride,
N-(7-Morpholin-4-yl-1-benzofuran-5-yl)benzenesulfonamide hydrochloride,
3,4-Dimethoxy-N-(7-morpholin-4-yl-1-benzofuran-5-yl)benzenesulfonamide,
2-Methoxy-5-methyl-N-(7-pyridin-4-yl-1-benzofuran-5-yl)benzenesulfonamide,
N-(7-Pyridin-3-yl-1-benzofuran-5-yl)benzenesulfonamide trifluoroacetate,
2-Methoxy-5-methyl-N-(7-pyridin-3-yl-1-benzofuran-5-yl)benzenesulfonamide trifluoroacetate,
N-(7-Pyrazin-2-yl-1-benzofuran-5-yl)benzenesulfonamide trifluoroacetate,
N-(7-Pyrimidine-5-yl-1-benzofuran-5-yl)benzenesulfonamide hydrochloride, and,
N-[7-(1-Aza-bicyclo[2.2.2]oct-2-en-3-yl)-benzofuran-5-yl]-2-methoxy-5-methylbenzenesulfonamide hydrochloride,
2-[4-(5-{[(2-Chlorophenyl)sulfonyl]amino}-1-benzofuran-7-yl)piperazin-1-yl]-N,N-diethylacetamide hydrochloride,
N,N-diethyl-2-[4-(5-{[(2-methoxy-5-methylphenyl)sulfonyl]amino}-1-benzofuran-7-yl)piperazin-1-yl]acetamide hydrochloride,
N-[7-(1-Azabicyclo[2.2.2]oct-3-yloxy)-1-benzofuran-5-yl]benzenesulfonamide hydrochloride,
N-[7-(1-Azabicyclo[2.2.2]oct-3-yloxy)-1-benzofuran-5-yl]-2-chlorobenzenesulfonamide hydrochloride,
N-[7-(1-Azabicyclo[2.2.2]oct-3-yloxy)-1-benzofuran-5-yl]-2-methoxy-5-benzenesulfonamide hydrochloride,
N-{7-[(2-Morpholin-4-ylethyl)amino]-1-benzofuran-5-yl}benzenesulfonamide hydrochloride,
2-Methoxy-5-methyl-N-{7-[(2-morpholin-4-ylethyl)amino]-1-benzofuran-5-yl}benzenesulfonamide hydrochloride,
N-{7-[(2-Morpholin-4-ylethyl)amino]-1-benzofuran-5-yl}-2-(trifluoromethyl)benzenesulfonamide hydrochloride,
2,6-Dichloro-N-{7-[(2-morpholin-4-ylethyl)amino]-1-benzofuran-5-yl}benzenesulfonamide hydrochloride,
N-(7-{[2(Dimethylamino)ethyl]amino}-1-benzofuran-5-yl)-2-methoxy-5-benzenesulfonamide hydrochloride,
2-Chloro-N(7-{[2-(dimethylamino)}-1-benzofuran-5-yl)benzenesulfonamide hydrochloride,
N-[7-(Pyridin-4-ylamino)-1-benzofuran-5-yl]benzenesulfonamide hydrochloride,
2-Chloro-N-[7-(pyridin-4-ylamino)-1-benzofuran-5-yl]benzenesulfonamide hydrochloride,
2-Methoxy-5-methyl-N-[7-(pyridin-4-ylamino)-1-benzofuran-5-yl]benzenesulfonamide hydrochloride,
2-Methoxy-5-methyl-N-[7-(piperazin-1-ylcarbonyl)-1-benzofuran-5-yl]benzenesulfonamide hydrochloride,
2-Methoxy-5-methyl-N-[7-(piperazin-1-ylmethyl)-1-benzofuran-5-yl]benzenesulfonamide hydrochloride,
N-{7-[(3-Aminopyrrolidin-1-yl)methyl]-1-benzofuran-5-yl}-2-methoxy-5-methylbenzenesulfonamide hydrochloride,
N-[7(6,6-Dioxidohexahydrothieno[3,4-b]pyrazin-1(2H)-yl)-1-benzofuran-5-yl]-2-methoxy-5-methylbenzenesulfonamide hydrochloride,
N-[7(6,6-Dioxidohexahydrothieno[3,4-b]pyrazin-1(2H)-yl)-1-benzofuran-5-yl]benzenesulfonamide hydrochloride,
N-{7-[(2-Pyrrolidin-1-ylethyl)amino]-1-benzofuran-5-yl}benzenesulfonamide hydrochloride,
2-Methoxy-5-methyl-N-{7-[(2-pyrrolidin-1-ylethyl)amino]-1-benzofuran-5-yl}benzenesulfonamide hydrochloride,
N-{7-[(2-Pyrrolidin-1-ylethyl)amino]-1-benzofuran-5-yl}-2-(trifluoromethyl)benzenesulfonamide hydrochloride,
3-Chloro-4-methyl-N-{7-[(2-pyrrolidin-1-ylethyl)amino]-1-benzofuran-5-yl}benzenesulfonamide hydrochloride,
2-Methoxy-5-methyl-N-{7-[(3-morpholin-4-ylpropyl)amino]-1-benzofuran-5-yl}benzenesulfonamide hydrochloride,
N-{7-[(3-Morpholin-4-ylpropyl)amino]-1-benzofuran-5-yl}-2-(trifluoromethyl)benzenesulfonamide hydrochloride,
3-Chloro-4-methyl-N-{7-[(3-morpholin-4-ylpropyl)amino]-1-benzofuran-5-yl}benzenesulfonamide hydrochloride,
N-[7-({[(2R)-1-Ethylpyrrolidin-2-yl]methyl}amino)-1-benzofuran-5-yl]benzenesulfonamide hydrochloride,
N-[7-({[(2R)-1-Ethylpyrrolidin-2-yl]methyl}amino)-1-benzofuran-5-yl]-2-methoxy-5-methylbenzenesulfonamide hydrochloride,
N-[7-({[(2R)-1-Ethylpyrrolidin-2-yl]methyl}amino)-1-benzofuran-5-yl]-2-(trifluoromethyl)benzenesulfonamide hydrochloride,
N-[7-({[(2R)-1-Ethylpyrrolidin-2-yl]methyl}amino)-1-benzofuran-5-yl]-3-methylbenzenesulfonamide hydrochloride,
N-[7-({[(2R)-1-Ethylpyrrolidin-2-yl]methyl}amino)-1-benzofuran-5-yl]thiophene-2-sulfonamide hydrochloride,
5-Chloro-N-[7-({[(2R)-1-ethylpyrrolidin-2-yl]methyl}amino)-1-benzofuran-5-yl]thiophene-2-sulfonamide hydrochloride,
5-Chloro-N-[7-({[(2R)-1-ethylpyrrolidin-2-yl]methyl}amino)-1-benzofuran-5-yl]-1,3-dimethyl-1H-pyrazole-4-sulfonamide hydrochloride,
N-(7-{[3-(2-Methylpiperidin-1-yl)propyl]amino}-1-benzofuran-5-yl)benzenesulfonamide hydrochloride,
2-Methoxy-5-methyl-N-(7-{[3-(2-methylpiperidin-1-yl)propyl]amino}-1-benzofuran-5-yl)benzenesulfonamide hydrochloride,
N-(7-{[3-(2-Methylpiperidin-1-yl)propyl]amino}-1-benzofuran-5-yl)-2-(trifluoromethyl)benzenesulfonamide hydrochloride,
5-Chloro-1,3-dimethyl-N-(7-{[3-(2-methylpiperidin-1-yl)propyl]amino}-1-benzofuran-5-yl)-1H-pyrazole-4-sulfonamide hydrochloride,
N-[7-(6-Aminopyridin-3-yl)-1-benzofuran-5-yl]-2-methoxy-5-methylbenzenesulfonamide,
N-{7-[4-(Cyclopropylmethyl)piperazin-1-yl]-1-benzofuran-5-yl}-2-methoxy-5-methylbenzenesulfonamide hydrochloride,
2-Methoxy-5-methyl-N-{7-[4-(3,3,3-trifluoropropyl)piperazin-1-yl]-1-benzofuran-5-yl}benzenesulfonamide hydrochloride,
2-Methoxy-5-methyl-N-{7-[3-(trifluoromethyl)piperazin-1-yl]-1-benzofuran-5-yl}benzenesulfonamide hydrochloride,
N-[7-(Aminopiperidin-1-yl)-1-benzofuran-5-yl]-2-(trifluoromethyl)benzenesulfonamide hydrochloride,
N-[7-(Aminopiperidin-1-yl)-1-benzofuran-5-yl]-benzenesulfonamide hydrochloride,
N-[7-(Aminopiperidin-1-yl)-1-benzofuran-5-yl]-2-chlorobenzenesulfonamide hydrochloride, N-[7-(Aminopiperidin-1-yl)-1-benzofuran-5-yl]-2-methoxy-5-methylbenzenesulfonamide hydrochloride,
N-(7-{[cis-3-Fluoropiperidin-4-yl]oxy}-1-benzofuran-5-yl)-2-methoxy-5-methylbenzenesulfonamide hydrochloride,
N-(7-{trans-3-Fluoropiperidin-4-yl]oxy}-1-benzofuran-5-yl)-2-methoxy-5-methylbenzenesulfonamide hydrochloride,
N-(7-{[cis-3-Fluoropiperidin-4-yl]oxy}-1-benzofuran-5-yl)-2-(trifluoromethyl)benzenesulfonamide hydrochloride,
N-(7-{[trans-3-Fluoropiperidin-4-yl]oxy}-1-benzofuran-5-yl)-2-(trifluoromethyl)benzenesulfonamide hydrochloride,
2-Chloro-N-(7-{[trans-3-fluoropiperidin-4-yl]oxy}-1-benzofuran-5-yl)benzenesulfonamide hydrochloride,
N-(7-{[trans-3-Fluoropiperidin-4-yl]oxy}-1-benzofuran-5-yl)-3-methylbenzenesulfonamide hydrochloride,
3,6-Dichloro-N-(7-{[trans-3-fluoropiperidin-4-yl]oxy}-1-benzofuran-5-yl)-2-methylbenzenesulfonamide hydrochloride,
2-Chloro-5-fluoro-N-(7-{[trans-3-fluoropiperidin-4-yl]oxy}-1-benzofuran-5-yl)benzenesulfonamide hydrochloride,
N-(2-Methoxy-5-methylphenyl)-7-[(3-methylpiperazin-1-yl)methyl]-1-benzofuran-5-sulfonamide hydrochloride,
N-(2-Methylphenyl)-7-(piperazin-1-ylmethyl)-1-benzofuran-5-sulfonamide, trifluoroacetate,
7-[(3,5-Dimethylpiperazin-1-yl)methyl]-N-(2-methylphenyl)-1-benzofuran-5-sulfonamide, trifluoroacetate,
N-(2-Methylphenyl)-7-[(3-methylpiperazin-1-yl)methyl]-1-benzofuran-5-sulfonamide, trifluoroacetate,
7-(1,4-Diazepan-1-ylmethyl)-N-(2-methylphenyl)-1-benzofuran-5-sulfonamide, trifluoroacetate,
7-{(trans-2,5-Dimethylpiperazin-1-yl)methyl}-N-(2-methylphenyl)-1-benzofuran-5-sulfonamide, trifluoroacetate,
N-(2-Methylphenyl)-7-{[(2R)-2-methylpiperazin-1-yl]methyl}-1-benzofuran-5-sulfonamide, trifluoroacetate,
N-(2-Methoxy-5-methylphenyl)-7-[(3-methylpiperazin-1-yl)methyl]-1-benzofuran-5-sulfonamide, trifluoroacetate,
7-(1,4-Diazepan-1-ylmethyl)-N-(2-methoxy-5-methylphenyl)-1-benzofuran-5-sulfonamide, trifluoroacetate,
N-(2-Methoxy-5-methylphenyl)-7-(piperazin-1-ylmethyl)-1-benzofuran-5-sulfonamide, trifluoroacetate,
7-{(cis-3,5-Dimethylpiperazin-1-yl)methyl}-N-(2-methoxy-5-methylphenyl)-1-benzofuran-5-sulfonamide, trifluoroacetate,
7-{[trans-2,5-Dimethylpiperazin-1-yl]methyl}-N-(2-methoxy-5-methylphenyl)-1-benzofuran-5-sulfonamide, trifluoroacetate,
7-[(1S,4S)-2,5-Diazabicyclo[2.2.1]hept-2-ylmethyl]-N-(2-methoxy-5-methylphenyl)-1-benzofuran-5-sulfonamide, trifluoroacetate,
N-(2-Methoxy-5-methylphenyl)-7-[(2-methylpiperazin-1-yl)methyl]-1-benzofuran-5-sulfonamide, trifluoroacetate,
2-Chloro-N-[7-(piperazin-1-ylmethyl)-1-benzofuran-5-yl]benzenesulfonamide dihydrochloride,
2-Methyl-N-[7-(piperazin-1-ylmethyl)-1-benzofuran-5-yl]benzenesulfonamide, dihydrochloride,
N-[7-(piperazin-1-ylmethyl)-1-benzofuran-5-yl]thiophene-2-sulfonamide, dihydrochloride,
2-Chloro-N-[7-(1,4-diazepan-1-ylmethyl)-1-benzofuran-5-yl]benzenesulfonamide dihydrochloride,
N-[7-(1,4-Diazepan-1-ylmethyl)-1-benzofuran-5-yl]-2-methylbenzenesulfonamide, dihydrochloride,
N-[7-(1,4-Diazepan-1-ylmethyl)-1-benzofuran-5-yl]thiophene-2-sulfonamide dihydrochloride,
2-Methoxy-5-methyl-N-{7-[(2-methylpiperazin-1-yl)methyl]-1-benzofuran-5-yl}benzenesulfonamide, dihydrochloride,
2-Methyl-N-{7-[(2-methylpiperazin-1-yl)methyl]-1-benzofuran-5-yl}benzenesulfonamide dihydrochloride,
2,5-Dichloro-N-{7-[(2-methylpiperazin-1-yl)methyl]-1-benzofuran-5-yl}thiophene-3-sulfonamide dihydrochloride,
2-Methoxy-5-methyl-N-{7-[(3-methylpiperazin-1-yl)methyl]-1-benzofuran-5-yl}benzenesulfonamide, dihydro chloride,
N-{7-[(3-Methylpiperazin-1-yl)methyl]-1-benzofuran-5-yl}-2-(trifluoromethyl)benzenesulfonamide, dihydrochloride,
2-Chloro-N-{7-[(3-methylpiperazin-1-yl)methyl]-1-benzofuran-5-yl}benzenesulfonamide, dihydrochloride,
N-{7-[(1S,4S)-2,5-Diazabicyclo[2.2.1]hept-2-ylmethyl]-1-benzofuran-5-yl}-2-methoxy-5-methylbenzenesulfonamide, dihydrochloride,
N-{7-[(1S,4S)-2,5-Diazabicyclo[2.2.1]hept-2-ylmethyl]-1-benzofuran-5-yl}-2-(trifluoromethyl)benzenesulfonamide, dihydrochloride,
N-{7-[(1S,4S)-2,5-Diazabicyclo[2.2.1]hept-2-ylmethyl]-1-benzofuran-5-yl}-2-methylbenzenesulfonamide, dihydrochloride,
2-Methoxy-5-methyl-N-{7-[(trans-2,5-dimethylpiperazin-1-yl)methyl]-1-benzofuran-5-yl}benzenesulfonamide, bistrifluoroacetate,
2-Methyl-N-{7-[(trans-2,5-dimethylpiperazin-1-yl)methyl]-1-benzofuran-5-yl}benzenesulfonamide, bistrifluoroacetate,
2-Chloro-N-{7-[(trans-2,5-dimethylpiperazin-1-yl)methyl]-1-benzofuran-5-yl}benzenesulfonamide, bistrifluoroacetate,
1-({5-[(2-Methoxy-5-methylphenyl)sulfonyl]-1-benzofuran-7-yl}methyl)piperazine, trifluoroacetate,
1-{[5-(Phenylsulfonyl)-1-benzofuran-7-yl]methyl}piperazine, trifluoroacetate,
1-({5-[(4-Methylphenyl)sulfonyl]-1-benzofuran-7-yl}methyl)piperazine, trifluoroacetate,
1-({5-[(2-Methoxy-5-methylphenyl)sulfonyl]-1-benzofuran-7-yl}methyl)-1,4-diazepane, trifluoroacetate,
1-{[5-(Phenylsulfonyl)-1-benzofuran-7-yl]methyl}-1,4-diazepane, trifluoroacetate,
1-({5-[(4-Methylphenyl)sulfonyl]-1-benzofuran-7-yl}methyl)-1,4-diazepane, trifluoroacetate,
1-({5-[(2-Methoxy-5-methylphenyl)sulfonyl]-1-benzofuran-7-yl}methyl)-2-methylpiperazine, trifluoroacetate,
1-({5-[(2-Methoxy-5-methylphenyl)sulfonyl]-1-benzofuran-7-yl}methyl)-3-methylpiperazine, trifluoroacetate,
N-(2-Methylphenyl)-7-{[(3R)-pyrrolidin-3-ylamino]methyl}-1-benzofuran-5-sulfonamide, trifluoroacetate,
N-(2-Methylphenyl)-7-(piperidin-4-ylmethyl)-1-benzofuran-5-sulfonamide, trifluoroacetate,
N-(2-Methylphenyl)-7-(pyrrolidin-3-ylmethyl)-1-benzofuran-5-sulfonamide, trifluoroacetate,
N-(2-Methylphenyl)-7-(piperidin-3-ylmethyl)-1-benzofuran-5-sulfonamide, trifluoroacetate,
2-Methoxy-5-methyl-N-[7-(piperidin-4-ylmethyl)-1-benzofuran-5-yl]benzenesulfonamide, trifluoroacetate,
3-({5-[(4-Methylphenyl)sulfonyl]-1-benzofuran-7-yl}methyl)pyrrolidine, trifluoroacetate,
2-Methoxy-5-methyl-N-[5-(piperidin-4-ylmethyl)-1-benzofuran-7-yl]benzenesulfonamide, trifluoroacetate,
2-Methoxy-5-methyl-N-{5-[(3-methylpiperazin-1-yl)methyl]-1-benzofuran-7-yl}benzenesulfonamide, bis(trifluoroacetate, and 2-Methoxy-5-methyl-N-[5-(piperidin-4-ylmethyl)-1-benzofuran-7-yl]benzenesulfonamide, trifluoroacetate.

In another aspect, this invention related to processes for the preparation of a compound described herein, the process includes:

(a) halogenation of 4-nitrophenol to give a dihalogenated 4-nitrophenol, (b) ring closure of a dihalogenated 4-nitrophenol using trimethylsilylacetylene to give a halogenated nitrobenzofuran, (c) nucleophilic displacement of a halogenated nitrobenzofuran with an amine to give an amine-substituted nitrobenzofuran, (d) BOC-protection of an amine-substituted benzofuran to give a BOC-protected amine-substituted nitrobenzofuran, (e) reduction of a BOC-protected amine-substituted nitrobenzofuran to give a BOC-protected amine-substituted aminobenzofuran, (f) coupling of a halogenated nitrobenzofuran with a tributylstannylheterocycle, tributylstannylheteroaryl compound, or heteroaryl boronic acid or heteroaryl boronic ester to give a heterocycle-substituted or heteroaryl-substituted nitrobenzofuran, (g) reduction of a heterocycle-substituted or aryl-substituted nitrobenzofuran to give a heterocycle-substituted or heteroaryl-substituted aminobenzo furan, (h) arylsulfonylation of a heterocycle-substituted or heteroaryl-substituted aminobenzofuran to give a heterocycle-substituted or heteroaryl-substituted arylsulfonylaminobenzofuran, (i) arylsulfonylation of a BOC-protected amine-substituted aminobenzofuran to give a BOC-protected amine-substituted arylsulfonylaminobenzofuran, (j) removal of the BOC-protecting group from a BOC-protected amine-substituted arylsulfonylaminobenzofuran, (k) benzylation of a BOC-protected amine-substituted aminobenzofuran to give a BOC-protected amine-substituted benzylaminobenzofuran, (l) removal of the BOC-protecting group from a BOC-protected amine-substituted benzylaminobenzofuran, (m) benzoylation of a BOC-protected amine-substituted aminobenzofuran to give a BOC-protected amine-substituted benzoylaminobenzofuran, (n) removal of the BOC-protecting group from a BOC-protected amine-substituted benzoylaminobenzofuran, (o) reaction of a BOC-protected amine-substituted aminobenzofuran with an aryl isocyanate to give a BOC-protected amine-substituted phenylaminocarbonylaminobenzofuran, and (p) removal of the BOC-protecting group from a BOC-protected amine-substituted phenylaminocarbonylaminobenzofuran.

Additional synthetic steps that can be used to prepare the compounds of the invention are described in Schemes 7-14.

In a further aspect, this invention relates to compounds described herein for use in therapy, e.g., for use in the treatment or prophylaxis of a 5-HT$_6$ receptor-related disorder, to achieve reduction of body weight and of body weight gain.

In one aspect, this invention relates to pharmaceutical formulations that include a compound as described herein as active ingredient, in combination with a pharmaceutically acceptable diluent or carrier, e.g., for use in the treatment or prophylaxis of a 5-HT$_6$ receptor-related disorder, to achieve reduction of body weight and of body weight gain.

In another aspect, this invention relates to methods for treating a human or animal subject suffering from a 5-HT$_6$ receptor-related disorder, to achieve reduction of body weight and of body weight gain. The method can include administering to a subject (e.g., a human or an animal, dog, cat, horse, cow) in need thereof an effective amount of one or more compounds of any of the formulae herein, their salts, or compositions containing the compounds or salts.

The methods delineated herein can also include the step of identifying that the subject is in need of treatment of the 5-HT$_6$ receptor-related disorder, to achieve reduction of body weight and of body weight gain. Identifying a subject in need of such treatment can be in the judgment of a subject or a health care professional and can be subjective (e.g., opinion) or objective (e.g., measurable by a test or diagnostic method).

In a further aspect, this invention relates to methods for the treatment or prophylaxis of a 5-HT$_6$ receptor-related disorder, to achieve reduction of body weight and of body weight gain, which include administering to a subject in need of such treatment an effective amount of a compound as mentioned above.

In one aspect, this invention relates to methods for modulating (e g inhibiting or promoting) 5-HT$_6$ receptor activity, which include administering to a subject in need of such treatment an effective amount of a compound as mentioned above.

In another aspect, this invention relates to the use of a compound as mentioned above for the manufacture of a medicament for use in the prophylaxis or treatment of a 5-HT$_6$ receptor-related disorder, to achieve reduction of body weight and of body weight gain.

The compounds as mentioned above may be agonists, partial agonists or antagonists for the 5-HT$_6$ receptor. Preferably, the compounds act as partial agonists or antagonists for the 5-HT$_6$ receptor.

In a further aspect, this invention relates to a cosmetic composition that includes a compound as mentioned above as active ingredient, in combination with a cosmetically acceptable diluent or carrier, e.g., for use in the prophylaxis or treatment of a 5-HT$_6$ receptor-related disorder, to achieve reduction of body weight and of body weight gain.

In one aspect, this invention relates to methods for the prophylaxis or treatment of a 5-HT$_6$ receptor-related disorder or to achieve reduction of body weight and of body weight gain. The methods can include administering to a subject (e.g., a human or an animal, dog, cat, horse, cow) in need thereof an effective amount of one or more compounds of any of the formulae herein, their salts, or compositions containing the compounds or salts.

In another aspect, this invention relates to methods for the prophylaxis or treatment of a 5-HT$_6$ receptor-related disorder. The method can include administering to a subject (e.g., a human or an animal, dog, cat, horse, cow) in need thereof an effective amount of one or more compounds of any of the formulae herein, their salts, or compositions containing the compounds or salts.

In a further aspect, this invention relates to methods for achieving reduction of body weight and of body weight gain. The method can include administering to a subject (e.g., a human or an animal, dog, cat, horse, cow) in need thereof an effective amount of one or more compounds of any of the formulae herein, their salts, or compositions containing the compounds or salts.

The disorder can be selected from obesity; type II diabetes; or a disorder of the central nervous system.

The disorder can be obesity.

The disorder can be type II diabetes.

The disorder can be a disorder of the central nervous system (e.g., selected from anxiety, depression, panic attacks, memory disorders, cognitive disorders, epilepsy, sleep disorders, migraine, anorexia, bulimia, binge eating disorders, obsessive compulsive disorders, psychoses, Alzheimer's disease, Parkinson's disease, Huntington's chorea, schizophrenia, attention deficit hyperactive disorder, withdrawal from drug abuse, neurodegenerative diseases characterized by impaired neuronal growth, and pain).

The formulations and compositions described herein can include an amount of the compound of claim 1 that is effective for the prophylaxis or treatment of a 5-HT$_6$ receptor-related disorder or to achieve reduction of body weight and of body weight gain.

Examples of 5-HT$_6$ receptor-related disorders are obesity; type II diabetes; disorders of the central nervous system such as anxiety, depression, panic attacks, memory disorders, cognitive disorders, epilepsy, sleep disorders, migraine, anorexia, bulimia, binge eating disorders, obsessive compulsive disorders, psychoses, Alzheimer's disease, Parkinson's disease, Huntington's chorea, schizophrenia, attention deficit hyperactive disorder (ADHD), withdrawal from drug abuse, neurodegenerative diseases characterized by impaired neuronal growth, and pain.

The compounds and compositions are useful for treating diseases, to achieve reduction of body weight and of body weight gain. The diseases include obesity; type II diabetes; disorders of the central nervous system such as anxiety, depression, panic attacks, memory disorders, cognitive disorders, epilepsy, sleep disorders, migraine, anorexia, bulimia, binge eating disorders, obsessive compulsive disorders, psychoses, Alzheimer's disease, Parkinson's disease, Huntington's chorea, schizophrenia, attention deficit hyperactive disorder (ADHD), withdrawal from drug abuse, neurodegenerative diseases characterized by impaired neuronal growth, and pain. In one aspect, the invention relates to a method for treating or preventing an aforementioned disease comprising administering to a subject in need of such treatment an effective amount or composition delineated herein.

The following definitions shall apply throughout the specification and the appended claims.

Unless otherwise stated or indicated, the term "$C_{1-6}$-alkyl" denotes a straight or branched alkyl group having from 1 to 6 carbon atoms. Examples of said $C_{1-6}$-alkyl include methyl, ethyl, n-propyl, iso-propyl, n-butyl, iso-butyl, sec-butyl, t-butyl and straight- and branched-chain pentyl and hexyl. For parts of the range "$C_{1-6}$-alkyl" all subgroups thereof are contemplated such as $C_{1-5}$-alkyl, $C_{1-4}$-alkyl, $C_{1-3}$-alkyl, $C_{1-2}$-alkyl, $C_{2-6}$-alkyl, $C_{2-5}$-alkyl, $C_{2-4}$-alkyl, $C_{2-3}$-alkyl, $C_{3-6}$-alkyl, $C_{4-5}$-alkyl, etc. "Halo-$C_{1-6}$-alkyl" means a $C_{1-6}$-alkyl group substituted by one or more halogen atoms. Examples of said halo-$C_{1-6}$-alkyl include 2-fluoroethyl, fluoromethyl, trifluoromethyl and 2,2,2-trifluoroethyl. Likewise, "aryl-$C_{1-6}$-alkyl" means a $C_{1-6}$-alkyl group substituted by one or more aryl groups.

Unless otherwise stated or indicated, the term "hydroxy-$C_{1-6}$-alkyl" denotes a straight or branched alkyl group that has a hydrogen atom thereof replaced with OH. Examples of said hydroxy-$C_{1-6}$-alkyl include hydroxymethyl, 2-hydroxyethyl, 2-hydroxypropyl and 2-hydroxy-2-methylpropyl.

Unless otherwise stated or indicated, the term "$C_{1-6}$-alkoxy" denotes a straight or branched alkoxy group having from 1 to 6 carbon atoms. Examples of said $C_{1-6}$-alkoxy include methoxy, ethoxy, n-propoxy, iso-propoxy, n-butoxy, iso-butoxy, sec-butoxy, t-butoxy and straight- and branched-chain pentoxy and hexoxy. For parts of the range "$C_{1-6}$-alkoxy" all subgroups thereof are contemplated such as $C_{1-5}$-alkoxy, $C_{1-4}$-alkoxy, $C_{1-3}$-alkoxy, $C_{1-2}$-alkoxy, $C_{2-6}$-alkoxy, $C_{2-5}$-alkoxy, $C_{2-4}$-alkoxy, $C_{2-3}$-alkoxy, $C_{3-6}$-alkoxy, $C_{4-5}$-alkoxy, etc.

Unless otherwise stated or indicated, the term $C_{1-6}$-alkoxy-$C_{1-6}$-alkyl denotes a straight or branched alkoxy group having from 1 to 6 carbon atoms connected to an alkyl group having from 1 to 6 carbon atoms. Examples of said $C_{1-6}$-alkoxy-$C_{1-6}$-alkyl include methoxymethyl, ethoxymethyl, iso-propoxymethyl, n-butoxymethyl, t-butoxymethyl and straight- and branched-chain pentoxymethyl. For parts of the range "$C_{1-6}$-alkoxy-$C_{1-6}$-alkyl" all subgroups thereof are contemplated such as $C_{1-5}$-alkoxy-$C_{1-6}$-alkyl, $C_{1-4}$-alkoxy-$C_{1-6}$-alkyl, $C_{1-3}$-alkoxy-$C_{1-6}$-alkyl, $C_{1-2}$-alkoxy-$C_{1-6}$-alkyl, $C_{2-6}$-alkoxy-$C_{1-6}$-alkyl, $C_{2-5}$-alkoxy-$C_{1-6}$-alkyl, $C_{2-4}$-alkoxy-$C_{1-6}$-alkyl, $C_{2-3}$-alkoxy-$C_{1-6}$-alkyl, $C_{3-6}$-alkoxy-$C_{1-6}$-alkyl, $C_{4-5}$-alkoxy-$C_{1-6}$-alkyl, $C_{1-6}$-alkoxy-$C_{1-5}$-alkyl, $C_{1-6}$-alkoxy-$C_{1-4}$-alkyl, etc.

Unless otherwise stated or indicated, the term "$C_{2-6}$-alkenyl" denotes a straight or branched alkenyl group having from 2 to 6 carbon atoms. Examples of said $C_{2-6}$-alkenyl include vinyl, allyl, 2,3-dimethylallyl, 1-butenyl, 1-pentenyl, and 1-hexenyl. For parts of the range "$C_{2-6}$-alkenyl" all subgroups thereof are contemplated such as $C_{2-5}$-alkenyl, $C_{2-4}$-alkenyl, $C_{2-3}$-alkenyl, $C_{3-6}$-alkenyl, $C_{4-5}$-alkenyl, etc. Likewise, "aryl-$C_{2-6}$-alkenyl" means a $C_{2-6}$-alkenyl group substituted by one or more aryl groups. Examples of said aryl-$C_{2-6}$-alkenyl include styryl and cinnamyl.

The term "oxo" denotes =O

Unless otherwise stated or indicated, the term "$C_{2-6}$-alkynyl" denotes a straight or branched alkynyl group having from 2 to 6 carbon atoms. Examples of said $C_{2-6}$-alkynyl include ethynyl, 1-propynyl, 1-butynyl, and 1-hexynyl. For parts of the range "$C_{2-6}$-alkynyl" all subgroups thereof are contemplated such as $C_{2-5}$-alkynyl, $C_{2-4}$-alkynyl, $C_{2-3}$-alkynyl, $C_{3-6}$-alkynyl, $C_{4-5}$-alkynyl, etc.

Unless otherwise stated or indicated, the term "$C_{3-7}$-cycloalkyl" denotes a cyclic alkyl group having a ring size from 3 to 7 carbon atoms. Examples of said cycloalkyl include cyclopropyl, cyclobutyl, cyclopentyl, cyclohexyl, methylcyclohexyl, and cycloheptyl. For parts of the range "$C_{3-7}$-cycloalkyl" all subgroups thereof are contemplated such as $C_{3-6}$-cycloalkyl, $C_{3-5}$-cycloalkyl, $C_{3-4}$-cycloalkyl, $C_{4-7}$-cycloalkyl, $C_{4-6}$-cycloalkyl, $C_{4-5}$-cycloalkyl, $C_{5-7}$-cycloalkyl, $C_{6-7}$-cycloalkyl, etc.

Unless otherwise stated or indicated, the term "aryl" refers to a hydrocarbon ring system having at least one aromatic ring. Examples of aryls are phenyl, indenyl, indanyl, 1,2,3,4-tetrahydronaphthyl, 1-naphthyl, 2-naphthyl, and fluorenyl.

Likewise, aryloxy refers to an aryl group bonded to an oxygen atom.

The term "heteroaryl" refers to a mono- or bicyclic aromatic ring system, only one ring need be aromatic, and the said heteroaryl moiety can be linked to the remainder of the molecule via a carbon or nitrogen atom in any ring, and having from 5 to 10 ring atoms (mono- or bicyclic), in which one or more of the ring atoms are other than carbon, such as nitrogen, sulphur, oxygen and selenium. Examples of such heteroaryl rings include furyl, pyrrolyl, thienyl, oxazolyl, isoxazolyl, imidazolyl, thiazolyl, isothiazolyl, pyridinyl, pyrimidinyl, pyrazinyl, chromanyl, quinazolinyl, indolyl, isoindolyl, indolinyl, isoindolinyl, indazolyl, pyrazolyl, pyridazinyl, quinolinyl, isoquinolinyl, benzofuranyl, 2,3-dihydrobenzofuranyl, 1,2,3,4-tetrahydroquinolinyl, 1,2,3,4-tetrahydroisoquinolinyl, benzodioxolyl, benzodioxinyl, benzothienyl, benzimidazolyl, benzothiazolyl, benzothiadiazolyl, benzotriazolyl, and 2,1,3-benzoxadiazolyl groups. If a bicyclic heteroaryl ring is substituted, it may be substituted in any ring.

Unless otherwise stated or indicated, the term "heterocyclic" refers to a non-aromatic (i.e., partially or fully saturated) mono- or bicyclic ring system having 4 to 10 ring atoms with at least one heteroatom such as O, N, or S, and the remaining ring atoms are carbon. Examples of heterocyclic groups include piperidyl, tetrahydropyranyl, tetrahydrofuranyl, azepinyl, azetidinyl, pyrrolidinyl, morpholinyl, imidazolinyl, thiomorpholinyl, pyranyl, dioxanyl, piperazinyl, octahydrofuro[3,4b]pyrazinyl, and 1-azabicyclo[2.2.2]oct-2-en-3-yl groups. When present, the sulfur atom may be in an oxidized form (i.e., S=O or O=S=O). Examples of heterocyclic groups containing sulfur in oxidized form include octahydrothieno[3,4b]pyrazine 6,6-dioxide and thiomorpholine 1,1-dioxide.

Unless otherwise stated or indicated, the term "halogen" shall mean fluorine, chlorine, bromine or iodine.

The term —S(O)$_x$— in Formula (IV), wherein x is 0, 1 or 2, has the meaning as illustrated by Formula (IX)-(XI):

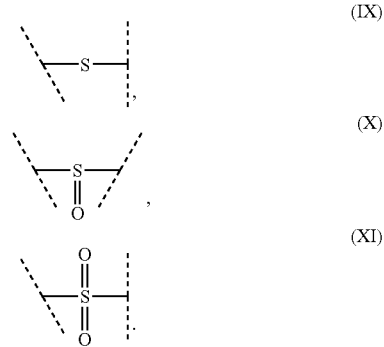

The term "leaving group" refers to a group to be displaced from a molecule during a nucleophilic displacement reaction. Examples of leaving groups are iodide, bromide, chloride, methanesulphonate, hydroxy, methoxy, thiomethoxy, tosyl, or suitable protonated forms thereof (e.g., H$_2$O, MeOH), especially bromide and methanesulphonate.

"Optional" or "optionally" means that the subsequently described event or circumstance may but need not occur, and that the description includes instances where the event or circumstance occurs and instances in which it does not.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

The term "prodrug forms" means a pharmacologically acceptable derivative, such as an ester or an amide, which derivative is biotransformed in the body to form the active drug. Reference is made to Goodman and Gilman's, The Pharmacological basis of Therapeutics, 8$^{th}$ ed., Mc-Graw-Hill, Int. Ed. 1992, "Biotransformation of Drugs", p. 13-15; and "The Organic Chemistry of Drug Design and Drug Action" by Richard B. Silverman. Chapter 8, p 352. (Academic Press, Inc. 1992. ISBN 0-12-643730-0).

The following abbreviations have been used:
BINAP means 2,2'-bis(diphenylphosphino)-1-1'-binaphthyl,
BOC means tert-butyloxycarbonyl,
CV means Coefficient of Variation,
DCM means dichloromethane,
DME means 1,2-dimethoxyethane,
DMSO means dimethyl sulphoxide,
EDTA means ethylenediamine tetraacetic acid,
EtOH means ethanol,
EtOAc means ethyl acetate,
EGTA means ethylenebis(oxyethylenenitrilo)tetraacetic acid,
HEPES means 4-(2-hydroxyethyl)-1-piperazineethanesulfonic acid,
HPLC means high performance liquid chromatography,
LSD means lysergic acid, diethylamide,
MeCN means acetonitrile,
SPA means Scintillation Proximity Assay,
t-BuOK means potassium tert-butoxide,
TEA means triethylamine,
TFA means trifluoroacetic acid,
THF means tetrahydrofuran, and
Xantphos means 4,5-bis(diphenylphosphino)-9,9-dimethylxanthene.

The details of one or more embodiments of the invention are set forth in the accompanying description below. Other features and advantages are in the claims.

DETAILED DESCRIPTION

All isomeric forms possible (pure enantiomers, diastereomers, tautomers, racemic mixtures and unequal mixtures of two enantiomers) for the compounds delineated are within the scope of the invention. Such compounds can also occur as cis- or trans-, E- or Z-double bond isomer forms. All isomeric forms are contemplated.

The compounds of the formula (I) may be used as such or, where appropriate, as pharmacologically acceptable salts (acid or base addition salts) thereof. The pharmacologically acceptable addition salts mentioned above are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine.

For example, sulfonamide derivatives of Formula (I) wherein P is selected from a substituent of Formula (II) and (III) and wherein R$^2$ is hydrogen may be converted into their corresponding potassium, sodium or calcium salts, or salts of other alkali metals or alkaline earth metals. The term addition salt as used herein also comprises solvates which the compounds and salts thereof are able to form, such as, for example, hydrates, alcoholates and the like.

For clinical use, the compounds of the invention are formulated into pharmaceutical formulations for oral, rectal, parenteral or other mode of administration. Pharmaceutical formulations are usually prepared by mixing the active substance, or a pharmaceutically acceptable salt thereof, with conventional pharmaceutical excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parental use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

In a further aspect the invention relates to methods of making compounds of any of the formulae herein comprising reacting any one or more of the compounds of the formulae delineated herein, including any processes delineated herein. The compounds of the formula (I) above may be prepared by, or in analogy with, conventional methods.

The processes described above may be carried out to give a compound of the invention in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are mentioned above.

The compounds of formula (I) may possess one or more chiral carbon atoms, and they may therefore be obtained in the form of optical isomers, e.g. as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The chemicals used in the synthetic routes delineated herein may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The necessary starting materials for preparing the compounds of formula (I) are either known or may be prepared in analogy with the preparation of known compounds. The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

The invention will now be further illustrated by the following non-limiting Examples.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Methods $^1$H nuclear magnetic resonance (NMR) and $^{13}$C NMR were recorded on Bruker Advance DPX 400, Bruker DRX-500, JEOL JNM-EX 270 or Varian MERCURY plus 400 MHz spectrometers. All spectra were recorded using residual solvent or tetramethylsilane (TMS) as internal standard. Ionspray mass spectrometry (MS) spectra were obtained on a Perkin-Elmer API 150EX mass spectrometer. Preparative HPLC/MS was performed on a Waters/Micromass Platform ZQ system equipped with System A: ACE 5 C8 column (19×50 mm) or System B: Xterra MS C18, 5 μm column (19×50 mm). The following HPLC setups have also been used: System C: Gilson/YMC AQ C18; 150×30 mm; System D: Gilson Finnigan/YMC ODS AQ 5 μm column (20×50 mm); System E: Gyncotech HPLC-UV "SYS-2"; Ace C8, 5 μm column (21×50 mm) and System F: Gyncotech HPLC-UV "SYS-2"; Ace C8, 5 μm column (30×150 mm). Eluents used for System A, C-F: MeCN in milliQ-water with 0.1% TFA. Eluents used for System B: MilliQ water, MeCN and NH$_4$HCO$_3$ (100 mM). Analytical HPLC were performed on Agilent 1100, column: ACE 3 C8 (System A) or column: YMC ODS-AQ (System B) or column: Chromolith C18 (50× 4.6 mm) (System C), eluents: MilliQ/0.1% TFA and MeCN. Preparative flash chromatography was performed on Merck silica gel 60 (230-400 mesh). Reactions conducted under controlled microwave energy were performed with a Personal Chemistry Smith Creator using 0.5-2 mL, 2-5 mL or 20 mL Smith Process Vials fitted with aluminium caps and septa.

TABLE 1

| EXAMPLE | | P | R3 |
|---|---|---|---|
| 1 | N-(7-{Methyl[3-(methylamino)propyl]amino}-1-benzofuran-5-yl)benzenesulfonamide hydrochloride | phenyl-SO2-NH- | -N(CH3)-CH2CH2CH2-NH(CH3) |
| 2 | N-(7-Piperidin-1-yl-1-benzofuran-5-yl)benzenesulfonamide | phenyl-SO2-NH- | piperidin-1-yl |
| 3 | 4-Fluoro-N-(7-piperidin-1-yl-1-benzofuran-5-yl)benzenesulfonamide | 4-F-phenyl-SO2-NH- | piperidin-1-yl |
| 4 | 3,4-Dimethoxy-N-(7-piperidin-1-yl-1-benzofuran-5-yl)benzenesulfonamide hydrochloride | 3,4-dimethoxy-phenyl-SO2-NH- | piperidin-1-yl |

TABLE 1-continued

| EXAMPLE | | P | R3 |
|---|---|---|---|
| 5 | 3,4-Dimethoxy-N-(7-pyrrolidin-1-yl-1-benzofuran-5-yl)benzenesulfonamide | 3,4-dimethoxyphenyl-SO$_2$-NH- | pyrrolidin-1-yl |
| 6 | N-(7-Pyrrolidin-1-yl-1-benzofuran-5-yl)benzenesulfonamide | phenyl-SO$_2$-NH- | pyrrolidin-1-yl |
| 7 | 4-Fluoro-N-(7-pyrrolidin-1-yl-1-benzofuran-5-yl)benzenesulfonamide hydrochloride | 4-fluorophenyl-SO$_2$-NH- | pyrrolidin-1-yl |
| 8 | 4-Fluoro-N-(7-morpholin-4-yl-1-benzofuran-5-yl)benzenesulfonamide hydrochloride | 4-fluorophenyl-SO$_2$-NH- | morpholin-4-yl |

TABLE 1-continued

| EXAMPLE | | P | R3 |
|---|---|---|---|
| 9 | N-(7-Morpholin-4-yl-1-benzofuran-5-yl)benzenesulfonamide hydrochloride | phenyl-SO2-NH- | morpholin-4-yl |
| 10 | 3,4-Dimethoxy-N-(7-morpholin-4-yl-1-benzofuran-5-yl)benzenesulfonamide | (3,4-dimethoxyphenyl)-SO2-NH- | morpholin-4-yl |
| 11 | N-(3,5-Dimethylbenzyl)-7-piperazin-1-yl-1-benzofuran-5-amine hydrochloride | (3,5-dimethylbenzyl)-NH- | piperazin-1-yl |
| 12 | N-(3,4-Difluorobenzyl)-7-piperazin-1-yl-1-benzofuran-5-amine hydrochloride | (3,4-difluorobenzyl)-NH- | piperazin-1-yl |
| 13 | N-(3,5-Dimethoxybenzyl)-7-piperazin-1-yl-1-benzofuran-5-amine hydrochloride | (3,5-dimethoxybenzyl)-NH- | piperazin-1-yl |
| 14 | N-Benzyl-7-piperazin-1-yl-1-benzofuran-5-amine hydrochloride | benzyl-NH- | piperazin-1-yl |

TABLE 1-continued

| EXAMPLE | | P | R3 |
|---|---|---|---|
| 15 | N-(7-piperazin-1-yl-1-benzofuran-5-yl)benzamide hydrochloride | 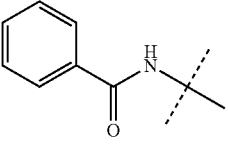 | 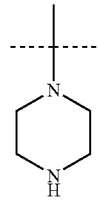 |
| 16 | 4-Methoxy-N-(7-piperazin-1-yl-1-benzofuran-5-yl)benzamide hydrochloride | 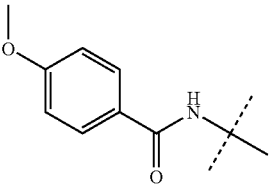 | 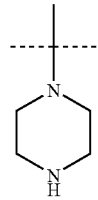 |
| 17 | 2-Bromo-5-methoxy-N-(7-piperazin-1-yl-1-benzofuran-5-yl)benzamide hydrochloride | 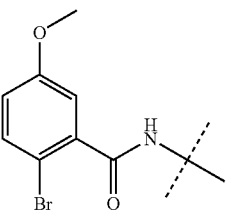 | 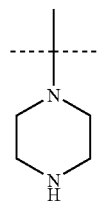 |
| 18 | 3-Methyl-N-(7-piperazin-1-yl-1-benzofuran-5-yl)benzamide hydrochloride | 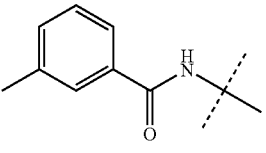 | 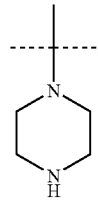 |
| 19 | N-(7-Piperazin-1-yl-1-benzofuran-5-yl)-3-(trifluoromethyl)benzamide hydrochloride | 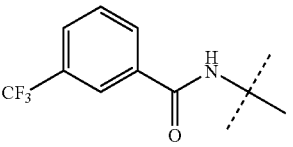 | 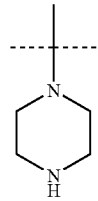 |
| 20 | 2,4-Dichloro-N-(7-piperazin-1-yl-1-benzofuran-5-yl)benzamide hydrochloride | 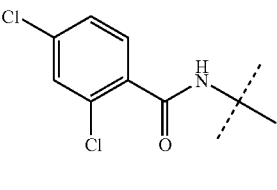 | 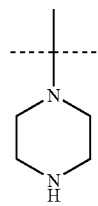 |

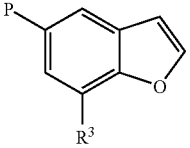

TABLE 1-continued

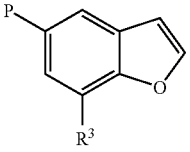

| EXAMPLE | | P | R3 |
|---|---|---|---|
| 21 | 3,5-Dimethoxy-N-(7-piperazin-1-yl-1-benzofuran-5-yl)benzamide hydrochloride | 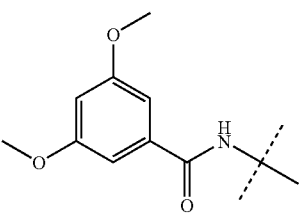 | 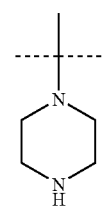 |
| 22 | N-(3,5-Dimethoxyphenyl)-N'-(7-piperazin-1-yl-benzofuran-5-yl)urea hydrochloride | 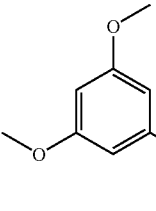 | 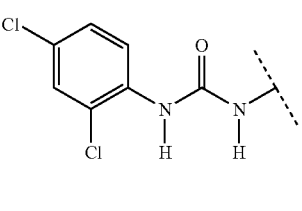 |
| 23 | N-(2,4-Dichlorophenyl)-N'-(7-piperazin-1-yl-benzofuran-5-yl)urea hydrochloride | 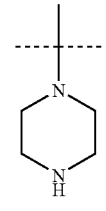 | 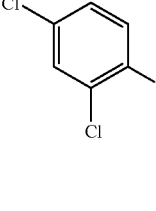 |
| 24 | N-(2-Methoxyphenyl)-N'-(7-piperazin-1-benzofuran-5-yl)urea hydrochloride | 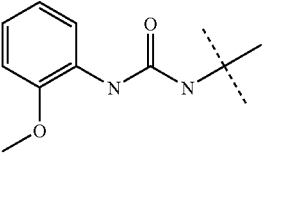 | 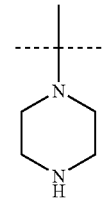 |
| 25 | N-Phenyl-N'-(7-piperazin-1-yl-1-benzofuran-5-yl)urea hydrochloride | 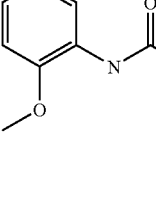 | 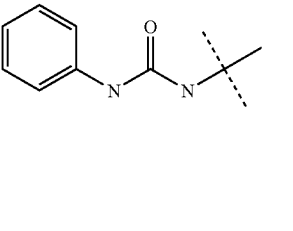 |
| 26 | N-(3-Fluorophenyl)-N'-(7-piperazin-1-yl-benzofuran-5-yl)urea hydrochloride | 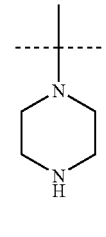 | 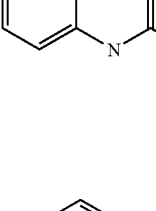 |

TABLE 1-continued

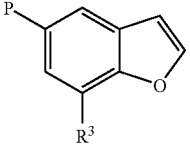

| EXAMPLE | | P | R3 |
|---|---|---|---|
| 27 | N-(7-Piperazin-1-yl-1-benzofuran-5-yl-)-N'-[trifuoromethyl)phenyl]urea hydrochloride | 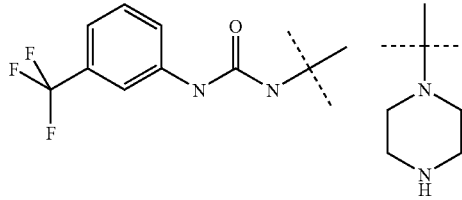 | 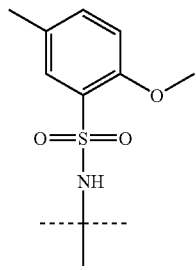 |
| 28 | 2-Methoxy-5-methyl-N-(7-pyridin-4-yl-1-benzofuran-5-yl)benzenesulfonamide | 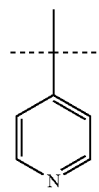 | 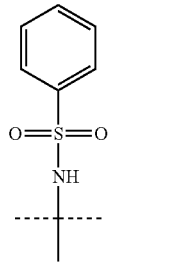 |
| 29 | N-(7-Pyridin-3-yl-1-benzofuran-5-yl)benzenesulfonamide trifluoroacetate | 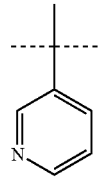 | 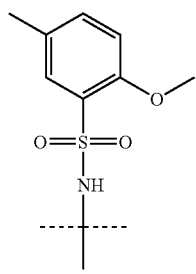 |
| 30 | 2-Methoxy-5-methyl-N-(7-pyridin-3-yl-1-benzofuran-5-yl)benzenesulfonamide trifluoroacetate | 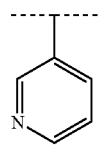 | 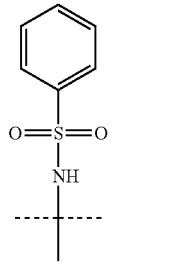 |
| 31 | N-(7-Pyrazin-2-yl-1-benzofuran-5-yl)benzenesulfonamide trifluoroacetate | 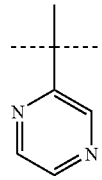 | |

TABLE 1-continued

| EXAMPLE | | P | R3 |
|---|---|---|---|
| 32 | N-(7-Pyrimidin-5-yl-1-benzofuran-5-yl)benzenesulfonamide hydrochloride | phenyl-SO2-NH- | pyrimidin-5-yl |
| 33 | N-[7-(1-Aza-bicyclo[2.2.2]oct-2-en-3-yl)-benzofuran-5-yl]-2-methoxy-5-methyl-benzenesulfonamide hydrochloride | (2-methoxy-5-methylphenyl)-SO2-NH- | 1-azabicyclo[2.2.2]oct-2-en-3-yl |
| 34 | 2-[4-(5-{[(2-Chlorophenyl)sulfonyl]amino}-1-benzofuran-7-yl)piperazin-1-yl]-N,N-diethylacetamide hydrochloride | (2-chlorophenyl)-SO2-NH- | 4-[2-(N,N-diethylamino)-2-oxoethyl]piperazin-1-yl |
| 35 | N,N-diethyl-2-[4-(5-{[(2-methoxy-5-methylphenyl)sulfonyl]amino}-1-benzofuran-7-yl)piperazin-1-yl]acetamide hydrochloride | (2-methoxy-5-methylphenyl)-SO2-NH- | 4-[2-(N,N-diethylamino)-2-oxoethyl]piperazin-1-yl |
| 38 | N-[7-(1-Azabicyclo[2.2.2.]oct-3-yloxy)-1-benzofuran-5-yl]benzenesulfonamide hydrochloride | phenyl-SO2-NH- | 1-azabicyclo[2.2.2]oct-3-yloxy |

TABLE 1-continued

| EXAMPLE | | P | R3 |
|---|---|---|---|
| 39 | N-[7-(1-Azabicyclo[2.2.2.]oct-3-yloxy)-1-benzofuran-5-yl]-2-chlorobenzenesulfonamidehydrochloride | 2-chlorophenylsulfonamide | 1-azabicyclo[2.2.2]oct-3-yloxy |
| 40 | N-[7-(1-Azabicyclo[2.2.2.]oct-3-yloxy)-1-benzofuran-5-yl]-2-methoxy-5-benzenesulfonamide hydrochloride | 2-methoxy-5-methylphenylsulfonamide | 1-azabicyclo[2.2.2]oct-3-yloxy |
| 41 | N-{7-[(2-Morpholin-4-ylethyl)amino]-1-benzofuran-5-yl}benzenesulfonamide hydrochloride | phenylsulfonamide | 2-(morpholin-4-yl)ethylamino |
| 42 | 2-Methoxy-5-methyl-N-{7-[(2-morpholin-4-ylethyl)amino]-1-benzofuran-5-yl}benzenesulfonamide hydrochloride | 2-methoxy-5-methylphenylsulfonamide | 2-(morpholin-4-yl)ethylamino |
| 43 | N-{7-[(2-Morpholin-4-ylethyl)amino]-1-benzofuran-5-yl}-2-(trifluoromethyl)benzenesulfonamide hydrochloride | 2-(trifluoromethyl)phenylsulfonamide | 2-(morpholin-4-yl)ethylamino |

TABLE 1-continued

| EXAMPLE | | P | R3 |
|---|---|---|---|
| 44 | 2,6-Dichloro-N-{7-[(2-morpholin-4-ylethyl)amino]-1-benzofuran-5-yl}benzenesulfonamide hydrochloride | 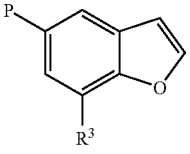 | 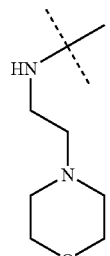 |
| 45 | 2-Methoxy-5-methyl-N-[7-(2-morpholin-4-ylethoxy)-1-benzofuran-5-yl]benzenesulfonamide hydrochloride | 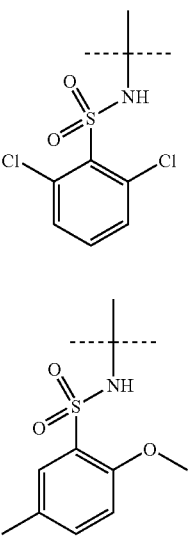 | 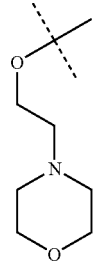 |
| 46 | 3-Methyl-N-[7-(2-morpholin-4-ylethoxy)-1-benzofuran-5-yl]benzenesulfonamide hydrochloride | 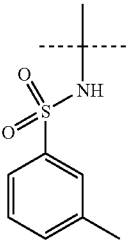 | 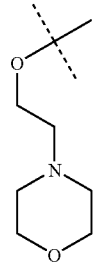 |
| 47 | 3-Chloro-4-methyl-N-[7-(2-morpholin-4-ylethoxy)-1-benzofuran-5-yl]benzenesulfonamide hydrochloride | 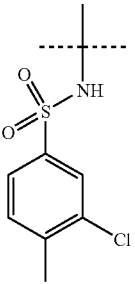 | 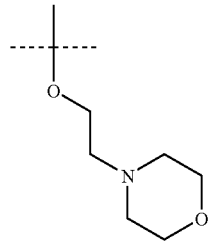 |
| 48 | N-(7-{[2(Dimethylamino)ethyl]amino}-1-benzofuran-5-yl)-2-methoxy-5-benzenesulfonamide hydrochloride | 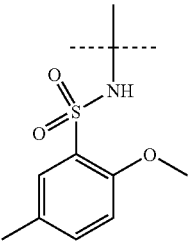 | 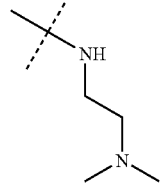 |

TABLE 1-continued

| EXAMPLE | | P | R3 |
|---|---|---|---|
| 49 | 2-Chloro-N(7-{[2-(dimethylamino)}-1-benzofuran-5-yl)benzenesulfonamide hydrochloride | 2-chlorobenzenesulfonyl-NH- | -C(CH₃)₂-NH-CH₂CH₂-N(CH₃)₂ (dimethylaminoethylamino group attached via quaternary carbon) |
| 50 | N-[7-(Pyridin-4-ylamino)-1-benzofuran-5-yl]benzenesulfonamide hydrochloride | benzenesulfonyl-NH- | 4-pyridinyl-NH- |
| 51 | 2-Chloro-N-[7-(pyridin-4-ylamino)-1-benzofuran-5-yl]benzenesulfonamide hydrochloride | 2-chlorobenzenesulfonyl-NH- | 4-pyridinyl-NH- |
| 52 | 2-Methoxy-5-methyl-N-[7-(pyridin-4-ylamino)-1-benzofuran-5-yl]benzenesulfonamide hydrochloride | 2-methoxy-5-methylbenzenesulfonyl-NH- | 4-pyridinyl-NH- |
| 53 | 2-Methoxy-5-methyl-N-[7-(piperazin-1-ylcarbonyl)-1-benzofuran-5-yl]benzenesulfonamide hydrochloride | 2-methoxy-5-methylbenzenesulfonyl-NH- | piperazin-1-ylcarbonyl |

TABLE 1-continued

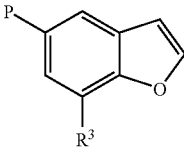

| EXAMPLE | | P | R3 |
|---|---|---|---|
| 54 | 2-Methoxy-5-methyl-N-[7-(piperazin-1-ylmethyl)-1-benzofuran-5-yl]benzenesulfonamide hydrochloride | | |
| 55 | N-{7-[(3-Aminopyrrolidin-1-yl)methyl]-1-benzofuran-5-yl}-2-methoxy-5-methylbenzenesulfonamide hydrochloride | | |
| 56 | N-[7(6,6-Dioxidohexahydrothieno[3,4-b]pyrazin-1(2H)-yl)-1-benzofuran-5-yl]-2-methoxy-5-methylbenzenesulfonamide hydrochloride | | |
| 57 | N-[7(6,6-Dioxidohexahydrothieno[3,4-b]pyrazin-1(2H)-yl)-1-benzofuran-5-yl]benzenesulfonamide hydrochloride | | |
| 58 | N-{7-[(2-Pyrrolidin-1-ylethyl)amino]-1-benzofuran-5-yl}benzenesulfonamide hydrochloride | | |

TABLE 1-continued

| EXAMPLE | | P | R3 |
|---|---|---|---|
| 59 | 2-Methoxy-5-methyl-N-{7-[(2-pyrrolidin-1-ylethyl)amino]-1-benzofuran-5-yl}benzenesulfonamide hydrochloride | 2-methoxy-5-methylphenylsulfonamide | 2-(pyrrolidin-1-yl)ethylamino |
| 60 | N-{7-[(2-Pyrrolidin-1-ylethyl)amino]-1-benzofuran-5-yl}-2-(trifluoromethyl)benzenesulfonamide hydrochloride | 2-(trifluoromethyl)phenylsulfonamide | 2-(pyrrolidin-1-yl)ethylamino |
| 61 | 3-Chloro-4-methyl-N-{7-[(2-pyrrolidin-1-ylethyl)amino]-1-benzofuran-5-yl}benzenesulfonamide hydrochloride | 3-chloro-4-methylphenylsulfonamide | 2-(pyrrolidin-1-yl)ethylamino |
| 62 | 2-Methoxy-5-methyl-N-{7-[(3-morpholin-4-ylpropyl)amino]-1-benzofuran-5-yl}benzenesulfonamide hydrochloride | 2-methoxy-5-methylphenylsulfonamide | 3-(morpholin-4-yl)propylamino |
| 63 | N-{7-[(3-Morpholin-4-ylpropyl)amino]-1-benzofuran-5-yl}-2-(trifluoromethyl)benzenesulfonamide hydrochloride | 2-(trifluoromethyl)phenylsulfonamide | 3-(morpholin-4-yl)propylamino |

TABLE 1-continued

| EXAMPLE | | P | R3 |
|---|---|---|---|
| 64 | 3-Chloro-4-methyl-N-{7-[(3-morpholin-4-ylpropyl)amino]-1-benzofuran-5-yl}benzenesulfonamide hydrochloride | 3-chloro-4-methylphenylsulfonamide | 3-(morpholin-4-yl)propylamino |
| 65 | N-[7-({[(2R)-1-Ethylpyrrolidin-2-yl]methyl}amino)-1-benzofuran-5-yl]benzenesulfonamide hydrochloride | phenylsulfonamide | [(2R)-1-ethylpyrrolidin-2-yl]methylamino |
| 66 | N-[7-({[(2R)-1-Ethylpyrrolidin-2-yl]methyl}amino)-1-benzofuran-5-yl]-2-methoxy-5-methylbenzenesulfonamide hydrochloride | 2-methoxy-5-methylphenylsulfonamide | [(2R)-1-ethylpyrrolidin-2-yl]methylamino |
| 67 | N-[7-({[(2R)-1-Ethylpyrrolidin-2-yl]methyl}amino)-1-benzofuran-5-yl]-2-(trifluoromethyl)benzenesulfonamide hydrochloride | 2-(trifluoromethyl)phenylsulfonamide | [(2R)-1-ethylpyrrolidin-2-yl]methylamino |
| 68 | N-[7-({[(2R)-1-Ethylpyrrolidin-2-yl]methyl}amino)-1-benzofuran-5-yl]-3-methylbenzenesulfonamide hydrochloride | 3-methylphenylsulfonamide | [(2R)-1-ethylpyrrolidin-2-yl]methylamino |

TABLE 1-continued

| EXAMPLE | | P | R3 |
|---|---|---|---|
| 69 | N-[7-({[(2R)-1-Ethylpyrrolidin-2-yl]methyl}amino)-1-benzofuran-5-yl]thiophene-2-sulfonamide hydrochloride | thiophene-2-sulfonamide | (2R)-1-ethylpyrrolidin-2-ylmethylamino |
| 70 | 5-Chloro-N-[7-({[(2R)-1-ethylpyrrolidin-2-yl]methyl}amino)-1-benzofuran-5-yl]thiophene-2-sulfonamide hydrochloride | 5-chlorothiophene-2-sulfonamide | (2R)-1-ethylpyrrolidin-2-ylmethylamino |
| 71 | 5-Chloro-N-[7-({[(2R)-1-ethylpyrrolidin-2-yl]methyl}amino)-1-benzofuran-5-yl]-1,3-dimethyl-1H-pyrazole-4-sulfonamide hydrochloride | 5-chloro-1,3-dimethyl-1H-pyrazole-4-sulfonamide | (2R)-1-ethylpyrrolidin-2-ylmethylamino |
| 72 | N-(7-{[3-(2-Methylpiperidin-1-yl)propyl]amino}-1-benzofuran-5-yl)benzenesulfonamide hydrochloride | benzenesulfonamide | 3-(2-methylpiperidin-1-yl)propylamino |
| 73 | 2-Methoxy-5-methyl-N-(7-{[3-(2-methylpiperidin-1-yl)propyl]amino}-1-benzofuran-5-yl)benzenesulfonamide hydrochloride | 2-methoxy-5-methylbenzenesulfonamide | 3-(2-methylpiperidin-1-yl)propylamino |

TABLE 1-continued

| EXAMPLE | | P | R3 |
|---|---|---|---|
| 74 | N-(7-{[3-(2-Methylpiperidin-1-yl)propyl]amino}-1-benzofuran-5-yl)-2-(trifluoromethyl)benzenesulfonamide hydrochloride | benzenesulfonamide with 2-CF3 | 3-(2-methylpiperidin-1-yl)propylamino |
| 75 | 5-Chloro-1,3-dimethyl-N-(7-{[3-(2-methylpiperidin-1-yl)propyl]amino}-1-benzofuran-5-yl)-1H-pyrazole-4-sulfonamide hydrochloride | 5-chloro-1,3-dimethyl-1H-pyrazole-4-sulfonamide | 3-(2-methylpiperidin-1-yl)propylamino |
| 76 | N-[7-(6-Aminopyridin-3-yl)-1-benzofuran-5-yl]-2-methoxy-5-methylbenzenesulfonamide | 2-methoxy-5-methylbenzenesulfonamide | 6-aminopyridin-3-yl |
| 77 | N-{7-[4-(Cyclopropylmethyl)piperazin-1-yl]-1-benzofuran-5-yl}-2-methoxy-5-methylbenzenesulfonamide hydrochloride | 2-methoxy-5-methylbenzenesulfonamide | 4-(cyclopropylmethyl)piperazin-1-yl |
| 78 | 2-Methoxy-5-methyl-N-{7-[4-(3,3,3-trifluoropropyl)piperazin-1-yl]-1-benzofuran-5-yl}benzenesulfonamide hydrochloride | 2-methoxy-5-methylbenzenesulfonamide | 4-(3,3,3-trifluoropropyl)piperazin-1-yl |

TABLE 1-continued

| EXAMPLE | | P | R3 |
|---|---|---|---|
| 79 | 2-Methoxy-5-methyl-N-{7-[3-(trifluoromethyl)piperazin-1-yl]-1-benzofuran-5-yl}benzenesulfonamide hydrochloride | 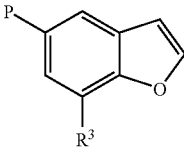 | 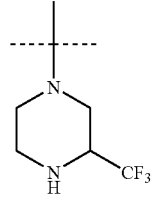 |
| 80 | N-[7-(Aminopiperidin-1-yl)-1-benzofuran-5-yl]-2-(trifluoromethyl)benzenesulfonamide hydrochloride | 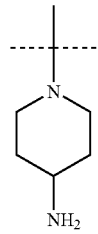 | |
| 81 | N-[7-(Aminopiperidin-1-yl)-1-benzofuran-5-yl]-benzenesulfonamide hydrochloride | 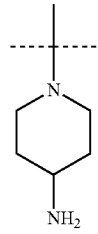 | |
| 82 | N-[7-(Aminopiperidin-1-yl)-1-benzofuran-5-yl]-2-chlorobenzenesulfonamide hydrochloride | 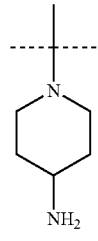 | |
| 83 | N-[7-(Aminopiperidin-1-yl)-1-benzofuran-5-yl]-2-methoxy-5-methylbenzenesulfonamide hydrochloride | 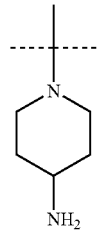 | |

TABLE 1-continued

| EXAMPLE | | P | R3 |
|---|---|---|---|
| 84 | N-(7-{[cis-3-Fluoropiperidin-4-yl]oxy}-1-benzofuran-5-yl)-2-methoxy-5-methylbenzenesulfonamide hydrochloride | | |
| 85 | N-(7-{trans-3-Fluoropiperidin-4-yl]oxy}-1-benzofuran-5-yl)-2-methoxy-5-methylbenzenesulfonamide hydrochloride | | |
| 86 | N-(7-{[cis-3-Fluoropiperidin-4-yl]oxy}-1-benzofuran-5-yl)-2-(trifluoromethyl)benzenesulfonamide hydrochloride | | |
| 87 | N-(7-{[trans-3-Fluoropiperidin-4-yl]oxy}-1-benzofuran-5-yl)-2-(trifluoromethyl)benzenesulfonamide hydrochloride | | |
| 88 | 2-Chloro-N-(7-{[trans-3-fluoropiperidin-4-yl]oxy}-1-benzofuran-5-yl)benzenesulfonamide hydrochloride | | |

TABLE 1-continued

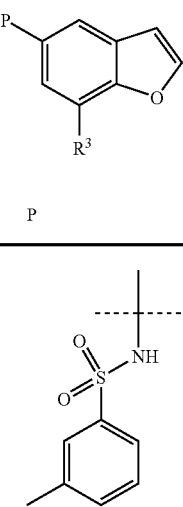

| EXAMPLE | | P | R3 |
|---|---|---|---|
| 89 | N-(7-{[trans-3-Fluoropiperidin-4-yl]oxy}-1-benzofuran-5-yl)-3-methylbenzenesulfonamide hydrochloride | 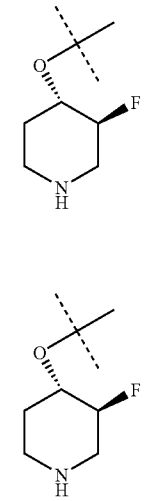 | 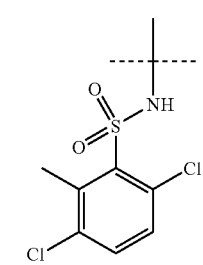 |
| 90 | 3,6-Dichloro-N-(7-{[trans-3-fluoropiperidin-4-yl]oxy}-1-benzofuran-5-yl)-2-methylbenzenesulfonamide hydrochloride | 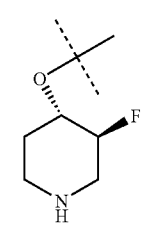 | 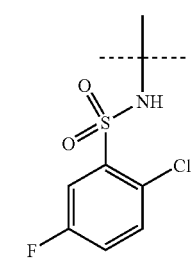 |
| 91 | 2-Chloro-5-fluoro-N-(7-{[trans-3-fluoropiperidin-4-yl]oxy}-1-benzofuran-5-yl)benzenesulfonamide hydrochloride | 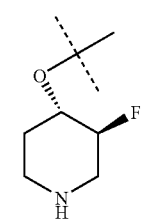 | 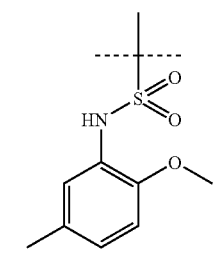 |
| 92 | N-(2-Methoxy-5-methylphenyl)-7-[(3-methylpiperazin-1-yl)methyl]-1-benzofuran-5-sulfonamide hydrochloride | 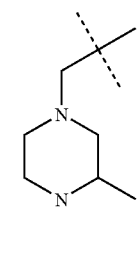 | 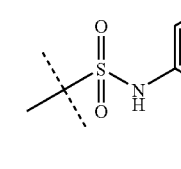 |
| 93 | N-(2-Methylphenyl)-7-(piperazin-1-ylmethyl)-1-benzofuran-5-sulfonamide, trifluoroacetate | 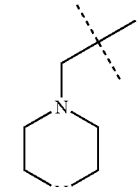 | |

TABLE 1-continued

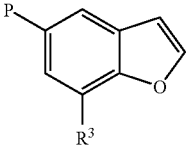

| EXAMPLE | | P | R3 |
|---|---|---|---|
| 94 | 7-[(3,5-Dimethylpiperazin-1-yl)methyl]-N-(2-methylphenyl)-1-benzofuran-5-sulfonamide, trifluoroacetate | 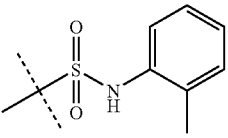 | 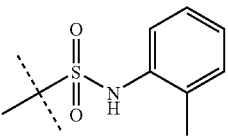 |
| 95 | N-(2-Methylphenyl)-7-[(3-methylpiperazin-1-yl)methyl]-1-benzofuran-5-sulfonamide, trifluoroacetate | 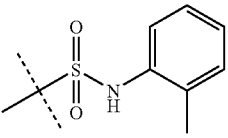 | 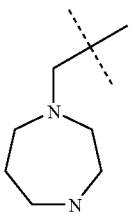 |
| 96 | 7-(1,4-Diazepan-1-ylmethyl)-N-(2-methylphenyl)-1-benzofuran-5-sulfonamide, trifluoroacetate | 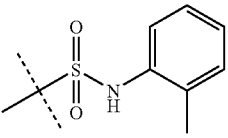 | 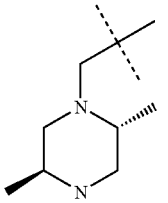 |
| 97 | 7-{(trans-2,5-Dimethylpiperazin-1-yl)methyl}-N-(2-methylphenyl)-1-benzofuran-5-sulfonamide, trifluoroacetate | 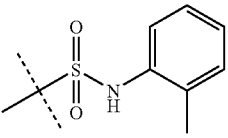 | 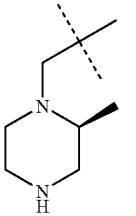 |
| 98 | N-(2-Methylphenyl)-7-{[(2R)-2-methylpiperazin-1-yl]methyl}-1-benzofuran-5-sulfonamide, trifluoroacetate | 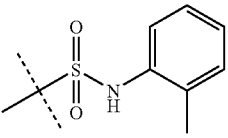 | 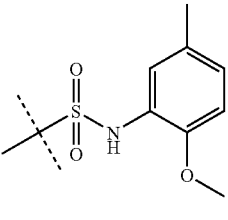 |
| 99 | N-(2-Methoxy-5-methylphenyl)-7-[(3-methylpiperazin-1-yl)methyl]-1-benzofuran-5-sulfonamide, trifluoroacetate | | 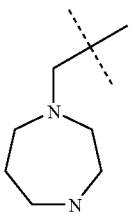 |

TABLE 1-continued

| EXAMPLE | | P | R3 |
|---|---|---|---|
| 100 | 7-(1,4-Diazepan-1-ylmethyl)-N-(2-methoxy-5-methylphenyl)-1-benzofuran-5-sulfonamide, trifluoroacetate | | |
| 101 | N-(2-Methoxy-5-methylphenyl)-7-(piperazin-1-ylmethyl)-1-benzofuran-5-sulfonamide, trifluoroacetate | | |
| 102 | 7-{(cis-3,5-Dimethylpiperazin-1-yl)methyl}-N-(2-methoxy-5-methylphenyl)-1-benzofuran-5-sulfonamide, trifluoroacetate | | |
| 103 | 7-{[trans-2,5-Dimethylpiperazin-1-yl]methyl}-N-(2-methoxy-5-methylphenyl)-1-benzofuran-5-sulfonamide, trifluoroacetate | | |
| 104 | 7-(2,5-Diazabicyclo[2.2.1]hept-2-ylmethyl)-N-(2-methoxy-5-methylphenyl)-1-benzofuran-5-sulfonamide, trifluoroacetate | | |
| 105 | N-(2-Methoxy-5-methylphenyl)-7-[(2-methylpiperazin-1-yl)methyl]-1-benzofuran-5-sulfonamide, trifluoroacetate | | |

TABLE 1-continued

| EXAMPLE | | P | R3 |
|---|---|---|---|
| 106 | 2-Chloro-N-[7-(piperazin-1-ylmethyl)-1-benzofuran-5-yl]benzenesulfonamide dihydrochloride | *N-t-Bu-SO2-(2-chlorophenyl)* | *piperazin-1-ylmethyl* |
| 107 | 2-Methyl-N-[7-(piperazin-1-ylmethyl)-1-benzofuran-5-yl]benzenesulfonamide, dihydrochloride | *N-t-Bu-SO2-(2-methylphenyl)* | *piperazin-1-ylmethyl* |
| 108 | N-[7-(Piperazin-1-ylmethyl)-1-benzofuran-5-yl]thiophene-2-sulfonamide, dihydrochloride | *thiophene-2-SO2-NH-t-Bu* | *piperazin-1-ylmethyl* |
| 109 | 2-Chloro-N-[7-(1,4-diazepan-1-ylmethyl)-1-benzofuran-5-yl]benzenesulfonamide dihydrochloride | *N-t-Bu-SO2-(2-chlorophenyl)* | *1,4-diazepan-1-ylmethyl* |
| 110 | N-[7-(1,4-Diazepan-1-ylmethyl)-1-benzofuran-5-yl]-2-methylbenzenesulfonamide, dihydrochloride | *N-t-Bu-SO2-(2-methylphenyl)* | *1,4-diazepan-1-ylmethyl* |
| 111 | N-[7-(1,4-Diazepan-1-ylmethyl)-1-benzofuran-5-yl]thiophene-2-sulfonamide dihydrochloride | *thiophene-2-SO2-NH-t-Bu* | *1,4-diazepan-1-ylmethyl* |

US 7,820,675 B2

TABLE 1-continued

| EXAMPLE | | P | R3 |
|---|---|---|---|
| 112 | 2-Methoxy-5-methyl-N-{7-[(2-methylpiperazin-1-yl)methyl]-1-benzofuran-5-yl}benzenesulfonamide, dihydrochloride | | |
| 113 | 2-Methyl-N-{7-[(2-methylpiperazin-1-yl)methyl]-1-benzofuran-5-yl}benzenesulfonamide dihydrochloride | | |
| 114 | 2,5-Dichloro-N-{7-[(2-methylpiperazin-1-yl)methyl]-1-benzofuran-5-yl}thiophene-3-sulfonamide dihydrochloride | | |
| 115 | 2-Methoxy-5-methyl-N-{7-[(3-methylpiperazin-1-yl)methyl]-1-benzofuran-5-yl}benzenesulfonamide, dihydrochloride | | |
| 116 | N-{7-[(3-Methylpiperazin-1-yl)methyl]-1-benzofuran-5-yl}-2-(trifluoromethyl)benzenesulfonamide, dihydrochloride | | |
| 117 | 2-Chloro-N-{7-[(3-methylpiperazin-1-yl)methyl]-1-benzofuran-5-yl}benzenesulfonamide, dihydrochloride | | |

TABLE 1-continued

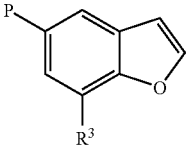

| EXAMPLE | | P | R3 |
|---|---|---|---|
| 118 | N-[7-(2,5-Diazabicyclo[2.2.1]hept-2-ylmethyl)-1-benzofuran-5-yl]-2-methoxy-5-methylbenzenesulfonamide, dihydrochloride | 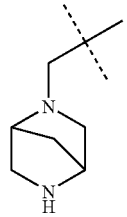 | 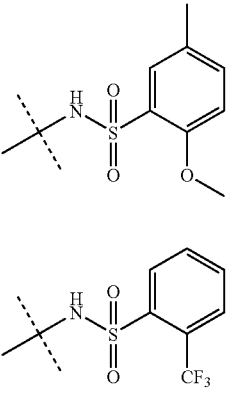 |
| 119 | N-[7-(2,5-Diazabicyclo[2.2.1]hept-2-ylmethyl)-1-benzofuran-5-yl]-2-(trifluoromethyl)benzenesulfonamide, dihydrochloride | 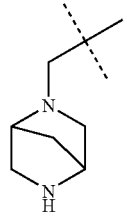 | 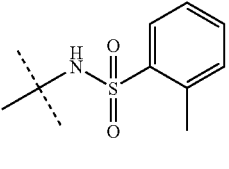 |
| 120 | N-[7-(2,5-Diazabicyclo[2.2.1]hept-2-ylmethyl)-1-benzofuran-5-yl]-2-methylbenzenesulfonamide, dihydrochloride | 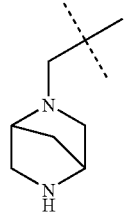 | 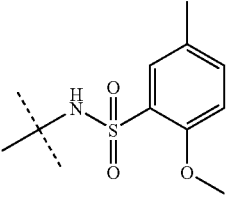 |
| 121 | 2-Methoxy-5-methyl-N-{7-[(trans-2,5-dimethylpiperazin-1-yl)methyl]-1-benzofuran-5-yl}benzenesulfonamide, bistrifluoroacetate | 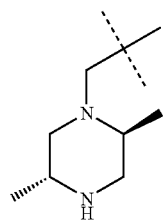 | 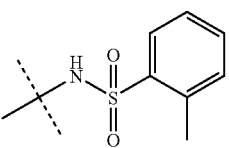 |
| 122 | 2-Methyl-N-{7-[(trans-2,5-dimethylpiperazin-1-yl)methyl]-1-benzofuran-5-yl}benzenesulfonamide, bistrifluoroacetate | 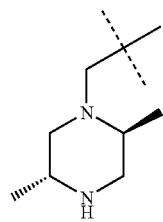 | 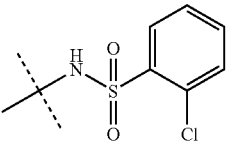 |
| 123 | 2-Chloro-N-{7-[(trans-2,5-dimethylpiperazin-1-yl)methyl]-1-benzofuran-5-yl}benzenesulfonamide, bistrifluoroacetate | 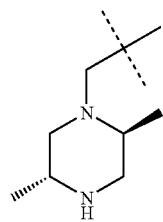 | |

TABLE 1-continued

| EXAMPLE | | P | R3 |
|---|---|---|---|
| 124 | 1-({5-[(2-Methoxy-5-methylphenyl)sulfonyl]-1-benzofuran-7-yl}methyl)piperazine, trifluoroacetate | 2-methoxy-5-methylphenylsulfonyl | piperazin-1-ylmethyl |
| 125 | 1-{[5-(Phenylsulfonyl)-1-benzofuran-7-yl]methyl}piperazine, trifluoroacetate | phenylsulfonyl | piperazin-1-ylmethyl |
| 126 | 1-({5-[(4-Methylphenyl)sulfonyl]-1-benzofuran-7-yl}methyl)piperazine, trifluoroacetate | 4-methylphenylsulfonyl | piperazin-1-ylmethyl |
| 127 | 1-({5-[(2-Methoxy-5-methylphenyl)sulfonyl]-1-benzofuran-7-yl}methyl)-1,4-diazepane, trifluoroacetate | 2-methoxy-5-methylphenylsulfonyl | 1,4-diazepan-1-ylmethyl |
| 128 | 1-{[5-(Phenylsulfonyl)-1-benzofuran-7-yl]methyl}-1,4-diazepane, trifluoroacetate | phenylsulfonyl | 1,4-diazepan-1-ylmethyl |
| 129 | 1-({5-[(4-Methylphenyl)sulfonyl]-1-benzofuran-7-yl}methyl)-1,4-diazepane, trifluoroacetate | 4-methylphenylsulfonyl | 1,4-diazepan-1-ylmethyl |

TABLE 1-continued

| EXAMPLE | | P | R3 |
|---|---|---|---|
| 130 | 1-({5-[(2-Methoxy-5-methylphenyl)sulfonyl]-1-benzofuran-7-yl}methyl)-2-methylpiperazine, trifluoroacetate | | |
| 131 | 1-({5-[(2-Methoxy-5-methylphenyl)sulfonyl]-1-benzofuran-7-yl}methyl)-3-methylpiperazine, trifluoroacetate | | |
| 134 | N-(2-Methylphenyl)-7-{[(3R)-pyrrolidin-3-ylamino]methyl}-1-benzofuran-5-sulfonamide, trifluoroacetate | | |
| 135 | N-(2-Methylphenyl)-7-(piperidin-4-ylmethyl)-1-benzofuran-5-sulfonamide, trifluoroacetate | | |
| 136 | N-(2-Methylphenyl)-7-(pyrrolidin-3-ylmethyl)-1-benzofuran-5-sulfonamide, trifluoroacetate | | |
| 137 | N-(2-Methylphenyl)-7-(piperidin-3-ylmethyl)-1-benzofuran-5-sulfonamide, trifluoroacetate | | |

TABLE 1-continued

| EXAMPLE | | P | R3 |
|---|---|---|---|
| 138 | 2-Methoxy-5-methyl-N-[7-(piperidin-4-ylmethyl)-1-benzofuran-5-yl]benzenesulfonamide, trifluoroacetate | | |
| 139 | 3-({5-[(4-Methylphenyl)sulfonyl]-1-benzofuran-7-yl}methyl)pyrrolidine, trifluoroacetate | | |

TABLE 2

| EXAMPLE | | R7 | R2 |
|---|---|---|---|
| 36 | N-[2-(1-Azabicyclo[2.2.2]oct-2-en-3-yl)-1-benzofuran-7-yl]benzenesulfonamide hydrochloride | | |
| 37 | N-[2-(1-Azabicyclo[2.2.2]oct-2-en-3-yl)-1-benzofuran-7-yl]-2-methoxy-5-methylbenzenesulfonamide hydrochloride | | |

TABLE 3

| EXAMPLE | | R⁷ | R⁵ |
|---|---|---|---|
| 132 | 2-Methoxy-5-methyl-N-[5-(piperidin-4-ylmethyl)-1-benzofuran-7-yl]benzenesulfonamide, trifluoroacetate | | |
| 133 | 2-Methoxy-5-methyl-N-{5-[(3-methylpiperazin-1-yl)methyl]-1-benzofuran-7-yl}benzenesulfonamide, bis(trifluoroacetate) | | |
| 140 | 2-Methoxy-5-methyl-N-[5-(piperidin-4-ylmethyl)-1-benzofuran-7-yl]benzenesulfonamide, trifluoroacetate | | |

The preparation of the compounds of Formula (I) according to the Examples may in particular be illuminated by the following Schemes 1-6, wherein steps (a) to (s) are detailed below.

The experimental details are given for each of the specific synthetic examples. Schemes 1-6 are merely illustrative of some methods by which the compounds of the present invention may be synthesized, and various modifications to these synthetic reaction schemes may be made. Any primary or secondary amine nitrogen, if present, in R³ may optionally be protected with a nitrogen protecting group, such as tert-butoxycarbonyl (t-BOC) or benzyl, in reactions targeting a compound of Formula (I). Subsequent N-deprotection is carried out by conventional methods such as those described in Protective Groups in Organic Synthesis, John Wiley & Sons, 1991.

Scheme 1

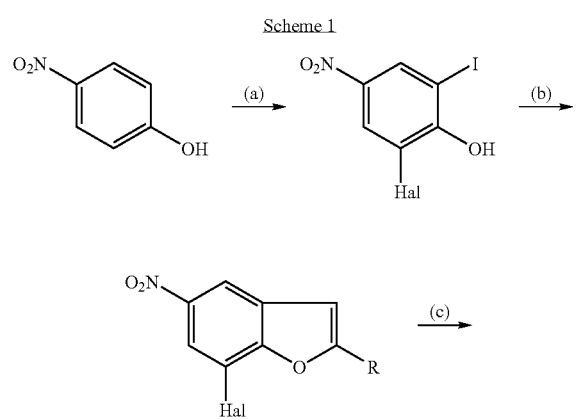

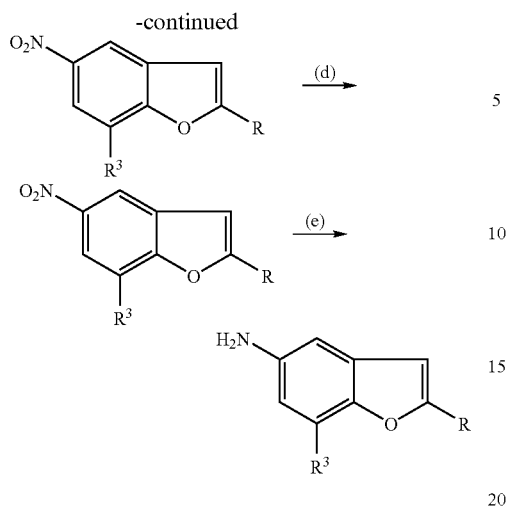

R=H or SiMe₃
Hal=Cl, Br, or I
R³ is as defined for Formula (I).

Scheme 2

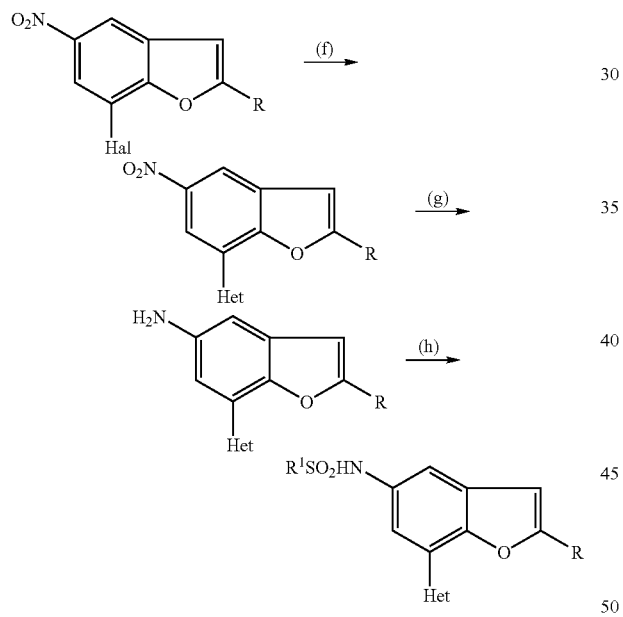

R=H or SiMe₃
Hal=Cl, Br, or I
Het=a heteroaryl group or a heterocyclic group within the scope of R³ as defined for Formula (I). Exemplary heteroaryl or heterocyclic groups are selected from 3-pyridyl, 4-pyridyl, pyrazinyl, 5-pyrimidyl, and 1-azabicyclo[2.2.2]oct-3-en-2-yl
R¹ is as defined for Formula (I).

Scheme 3

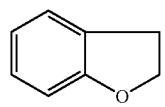

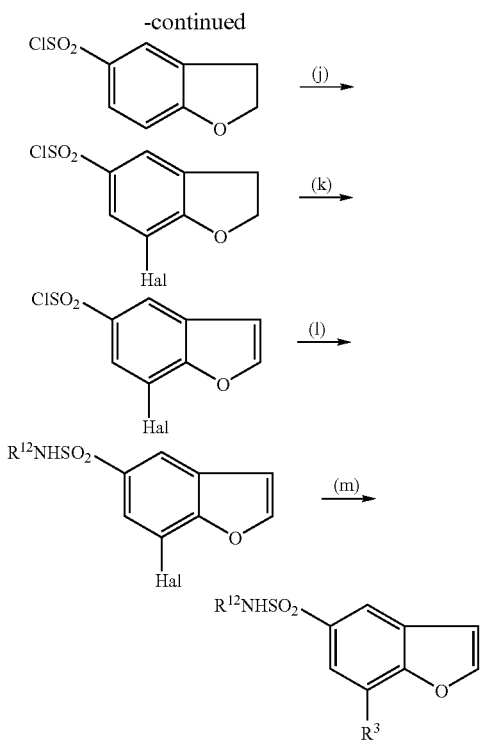

Hal=Cl, Br, or I
R³ and R¹² are as defined for Formula (I)

Scheme 4

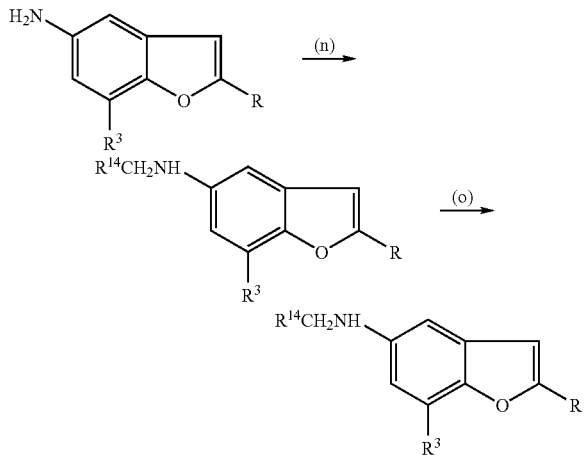

R=H or SiMe₃
R³ and R¹⁴ are as defined for Formula (I).

Scheme 5

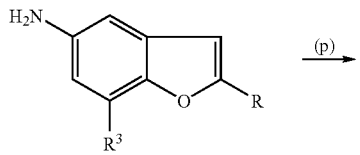

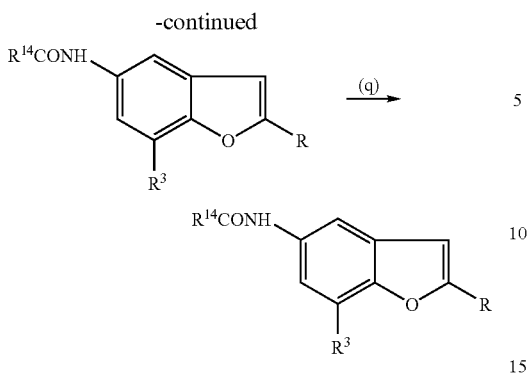
R=H or SiMe₃
R³ and R¹⁴ are as defined for Formula (I).
Scheme 6
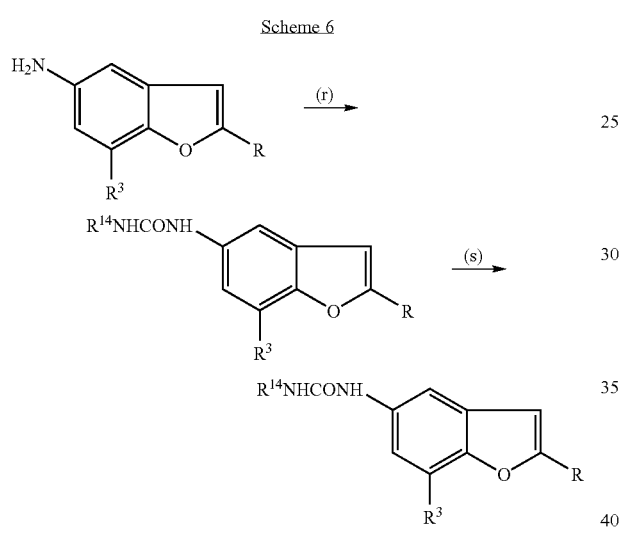
R=H or SiMe₃
R³ and R¹⁴ are as defined for Formula (I).
Scheme 7
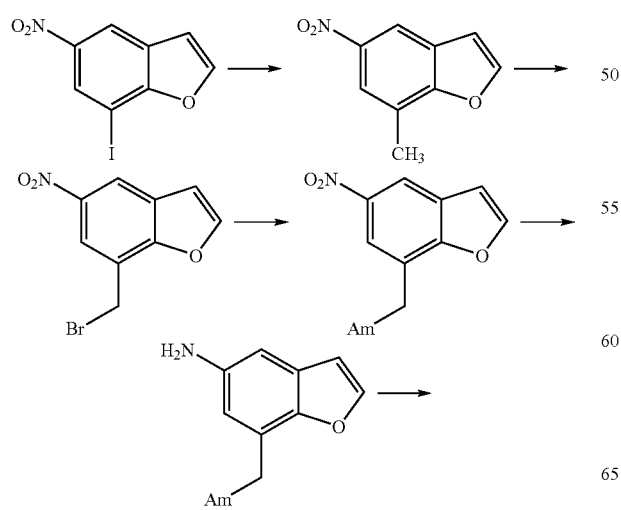
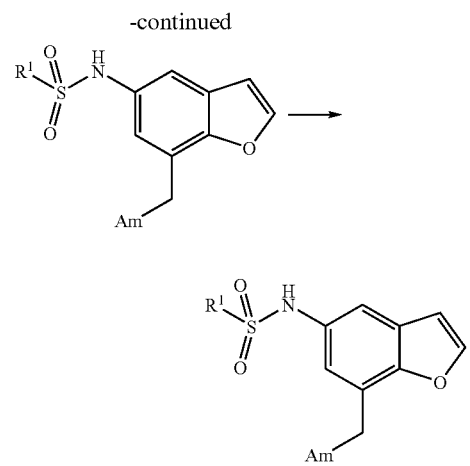
$R^1$ is as defined for formula (I) and Am is attached to the remainder of the molecule via a nitrogen atom. Exemplary Am groups are depicted in Scheme 7-A.
Scheme 7-A
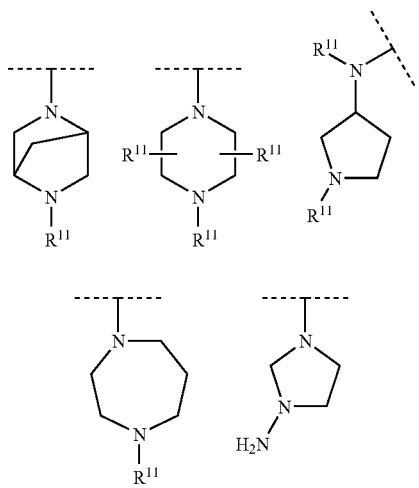
wherein $R^{11}$ is each independently selected from hydrogen or methyl.
Scheme 8
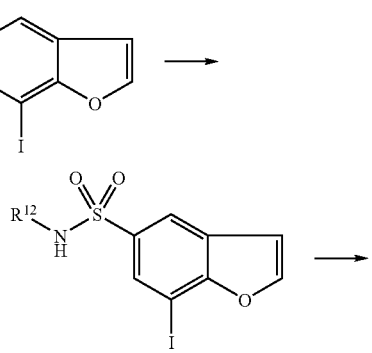

-continued

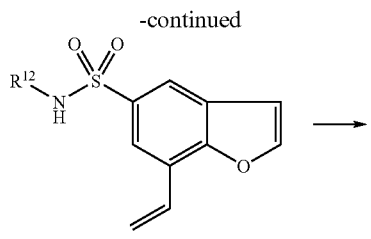

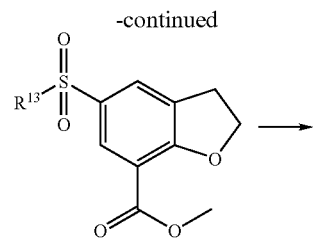

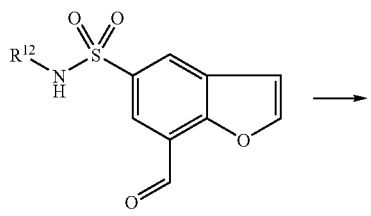

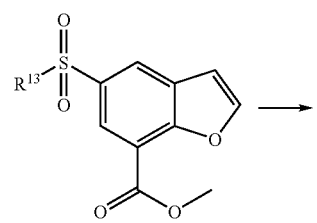

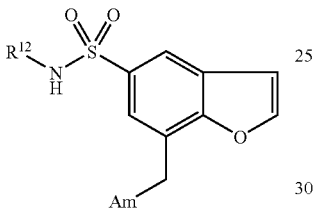

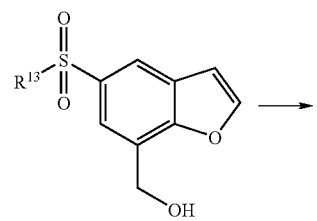

$R^{12}$ is as defined for formula (I) and Am is attached to the remainder of the molecule via a nitrogen atom. Exemplary Am groups are shown in Scheme 7-A.

Scheme 9

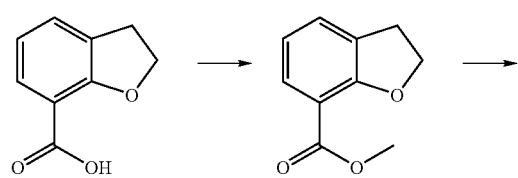

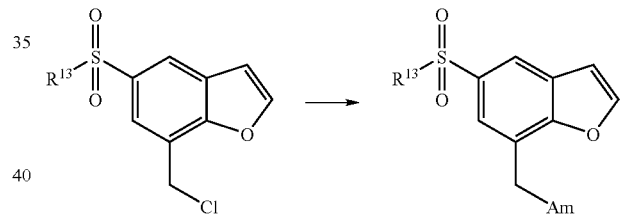

$R^{12}$ is as defined for formula (I) and Am is attached to the remainder of the molecule via a nitrogen atom. Exemplary Am groups are shown in Scheme 7-A.

Scheme 10

$R^{12}$ is as defined for formula(I); P is a suitable protecting group such as t-BOC

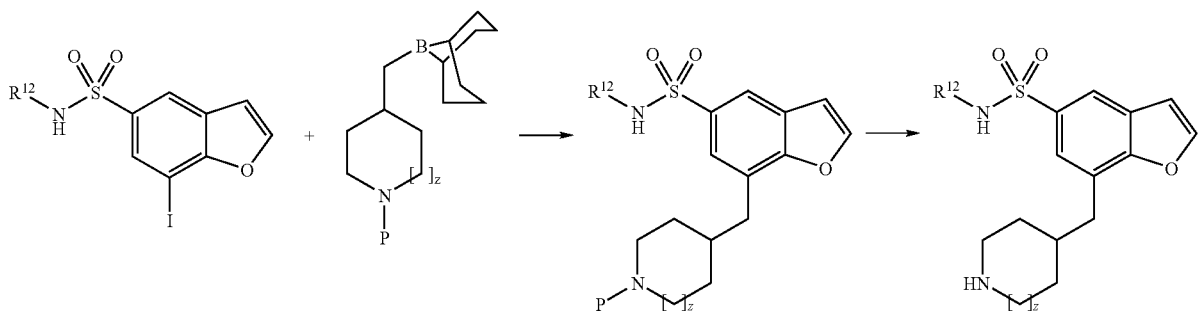

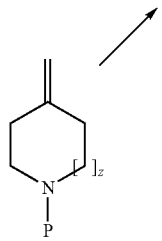
and z=0, 1 or 2.
Scheme 11
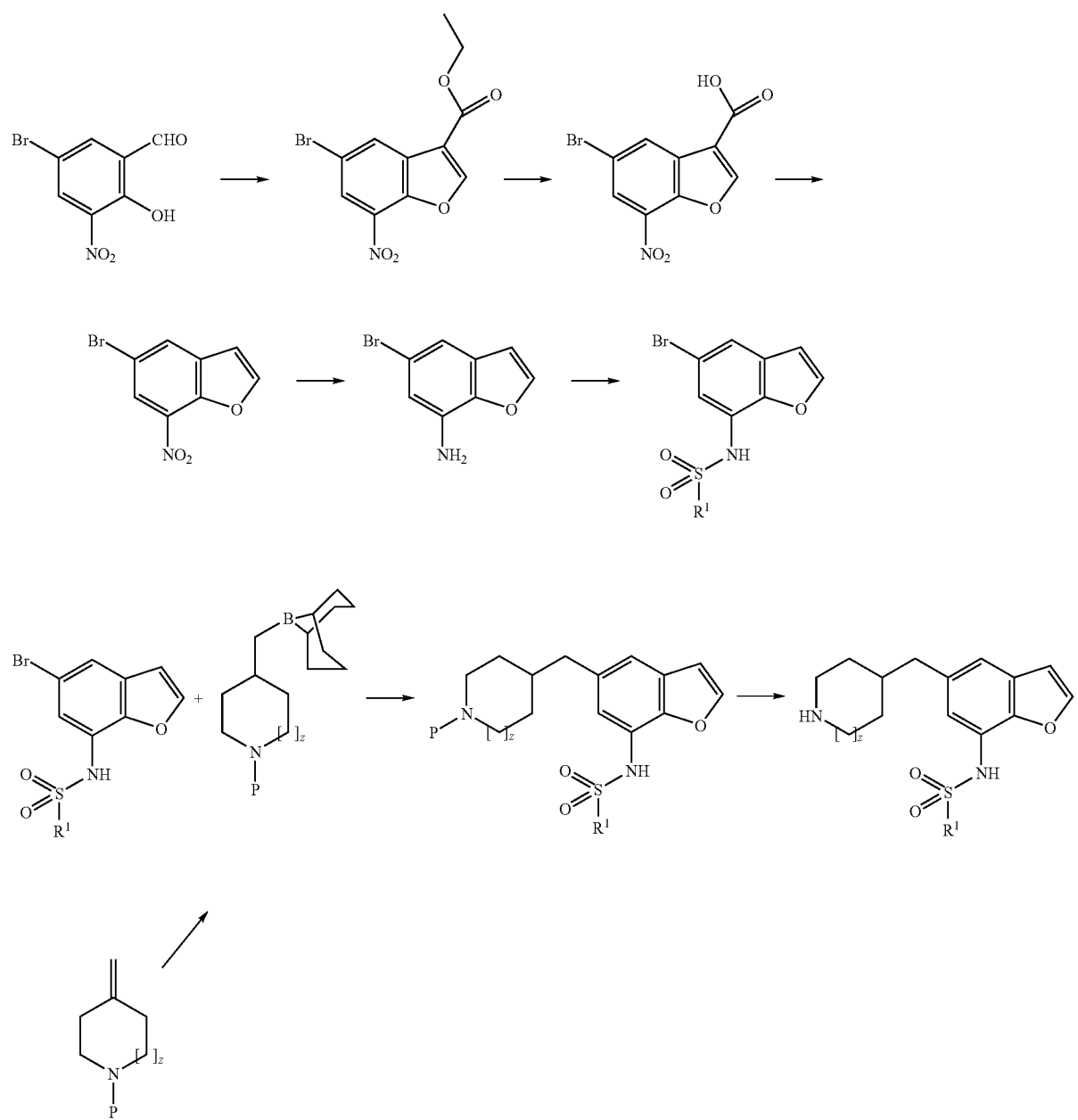

103

R[1] is as defined for formula (I);
P is a suitable protecting group such as t-BOC; and
z=0, 1 or 2.

104

R[1] is as defined for formula (I) and Am is attached to the remainder of the molecule via a nitrogen atom. Exemplary Am groups are shown in Scheme 7-A.

Scheme 12

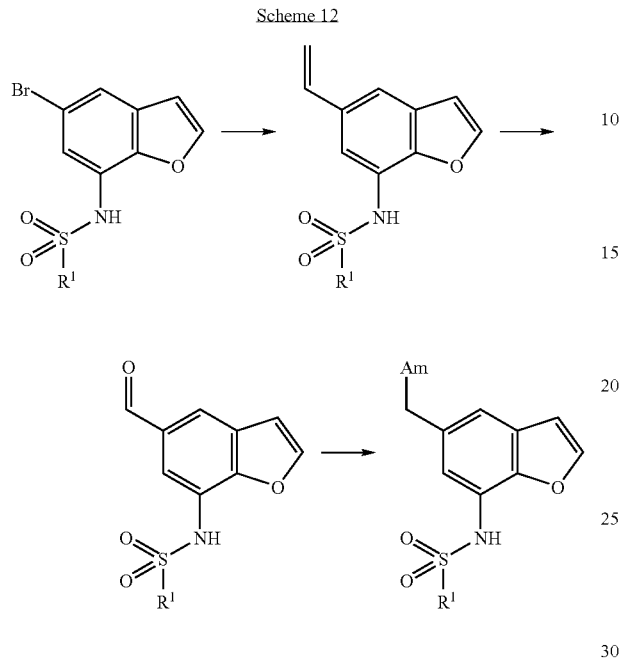

R[1] is as defined for formula (I) and Am is attached to the remainder of the molecule via a nitrogen atom. Exemplary Am groups are shown in Scheme 7-A.

Scheme 14

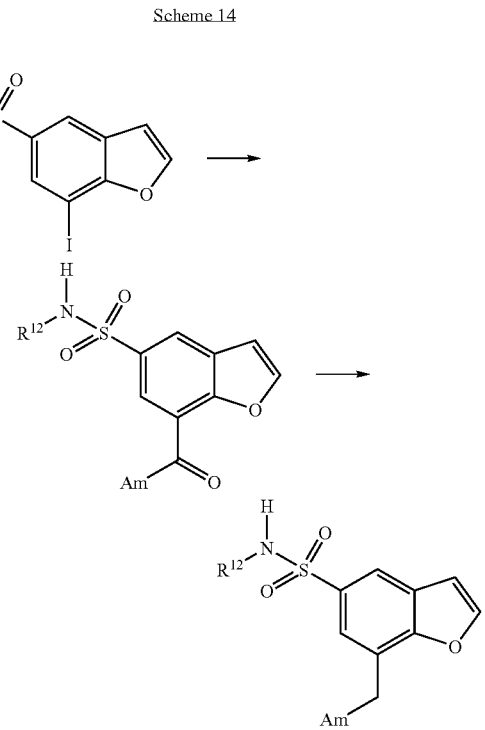

Scheme 13

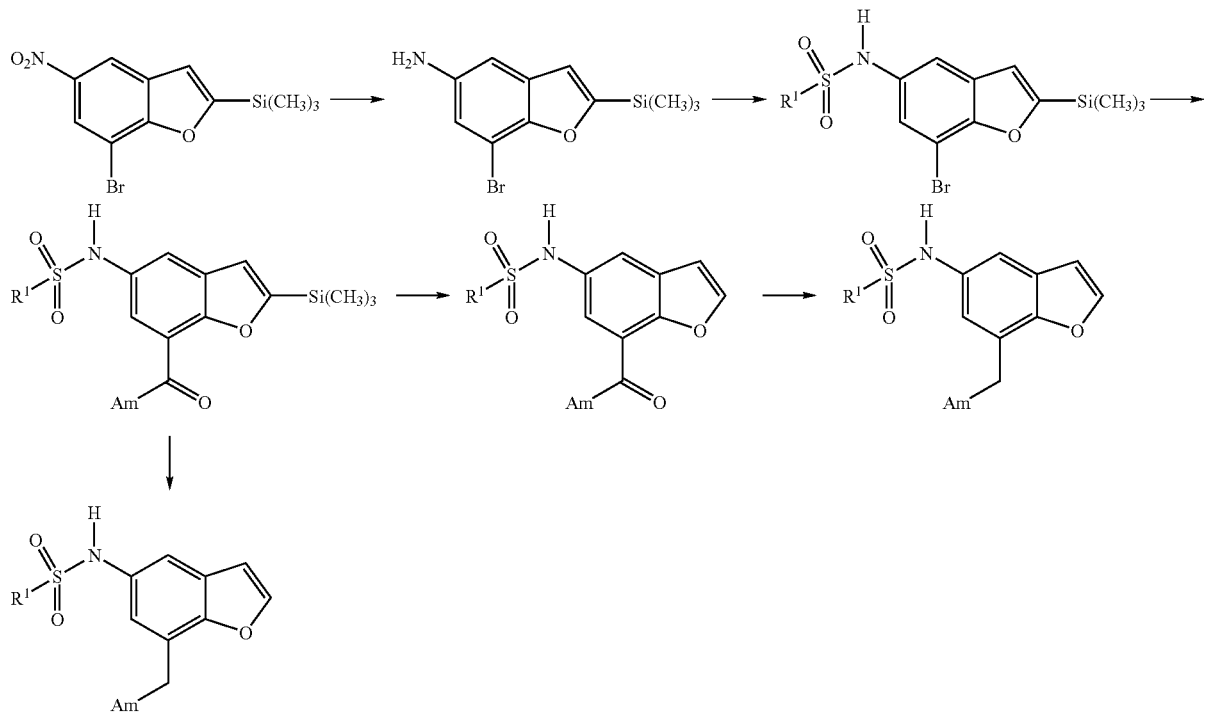

$R^{12}$ is as defined for formula (I) and Am is attached to the remainder of the molecule via a nitrogen atom. Exemplary Am groups are shown in Scheme 7-A.

Intermediate 1

N,N'-Dimethyl-N-(5-nitro-1-benzofuran-7-yl)-propyl-1,3-diamine

To a mixture of 7-iodo-5-nitro-1-benzofuran (prepared according to the following procedures Castro, C. E.; Stephens, R. D. *J. Org. Chem.* 1963, 28, 2163 and Doad, G. J. S.; Barltrop, J. A.; Petty, C. M.; Owen, T. C. *Tetrahedron Lett.* 1989, 30, 1597-1598) (300 mg, 1.0 mmol), Xantphos (60 mg, 0.1 mmol), Pd$_2$(dba)$_3$ (23 mg, 25 mmol), sodium tert-butoxide (125 mg, 1.3 mmol) in xylene (10 mL) was added N,N'-dimethylpropane-1,3-diamine (540 µL, 5 mmol). The mixture was stirred at 120° C. for 2 h, allowed to cool and filtered through a Celite pad. The filtrate was concentrated in vacuo to give the crude title compound. MS m/z 264 (M+H)$^+$.

Intermediate 2 tert-Butyl 3-[(5-amino-1-benzofuran-7-yl)(methyl)amino]propyl(methyl)carbamate

The crude N,N'-dimethyl-N-(5-nitro-1-benzofuran-7-yl) propyl-1,3-diamine (Intermediate 1) was dissolved in DCM (10 mL) and di-tert-butyl dicarbonate (327 mg, 1.5 mmol) in DCM (5 mL) was added at 0° C. The mixture was stirred at 0° C. for 15 min, after which time the ice-bath was removed and the mixture was stirred for 2 h at room temperature. Water was added. The organic material was extracted with chloroform (2×), the combined organic layers were dried (MgSO$_4$) and filtered. The volatiles were evaporated to give a yellow oil which was filtered through silica gel eluting with EtOAc. The volatiles were evaporated and the crude material of tert-butyl methyl[3-(methyl{5-nitro-1-benzofuran-7-yl}amino)]propyl]carbamate was dissolved in EtOH and an excess of Raney Ni as a suspension in EtOH (4 mL) was added followed by the addition of hydrazine hydrate (300 µL, 6 mmol). The reaction mixture was stirred at room temperature for 2 h followed by filtration through a Celite pad pre-treated with water. The Celite pad was washed with MeOH and the filtrate was concentrated in vacuo to give the title compound (250 mg) as a crude, which was used directly in the next step.

Intermediate 3 tert-Butyl methyl[3-(methyl{5-[(phenylsulfonyl)amino]-1-benzofuran-7-yl}amino)propyl]carbamate Benzenesulfonyl chloride (115 µL, 0.9 mmol) was added to a mixture of tert-butyl 3-[(5-amino-1-benzofuran-7-yl)(methyl)amino]propyl(methyl)carbamate (Intermediate 2; 250 mg, 0.75 mmol) in DCM (2 mL) followed by addition of pyridine (1 mL). The reaction mixture was stirred at room temperature for 4 h. The volatiles were evaporated in vacuo and the residue obtained was purified using RP-HPLC (Gilson/YMC AQ C18; 150×30 mm) to give the title compound as a beige oil (202 mg, 43% over 4 steps); HPLC 93%, R$_T$: 2.49 min (System A); 95%, R$_T$: 2.27 min (System B); $^1$H NMR (CDCl$_3$) δ ppm 1.41 (s, 9H), 1.60-1.75 (m, 2H), 2.74 (s, 3H), 2.93 (s, 3H), 3.13-3.25 (m, 2H), 3.42-3.53 (m, 2H), 6.19-6.69 (m, 2H), 6.87-7.06 (m, 1H), 7.33-7.58 (m, 4H), 7.71-7.79 (m, 2H); MS m/z 474 (M+H)$^+$.

Example 1

N-(7-{Methyl[3-(methylamino)propyl]amino}-1-benzofuran-5-yl)benzenesulfonamide hydrochloride tert-Butyl methyl[3-(methyl{5-[(phenylsulfonyl)amino]-1-benzofuran-7-yl}amino)propyl]carbamate (Intermediate 3; 202 mg, 0.43 mmol) in DCM (2 mL) was treated with TFA (2 mL) at 0° C. for 10 min and was stirred for an additional 30 min at room temperature. After concentration in vacuo, the residue was re-dissolved in MeOH and treated with an excess of 1M HCl in diethyl ether. Removal of the solvents gave the title compound (173 mg, 98%) as a white solid; HPLC 100%, R$_T$: 1.65 min (System A); 100%, R$_T$: 0.630 min (System B); $^1$H NMR (methanol-d$_4$) δ ppm 1.85-2.00 (m, 2H), 2.67 (s, 3H), 3.04-3.17 (m, 5H), 3.64-3.73 (m, 2H), 6.81-6.84 (m, 1H), 6.95-6.98 (m, 1H), 7.06-7.09 (m, 1H), 7.43-7.60 (m, 3H), 7.72-7.78 (m, 2H), 7.81-7.85 (m, 1H); MS m/z 374 (M+H)$^+$.

Intermediate 4

1-(5-Nitro-1-benzofuran-7-yl)piperidine

Step 1. 2-Bromo-6-iodo-4-nitrophenol. A solution of 4-nitrophenol (130 g, 0.96 mol) in acetonitrile (500 mL) was cooled to 0° C. While keeping the temperature below 5° C., chlorosulfonic acid (120 g, 1.03 mol) was added. The resulting mixture was stirred for 30 min at 0-5° C. N-bromosuccinimide (181 g, 1.01 mol) was added portionwise to the mixture during 7 h, while keeping the temperature below 8° C. The reaction was then quenched by addition of a solution of NaHSO$_3$ (250 g, 2.4 mol) in water (600 mL) while the temperature was kept below 20° C. The water phase was removed and the remaining organic phase was concentrated to 300 mL by distillation. The residue was diluted with acetic acid (381 mL, 6.6 mol) and potassium acetate (212 g, 2.16 mol) was added. The temperature was adjusted to 50° C. and ICl (152 g, 0.936 mol) was added while the temperature was maintained between 50 and 80° C. When the addition was completed, the product was precipitated by addition of water (1000 mL). After cooling to 10° C., the product was isolated by filtration, to yield 290 g (90%) of 2-bromo-6-iodo-4-nitrophenol. $^1$H NMR (270 MHz, CDCl$_3$) δ ppm 6.53 (s, 1H) 8.42 (d, J=2.72 Hz, 1H) 8.58 (d, J=2.72 Hz, 1H).

Step 2. 7-Bromo-5-nitro-2-(trimethylsilyl)benzofuran. To a solution of 2-bromo-6-iodo-4-nitrophenol (200 g, 581.56 mmol; obtained in Step 1) in acetonitrile (2800 mL) were added CuI (2.22 g, 11.63 mmol) and Et$_3$N (117.70 g, 1163.12 mmol). N$_2$ atmosphere was established and PdCl$_2$(PPh$_3$)$_2$ (4.08 g, 5.82 mmol) was added followed by slow addition of (trimethylsilyl)acetylene (59.98 g, 610.64 mmol) during 2 h. The reaction mixture was stirred overnight until complete formation of intermediate 2-bromo-4-nitro-6-[(trimethylsilyl)ethynyl]phenol and then heated to 85° C. for 8 h. The mixture was diluted with acetonitrile (1500 mL) and activated carbon (6 g) was added followed by water (600 mL). The resulting suspension was heated to 85° C. and the carbon was removed by filtration. The volume was adjusted to 1950 mL by distillation followed by the addition of water (1600 mL). The product was obtained as an oily precipitation that solidified upon cooling. The liquid was decanted off and the solid residue was dissolved in acetonitrile (500 mL). The volatiles were eliminated to give 149.7 g (82%) of 7-bromo-5-nitro-2-(trimethylsilyl)-benzofuran. $^1$H NMR (270 MHz, CDCl$_3$) δ ppm 0.39 (s, 9H) 7.12 (s, 1H) 8.38 (d, J=2.23 Hz, 1H) 8.42 (d, J=2.23 Hz, 1H).

Step 3. 1-(5-Nitro-1-benzofuran-7-yl)piperidine. A mixture of 7-bromo-5-nitro-2-(trimethylsilyl)benzofuran (1.57 g, 5 mmol; obtained in Step 2), piperidine (0.47 g, 5.5 mmol), Pd(OAc)$_2$ (56 mg, 0.25 mmol), BINAP (0.31 g, 0.5 mmol) and NaOtBu (0.96 g, 10 mmol) in xylene (15 mL) was stirred at 110° C. for 6 h. The cooled mixture was filtered through Celite and concentrated to give an oil that was put on a SiO$_2$-column and eluted with EtOAc/hexane (25:75) to give 1-(5-nitro-1-benzofuran-7-yl)piperidine. Yield: 650 mg (53%). $^1$H NMR (400 MHz, CDCl$_3$) δ ppm 1.62-1.70 (m, 2H), 1.77-1.85 (m, 4H), 3.36 (t, 4H), 6.86 (d, 1H), 7.64 (d, 1H), 7.73 (d, 1H), 8.09 (d, 1H); GC-MS (EI+) for C$_{13}$H$_{14}$N$_2$O$_3$ m/z 246 M$^+$.

Intermediate 5

4-(5-Nitro-1-benzofuran-7-yl)morpholine

Prepared according to the procedure of Intermediate 4 (Step 3) starting from morpholine. Yield: 460 mg (37%); $^1$H NMR (400 MHz, CDCl$_3$) δ ppm 3.40-3.45 (m, 4H), 3.94-3.98 (m, 4H), 6.90 (d, 1H), 7.64 (d, 1H), 7.74 (d, 1H), 8.15 (d, 1H); GC-MS (EI+) for C$_{12}$H$_{12}$N$_2$O$_4$ m/z 248 (M)$^+$.

Intermediate 6

7-Piperidin-1-yl-1-benzofuran-5-amine 1-(5-Nitro-1-benzofuran-7-yl)piperidine (630 mg, 2.56 mmol; Intermediate 4) was dissolved in EtOAc (50 mL), PtO$_2$ added and the mixture stirred under H$_2$ for 36 h. Filtration through Celite and concentration of the filtrate furnished 7-piperidin-1-yl-1-benzofuran-5-amine. Yield: 540 mg (98%). $^1$H NMR (400 MHz, CDCl$_3$) δ ppm 1.59-1.65 (m, 2H), 1.71-1.83 (m, 4H), 3.21-3.26 (m, 4H), 3.55 (br s, 2H), 6.19 (d, 1H), 6.45 (d, 1H), 6.56 (d, 1H), 7.51 (d, 1H); GC-MS (EI+) for C$_{13}$H$_{16}$N$_2$O m/z 216 M$^+$.

Intermediate 7

7-Morpholin-4-yl-1-benzofuran-5-amine

Prepared according to the procedure of Intermediate 6 starting from 4-(5-nitro-1-benzofuran-7-yl)morpholine (Intermediate 5). Yield: 520 mg (98%); $^1$H NMR (400 MHz, CDCl$_3$) δ ppm 3.28-3.32 (m, 4H), 3.56 (br s, 2H), 3.91-3.95 (m, 4H), 6.17 (d, 1H), 6.50 (d, 1H), 6.58 (d, 1H), 7.50 (d, 1H); GC-MS (EI+) for C$_{12}$H$_{14}$N$_2$O$_2$ m/z 218 (M)$^+$.

Example 2

N-(7-Piperidin-1-yl-1-benzofuran-5-yl)benzenesulfonamide

The synthesis was performed according to the procedure of Intermediate 3 starting from 7-piperidin-1-yl-1-benzofuran-5-amine (Intermediate 6). Yield: 70 mg (39%). $^1$H NMR (400 MHz, CDCl$_3$) δ ppm 1.57-1.62 (m, 2H), 1.70-1.78 (m, 4H), 3.16 (t, 4H), 6.39 (br s, 1H), 6.41 (d, 1H), 6.63 (d, 1H), 6.83 (d, 1H), 7.37-7.43 (m, 2H), 7.49-7.54 (m, 1H), 7.57 (d, 1H), 7.68-7.72 (m, 2H); MS (ESI+) for C$_{19}$H$_{20}$N$_2$O$_3$S m/z 357 (M+H)$^+$; HPLC 97% (System A).

Example 3

4-Fluoro-N-(7-piperidin-1-yl-1-benzofuran-5-yl)benzenesulfonamide

The synthesis was performed according to the procedure of Intermediate 3 starting from 7-piperidin-1-yl-1-benzofuran-5-amine (Intermediate 6). Yield: 55 mg (29%). $^1$H NMR (400 MHz, CDCl$_3$) δ ppm 1.56-1.65 (m, 2H), 1.70-1.79 (m, 4H), 3.19 (t, 4H), 6.43 (d, 1H), 6.48 (br s, 1H), 6.63 (d, 1H), 6.81 (d, 1H), 7.04-7.10 (m, 2H), 7.58 (d, 1H), 7.68-7.74 (m, 2H); $^{13}$C NMR (100 MHz, CDCl$_3$) δ 24.30, 25.88, 50.90, 107.00, 108.11, 108.42, 115.96, 116.19, 128.67, 130.01, 131.52, 134.89, 138.76, 144.80, 145.16, 163.85, 166.39; MS (ESI+) for C$_{19}$H$_{19}$FN$_2$O$_3$S m/z 375 (M+H)$^+$. HPLC 100% (System A).

Example 4

3,4-Dimethoxy-N-(7-piperidin-1-yl-1-benzofuran-5-yl)benzenesulfonamide hydrochloride The synthesis was performed according to the procedure of Intermediate 3 starting from 7-piperidin-1-yl-1-benzofuran-5-amine (Intermediate 6). Yield: 100 mg (48%). $^1$H NMR (400 MHz, CDCl$_3$) δ ppm 1.52-1.57 (m, 2H), 1.62-1.66 (m, 4H), 3.09-3.15 (m, 4H), 3.69 (s, 3H), 3.75 (s, 3H), 6.50-6.55 (m, 1H), 6.82 (d, 1H), 6.88 (d, 1H), 7.01 (d, 1H), 7.20-7.26 (m, 2H), 7.87 (d, 1H), 9.80 (br s, 1H); MS (ESI+) for C$_{21}$H$_{24}$N$_2$O$_5$S m/z 417 (M+H)$^+$; HPLC 100% (System A).

Intermediate 8

1-(5-Nitro-1-benzofuran-7-yl)pyrrolidine

The synthesis was performed as described for Intermediate 4 (Step 3). Yield 26%. $^1$H NMR (400 MHz, CDCl$_3$) δ ppm 2.03-2.08 (m, 4H), 3.66-3.72 (m, 4H), 6.82 (d, 1H), 7.23 (d, 1H), 7.67 (d, 1H), 7.81 (d, 1H); GC-MS (EI+) for C$_{12}$H$_{12}$N$_2$O$_3$ m/z 232 M$^+$.

Intermediate 9

7-Pyrrolidin-1-yl-1-benzofuran-5-amine

The synthesis was performed as described for Intermediate 6. Yield 48%. MS (ESI+) for C$_{12}$H$_{14}$N$_2$O m/z 203 (M+H)$^+$.

Example 5

3,4-Dimethoxy-N-(7-pyrrolidin-1-yl-1-benzofuran-5-yl)benzenesulfonamide

The title compound was prepared according to the procedure of Intermediate 3 starting from 7-pyrrolidin-1-yl-1-benzofuran-5-amine (Intermediate 9). Yield: 70 mg (43%). $^1$H NMR (400 MHz, DMSO-d$_6$) δ ppm 1.88-1.93 (m, 4H), 3.38-3.43 (m, 4H), 3.71 (s, 3H), 3.75 (s, 3H), 6.16 (d, 1H), 6.60 (d, 1H), 6.75 (d, 1H), 7.01 (d, 1H), 7.24-7.29 (m, 2H), 7.80 (d, 1H), 9.71 (s, 1H); $^{13}$C NMR (100 MHz, DMSO-d$_6$) δ 24.72, 48.82, 55.62, 55.71, 100.66, 101.57, 106.96, 109.54, 110.91, 120.58, 128.29, 131.10, 134.01, 134.58, 140.65, 145.37, 148.33, 151.89; MS (ESI+) for $C_{20}H_{22}N_2O_5S$ m/z 403 $(M+H)^+$; HPLC 98% (System A).

Example 6

N-(7-Pyrrolidin-1-yl-1-benzofuran-5-yl)benzenesulfonamide

The title compound was prepared according to the procedure of Intermediate 3 starting from 7-pyrrolidin-1-yl-1-benzofuran-5-amine (Intermediate 9). Yield: 30 mg (22%). $^1$H NMR (400 MHz, DMSO-$d_6$) δ ppm 1.86-1.93 (m, 4H), 3.36-3.43 (m, 4H), 6.13 (br s, 1H), 6.59 (br s, 1H), 6.73 (d, 1H), 7.45-7.60 (m, 3H), 7.73 (d, 2H), 7.79 (d, 1H), 9.92 (s, 1H); $^{13}$C NMR (100 MHz, DMSO-$d_6$) δ ppm 24.73, 48.79, 100.68, 101.51, 106.97, 126.74, 128.33, 129.05, 132.58, 133.70, 134.62, 139.67, 140.68, 145.40; MS (ESI+) for $C_{18}H_{18}N_2O_3S$ m/z 343 $(M+H)^+$; HPLC 95% (System A).

Example 7

4-Fluoro-N-(7-pyrrolidin-1-yl-1-benzofuran-5-yl)benzenesulfonamide hydrochloride The title compound was prepared according to the procedure of Intermediate 3 starting from 7-pyrrolidin-1-yl-1-benzofuran-5-amine (Intermediate 9). Yield: 65 mg (41%). $^1$H NMR (400 MHz, DMSO-$d_6$) δ ppm 1.87-1.94 (m, 4H), 3.38-3.44 (m, 4H), 6.13 (d, 1H), 6.58 (d, 1H), 6.75 (d, 1H), 7.34-7.40 (m, 2H), 7.74-7.80 (m, 2H), 7.81 (d, 1H), 9.94 (s, 1H); $^{13}$C NMR (100 MHz, DMSO-$d_6$) δ 24.73, 48.85, 100.97, 101.73, 106.99, 116.13, 116.36, 128.38, 129.71, 1129.80, 133.51, 134.59, 135.99, 140.77, 145.48, 162.88, 165.38; MS (ESI+) for $C_{18}H_{17}FN_2O_3S$ m/z 361.0 $(M+H)^+$; HPLC 98%.

Example 8

4-Fluoro-N-(7-morpholin-4-yl-1-benzofuran-5-yl)benzenesulfonamide hydrochloride The title compound was prepared according to the procedure of Intermediate 3 starting from Intermediate 7. Yield: 100 mg (53%); $^1$H NMR (400 MHz, DMSO-$d_6$) δ ppm 3.08-3.14 (m, 4H), 3.72-3.78 (m, 4H), 6.47 (d, 1H), 6.83 (d, 1H), 6.88 (d, 1H), 7.32-7.40 (m, 2H), 7.74-7.78 (m, 2H), 7.88 (d, 1H), 10.07 (s, 1H); $^{13}$C NMR (100 MHz, DMSO-$d_6$) δ ppm 49.31, 65.98, 105.45, 106.13, 107.14, 116.20, 116.43, 128.52, 129.85, 133.24, 135.70, 137.00, 143.09, 145.74, 162.96, 165.46; MS (ESI+) for $C_{18}H_{17}FN_2O_4S$ m/z 377.2 $(M+H)^+$; HPLC 100%.

Example 9

N-(7-Morpholin-4-yl-1-benzofuran-5-yl)benzenesulfonamide hydrochloride,

The title compound was prepared according to the procedure of Intermediate 3 starting from Intermediate 7. Yield: 75 mg (42%); $^1$H NMR (400 MHz, DMSO-$d_6$) δ ppm 3.06-3.12 (m, 4H), 3.71-3.78 (m, 4H), 6.46 (d, 1H), 6.82 (d, 1H), 6.88 (d, 1H), 7.48-7.54 (m, 2H), 7.54-7.60 (m, 1H), 7.71 (d, 2H), 7.87 (d, 1H), 10.03 (s, 1H); $^{13}$C NMR (100 MHz, DMSO-$d_6$) δ 49.29, 65.98, 105.30, 105.90, 107.10, 126.75, 128.46, 129.11, 132.71, 133.40, 136.93, 139.37, 142.99, 145.67; MS (ESI+) for $C_{18}H_{18}N_2O_4S$ m/z 359.2 $(M+H)^+$; HPLC 97%.

Example 10

3,4-Dimethoxy-N-(7-morpholin-4-yl-1-benzofuran-5-yl)benzenesulfonamide

The title compound was prepared according to the procedure of Intermediate 3 starting from Intermediate 7. Yield: 45 mg (21%); $^1$H NMR (400 MHz, CDCl$_3$) δ ppm 3.23-3.28 (m, 4H), 3.75 (s, 3H), 3.89 (s, 3H), 3.89-3.93 (m, 4H), 6.53 (br s, 1H), 6.65 (d, 1H), 6.76 (br s, 1H), 6.82 (d, 1H), 6.89 (br s, 1H), 7.18 (d, 1H), 7.35 (dd, 1H), 7.57 (d, 1H); MS (ESI+) for $C_{20}H_{22}N_2O_6S$ m/z 419.0 $(M+H)^+$; HPLC 88%.

Intermediate 10 tert-Butyl 4-(5-amino-1-benzofuran-7-yl)piperazine-1-carboxylate tert-Butyl 4-(5-nitro-1-benzofuran-7-yl)piperazine-1-carboxylate* (1 g, 2.9 mmol) was dissolved in THF/EtOH (1:4). An excess of Raney-Ni (slurry in ethanol) was added followed by hydrazine-hydrate (0.58 g, 11.5 mmol). The reaction mixture was stirred at room temperature overnight. Filtration and evaporation afforded 1.19 g of the title product that was used in the next step without further purification. HPLC purity 93%, $R_T$=1.71 min (System A; 10-97% MeCN over 3 min).

*Previously described in WO 2002100822.

General Procedure A: Alkylation of tert-butyl 4-(5-amino-1-benzofuran-7-yl)piperazine-1-carboxylate A stock solution of tert-butyl 4-(5-amino-1-benzofuran-7-yl)piperazine-1-carboxylate (0.12 g, 0.378 mmol; Intermediate 10) in acetonitrile was added together with $K_2CO_3$ (52 mg, 0.378 mmol) to respective benzyl bromide (0.378 mmol). The mixtures were shaken at room temperature for 3 h. The reaction progress was controlled with LC-MS. Workup: filtration and purification by preparative HPLC using acetonitrile-water gradients containing 0.1% trifluoroacetic acid. N-deprotection was carried out according to the procedure of Example 1 and the target hydrochloride salt was obtained following treatment with 2 M HCl in ether.

Example 11

N-(3,5-Dimethylbenzyl)-7-piperazin-1-yl-1-benzofuran-5-amine hydrochloride

Prepared by general procedure A from 1-(bromomethyl)-3,5-dimethylbenzene (75 mg, 0.378 mmol). Yield: 8 mg (6%). HPLC 93%, $R_T$: 1.240 (System A; 10-97% MeCN over 3 min). $^1$H NMR (270 MHz, methanol-$d_4$) δ ppm 2.30 (s, 6H) 3.47-3.64 (m, 8H) 4.52 (s, 2H) 6.86-6.95 (m, 2H) 7.08-7.09 (m, 3H) 7.32 (s, 1H) 7.93 (s, 1H). LC-MS 336 $(M+H)^+$.

Example 12

N-(3,4-Difluorobenzyl)-7-piperazin-1-yl-1-benzofuran-5-amine hydrochloride

Prepared by general procedure A from 4-(bromomethyl)-1,2-difluorobenzene (78 mg, 0.378 mmol). Yield: 6 mg (5%). HPLC 97%, $R_T$: 1.499 (System A; 10-97% MeCN over 3 min). ¹H NMR (270 MHz, methanol-d₄) δ ppm 3.46-3.63 (m, 8H) 4.73 (s, 2H) 6.86-6.94 (m, 2H) 7.36 (s, 1H) 7.49-7.64 (m, 2H) 7.91-8.00 (m, 2H). LC-MS 344 (M+H)⁺.

Example 13

N-(3,5-Dimethoxybenzyl)-7-piperazin-1-yl-1-benzofuran-5-amine hydrochloride

Prepared by general procedure A from 1-(bromomethyl)-3,5-dimethoxybenzene (87 mg, 0.378 mmol). Yield: 8 mg (6%). HPLC 93%, $R_T$: 1.355 (System A; 10-97% MeCN over 3 min). ¹H NMR (270 MHz, methanol-d₄) δ ppm 3.47-3.65 (m, 8H) 3.76 (s, 6H) 4.56 (s, 2H) 6.54 (s, 1H) 6.64 (s, 2H) 6.89 (s, 1H) 6.95 (s, 1H) 7.35 (s, 1H) 7.92 (s, 1H). LC-MS 368 (M+H)⁺.

Example 14

N-Benzyl-7-piperazin-1-yl-1-benzofuran-5-amine hydrochloride

A stock solution of tert-butyl 4-(5-amino-1-benzofuran-7-yl)piperazine-1-carboxylate (0.12 g, 0.378 mmol; Intermediate 10) in acetonitrile was added, together with K₂CO₃ (52 mg, 0.378 mmol), to benzyl bromide (65 mg, 0.378 mmol). The mixture was shaken at room temperature for 3 h. The product was controlled with LC-MS, filtered and purified by preparative HPLC using acetonitrile-water gradients containing 0.1% trifluoroacetic acid. N-deprotection and conversion into the hydrochloride salt was performed by treatment with 2 M HCl in ether. Yield: 19 mg (16.4%). HPLC 92%, $R_T$: 1.240 (System A; 10-97% MeCN over 3 min). ¹H NMR (270 MHz, methanol-d₄) δ ppm 3.56 (d, 8H) 4.65 (s, 2H) 6.94 (s, 2H) 7.43 (s, 6H) 7.92 (s, 1H). LC-MS 308 (M+H)⁺.

General Procedure B: Amidation of tert-butyl 4-(5-amino-1-benzofuran-7-yl)piperazine-1-carboxylate Pyridine (274 µl, 3.40 mmol) and a stock solution of tert-butyl 4-(5-amino-1-benzofuran-7-yl)piperazine-1-carboxylate (0.12 g, 0.378 mmol; Intermediate 10) in DCM (2 mL) were added to the respective benzoyl chloride (0.454 mmol). The mixtures were shaken at room temperature for 2 h. The products were controlled with LC-MS and the solvent was removed. Purification of the products was done by preparative HPLC using acetonitrile-water gradients containing 0.1% trifluoroacetic acid. The final products were obtained following N-deprotection according to the procedure of Example 1 and conversion into the corresponding hydrochloride salt by treatment with 2 M HCl in ether.

Example 15

N-(7-piperazin-1-yl-1-benzofuran-5-yl)benzamide hydrochloride

Prepared by general procedure B from tert-butyl 4-(5-amino-1-benzofuran-7-yl)piperazine-1-carboxylate (64 mg, 0.454 mmol; Intermediate 10). Yield: 3 mg (3%). HPLC 94%, $R_T$: 1.534 (System A; 10-97% MeCN over 3 min). ¹H NMR (270 MHz methanol-d₄) δ ppm 3.46-3.61 (m, 8H) 6.85 (d, J=2.23 Hz, 1H) 7.28 (d, J=1.24 Hz, 1H) 7.52-7.59 (m, 4H) 7.78 (d, J=1.98 Hz, 1H) 7.95 (d, J=6.68 Hz, 2H). LC-MS 322 (M+H)⁺.

Example 16

4-Methoxy-N-(7-piperazin-1-yl-1-benzofuran-5-yl)benzamide hydrochloride

Prepared by general procedure B from 4-methoxybenzoyl chloride (77 mg, 0.454 mmol). Yield: 2 mg (1.5%). HPLC 99%, $R_T$: 1.568 (System A; 10-97% MeCN over 3 min). ¹H NMR (270 MHz, methanol-d₄) δ ppm 3.44-3.61 (m, 8H) 3.87 (s, 2H) 6.84 (d, J=2.23 Hz, 1H) 7.04 (d, J=8.91 Hz, 2H) 7.27 (d, J=1.48 Hz, 1H) 7.52 (d, J=1.73 Hz, 1H) 7.77 (d, J=1.98 Hz, 1H) 7.93 (d, J=8.91 Hz, 2H). LC-MS 352 (M+H)⁺.

Example 17

2-Bromo-5-methoxy-N-(7-piperazin-1-yl-1-benzofuran-5-yl)benzamide hydrochloride

Prepared by general procedure B from 2-bromo-5-methoxybenzoyl chloride (113 mg, 0.454 mmol). Yield: 10 mg (6.2%). HPLC 85%, $R_T$: 1.685 (System A; 10-97% MeCN over 3 min). ¹H NMR (270 MHz, methanol-d₄) δ ppm 3.46-3.48 (m, 4H) 3.59-3.61 (m, 4H) 3.84 (s, 3H) 6.84 (d, J=1.98 Hz, 1H) 6.97 (dd, J=8.66, 2.72 Hz, 1H) 7.10 (d, J=2.97 Hz, 1H) 7.23 (s, 1H) 7.54-7.59 (m, 2H) 7.78 (d, J=1.98 Hz, 1H). LC-MS 430 (M+H)⁺.

Example 18

3-Methyl-N-(7-piperazin-1-yl-1-benzofuran-5-yl)benzamide hydrochloride

Prepared by general procedure B from 3-methylbenzoyl chloride (70 mg, 0.454 mmol). Yield: 14 mg (11.1%). HPLC 93%, $R_T$: 1.666 (System A; 10-97% MeCN over 3 min). ¹H NMR (270 MHz, methanol-d₄) δ ppm 2.43 (s, 3H) 3.46-3.62 (m, 8H) 6.84 (d, J=1.73 Hz, 1H) 7.39 (d, J=4.21 Hz, 2H) 7.76 (d, J=10.14 Hz, 3H). LC-MS 336 (M+H)⁺.

Example 19

N-(7-piperazin-1-yl-1-benzofuran-5-yl)-3-(trifluoromethyl)benzamide hydrochloride Prepared by general procedure B from 3-(trifluoromethyl)benzoyl chloride (95 mg, 0.454 mmol). Yield: 12 mg (8.2%). HPLC 88%, $R_T$: 1.779 (System A; 10-97% MeCN over 3 min). ¹H NMR (270 MHz, methanol-d₄) δ ppm 3.45-3.63 (m, 8H) 6.86 (d, J=2.23 Hz, 1H) 7.31 (d, J=1.73 Hz, 1H) 7.58 (s, 1H) 7.75-7.79 (m, 2H) 7.92 (s, 1H) 8.24 (m, 2H). LC-MS 390.1 (M+H)⁺.

Example 20

2,4-Dichloro-N-(7-piperazin-1-yl-1-benzofuran-5-yl)benzamide hydrochloride

Prepared by general procedure B from 2,4-dichlorobenzoyl chloride (95 mg, 0.454 mmol). Yield: 19 mg (12.9%). HPLC 93%, $R_T$: 1.803 (System A; 10-97% MeCN over 3 min). ¹H NMR (270 MHz, methanol-d₄) δ ppm 3.47-3.62 (m, 8H) 6.84 (d, J=2.23 Hz, 1H) 7.21 (d, J=2.23 Hz, 1H) 7.44-7.78 (m, 5H). LC-MS 390 (M+H)⁺.

Example 21

3,5-Dimethoxy-N-(7-piperazin-1-yl-1-benzofuran-5-yl)benzamide hydrochloride

Prepared by general procedure B from 3,5-dimethoxybenzoyl chloride (91 mg, 0.454 mmol). Yield: 18.3 mg (12.7%). HPLC 91%, $R_T$: 1.666 (System A; 10-97% MeCN over 3 min). $^1$H NMR (270 MHz, methanol-$d_4$) δ ppm 2.76-7.82 (m, 8H) 3.04 (s, 6H) 5.87 (s, 1H) 6.02 (d, J=1.57 Hz, 1H) 6.30 (d, J=1.57 Hz, 2H) 6.41-6.49 (m, 1H) 6.78-6.79 (m, 1H) 6.98-6.69 (m, 1H). LC-MS 382 (M+H)$^+$.

General Procedure C: Synthesis of Urea Derivatives from tert-butyl 4-(5-amino-1-benzofuran-7-yl)piperazine-1-carboxylate. Method A A stock solution of tert-butyl 4-(5-amino-1-benzofuran-7-yl)piperazine-1-carboxylate (0.12 g, 0.378 mmol; Intermediate 10) in acetonitrile (2 mL) and pyridine (274 µl, 3.4 mmol) were added to the respective aryl isocyanate (0.416 mmol). The mixtures were shaken at room temperature over night. The reaction progress was controlled with LC-MS. Workup: filtration and purification by preparative HPLC using acetonitrile-water gradients containing 0.1% trifluoroacetic acid. The final products were obtained following N-deprotection according to the procedure of Example 1 and conversion into the hydrochloride salt by treatment with 2 M HCl in ether.

Example 22

N-(3,5-Dimethoxyphenyl)-N'-(7-piperazin-1-yl-benzofuran-5-yl)urea hydrochloride Prepared by general procedure C (method A) from 1-isocyanato-3,5-dimethoxybenzene (75 mg, 0.416 mmol). Yield: 11 mg (8%). HPLC 100%, $R_T$: 1.673 (System A; 10-97% MeCN over 3 min). $^1$H NMR (270 MHz, methanol-$d_4$) δ ppm 3.44-3.46 (m, 4H) 3.56-3.57 (m, 4H) 3.75 (s, 6H) 6.78 (d, J=1.98 Hz, 2H) 7.03 (s, 2H) 7.27 (d, J=1.48 Hz, 1H) 7.72 (d, J=1.98 Hz, 2H). LC-MS 397 (M+H)$^+$.

Example 23

N-(2,4-Dichlorophenyl)-N'-(7-piperazin-1-yl-benzofuran-5-yl)urea hydrochloride Prepared by general procedure C (method A) from 2,4-dichloro-1-isocyanatobenzene (78 mg, 0.416 mmol). Yield: 9 mg (6%). HPLC 100%, $R_T$: 1.775 (System A; 10-97% MeCN over 3 min). $^1$H NMR (270 MHz, methanol-$d_4$) δ ppm 3.46-3.47 (m, 4H) 3.58-3.59 (m, 4H) 6.80 (d, J=1.98 Hz, 1H) 7.06-7.07 (m, 1H) 7.26 (d, J=2.23 Hz, 1H) 7.29 (d, J=2.47 Hz, 1H) 7.46 (d, J=2.47 Hz, 1H) 7.74 (d, J=1.98 Hz, 1H) 8.13 (d, J=8.91 Hz, 1H). LC-MS 405 (M+H)$^+$.

General Procedure C: Synthesis of Urea Derivatives from tert-butyl 4-(5-amino-1-benzofuran-7-yl)piperazine-1-carboxylate. Method B A stock solution of tert-butyl 4-(5-amino-1-benzofuran-7-yl)piperazine-1-carboxylate (0.12 g, 0.378 mmol; Intermediate 10) in acetonitrile was added, together with triethylamine (158 µL, 1.13 mmol), to respective isocyanate (0.416 mmol). The mixtures were shaken at room temperature overnight. The reaction progress was controlled with LC-MS. Workup: filtration and purification by preparative HPLC using acetonitrile-water gradients containing 0.1% trifluoroacetic acid. The final products were obtained following N-deprotection according to the procedure of Example 1 and conversion into the corresponding hydrochloride salt by treatment with 2 M HCl in ether.

Example 24

N-(2-Methoxyphenyl)-N'-(7-piperazin-1-yl-1-benzofuran-5-yl)urea hydrochloride Prepared by the general procedure above (Method B) from 1-isocyanato-2-methoxybenzene (60 mg, 0.416 mmol). Yield: 33 mg (23.8%). HPLC 93%, $R_T$: 1.673 (System A; 10-97% MeCN over 3 min). $^1$H NMR (270 MHz, methanol-$d_4$) δ ppm 3.44-3.60 (m, 8H) 3.92 (s, 3H) 6.79-6.99 (m, 5H) 7.12-7.21 (m, 1H) 7.73 (d, J=2.23 Hz, 1H) 8.05 (d, J=7.67 Hz, 1H). LC-MS 367.1 (M+H)$^+$.

Example 25

N-Phenyl-N'-(7-piperazin-1-yl-1-benzofuran-5-yl)urea hydrochloride

Prepared by the general procedure above (Method B) from isocyanatobenzene (50 mg, 0.416 mmol). Yield: 31 mg (24.4%). HPLC 93%, $R_T$: 1.583 (System A; 10-97% MeCN over 3 min). $^1$H NMR (270 MHz, methanol-$d_4$) δ ppm 3.43-3.47 (m, 4H) 3.56-3.60 (m, 4H) 6.80 (d, J=2.23 Hz, 1H) 7.09-7.21 (m, 2H) 7.22-7.31 (m, 3H) 7.43 (d, J=8.41 Hz, 2H) 7.74 (d, J=2.23 Hz, 1H). LC-MS 337 (M+H)$^+$.

Example 26

N-(3-Fluorophenyl)-N'-(7-piperazin-1-yl-benzofuran-5-yl)urea hydrochloride

Prepared by the general procedure above (Method B) from 1-fluoro-3-isocyanatobenzene (57 mg, 0.416 mmol). Yield: 5 mg (3.7%). HPLC 93%, $R_T$: 1.700 (System A; 10-97% MeCN over 3 min). $^1$H NMR (270 MHz, methanol-$d_4$) δ ppm 3.46-3.47 (m, 4H) 3.57-3.60 (m, 4H) 6.77-6.81 (m, 2H) 7.08-7.09 (m, 2H) 7.22-7.28 (m, 2H) 7.42-7.47 (m, 1H) 7.74 (d, J=1.98 Hz, 1H). LC-MS 355 (M+H)$^+$.

Example 27

N-(7-piperazin-1-yl-1-benzofuran-5-yl-)-N'-[trifluoromethyl)phenyl]urea hydrochloride Prepared by the general procedure above (Method B) from 1-isocyanato-3-(trifluoromethyl)benzene (78 mg, 0.416 mmol). Yield: 27 mg (17.7%). HPLC 91%, $R_T$: 1.932 (System A; 10-97% MeCN over 3 min). $^1$H NMR (270 MHz, methanol-$d_4$) δ ppm 3.44-3.47 (m, 4H) 3.57-3.61 (m, 4H) 6.81 (d, J=2.23 Hz, 1H) 7.12-7.30 (m, 3H) 7.51 (m, 2H) 7.74 (d, J=2.23 Hz, 1H) 7.96 (s, 1H). LC-MS 405 (M+H)$^+$.

Intermediate 11

4-(5-Nitro-1-benzofuran-7-yl)pyridine

7-Iodo-5-nitrobenzofuran (2.00 g, 0.00692 mol), 4-tributylstannylpyridine (2.80 g, 0.00761 mol), copper(I)iodide (132 mg, 0.692 mmol) and dichlorobis(triphenylphosphine)palladium(II) (49 mg, 0.0692 mmol) were added to a 50 mL test tube followed by DMF (20 mL). The mixture was heated at 100° C. overnight in a StemBlock. After cooling to room temperature, aqueous sodium hydroxide (2 M; 4 mL) was added and the solution was stirred for 15 min. Chloroform (20 mL) was added and the mixture was filtered through Celite. The aqueous layer was then extracted with chloroform (3×) and the combined organic phases were evaporated. The residue was then triturated with ether and the precipitate was dried in vacuo overnight to yield a light brown solid. Yield: 686 mg (41%); HLPC (System A) purity=99%, m/z=241 (M+H)$^+$, $^1$H NMR (270 MHz, DMSO-d$_6$) δ ppm 7.33 (d, J=2.23 Hz, 1H) 7.98 (m, 2H) 8.38 (d, J=2.23 Hz, 1H) 8.50 (d, J=2.47 Hz, 1H) 8.75 (d, J=2.23 Hz, 1H) 8.79 (m, 2H).

Intermediate 12

3-(5-Nitro-1-benzofuran-7-yl)pyridine

The title compound was prepared according to the procedure described for Intermediate 11 using 3-tributylstannylpyridine. Yield: 145 mg (35%); HLPC (System A) purity=97%, m/z=241 (M+H)$^+$, $^1$H NMR (270 MHz, DMSO-d$_6$) δ ppm 7.32 (d, J=2.23 Hz, 1H) 7.63 (dd, J=7.79, 4.82 Hz, 1H) 8.33 (m, 1H) 8.36 (d, J=2.23 Hz, 1H) 8.44 (d, J=2.47 Hz, 1H) 8.72 (m, 2H) 9.14 (d, J=1.73 Hz, 1H).

Intermediate 13

2-(5-Nitro-1-benzofuran-7-yl)pyridine

The title compound was prepared according to the procedure described for Intermediate 11 using 2-tributylstannylpyridine. Yield: 282 mg (42%); HLPC (System A) purity=98%, m/z=241 (M+H)$^+$, $^1$H NMR (270 MHz, DMSO-d$_6$) δ ppm 7.33 (d, J=2.23 Hz, 1H) 7.53 (m, 1H) 8.06 (m, 1H) 8.41 (m, 2H) 8.72 (d, J=2.47 Hz, 1H) 8.84 (m, 1H) 8.99 (d, J=2.47 Hz, 1H).

Intermediate 14

2-(5-Nitro-1-benzofuran-7-yl)pyrazine

The title compound was prepared according to the procedure described for Intermediate 11 using 2-tributylstannylpyrazine. Yield: 238 mg (57%); HLPC (System A) purity=97%, m/z=242 (M+H)$^+$, $^1$H NMR (270 MHz, DMSO-d$_6$) δ ppm 7.35 (d, J=2.23 Hz, 1H) 8.43 (d, J=2.23 Hz, 1H) 8.78 (m, 2H) 8.92 (m, 2H) 9.58 (s, 1H).

Intermediate 15

2-(5-Nitro-1-benzofuran-7-yl)pyrimidine

The title compound was prepared according to the procedure described for Intermediate 11 using 2-tributylstannylpyrimidine. Yield: 219 mg (52%); HLPC (System A) purity=97%, m/z=242 (M+H)$^+$, $^1$H NMR (270 MHz, DMSO-d$_6$) δ ppm 7.32 (d, J=2.23 Hz, 1H) 7.61 (t, J=4.95 Hz, 1H) 8.40 (d, J=2.23 Hz, 1H) 8.81 (d, J=2.47 Hz, 1H) 9.07 (m, 3H).

Intermediate 16

4-(5-Amino-1-benzofuran-7-yl)pyridine 4-(5-Nitro-1-benzofuran-7-yl)pyridine (125 mg, 0.520 mmol; Intermediate 11) was dissolved in 1,4-dioxane (15 mL). After addition of ethanol (20 mL), Raney-nickel (slurry in ethanol; 2 mL) and hydrazine hydrate (4 mL) were added and the mixture was left stirring at room temperature overnight. The product was used directly in the subsequent reaction after filtration through Celite and evaporation of solvent.

Example 28

2-Methoxy-5-methyl-N-(7-pyridin-4-yl-1-benzofuran-5-yl)benzenesulfonamide 4-(5-Amino-1-benzofuran-7-yl)pyridine (55 mg, 0.260 mmol; Intermediate 16) and 6-methoxy-m-toluenesulfonyl chloride (69 mg, 0.312 mmol) was dissolved in dichloromethane (5 mL). Triethylamine (73 µL, 0.520 mmol) was added and the mixture was shaken for 2 h. After concentration, the residue was triturated with cold acetonitrile and the precipitate was collected and dried in vacuo. Yield: 56 mg (55%); HLPC (System A) purity=98%, m/z=395 (M+H)$^+$, $^1$H NMR (270 MHz, DMSO-d$_6$) δ ppm 2.21 (s, 3H) 3.87 (s, 3H) 7.09 (m, 2H) 7.35 (dd, J=8.54, 2.10 Hz, 1H) 7.56 (m, 2H) 8.14 (d, J=2.23 Hz, 1H) 8.25 (d, J=6.68 Hz, 2H) 8.98 (d, J=6.68 Hz, 2H) 10.13 (s, 1H).

Example 29

N-(7-Pyridin-3-yl-1-benzofuran-5-yl)benzenesulfonamide trifluoroacetate

The title compound was prepared according to the procedure described for Example 28 using 3-(S-amino-1-benzofuran-7-yl)pyridine* and purified by preparative HPLC. Yield: 63 mg (51%); HLPC (System A) purity=95%, m/z=351 (M+H)$^+$, $^1$H NMR (270 MHz, methanol-d$_4$) δ ppm 6.90 (d, J=2.23 Hz, 1H) 7.49 (m, 5H) 7.74 (m, 2H) 7.89 (d, J=2.23 Hz, 1H) 8.01 (m, 1H) 8.77 (m, 2H) 9.19 (d, J=1.73 Hz, 1H).
*Prepared according to the procedure of Intermediate 16 using 3-(5-nitro-1-benzofuran-7-yl)pyridine (Intermediate 12).

Example 30

2-Methoxy-5-methyl-N-(7-pyridin-3-yl-1-benzofuran-5-yl)benzenesulfonamide trifluoroacetate The title compound was prepared according to the procedure described for Example 28, using 3-(S-amino-1-benzofuran-7-yl)pyridine* and purified by preparative HPLC (System D). Yield: 67 mg (50%); HLPC (System A) purity=97%, m/z=395 (M+H)$^+$, $^1$H NMR (270 MHz, methanol-d$_4$) δ ppm 2.17 (s, 3H) 3.95 (s, 3H) 6.88 (d, J=2.23 Hz, 1H) 7.01 (d, J=8.41 Hz, 1H) 7.29 (m, 1H) 7.48 (d, J=2.23 Hz, 2H) 7.54 (m, 1H) 7.86 (d, J=2.23 Hz, 1H) 8.10 (m, 1H) 8.84 (m, 2H) 9.24 (d, J=1.98 Hz, 1H).
*Prepared according to the procedure of Intermediate 16 using 3-(5-nitro-1-benzofuran-7-yl)pyridine (Intermediate 12).

Example 31

N-(7-Pyrazin-2-yl-1-benzofuran-5-yl)benzenesulfonamide trifluoroacetate

The title compound was prepared according to the procedure described for Example 28 using 2-(5-amino-1-benzofuran-7-yl)pyrazine* and purified by preparative HPLC (System D). Yield: 20 mg (17%), HLPC (System A) purity=98%, m/z=352 (M+H)$^+$, $^1$H NMR (270 MHz, DMSO-d$_6$) δ ppm 7.07 (d, J=2.23 Hz, 1H) 7.53 (m, 3H) 7.76 (m, 2H) 7.91 (d, J=1.98 Hz, 1H) 8.14 (d, J=2.23 Hz, 1H) 8.67 (d, J=2.47 Hz, 1H) 8.82 (m, 1H) 9.45 (d, J=1.73 Hz, 1H) 10.39 (s, 1H).
*Prepared according to the procedure of Intermediate 16 using 2-(5-nitro-1-benzofuran-7-yl)pyrazine (Intermediate 14).

Intermediate 17

5-(5-Nitro-1-benzofuran-7-yl)pyrimidine $Pd(PPh_3)_4$ (240 mg, 209 mmol) was added to 7-iodo-5-nitro-1-benzofurane (1.00 g, 3.45 mmol) in DME (11 mL) and the resulting mixture was stirred for 10 min. The color went from dark red to mustard yellow. Pyrimidine-5-boronic acid (0.24 g, 0.21 mmol) and 1 M $Na_2CO_3$ (5 mL) were added and the reaction mixture was refluxed at 100° C. for 2.5 h. The mixture was concentrated in vacuo and the residue was dissolved in 1 M HCl (50 mL) and washed with diethyl ether (50 mL). The aqueous layer was made basic (pH 8), by addition of $K_2CO_3$, and extracted with chloroform (3×). The combined organic layers were dried with $K_2CO_3$, filtered and concentrated to afford 0.455 g (55%) of a yellow solid. HPLC 100%, $R_T$: 1.870 min (System A; 10-97% over 3 min). $^1$H NMR (270 MHz, $CDCl_3$) δ ppm 7.06 (d, J=2.47 Hz, 1H) 7.90 (d, J=2.23 Hz, 1H) 8.45 (d, J=2.23 Hz, 1H) 8.63 (d, J=2.23 Hz, 1H) 9.28-9.31 (m, 3H). LC-MS 242 $(M+H)^+$.

Intermediate 18

7-Pyrimidin-5-yl-1-benzofuran-5-amine

Raney-nickel (slurry in ethanol; 2 mL) and hydrazine (0.378 g, 7.55 mmol) were added to 5-(5-nitro-1-benzofuran-7-yl)pyrimidine (0.455 g, 1.87 mmol, Intermediate 17) in ethanol/THF (100 mL:25 mL). The mixture was stirred at room temperature for 3 h, filtered through Celite and concentrated in vacuo to afford 0.317 g (80%) of the title compound as a yellow solid. HPLC 100%, $R_T$: 0.957 min (System A; 10-97% over 3 min). $^1$H NMR (270 MHz, methanol-$d_4$) δ ppm 6.77 (d, J=2.23 Hz, 1H) 7.05 (q, J=2.23 Hz, 2H) 7.76 (d, J=2.23 Hz, 1H) 9.14 (s, 1H) 9.26 (s, 2H). LC-MS 212 $(M+H)^+$.

Example 32

N-(7-Pyrimidin-5-yl-1-benzofuran-5-yl)benzenesulfonamide hydrochloride

Benzenesulfonyl chloride (0.093 g, 0.524 mmol) and pyridine (347 µL, 430 mmol) were added to 7-pyrimidin-5-yl-1-benzofuran-5-amine (0.100 g, 0.473 mmol; Intermediate 18) in dichloromethane (2 mL). The mixture was shaken at room temperature for 1 h and the solvent was removed. The crude product was purified by preparative HPLC using acetonitrile-water gradients containing 0.1% trifluoroacetic acid and then converted into the hydrochloride salt by treatment with 2 M HCL in diethyl ether. This gave 0.071 g (43%) of the title compound as a yellow solid. HPLC 97%, $R_T$: 1.863 min (System A; 10-97% over 3 min). $^1$H NMR (500 MHz, DMSO-$d_6$) δ ppm 6.98 (d, J=2.20 Hz, 1H) 7.34 (d, J=2.20 Hz, 1H) 7.50-7.54 (m, 3H) 7.58-7.60 (m, 1H) 7.80-7.82 (m, 1H) 7.97 (d, J=2.20 Hz, 1H) 9.10 (s, 2H) 9.20 (s, 1H) 9.87 (s, 1H). GC-MS 351 $(M^+)$.

Example 33

N-[7-(1-Aza-bicyclo[2.2.2]oct-2-en-3-yl)-benzofuran-5-yl]-2-methoxy-5-methylbenzenesulfonamide hydrochloride 3-Tributylstannanyl-1-aza-bicyclo[2.2.2]oct-2-ene (2.14 g, 5.36 mmol; prepared according to *Bioorg. Med. Chem. Lett.* 1994, 4, 2837-2840) was added to a mixture of 7-iodo-5-nitro-benzofuran (0.52 g, 1.79 mmol), $Pd(PPh_3)_4$ (0.206 g, 0.17 mmol) in DMF (10 mL). The mixture was heated at 160° C. for 10 min in a sealed reaction vessel using controlled microwave energy. The reaction mixture was diluted with $CHCl_3$ and then filtered through a pad of Celite and concentrated under reduced pressure. The residue was purified by repetitive chromatography on silica using gradient elution, ($CHCl_3$→$CHCl_3$+10% MeOH+0.4% $NH_3$) followed by $CHCl_3$+10% MeOH+0.4% $NH_3$ to give 399.5 mg of 3-(5-nitro-benzofuran-7-yl)-1-aza-bicyclo[2.2.2]oct-2-ene. This intermediate was dissolved in a solvent system of EtOH:THF (4:1; 20 mL) and Raney-Ni (~1.0 mL suspension in EtOH) was added followed by hydrazine monohydrate (6 equiv). The mixtures are stirred vigorously for 3 h and then filtered through Celite pre-treated with water. The filtrate was concentrated, followed by the addition of toluene and re-evaporation to yield 340 mg of the crude intermediate (7-(1-aza-bicyclo[2.2.2]oct-2-en-3-yl)-benzofuran-5-ylamine). Most of this material (325 mg; 1.35 mmol) was dissolved in DCM (5 mL). Pyridine (1.05 mL) was added followed by 2-methoxy-5-methyl-benzenesulfonyl chloride (267 mg, 1.20 mmol). The resultant mixture was stirred at room temperature for 16 h and then concentrated under reduced pressure. The residue was purified by column chromatography on silica using gradient elution ($CHCl_3$→$CHCl_3$+10% MeOH+0.4% $NH_3$) to give 230 mg of the free base of the title compound. The free base was dissolved in MeOH and 1 M HCl in ether was added to the solution. More ether was added and the precipitate was collected by filtration to give 182 mg of the HCl-salt. The product was dissolved in $CH_3CN$:MeOH (2:1) and then purified by preparative reversed phase HPLC. The pure HPLC fractions was pooled and then concentrated to give the TFA-salt of the final product. The TFA-salt was converted to the HCl-salt: yield 100 mg of N-[7-(1-aza-bicyclo[2.2.2]oct-2-en-3-yl)-benzofuran-5-yl]-2-methoxy-5-methyl-benzenesulfonamide hydrochloride; $^1$H NMR (270 MHz, DMSO-$d_6$) δ ppm 1.57-1.76 (m, 2H), 2.00-2.20 (m, 3H), 2.21 (s, 3H), 3.00-3.17 (m, 2H), 3.27-3.66 (m, obscured in part by solvent signal, 3H), 3.86 (s, 3H), 6.99-7.09 (m, 2H), 7.20-7.42 (m, 4H), 7.53-7.60 (m, 1H), 8.05-8.10 (m, 1H), 9.98 (m, s, 1H); GC-MS (EI+) for $C_{23}H_{24}N_2O_4S$ m/z 425 $(M)^+$.

Intermediate 19 tert-Butyl 4-(5-{[(2-chlorophenyl)sulfonyl]amino}-1-benzofuran-7-yl)piperazine-1-carboxylate tert-Butyl 4-(5-amino-1-benzofuran-7-yl)piperazine-1-carboxylate (0.59 g, 1.87 mmol; Intermediate 10) was dissolved in DCM. 2-Chlorobenzenesulfonyl chloride (0.59 g, 2.8 mmol) was added followed by pyridine (0.45 mL, 5.6 mmol). The reaction mixture was stirred at room temperature overnight. Filtration through a silica plug afforded 0.66 g (72%) of the title product. HPLC purity 92%, $R_T$=2.56 min (System A; 10-97% MeCN over 3 min). $^1$H NMR (400 MHz, CDCl$_3$) δ ppm 1.48 (s, 9H) 3.07-3.21 (m, 4H) 3.51-3.65 (m, 4H) 6.51 (d, J=2.0 Hz, 1H) 6.62 (d, J=2.3 Hz, 1H) 6.93 (d, J=2.0 Hz, 1H) 7.00 (s, 1H) 7.18-7.31 (m, 2H) 7.36-7.47 (m, 1H) 7.47-7.57 (m, 2H) 7.90 (dd, J=7.9, 1.6 Hz, 1H). MS (ESI+) m/z 492.2 (M+H)$^+$.

Intermediate 20

2-Chloro-N-(7-piperazin-1-yl-1-benzofuran-5-yl)benzenesulfonamide tert-Butyl 4-(5-{[(2-chlorophenyl)sulfonyl]amino}-1-benzofuran-7-yl)piperazine-1-carboxylate (0.66 g, 1.34 mmol; Intermediate 19) was dissolved in DCM (5 mL) and TFA was added (30% solution of TFA in DCM; 5 mL) and the mixture was stirred for 30 min. The solvents were evaporated. The residue was dissolved in water, pH adjusted to pH 8 and extracted with EtOAc. The organic layer was dried and evaporated to give 0.41 g (80%) of the title product that was used in the next step without further purification. HPLC purity 93%, $R_T$=1.61 min (System A; 10-97% MeCN over 3 min).

Intermediate 21

1-(5-Nitro-1-benzofuran-7-yl)piperazine

Removal of the N-t-BOC group in tert-butyl 4-(5-nitro-1-benzofuran-7-yl)piperazine-1-carboxylate* was performed according to the procedure of Intermediate 20 giving 2.3 g (80%) of the title compound as a yellow solid. HPLC purity 94%, $R_T$=1.37 min (System A; 10-97% MeCN over 3 min).
*Previously described in WO 2002100822.

Intermediate 22

N,N-Diethyl-2-[4-(5-nitro-1-benzofuran-7-yl)piperazin-1-yl]acetamide

A mixture of 1-(5-nitro-1-benzofuran-7-yl)piperazine (0.4 g, 1.6 mmol; Intermediate 21) and 2-chloro-N,N-diethylacetamide (0.48 g, 3.2 mmol) in the presence of K$_2$CO$_3$ (0.45 g, 3.2 mmol) in DMF was heated at 225° C. for 5 min using controlled microwave energy. The solvent was evaporated and the residue triturated with MeCN to give 0.31 g (54%) of the title compound as a yellow solid. HPLC purity 80%, $R_T$=1.63 min (System A; 10-97% MeCN over 3 min). $^1$H NMR (400 MHz, DMSO-d$_6$) δ ppm 1.02 (t, J=7.0 Hz, 3H) 1.14 (t, J=7.0 Hz, 3H) 2.58-2.77 (m, 4H) 3.14-3.50 (m, 10H) 7.14 (d, J=2.3 Hz, 1H) 7.53 (d, J=2.3 Hz, 1H) 8.18 (dd, J=12.5, 2.3 Hz, 2H).

Intermediate 23

2-[4-(5-Amino-1-benzofuran-7-yl)piperazin-1-yl]-N,N-diethylacetamide

Reduction of the nitro group in N,N-diethyl-2-[4-(5-nitro-1-benzofuran-7-yl)piperazin-1-yl]acetamide (0.3 g, 0.83 mmol; Intermediate 22) was performed according to the procedure of Intermediate 10. Yield: 0.19 g (70%). This material was used in the next step without further purification. MS (ESI+) m/z 331.2 (M+H)$^+$.

Example 34

2-[4-(5-{[(2-Chlorophenyl)sulfonyl]amino}-1-benzofuran-7-yl)piperazin-1-yl]-N,N-diethylacetamide hydrochloride 2-[4-(5-Amino-1-benzofuran-7-yl)piperazin-1-yl]-N,N-diethylacetamide (0.095 g, 0.29 mmol; Intermediate 23) was reacted with 2-chlorobenzenesulfonyl chloride according to the procedure of Intermediate 19. Yield: 0.06 g (41%) after purification by preparative HPLC (System E; 20-50% MeCN). $^1$H NMR (400 MHz, DMSO-d$_6$) δ ppm 1.08 (t, J=6.9 Hz, 3H) 1.15 (t, J=6.9 Hz, 3H) 3.09-3.43 (m, 7H) 3.55-3.65 (m, 2H) 3.67-3.76 (m, 2H) 4.39 (s, 2H) 6.62 (d, J=1.0 Hz, 1H) 6.86 (d, J=1.3 Hz, 1H) 6.93 (d, J=1.5 Hz, 1H) 7.47 (t, J=7.0 Hz, 1H) 7.60 (q, J=7.7 Hz, 2H) 7.91 (d, J=1.3 Hz, 1H) 8.01 (d, J=7.8 Hz, 1H) 10.08 (s, 1H) 10.46 (s, 1H). HPLC purity 92%, $R_T$=1.85 min (System A; 10-97% MeCN over 3 min). MS (ESI+) m/z 505.2 (M+H)$^+$.

Example 35

N,N-Diethyl-2-[4-(5-{[(2-methoxy-5-methylphenyl)sulfonyl]amino}-1-benzofuran-7-yl)piperazin-1-yl]acetamide hydrochloride 2-[4-(5-Amino-1-benzofuran-7-yl)piperazin-1-yl]-N,N-diethylacetamide (0.095 g, 0.29 mmol; Intermediate 23) was reacted with 2-methoxy-5-methylphenylsulfonyl chloride according to the procedure of Intermediate 19. Yield: 0.05 g (33%) after preparative HPLC (System F; 10-50% MeCN). HPLC purity 93%, $R_T$=1.87 min (System A; 10-97% MeCN over 3 min). $^1$H NMR (400 MHz, DMSO-d$_6$) δ ppm 1.08 (t, J=7.0 Hz, 3H) 1.16 (t, J=7.0 Hz, 3H) 2.20 (s, 3H) 3.08-3.45 (m, 7H) 3.58-3.73 (m, 4H) 3.87 (s, 3H) 4.40 (s, 2H) 6.61 (d, J=1.8 Hz, 1H) 6.85 (d, J=2.0 Hz, 1H) 6.93 (d, J=1.8 Hz, 1H) 7.04 (d, J=8.5 Hz, 1H) 7.32 (dd, J=8.8, 2.0 Hz, 1H) 7.52 (d, J=1.8 Hz, 1H) 7.89 (d, J=2.3 Hz, 1H) 9.75 (s, 1H) 10.07 (s, 1H) MS (ESI+) m/z 515.4 (M+H)$^+$.

Intermediate 24

3-(7-Bromo-1-benzofuran-2-yl)quinuclidin-3-ol

Step 1. 3-[(Trimethylsilyl)ethynyl]quinuclidin-3-ol
A mixture of 3-quinuclidinone hydrochloride (24.12 g, 0.149 mol) and Na$_2$CO$_3$ (27 g, 0.25 mol), in water (500 mL) was extracted with dichloromethane (500 mL). The organic phase was evaporated to dryness. The residue was dissolved in THF (200 g) and slowly added to a solution of TMS-Li-acetylide (1.1 equiv) in THF (200 g) at 0-5° C. When the addition was completed, a solution of NaHCO$_3$ in water (500 mL) was added. The organic phase was washed with additional water (500 mL) and evaporated to dryness to yield 20.89 g (63%) of the title compound as a white solid. $^1$H NMR (270 MHz, CDCl$_3$) δ ppm 0.15 (s, 9H) 1.27-1.46 (m, 1H) 1.47-1.73 (m, 1H) 1.80-2.14 (m, 3H) 2.61-3.02 (m, 5H) 3.17 (dd, J=13.86, 1.73 Hz, 1H) 4.14 (br s, 1H).

Step 2. 3-(7-Bromo-1-benzofuran-2-yl)quinuclidin-3-ol
2,6-Dibromonitrophenol (3.0 g, 0.0119 mol), 3-[(trimethylsilyl)ethynyl]quinuclidin-3-ol (2.66 g, 0.0119 mol; obtained in Step 1), Cu$_2$O (1.70 g, 0.0119 mol) and pyridine (200 mL) were added to a round bottom flask. The resulting mixture was heated at reflux overnight, filtered through Celite, and the solvent was evaporated. The residue was purified by chromatography on silica gel using ethyl acetate (250 mL) and methanol (500 mL) as eluents. The methanol fraction was evaporated to yield 1.12 g (29%) of the title compound. HPLC purity=90%, m/z=322 (M+H)$^+$.

Intermediate 25

3-(7-Bromo-1-benzofuran-2-yl)-1-azabicyclo[2.2.2]oct-2-ene 3-(7-Bromo-1-benzofuran-2-yl)quinuclidin-3-ol (600 mg, 1.86 mmol; Intermediate 24, Step 2) was dissolved in methanol (2 mL) and formic acid (40 mL) was added to the flask. The resulting mixture was heated at reflux overnight. Concentration in vacuo furnished 562 mg (99%) of the title product. HPLC purity=90%, m/z=305 (M+H)$^+$.

Intermediate 26

[2-(1-Azabicyclo[2.2.2]oct-2-en-3-yl)-1-benzofuran-7-yl]amine 3-(7-Bromo-1-benzofuran-2-yl)-1-azabicyclo[2.2.2]oct-2-ene (300 mg, 0.986 mmol; Intermediate 25) was dissolved in methanol (2 mL). A solution of concentrated aqueous ammonia (25%; 10 mL) and CuCl$_2$ (15 mg) were added and the resulting mixture was heated at 120° C. for 48 h. The mixture was run through a silica plug using methanol/ammonia solution (9:1) as eluent. Concentration in vacuo furnished 236 mg of the crude title product. This material was used directly in subsequent experiments.

Example 36

N-[2-(1-Azabicyclo[2.2.2]oct-2-en-3-yl)-1-benzofuran-7-yl]benzenesulfonamide hydrochloride

[2-(1-Azabicyclo[2.2.2]oct-2-en-3-yl)-1-benzofuran-7-yl]amine (118 mg, 0.493 mmol; Intermediate 26), benzenesulfonyl chloride (104 mg, 0.592 mmol) and triethylamine (137 μl, 0.986 mmol) were dissolved in ethanol (5 mL). The mixture was shaken for 2 hours. Purification was carried out by preparative HPLC (20-90% acetonitrile/TFA-water gradient). Evaporated to yield 47 mg TFA salt, which was converted to the HCl salt by stirring it in HCl/ether. Yield: 37 mg (18%), HPLC purity=99%, m/z=381 (M+H)$^+$, $^1$H NMR (270 MHz, methanol-d$_4$) δ ppm 1.74-1.91 (m, 2H) 2.10-2.26 (m, 2H) 3.15-3.29 (m, 2H) 3.49-3.57 (m, 1H) 3.64-3.78 (m, 2H) 6.97-7.01 (m, 1H) 7.13-7.28 (m, 3H) 7.38-7.57 (m, 4H) 7.70-7.76 (m, 2H).

Example 37

N-[2-(1-Azabicyclo[2.2.2]oct-2-en-3-yl)-1-benzofuran-7-yl]-2-methoxy-5-methylbenzenesulfonamide hydrochloride The title compound was prepared according to the same procedure as Example 36. Yield: 56 mg (25%), HPLC purity=99%, m/z=425 (M+H)$^+$, $^1$H NMR (270 MHz, CDCl$_3$) δ ppm 1.77-1.96 (m, 2H) 2.06-2.20 (m, 2H) 2.22 (s, 3H) 3.14-3.32 (m, 2H) 3.39-3.48 (m, 1H) 3.55-3.71 (m, 2H) 3.97 (s, 3H) 6.89-6.95 (m, 2H) 7.06-7.29 (m, 5H) 7.41 (dd, J=7.92, 0.99 Hz, 1H).

Example 38

N-[7-(1-Azabicyclo[2.2.2.]oct-3-yloxy)-1-benzofuran-5-yl]benzenesulfonamide hydrochloride Step 1. 3-[(5-nitro-1-benzofuran-7-yl)oxy]quinuclidine 7-Iodo-5-nitro-1-benzofuran (1.00 g, 3.46 mmol), quinuclidin-3-ol (1.10 g, 8.65 mmol), 1,10-phenanthroline (0.25 g, 1.38 mmol), CuI (0.13 g, 0.69 mmol) and toluene (20 mL) were mixed together and heated at 140° C. overnight. The solvent was removed in vacuo and the crude product was purified by flash chromatography (eluent: hexane and chloroform:MeOH:triethylamine; 9:0.9:0.1) to give 3-[(5-nitro-1-benzofuran-7-yl)oxy]quinuclidine (3.46 mmol).

Step 2. 7-(1-Azabicyclo[2.2.2]oct-3-yloxy)-1-benzofuran-5-amine

3-[(5-Nitro-1-benzofuran-7-yl)oxy]quinuclidine (1.38 g, 4.79 mmol; obtained in Step 1) was dissolved in ethanol:THF (100 mL: 25 mL) and Raney-nickel (slurry in ethanol; 6 mL) and hydrazine (891 μL, 0.18 mmol) were added. The mixture was stirred at room temperature for 3 h and then filtered through Celite and the solvent was removed in vacuo. The crude product was purified by flash chromatography [eluent: DCM:methanol (6:1) and chloroform:MeOH:triethylamine (9:1:0.1)] to give 7-(1-azabicyclo[2.2.2]oct-3-yloxy)-1-benzofuran-5-amine (500 mg; 40%).

Step 3. N-[7-(1-Azabicyclo[2.2.2.]oct-3-yloxy)-1-benzofuran-5-yl]benzenesulfonamide hydrochloride Benzenesulfonyl chloride (30 μL, 0.232 mmol) and pyridine (141 μL, 1.74 mmol) were added to 7-(1-azabicyclo[2.2.2]oct-3-yloxy)-1-benzofuran-5-amine (0.50 g, 0.194 mmol; obtained in Step 2) in DCM (2 mL). The mixture was shaken at room temperature for 2 h and then the solvent was removed in vacuo. Purification of the product was done by preparative HPLC using acetonitrile-water gradients containing 0.1% trifluoroacetic acid. The obtained TFA salt was converted into the hydrochloride salt by treatment with 2 M HCl in ether. Yield: 11.0 mg (11.8%). HPLC 100%, R$_T$: 1.680 (System B; 10-97% MeCN over 3 min). $^1$H NMR (270 MHz, methanol-d$_4$) δ ppm 0.91 (t, J=7.05 Hz, 1H) 1.31 (m, 1H) 1.89-2.36 (m, 5H) 3.32-3.46 (m, 4H) 3.77-3.87 (m, 1H) 6.68-6.74 (m, 2H) 6.94 (s, 1H) 7.43-7.56 (m, 3H) 7.68-7.73 (m, 3H). LC-MS 399 (M+H)$^+$.

Example 39

N-[7-(1-Azabicyclo[2.2.2.]oct-3-yloxy)-1-benzofuran-5-yl]-2-chlorobenzenesulfonamide hydrochloride The title compound was prepared according to the procedure of Example 38, Step 3, starting from 7-(1-azabicyclo[2.2.2]oct-3-yloxy)-1-benzofuran-5-amine (obtained in Example 38, Step 2) and 2-chlorobenzenesulfonyl chloride (0.49 g, 0.232 mmol). Yield: 55 mg (54%). HPLC 100%, R$_T$: 1.760 (System B; 10-97% MeCN over 3 min). $^1$H NMR (270 MHz, methanol-d$_4$) δ ppm 1.80-2.35 (m, 5H) 2.18 (d, J=7.42 Hz, 1H) 2.25 (s, 1H) 3.29-3.30 (m, 2H) 3.41 (t, J=8.04 Hz, 2H) 3.83 (dd, J=13.61, 7.92 Hz, 1H) 3.97 (s, 1H) 6.73-6.76

(m, 2H) 6.99-7.05 (m, 2H) 7.33-7.36 (m, 1H) 7.50-7.54 (m, 1H) 7.70 (t, J=2.60 Hz, 1H) 7.96 (d, J=7.67 Hz, 1H). LC-MS 433 (M+H)+.

Example 40

N-[7-(1-Azabicyclo[2.2.2.]oct-3-yloxy)-1-benzofuran-5-yl]-2-methoxy-5-methylbenzenesulfonamide hydrochloride The title compound was prepared according to the procedure of Example 38, Step 3, starting from 7-(1-azabicyclo[2.2.2]oct-3-yloxy)-1-benzofuran-5-amine (obtained in Example 38, Step 2) and 2-methoxy-5-methylbenzenesulfonyl chloride (0.51 g, 0.232 mmol). Yield: 80 mg (77%). HPLC 100%, $R_T$: 1.794 (System B; 10-97% MeCN over 3 min). $^1$H NMR (270 MHz, methanol-$d_4$) δ ppm 0.92 (d, J=7.92 Hz, 1H) 1.28-1.37 (m, 1H) 1.99 (d, J=11.13 Hz, 3H) 2.21 (s, 3H) 2.36 (s, 1H) 3.46-3.48 (m, 4H) 3.85 (d, J=7.18 Hz, 1H) 3.96 (s, 3H) 5.02-5.04 (m, 1H) 6.73-6.77 (m, 2H) 6.96 (s, 1H) 7.03 (d, J=8.41 Hz, 1H) 7.32 (d, J=7.42 Hz, 1H) 7.49 (s, 1H) 7.70 (d, J=1.48 Hz, 1H). LC-MS 443 (M+H)+.

Intermediate 27

(2-Morpholin-4-ylethyl)(5-nitro-1-benzofuran-7-yl)amine

7-Iodo-5-nitrobenzofuran (1.00 g, 3.46 mmol), 4-(2-aminoethyl)morpholine (0.54 g, 4.15 mmol), NaOt-Bu (0.47 g, 0.00484 mol), Xantphos (0.20 g, 0.346 mmol) and $Pd_2$ $dba_3$ (80 mg, 0.0865 mol) were heated in xylene (20 mL) at 120° C. for 1.5 hours. The reaction mixture was filtered through Celite and the solvent evaporated. The residue was run through a silica plug using dichloromethane (DCM) and then a 90:9:1 mixture of DCM/MeOH/$NH_3$ (aqueous 25%) as eluents. The product-containing fractions were concentrated to yield 0.978 g (97%) of the title compound as a dark yellow oil. HPLC purity=97%, m/z=292 (M+H)+, $^1$H NMR (270 MHz, $CDCl_3$) δ ppm 2.44-2.61 (m, 4H) 2.75 (t, J=5.81 Hz, 2H) 3.31-3.43 (m, 2H) 3.69-3.82 (m, 4H) 6.85 (d, J=1.98 Hz, 1H) 7.36 (d, J=1.98 Hz, 1H) 7.70 (d, J=1.98 Hz, 1H) 7.90 (d, J=2.23 Hz, 1H).

Intermediate 28

$N^7$-(2-Morpholin-4-ylethyl)-1-benzofuran-5,7-diamine (2-Morpholin-4-ylethyl)(5-nitro-1-benzofuran-7-yl)amine (450 mg, 1.545 mmol; Intermediate 27) was dissolved in THF (5 mL). After addition of ethanol (100 mL), Raney-nickel (cat.) and hydrazine hydrate (2 mL), the mixture was left stirring at room temperature for 2 h. The product was used directly in the subsequent reaction after filtration through Celite and evaporation of solvent.

Intermediate 29

4-{2-[(5-Nitro-1-benzofuran-7-yl)oxy]ethyl}morpholine

To a test tube was added 7-iodo-5-nitrobenzofuran (1.0 g, 0.00346 mol), 4-(2-hydroxyethyl)morpholine (0.91 g, 0.00692 mol), cesium carbonate (2.25 g, 0.00692 mol), 1,10-phenanthroline (0.25 g, 0.00138 mol) and CuI (130 mg, 0.692 mmol). Toluene (15 mL) was added and the solution was heated in a StemBlock for 72 h. After filtration through Celite, the crude material was purified by flash chromatography (EtOAc/DCM; 1:1). Yield: 32%, HPLC purity=90%, m/z=293 (M+H)+.

Intermediate 30

[7-(2-Morpholin-4-ylethoxy)-1-benzofuran-5-yl]amine

The title compound was prepared according to the same procedure as Intermediate 28 starting from Intermediate 29. The product was used directly in the subsequent reaction (Example 45).

Example 41

N-{7-[(2-Morpholin-4-ylethyl)amino]-1-benzofuran-5-yl}benzenesulfonamide hydrochloride To a solution of $N^7$-(2-Morpholin-4-ylethyl)-1-benzofuran-5,7-diamine (58 mg, 0.221 mmol; Intermediate 28) in dichloromethane (2 mL) were added triethylamine (62 μL, 0.442 mmol) and benzenesulfonyl chloride (39 mg, 0.221 mmol). The mixture was stirred at room temperature for 1 h and evaporated. The residue was purified by preparative HPLC (System D), evaporated pure fractions, and converted the resulting TFA salt to a HCl salt. Yield: 32%, HPLC purity=100%, m/z=402 (M+H)+, $^1$H NMR (270 MHz, methanol-$d_4$) δ ppm 3.43 (t, J=6.06 Hz, 2H) 3.40-3.61 (m, J=6.06, 6.06 Hz, 4H) 3.68 (t, J=6.06 Hz, 2H) 3.75-4.14 (m, 4H) 6.48-6.55 (m, 2H) 6.64 (d, J=2.23 Hz, 1H) 7.41-7.59 (m, 3H) 7.65-7.74 (m, 3H).

Example 42

2-Methoxy-5-methyl-N-{7-[(2-morpholin-4-ylethyl)amino]-1-benzofuran-5-yl}benzenesulfonamide hydrochloride The title compound was prepared according to the procedure of Example 41. Yield: 37%, HPLC purity=100%, m/z=446 (M+H)+, $^1$H NMR (270 MHz, methanol-$d_4$) δ ppm 2.18-2.24 (s, 3H) 3.35-3.60 (m, 4H) 3.43 (t, J=5.94 Hz, 2H) 3.67 (t, J=5.94 Hz, 2H) 3.74-4.07 (m, 4H) 3.94-3.99 (m, 3H) 6.51 (d, J=1.98 Hz, 1H) 6.63 (dd, J=4.08, 2.10 Hz, 2H) 7.03 (d, J=8.41 Hz, 1H) 7.32 (dd, J=8.78, 2.60 Hz, 1H) 7.49 (d, J=2.23 Hz, 1H) 7.64 (d, J=2.23 Hz, 1H).

Example 43

N-{7-[(2-Morpholin-4-ylethyl)amino]-1-benzofuran-5-yl}-2-(trifluoromethyl)benzenesulfonamide hydrochloride The title compound was prepared according to the procedure of Example 41. Yield: 38%, HPLC purity=100%, m/z=470 (M+H)+, $^1$H NMR (270 MHz, methanol-$d_4$) δ ppm 3.15-3.63 (m, 4H) 3.43 (t, J=5.94 Hz, 2H) 3.67 (t, J=6.06 Hz, 2H) 3.72-4.14 (m, 4H) 6.49 (d, J=1.73 Hz, 1H) 6.64 (dd, J=7.42, 1.98 Hz, 2H) 7.60-7.75 (m, 3H) 7.88-7.94 (m, 1H) 8.00-8.04 (m, 1H).

Example 44

2,6-Dichloro-N-{7-[(2-morpholin-4-ylethyl)amino]-1-benzofuran-5-yl}benzenesulfonamide hydrochloride The title compound was prepared according to the procedure of Example 41. Yield: 19%, HPLC purity=100%, m/z=470 (M+H)$^+$, $^1$H NMR (270 MHz, methanol-d$_4$) δ ppm 3.22-3.60 (m, 4H) 3.45 (t, J=5.94 Hz, 2H) 3.69 (t, J=5.94 Hz, 2H) 3.72-4.13 (m, 4H) 6.58 (d, J=1.98 Hz, 1H) 6.67 (dd, J=9.65, 1.98 Hz, 2H) 7.33-7.41 (m, 1H) 7.45-7.52 (m, 2H) 7.66 (d, J=1.98 Hz, 1H).

Example 45

2-Methoxy-5-methyl-N-[7-(2-morpholin-4-ylethoxy)-1-benzofuran-5-yl]benzenesulfonamide hydrochloride The title compound was prepared according to the procedure of Example 41 starting from [7-(2-morpholin-4-ylethoxy)-1-benzofuran-5-yl]amine (Intermediate 30). Yield: 32%, HPLC purity=99%, m/z=447 (M+H)$^+$, $^1$H NMR (270 MHz, methanol-d$_4$) δ ppm 2.20 (s, 3H) 3.26-3.74 (m, 4H) 3.66-3.72 (m, 2H) 3.75-4.15 (m, 4H) 3.96 (s, 3H) 4.49-4.57 (m, 2H) 6.73 (d, J=2.23 Hz, 1H) 6.85 (d, J=1.98 Hz, 1H) 6.96 (d, J=1.98 Hz, 1H) 6.99-7.04 (m, 1H) 7.27-7.34 (m, 1H) 7.51 (d, J=2.23 Hz, 1H) 7.70 (d, J=2.23 Hz, 1H).

Example 46

3-Methyl-N-[7-(2-morpholin-4-ylethoxy)-1-benzofuran-5-yl]benzenesulfonamide hydrochloride The title compound was prepared according to the procedure of Example 41 starting from [7-(2-morpholin-4-ylethoxy)-1-benzofuran-5-yl]amine (Intermediate 30). Yield: 28%, HPLC purity=98%, m/z=417 (M+H)$^+$, $^1$H NMR (270 MHz, methanol-d$_4$) δ ppm 2.28-2.36 (m, 3H) 3.24-3.69 (m, 4H) 3.67-3.73 (m, 2H) 3.76-4.17 (m, 4H) 4.51-4.59 (m, 2H) 6.74 (d, J=2.23 Hz, 1H) 6.82 (d, J=1.98 Hz, 1H) 6.89 (d, J=1.98 Hz, 1H) 7.27-7.40 (m, 2H) 7.46-7.57 (m, 2H) 7.73 (d, J=2.23 Hz, 1H).

Example 47

3-Chloro-4-methyl-N-[7-(2-morpholin-4-ylethoxy)-1-benzofuran-5-yl]benzenesulfonamide hydrochloride The title compound was prepared according to the procedure of Example 41 starting from [7-(2-morpholin-4-ylethoxy)-1-benzofuran-5-yl]amine (Intermediate 30). Yield: 11%, HPLC purity=99%, m/z=451 (M+H)$^+$, $^1$H NMR (270 MHz, methanol-d$_4$) δ ppm 2.36-2.39 (m, 3H) 3.31-3.71 (m, 4H) 3.68-3.74 (m, 2H) 3.75-4.22 (m, 4H) 4.54-4.61 (m, 2H) 6.77 (d, J=1.98 Hz, 1H) 6.87 (q, J=1.98 Hz, 2H) 7.35-7.40 (m, 1H) 7.48-7.54 (m, 1H) 7.66 (d, J=1.73 Hz, 1H) 7.75 (d, J=1.98 Hz, 1H).

Intermediate 31

[2-(Dimethylamino)ethyl](5-nitro-1-benzofuran-7-yl)amine

Xylene (75 mL) was added to 7-iodo-5-nitro-1-benzofuran (1.00 g, 3.46 mmol), N,N-dimethylethane-1,2-diamine (0.37 g, 4.15 mmol), Pd$_2$(dba)$_3$ (0.08 g, 0.87 mmol), Xantphos (0.20 g, 0.35 mmol) and Cs$_2$CO$_3$ (1.59 g, 4.84 mmol). The mixture was stirred at 120° C. overnight, filtered through Celite and the solvent was removed in vacuo. The crude product was purified by flash chromatography [eluent: DCM:MeOH (6:1) and DCM:MeOH:Et$_3$N (9:1:0.1)] to afford 0.378 g (44%) of the title compound. HPLC 90%, R$_T$: 1.430 (System A; 10-97% MeCN over 3 min). $^1$H NMR (270 MHz, methanol-d$_4$) δ ppm 2.44 (d, J=3.22 Hz, 6H) 2.81 (t, J=6.56 Hz, 2H) 3.52 (t, J=6.56 Hz, 2H) 6.97 (d, J=2.23 Hz, 1H) 7.40 (d, J=2.23 Hz, 1H) 7.89 (t, J=1.98 Hz, 2H). LC-MS 250 (M+H)$^+$.

Example 48

N-(7-{[2(Dimethylamino)ethyl]amino}-1-benzofuran-5-yl)-2-methoxy-5-benzenesulfonamide Step 1. N$^7$-[2-(Dimethylamino)ethyl]-1-benzofuran-5,7-diamine Raney-nickel (slurry in ethanol; 2 mL) and hydrazine (295 µL, 6.08 mmol) were added to [2-(dimethylamino)ethyl](5-nitro-1-benzofuran-7-yl)amine (0.378 g, 1.52 mmol; Intermediate 31) in a mixture of ethanol (100 mL) and THF (25 mL). The reaction mixture was stirred at room temperature for 2 h. Additional Raney-nickel (slurry in ethanol; 2 mL) and hydrazine (295 µL, 6.08 mmol) were added and stirring was continued overnight. The mixture was filtered through Celite and the solvent was removed. The crude product was used in the next step without further purification.

Step 2. N-(7-{[2(Dimethylamino)ethyl]amino}-1-benzofuran-5-yl)-2-methoxy-5-benzenesulfonamide 2-methoxy-5-methylbenzenesulfonyl chloride (0.145 g, 0.657 mmol) and pyridine (398 µL, 4.93 mmol) were added to N$^7$-[2-(dimethylamino)ethyl]-1-benzofuran-5,7-diamine (0.120 g, 0.547 mmol; from Step 1) in DCM (1 mL). The mixture was shaken at room temperature for 1 h, solvent was removed in vacuo and the product was purified by preparative HPLC using acetonitrile-water gradients containing 0.1% trifluoroacetic acid. The obtained TFA salt was converted into the hydrochloride salt by treatment with 2 M HCl in ether to afford 13.3 mg (6%) of the title product. HPLC 99%, R$_T$: 1.692 (System A; 10-97% MeCN over 3 min). $^1$H NMR (270 MHz, methanol-d$_4$) δ ppm 2.21 (s, 3H) 2.94 (s, 6H) 3.40 (t, J=5.69 Hz, 2H) 3.60-3.64 (m, 2H) 3.97 (s, 3H) 6.52 (s, 1H) 6.64 (t, J=2.10 Hz, 1H) 7.03 (d, J=8.41 Hz, 1H) 7.32 (d, J=6.19 Hz, 1H) 7.50 (d, J=1.98 Hz, 1H) 7.65 (d, J=2.23 Hz, 2H). LC-MS 404 (M+H)$^+$.

Example 49

2-Chloro-N-(7-{[2-(dimethylamino)}-1-benzofuran-5-yl)benzenesulfonamide hydrochloride 2-Chlorobenzenesulfonyl chloride (0.139 g, 0.657 mmol) and pyridine (398 µL, 4.93 mmol) were added to N$^7$-[2-(dimethylamino)ethyl]-1-benzofuran-5,7-diamine (0.120 g, 0.547 mmol; Example 48, Step 1) in DCM (1 mL). The mixture was shaken at room temperature for 1 h, solvent removed in vacuo, and the product was purified by preparative HPLC using acetonitrile-water gradients containing 0.1% trifluoroacetic acid. The obtained TFA salt was converted into the hydrochloride salt by treatment with 2 M HCl in ether to afford 22.8 mg (10%) of the title product. HPLC 99%, R$_T$: 1.651 (System A; 10-97% MeCN over 3 min). $^1$H NMR (270 MHz, methanol-d$_4$) δ ppm 2.94 (s, 6H) 3.40 (s, 2H) 3.65 (d, J=1.48 Hz, 2H) 6.65 (d, J=1.73 Hz, 1H) 7.36 (t, J=7.18 Hz, 2H) 7.50-7.56 (m, 3H) 7.66 (d, J=1.73 Hz, 1H) 7.97 (d, J=7.67 Hz, 1H). LC-MS 394 (M+H)$^+$.

Intermediate 32

N-(5-Nitro-1-benzofuran-7-yl)pyridin-4-yl-amine

A mixture of 7-iodo-5-nitro-1-benzofuran (1.00 g, 3.46 mmol), 4-aminopyridine (0.39 g, 4.15 mmol), Xantphos (0.20 g, 0.36 mmol), $Pd_2(dba)_3$ (0.08 g, 0.09 mmol), NaOtBu (0.47 g, 4.84 mmol) in xylene (200 mL) was heated at 120° C. overnight. The reaction mixture was filtered through Celite and a yellow precipitate was formed which was collected by filtration to yield 0.52 g (60%) of the title product. HPLC 96%, $R_T$: 1.344 (System A; 10-97% MeCN over 3 min). $^1$H NMR (270 MHz, methanol-$d_4$) δ ppm 6.91-7.12 (m, 4H) 8.00 (d, J=2.23 Hz, 1H) 8.15-8.24 (m, 2H) 8.37 (d, J=2.23 Hz, 1H). LC-MS 256 (M+H)$^+$.

Intermediate 33

5-Amino-1-benzofuran-7-yl)pyridin-4-yl-amine

Raney-nickel (slurry in ethanol; 2 mL) and hydrazine (404 μL, 8.33 mmol) were added to N-(5-nitro-1-benzofuran-7-yl) pyridin-4-yl-amine (0.52 g, 2.08 mmol; Intermediate 32) in ethanol (40 mL) and THF (10 mL). The mixture was stirred at room temperature for 3 h, filtered through Celite and the solvent was removed in vacuo to yield 0.27 g (53%) of the title product. HPLC 96%, $R_T$: 0.964 (System A; 10-97% MeCN over 3 min). $^1$H NMR (270 MHz, methanol-$d_4$) δ ppm 6.69 (d, J=2.23 Hz, 1H) 6.72 (d, J=2.23 Hz, 1H) 6.77 (d, J=1.98 Hz, 1H) 6.83 (dd, J=4.95, 1.48 Hz, 2H) 7.62 (d, J=1.98 Hz, 1H) 8.08-8.10 (m, 2H). LC-MS 226 (M+H)$^+$.

Example 50

N-[7-(Pyridin-4-ylamino)-1-benzofuran-5-yl]benzenesulfonamide hydrochloride

Benzenesulfonyl chloride (65 μL, 0.48 mmol) and pyridine (289 μL, 3.58 mmol) were added to (5-amino-1-benzofuran-7-yl)pyridin-4-yl-amine (90 mg, 0.40 mmol; Intermediate 33) in DCM (2 mL). The mixture was heated at 40° C. for 10 min, shaken at room temperature for 1 h, and solvent was removed in vacuo. The residue was purified by preparative HPLC using acetonitrile-water gradients containing 0.1% trifluoroacetic acid. The obtained TFA salt was converted into the hydrochloride salt by treatment with 2 M HCl in ether to afford 78.7 mg (45%) of the title product. HPLC 100%, $R_T$: 1.560 (System A; 10-97% MeCN over 3 min). $^1$H NMR (270 MHz, methanol-$d_4$) δ ppm 6.91 (s, 1H) 7.04 (d, J=2.23 Hz, 2H) 7.36 (d, J=1.98 Hz, 1H) 7.51-7.65 (m, 3H) 7.74-7.77 (m, 2H) 8.03 (d, J=1.98 Hz, 1H) 8.32 (d, J=6.93 Hz, 2H) 10.43 (s, 1H) 10.84 (s, 1H). LC-MS 366 (M+H)$^+$.

Example 51

2-Chloro-N-[7-(pyridin-4-ylamino)-1-benzofuran-5-yl]benzenesulfonamide hydrochloride Prepared by the same method as for N-[7-(pyridin-4-ylamino)-1-benzofuran-5-yl]benzenesulfonamide hydrochloride (Example 50) from 2-chlorobenzenesulfonyl chloride (101 mg, 0.48 mmol). This furnished 60.3 mg (32%) of 2-chloro-N-[7-(pyridin-4-ylamino)-1-benzofuran-5-yl]benzenesulfonamide hydrochloride. HPLC 100%, $R_T$: 1.639 (System A; 10-97% MeCN over 3 min). $^1$H NMR (270 MHz, methanol-$d_4$) δ ppm 6.92 (s, 1H) 7.03 (d, J=2.23 Hz, 1H) 7.09 (d, J=1.98 Hz, 1H) 7.36 (d, J=2.23 Hz, 1H) 7.48-7.53 (m, 1H) 7.60-7.68 (m, 2H) 8.02-8.06 (m, 2H) 8.33 (d, J=7.18 Hz, 2H) 10.74 (s, 1H) 10.86 (s, 1H). LC-MS 400 (M+H)$^+$.

Example 52

2-Methoxy-5-methyl-N-[7-(pyridin-4-ylamino)-1-benzofuran-5-yl]benzenesulfonamide hydrochloride Prepared by the same method as for N-[7-(pyridin-4-ylamino)-1-benzofuran-5-yl]benzenesulfonamide hydrochloride (Example 50) from 2-methoxy-5-methylbenzenesulfonyl chloride (105 mg, 0.48 mmol). This furnished 50.9 mg (26%) of 2-methoxy-5-methyl-N-[7-(pyridin-4-ylamino)-1-benzofuran-5-yl]benzenesulfonamide hydrochloride. HPLC 100%, $R_T$: 1.692 (System A; 10-97% MeCN over 3 min). $^1$H NMR (270 MHz, methanol-$d_4$) δ ppm 2.21 (s, 3H) 3.86 (s, 3H) 6.91 (s, 1H) 7.02-7.09 (m, 3H) 7.33-7.38 (m, 2H) 7.55 (d, J=1.73 Hz, 1H) 8.00 (d, J=1.98 Hz, 1H) 8.32 (d, J=6.93 Hz, 2H) 10.04 (s, 1H) 10.78 (s, 1H). LC-MS 410 (M+H)$^+$.

Example 53

2-Methoxy-5-methyl-N-[7-(piperazin-1-ylcarbonyl)-1-benzofuran-5-yl]benzenesulfonamide hydrochloride Step 1. 7-Bromo-2-trimethylsilanyl-benzofuran-5-ylamine 7-Bromo-5-nitro-2-trimethysilylbenzofuran (5.0 g, 15.9 mmol; Intermediate 4, Step 2) was reduced with $PtO_2$ (363 mg, 1.6 mmol) in EtOAc (100 mL) over 2.5 bar $H_2$ overnight. The resulting mixture was filtered through wetted Celite to yield 4.5 g (quantitative) of 7-bromo-2-trimethylsilanyl-benzofuran-5-ylamine.

Step 2. N-(7-Bromo-2-trimethylsilanyl-benzofuran-5-yl)-2-methoxy-5-methyl-benzenesulfonamide Coupling of the amine (4.5 g, 15.9 mmol) from Step 1 with 2-methoxy-5-methylphenylsulfonyl chloride (3.5 g, 15.9 mmol) in dichloromethane (200 mL) using pyridine as a base (3.2 mL, 40 mmol) required 2.5 hours at ambient temperature. Washing the resulting mixture with water, drying and concentration yielded 7.4 g (100%) of N-(7-bromo-2-trimethylsilanyl-benzofuran-5-yl)-2-methoxy-5-methyl-benzenesulfonamide as a dark orange solid.

Step 3. 4-[5-(2-Methoxy-5-methyl-benzenesulfonylamino)-benzofuran-7-carbonyl]-piperazine-1-carboxylic acid tert-butyl ester The Heck carbonylation was performed under controlled microwave heating at 150° C./15 min by mixing the above bromide (168 mg, 0.36 mmol) from Step 2, (tert-butoxycarbonyl)piperazine (134 mg, 0.72 mmol), $Mo(CO)_6$ (48 mg, 0.18 mmol), trans-di(acetato)bis[o-(di-o-tolylphosphino)benzyl]dipalladium (II) (Herrmann's catalyst, 36 mg, 0.04 mmol), aqueous $K_2CO_3$ (4 M; 300 μL, 1.3 mmol) and diglyme (1 mL). This yielded about 50% of product with TMS remaining (4-[5-(2-methoxy-5-methyl-benzenesulfonylamino)-2-trimethylsilanyl-benzofuran-7-carbonyl]-piperazine-1-carboxylic acid tert-butyl ester) and about 7% product with TMS absent, i.e., the title product. Both products were isolated pure by preparative HPLC (Gilson; using a gradient of 30-70% MeCN). Yield TMS product: 53 mg (24%) yellow oil. HPLC 100% $R_T$=2.06 (System C; 2-95% MeCN over 2 min). The TMS group was removed by allowing to stir in t-BuN$^+$F$^-$ (0.5 mL, 1 M in THF) in THF (3 mL) at ambient temperature for 1 h 20 min. Purification using preparative HPLC (gradient of 30-70% MeCN) gave additional material of the title product as a yellow oil.

Step 4. 2-Methoxy-5-methyl-N-[7-(piperazin-1-ylcarbonyl)-J-benzofuran-5-yl]benzenesulfonamide hydrochloride Deprotection of the N-t-BOC group in 4-[5-(2-methoxy-5-methyl-benzenesulfonylamino)-benzofuran-7-carbonyl]-piperazine-1-carboxylic acid tert-butyl ester (Step 3) was performed by adding HCl/ether to a solution of the said substrate in ethyl acetate and allowed to stir overnight at ambient temperature. Concentration of the solution gave the title product as a white solid. Yield: 31 mg. HPLC 96% $R_T$=2.73 min (System A; 30-80% MeCN over 3 min), 1.05 min (System C; 2-95% MeCN over 2 min). $^1$H NMR (400 Mz, methanol-d$_4$) δ ppm 2.17 (s, 3H), 3.19 (m, 2H), 3.34 (m, 2H), 3.49 (m, 2H), 3.91 (s, 3H), 4.01 (m, 2H), 6.80 (d, J=2.2 Hz, 1H), 6.99 (d, J=8.6 Hz, 1H), 7.20 (d, J=2.2 Hz, 1H), 7.28 (dd, J=8.6, 2.0 Hz, 1H), 7.45 (d, J=2.2 Hz, 1H), 7.49 (d, J=2.0 Hz, 1H), 7.76 (d, J=2.0 Hz, 1H). $^{13}$C NMR (400 Mz, MeOH-d$_4$) δ ppm 19.15, 55.60, 94.55, 106.86, 112.31, 116.62, 118.32, 118.44, 125.90, 129.07, 129.89, 130.51, 133.47, 135.37, 140.33, 147.22, 147.92, 154.75, 166.24 (C=O). MS (ESI) for $C_{21}H_{23}N_3O_5S$ m/z 430 (M+H).

Example 54

2-Methoxy-5-methyl-N-[7-(piperazin-1-ylmethyl)-1-benzofuran-5-yl]benzenesulfonamide hydrochloride To a solution of 4-[5-(2-methoxy-5-methyl-benzenesulfonylamino)-2-trimethylsilanyl-benzofuran-7-carbonyl]-piperazine-1-carboxylic acid tert-butyl ester (94 mg, 0.16 mmol; obtained in Example 53, Step 3) in THF was added LiAlH$_4$ (22 mg, 0.56 mmol) and allowed to stir overnight at 80° C. (only 50% conversion to t-BOC- and TMS-deprotected bisamine product after 3 hours). The solution was made neutral by addition of aqueous 1 M HCl and extracted with ethyl acetate, but little product in organic phase. The resulting aqueous phase was therefore made acidic, and then concentrated. Purification by preparative HPLC (Gilson; gradient of 20-50% MeCN) gave 14 mg of pure product as the TFA salt. Conversion to the HCl salt was done with aqueous 6 M HCl. Concentration gave the final product as a white solid. Yield: 15 mg. HPLC 100% $R_T$=2.51 min (System A; 30-80% MeCN over 3 min), 0.94 min (System C; 2-95% MeCN over 2 min). $^1$H NMR (400 Mz, MeOH-d$_4$) δ ppm 2.14 (s, 3H), 2.98 (s, 3H), 3.66 (br m, 9H), 4.69 (s, 2H), 6.80 (d, J=8.3 Hz, 1H), 6.82 (d, J=2.2 Hz, 1H), 7.14 (dd, J=8.3, 2.2 Hz, 1H), 7.38 (d, J=2.0 Hz, 1H), 7.40 (d, J=2.0 Hz, 1H), 7.52 (d, J=2.2 Hz, 1H), 7.82 (d, J=2.2 Hz, 1H). MS (ESI) for $C_{21}H_{25}N_3O_4S$ m/z 416 (M+H).

Example 55

N-{7-[(3-Aminopyrrolidin-1-yl)methyl]-1-benzofuran-5-yl}-2-methoxy-5-methylbenzenesulfonamide hydrochloride To a solution of {1-[5-(2-methoxy-5-methyl-benzenesulfonylamino)-2-trimethylsilanyl-benzofuran-7-carbonyl]-pyrrolidin-3-yl}-carbamic acid tert-butyl ester* (84 mg, 0.14 mmol) in THF was added LiAlH$_4$ (22 mg, 0.56 mmol) and the resulting mixture was allowed to stir for 4 h at 80° C. Ethyl acetate was added and the mixture was washed with 1 M aqueous HCl and then with water, dried and concentrated to yield 37 mg of the mono boc-protected diamine. (According to HPLC, 34% was reduced at the furan ring). Purification by preparative HPLC (Gilson; gradient of 40-80% MeCN) gave pure boc-protected diamine. N-Deprotection was performed cleanly overnight in 6 M aqueous HCl (attempts with HCl/ether at 60° C. overnight gave only 25% product and some biproducts) to give the product after evaporation as a yellow solid. Yield: 16 mg. HPLC 92% $R_T$=1.30 min (System A; 30-80% MeCN over 3 min), 1.03 min (System C; 2-95% MeCN over 2 min). The peaks in the proton NMR spectrum are broad due to the conformational flexibility of the pyrrolidine ring. $^1$H NMR (400 Mz, methanol-d$_4$) δ ppm 1.44 (br s, 1H), 2.17 (s, 3H), 2.38 (br s, 1H), 3.37-3.83 (br m, 4H), 3.97 (s, 3H), 4.08-4.73 (br m, 3H), 6.82 (br s, 1H), 7.03 (m, 1H), 7.22-7.34 (br m, 5H), 7.48 (m, 3H), 7.81 (br s, 1H). MS (ESI) for $C_{21}H_{25}N_3O_4S$ m/z 416 (M+H).

*Prepared from pyrrolidin-3-yl-carbamic acid tert-butyl ester according to the procedure of Example 53 (Step 3).

Intermediate 34

Octahydrothieno[3,4-b]pyrazine 6,6-dioxide* cis-3,4-Dichlorotetrahydrothiophene 1,1-dioxide (5.0 g, 26.0 mmol) in dioxane (40 mL) was added dropwise to ethane-1,2-diamine (10.4 g, 173.0 mmol) in dioxane (25 mL) at 0° C. The mixture was heated at 100° C. for 3 h, followed by cooling to room temperature and continued stirring overnight. The two layers were separated and the bottom layer, containing ethylene diamine and amine salt, was washed twice with dioxane. The dioxane layers were combined and the solvent was removed in vacuo. The crude product was recrystallized from toluene to afford 2.7 g (59%) of the title compound as white crystals. HPLC 98%, $R_T$: 0.292 (System B; 10-97% MeCN over 3 min). $^1$H NMR (270 MHz, methanol-d$_4$) δ ppm 2.67-2.76 (m, 2H) 2.86-2.96 (m, 2H) 3.13-3.20 (m, 2H) 3.33-3.44 (m, 2H) 3.63-3.70 (m, 2H). LC-MS 177 (M+H)$^+$.

*Previously described in U.S. Pat. No. 3,882,122.

Intermediate 35

1-(5-Nitro-1-benzofuran-7-yl)octahydrothieno[3,4-b]pyrazine 6,6-dioxide

Xylene (150 mL) was added to 7-iodo-5-nitro-1-benzofuran (1.00 g, 3.46 mmol), octahydrothieno[3,4-b]pyrazine 6,6-dioxide (0.73 g, 4.15 mmol; Intermediate 34), Pd$_2$(dba)$_3$ (0.08 g, 0.87 mmol), Xantphos (0.20 g, 0.35 mmol) and Cs$_2$CO$_3$ (1.59 g, 4.84 mmol). The resulting mixture was stirred at 120° C. overnight, filtered through Celite and the solvent was removed in vacuo. The crude product was purified by flash chromatography [eluent: DCM and DCM:MeOH (1:1)] and then recrystallized from MeOH to afford 0.354 g (8%) of the title product. HPLC 90%, $R_T$: 1.390 (System A; 10-97% MeCN over 3 min). $^1$H NMR (270 MHz, CDCl$_3$) δ ppm 2.85 (dd, J=12.62, 7.42 Hz, 1H) 3.16-3.49 (m, 6H) 3.71 (t, J=11.63 Hz, 1H) 4.02-4.05 (m, 1H) 5.17-5.25 (m, 1H) 6.93 (d, J=2.23 Hz, 1H) 7.62 (t, J=2.72 Hz, 1H) 7.77 (d, J=1.98 Hz, 1H) 8.19 (d, J=1.98 Hz, 1H). LC-MS 338 (M+H)$^+$.

Intermediate 36

7-(6,6-Dioxidohexahydrothieno[3,4-b]pyrazine-1 (2H)-yl-1-benzofuran-5-amine

Raney-nickel (slurry in ethanol; 2 mL) and hydrazine (204 mL, 4.20 mmol) were added to 1-(5-nitro-1-benzofuran-7-yl) octahydrothieno[3,4-b]pyrazine 6,6-dioxide (0.354 g, 1.05 mmol; Intermediate 35) in a mixture of THF (20 mL) and EtOH (80 mL). The resulting mixture was stirred at room temperature overnight and then more Raney-nickel (slurry in ethanol; 2 mL) and hydrazine (204 mL, 4.20 mmol) were added and stirring was continued overnight. The mixture was filtered through Celite and the solvent was removed in vacuo to afford 0.338 g (quantitative). HPLC 90%, $R_T$: 0.782 (System A; 10-97% MeCN over 3 min). $^1$H NMR (270 MHz, methanol-$d_4$) δ ppm 2.79 (dd, J=12.49, 7.30 Hz, 1H) 2.90-3.25 (m, 4H) 3.43-3.64 (m, 3H) 3.91-3.94 (m, 1H) 5.01-5.07 (m, 1H) 6.33 (d, J=1.98 Hz, 1H) 6.61 (dd, J=12.99, 2.10 Hz, 2H) 7.62 (d, J=1.98 Hz, 1H). LC-MS 308 (M+H)$^+$.

Example 56

N-[7(6,6-Dioxidohexahydrothieno[3,4-b]pyrazin-1(2H)-yl)-1-benzofuran-5-yl]-2-methoxy-5-methyl-benzenesulfonamide hydrochloride 2-Methoxy-5-methylbenzenesulfonyl chloride (0.094 g, 0.428 mmol) and pyridine (259 μL, 3.21 mmol) were added to 7-(6,6-dioxidohexahydrothieno[3,4-b]pyrazine-1(2H)-yl-1-benzofuran-5-amine (0.110 g, 0.357 mmol; Intermediate 36) in DCM (1 mL). The mixture was shaken at room temperature for 1 h, solvent removed in vacuo, and the residue was purified by preparative HPLC using acetonitrile-water gradients containing 0.1% trifluoroacetic acid. The obtained TFA salt was converted into the hydrochloride salt by treatment with 2 M HCl in ether to afford 20.0 mg (11%) of the title product. HPLC 98%, $R_T$: 1.483 (System A; 10-97% MeCN over 3 min). $^1$H NMR (270 MHz, methanol-$d_4$) δ ppm 3.08-3.12 (m, 2H) 3.37-3.79 (m, 6H) 3.96 (s, 3H) 4.55 (d, J=3.96 Hz, 1H) 6.77 (d, J=2.23 Hz, 1H) 6.84 (d, J=1.98 Hz, 1H) 7.03 (d, J=8.41 Hz, 1H) 7.12 (d, J=1.98 Hz, 1H) 7.31 (dd, J=8.78, 1.86 Hz, 1H) 7.51 (d, J=1.73 Hz, 1H) 7.74 (d, J=2.23 Hz, 1H). LC-MS 492 (M+H)$^+$.

Example 57

N-[7(6,6-Dioxidohexahydrothieno[3,4-b]pyrazin-1(2H)-yl)-1-benzofuran-5-yl]benzenesulfonamide hydrochloride Benzenesulfonyl chloride (0.076 g, 0.428 mmol) and pyridine (259 mL, 3.21 mmol) were added to 7-(6,6-dioxidohexahydrothieno[3,4-b]pyrazine-1(2H)-yl-1-benzofuran-5-amine
(0.110 g, 0.357 mmol; Intermediate 36) in DCM (1 mL). The mixture was shaken at room temperature for 1 h, solvent removed in vacuo, and the residue was purified by preparative HPLC using acetonitrile-water gradients containing 0.1% trifluoroacetic acid. The obtained TFA salt was converted into the hydrochloride salt by treatment with 2 M HCl in ether to afford 27.0 mg (17%) of the title product. HPLC 99%, $R_T$: 1.556 (System A; 10-97% MeCN over 3 min). $^1$H NMR (270 MHz, methanol-$d_4$) δ ppm 3.17 (d, J=6.68 Hz, 2H) 3.47-3.85 (m, 6H) 4.52-4.56 (m, 1H) 4.95-4.99 (m, 1H) 6.77-6.79 (m, 2H) 7.07 (d, J=1.98 Hz, 1H) 7.42-7.54 (m, 3H) 7.69-7.77 (m, 3H). LC-MS 448 (M+H)$^+$.

Example 58

N-{7-[(2-Pyrrolidin-1-ylethyl)amino]-1-benzofuran-5-yl}benzenesulfonamide hydrochloride To a test tube containing benzenesulfonyl chloride (42 mg, 0.235 mmol) was added a solution of $N^7$-(2-pyrrolidin-1-ylethyl)-1-benzofuran-5,7-diamine* (48 mg, 0.195 mmol) in dichloromethane (3 mL). After addition of triethylamine (55 μl, 0.391 mmol), the mixture was shaken for 1 h and then concentrated. The residue was purified by preparative HPLC. The resulting TFA-salt was treated with HCl/ether and evaporated to provide the title compound. Yield: 5%, HPLC purity=99%, m/z=386 (M+H)$^+$, $^1$H NMR (270 MHz, methanol-$d_4$) δ ppm 1.95-2.26 (m, 4H) 3.03-3.24 (m, 2H) 3.38-3.47 (m, 2H) 3.58-3.65 (m, 2H) 3.64-3.77 (m, 2H) 6.45-6.48 (m, 1H) 6.55-6.57 (m, 1H) 6.65 (d, J=2.23 Hz, 1H) 7.40-7.59 (m, 3H) 7.67 (d, J=2.23 Hz, 1H) 7.68-7.73 (m, 2H).

*Prepared in two steps starting from 2-pyrrolidin-1-yl-ethylamine: i) Pd-catalysed amination of 7-iodo-5-nitro-benzofuran according to the procedure of Intermediate 31 to provide (5-nitro-benzofuran-7-yl)-(2-pyrrolidin-1-yl-ethyl)-amine and ii) reduction of the nitro group of (5-nitro-benzofuran-7-yl)-(2-pyrrolidin-1-yl-ethyl)-amine to provide $N^7$-(2-pyrrolidin-1-ylethyl)-1-benzofuran-5,7-diamine according to the procedure of Example 48 (Step 1).

Example 59

2-Methoxy-5-methyl-N-{7-[(2-pyrrolidin-1-ylethyl)amino]-1-benzofuran-5-yl}benzenesulfonamide hydrochloride The title compound was prepared according to the procedure described for Example 58. Yield: 18%, HPLC purity=98%, m/z=430 (M+H)$^+$, $^1$H NMR (500 MHz, DMSO-$d_6$) δ ppm 1.81-1.92 (m, 2H) 1.96-2.08 (m, 2H) 2.18-2.22 (m, 3H) 3.00-3.12 (m, 2H) 3.31-3.37 (m, 2H) 3.39-3.45 (m, 2H) 3.55-3.63 (m, 2H) 3.87-3.90 (m, 3H) 6.34-6.37 (m, 1H) 6.59-6.63 (m, 1H) 6.77 (d, J=2.20 Hz, 1H) 7.03-7.07 (m, 1H) 7.32 (m, 1H) 7.48-7.50 (m, 1H) 7.83 (d, J=1.88 Hz, 1H).

Example 60

N-{7-[(2-Pyrrolidin-1-ylethyl)amino]-1-benzofuran-5-yl}-2-(trifluoromethyl)benzenesulfonamide hydrochloride The title compound was prepared according to the procedure described for Example 58. Yield: 31%, HPLC purity=99%, m/z=454 (M+H)$^+$, $^1$H NMR (270 MHz, methanol-$d_4$) δ ppm 1.92-2.26 (m, 4H) 3.07-3.22 (m, 2H) 3.39-3.48 (m, 2H) 3.56-3.64 (m, 2H) 3.61-3.75 (m, 2H) 6.49 (d, J=1.98 Hz, 1H) 6.63 (d, J=1.98 Hz, 1H) 6.66 (d, J=2.23 Hz, 1H) 7.60-7.76 (m, 3H) 7.88-7.95 (m, 1H) 7.99-8.05 (m, 1H).

Example 61

3-Chloro-4-methyl-N-{7-[(2-pyrrolidin-1-ylethyl)amino]-1-benzofuran-5-yl}benzenesulfonamide hydrochloride The title compound was prepared according to the procedure described for Example 58. Yield: 32%, HPLC purity=99%, m/z=433 (M+H)$^+$, $^1$H NMR (270 MHz, methanol-$d_4$) δ ppm 1.93-2.25 (m, 4H) 2.35-2.40 (m, 3H) 3.11-3.24 (m, 2H) 3.42-3.50 (m, 2H) 3.61-3.68 (m, 2H) 3.65-3.76 (m, 2H) 6.47-6.50 (m, 1H) 6.56-6.60 (m, 1H) 6.67 (d, J=2.23 Hz, 1H) 7.35-7.40 (m, 1H) 7.48-7.54 (m, 1H) 7.67 (d, J=1.98 Hz, 1H) 7.68 (d, J=1.98 Hz, 1H).

Example 62

2-Methoxy-5-methyl-N-{7-[(3-morpholin-4-ylpropyl)amino]-1-benzofuran-5-yl}benzenesulfonamide hydrochloride The title compound was prepared according to the procedure described for Example 58 using $N^7$-(3-morpholin-4-yl-propyl)-benzofuran-5,7-diamine.* Yield: 5%, HPLC purity=98%, m/z=460 (M+H)$^+$, $^1$H NMR (270 MHz, methanol-d$_4$) δ ppm 1.99-2.15 (m, 2H) 2.18-2.27 (m, 3H) 3.17-3.40 (m, 6H) 3.61-4.05 (m, 6H) 3.94-3.98 (m, 3H) 6.46 (d, J=1.73 Hz, 1H) 6.53-6.57 (m, 1H) 6.61 (d, J=2.23 Hz, 1H) 6.99-7.06 (m, 1H) 7.27-7.34 (m, 1H) 7.47-7.52 (m, 1H) 7.60 (d, J=2.23 Hz, 1H).

*Prepared in two steps starting from 3-morpholin-4-yl-propylamine: i) Pd-catalysed amination of 7-iodo-5-nitro-benzofuran according to the procedure of Intermediate 31 to provide (3-morpholin-4-yl-propyl)-(5-nitro-benzofuran-7-yl)-amine and ii) reduction of the nitro group of (3-morpholin-4-yl-propyl)-(5-nitro-benzofuran-7-yl)-amine to provide N$^7$-(3-morpholin-4-yl-propyl)-benzofuran-5,7-diamine according to the procedure of Example 48 (Step 1).

Example 63

N-{7-[(3-Morpholin-4-ylpropyl)amino]-1-benzofuran-5-yl}-2-(trifluoromethyl)benzenesulfonamide hydrochloride The title compound was prepared according to the procedure described for Example 58 using N$^7$-(3-morpholin-4-yl-propyl)-benzofuran-5,7-diamine. Yield: 13%, HPLC purity=99%, m/z=484 (M+H)$^+$, $^1$H NMR (270 MHz, methanol-d$_4$) δ ppm 1.99-2.15 (m, 2H) 3.03-3.38 (m, 6H) 3.38-3.57 (m, 2H) 3.62-3.85 (m, 2H) 3.89-4.14 (m, 2H) 6.44 (d, J=1.98 Hz, 1H) 6.53 (d, J=1.98 Hz, 1H) 6.62 (d, J=2.23 Hz, 1H) 7.60-7.75 (m, 3H) 7.89-7.94 (m, 1H) 7.99-8.05 (m, 1H).

Example 64

3-Chloro-4-methyl-N-{7-[(3-morpholin-4-ylpropyl)amino]-1-benzofuran-5-yl}benzenesulfonamide hydrochloride The title compound was prepared according to the procedure described for Example 58 using N$^7$-(3-morpholin-4-yl-propyl)-benzofuran-5,7-diamine. Yield: 15%, HPLC purity=99%, m/z=464 (M+H)$^+$, $^1$H NMR (270 MHz, methanol-d$_4$) δ ppm 2.04-2.18 (m, 2H) 2.35-2.40 (m, 3H) 3.06-3.24 (m, 2H) 3.27-3.41 (m, 4H) 3.44-3.57 (m, 2H) 3.65-3.81 (m, 2H) 3.98-4.13 (m, 2H) 6.43-6.49 (m, 2H) 6.63 (d, J=1.98 Hz, 1H) 7.34-7.40 (m, 1H) 7.47-7.52 (m, 1H) 7.65 (d, J=1.98 Hz, 1H) 7.66 (d, J=1.98 Hz, 1H).

Intermediate 37

{[(2R)-1-Ethylpyrrolidin-2-yl]methyl}(5-nitro-1-benzofuran-7-yl)amine

The title compound was prepared according to the procedure described for Intermediate 27 using (R)-2-aminomethyl-1-ethylpyrrolidine. Yield: 100%, HPLC purity=90%, m/z=290 (M+H)$^+$.

Intermediate 38

N$^7$-{[(2R)-1-Ethylpyrrolidin-2-yl]methyl}-1-benzofuran-5,7-diamine

The title compound was prepared according to the procedure described for Intermediate 28 using {[(2R)-1-ethylpyrrolidin-2-yl]methyl}(5-nitro-1-benzofuran-7-yl)amine (Intermediate 37). The obtained product was used directly in the subsequent reaction.

Example 65

N-[7-({[(2R)-1-Ethylpyrrolidin-2-yl]methyl}amino)-1-benzofuran-5-yl]benzenesulfonamide hydrochloride The title compound was prepared according to the procedure of Example 41 using N$^7$-{[(2R)-1-ethylpyrrolidin-2-yl]methyl}-1-benzofuran-5,7-diamine. Yield: 7 mg (8%), HPLC purity=95%, m/z=400 (M+H)$^+$, $^1$H NMR (270 MHz, methanol-d$_4$) δ ppm 1.29 (t, J=7.30 Hz, 3H) 1.83-2.39 (m, 4H) 3.05-3.28 (m, 2H) 3.37-3.54 (m, 1H) 3.54-3.61 (m, J=6.06, 3.34 Hz, 2H) 3.63-3.77 (m, 2H) 6.47 (d, J=1.73 Hz, 1H) 6.57 (d, J=1.98 Hz, 1H) 6.65 (d, J=2.23 Hz, 1H) 7.39-7.59 (m, 3H) 7.65-7.73 (m, 3H).

Example 66

N-[7-({[(2R)-1-Ethylpyrrolidin-2-yl]methyl}amino)-1-benzofuran-5-yl]-2-methoxy-5-methylbenzenesulfonamide hydrochloride The title compound was prepared according to the procedure of Example 41 using N$^7$-{[(2R)-1-ethylpyrrolidin-2-yl]methyl}-1-benzofuran-5,7-diamine. Yield: 16 mg (17%), HPLC purity=97%, m/z=444 (M+H)$^+$, $^1$H NMR (270 MHz, methanol-d$_4$) δ ppm 1.27 (t, J=7.18 Hz, 3H) 1.85-2.20 (m, 2H) 2.19-2.23 (s, 3H) 2.24-2.42 (m, 1H) 3.01-3.28 (m, 3H) 3.38-3.53 (m, 1H) 3.54-3.60 (m, 2H) 3.63-3.81 (m, 2H) 3.94-3.98 (s, 3H) 6.53 (d, J=1.73 Hz, 1H) 6.64 (dd, J=3.84, 1.86 Hz, 2H) 7.00-7.06 (m, 1H) 7.28-7.35 (m, 1H) 7.45-7.51 (m, 1H) 7.64 (d, J=1.98 Hz, 1H).

Example 67

N-[7-({[(2R)-1-Ethylpyrrolidin-2-yl]methyl}amino)-1-benzofuran-5-yl]-2-(trifluoromethyl)benzenesulfonamide hydrochloride The title compound was prepared according to the procedure of Example 41 using N$^7$-{[(2R)-1-ethylpyrrolidin-2-yl]methyl}-1-benzofuran-5,7-diamine. Yield: 21 mg (21%), HPLC purity=99%, m/z=468 (M+H)$^+$, $^1$H NMR (270 MHz, methanol-d$_4$) δ ppm 1.29 (t, J=7.30 Hz, 3H) 1.82-2.39 (m, 4H) 3.05-3.28 (m, 2H) 3.40-3.53 (m, 1H) 3.53-3.61 (m, 2H) 3.63-3.78 (m, 2H) 6.50 (d, J=1.98 Hz, 1H) 6.66 (dd, J=5.57, 2.10 Hz, 2H) 7.58-7.77 (m, 3H) 7.88-7.95 (m, 1H) 7.97-8.05 (m, 1H).

Example 68

N-[7-({[(2R)-1-Ethylpyrrolidin-2-yl]methyl}amino)-1-benzofuran-5-yl]-3-methylbenzenesulfonamide hydrochloride The title compound was prepared according to the procedure of Example 41 using N$^7$-{[(2R)-1-ethylpyrrolidin-2-yl]methyl}-1-benzofuran-5,7-diamine. Yield: 15 mg (16%), HPLC purity=96%, m/z=414 (M+H)$^+$, $^1$H NMR (270 MHz, methanol-d$_4$) δ ppm 1.29 (t, J=7.30 Hz, 3H) 1.81-2.38 (m, 4H) 2.30-2.34 (s, 3H) 3.02-3.27 (m, 2H) 3.39-3.54 (m, 1H) 3.54-3.61 (m, 2H) 3.64-3.79 (m, 2H) 6.47 (d, J=1.98 Hz, 1H) 6.57 (d, J=1.73 Hz, 1H) 6.66 (d, J=2.23 Hz, 1H) 7.26-7.41 (m, 2H) 7.44-7.55 (m, 2H) 7.67 (d, J=1.98 Hz, 3H).

Example 69

N-[7-({[(2R)-1-Ethylpyrrolidin-2-yl]methyl}amino)-1-benzofuran-5-yl]thiophene-2-sulfonamide hydrochloride The title compound was prepared according to the procedure of Example 41 using N$^7$-{[(2R)-1-ethylpyrrolidin-2-yl]methyl}-1-benzofuran-5,7-diamine. Yield: 17 mg (19%), HPLC purity=99%, m/z=406 (M+H)$^+$, $^1$H NMR (270 MHz, methanol-d$_4$) δ ppm 1.30 (t, J=7.30 Hz, 3H) 1.82-2.42 (m, 4H) 3.02-3.28 (m, 2H) 3.39-3.57 (m, 1H) 3.57-3.64 (m, 2H) 3.64-3.82 (m, 2H) 6.49-6.54 (m, J=1.98 Hz, 1H) 6.64 (d, J=1.98 Hz, 1H) 6.69 (d, J=1.98 Hz, 1H) 7.04 (dd, J=4.95, 3.71 Hz, 1H) 7.43 (dd, J=3.71, 1.24 Hz, 1H) 7.63-7.72 (m, 2H).

Example 70

5-Chloro-N-[7-({[(2R)-1-ethylpyrrolidin-2-yl]methyl}amino)-1-benzofuran-5-yl]thiophene-2-sulfonamide hydrochloride The title compound was prepared according to the procedure of Example 41 using N$^7$-{[(2R)-1-ethylpyrrolidin-2-yl]methyl}-1-benzofuran-5,7-diamine. Yield: 5 mg (5%), HPLC purity=99%, m/z=440 (M+H)$^+$, $^1$H NMR (270 MHz, methanol-d$_4$) δ ppm 1.32 (t, J=7.30 Hz, 3H) 1.84-2.42 (m, 4H) 3.06-3.28 (m, 2H) 3.44-3.58 (m, 1H) 3.59-3.65 (m, 2H) 3.65-3.82 (m, 2H) 6.52 (d, J=1.73 Hz, 1H) 6.68 (d, J=1.98 Hz, 1H) 6.73 (d, J=2.23 Hz, 1H) 6.95-6.99 (m, 1H) 7.22-7.26 (m, 1H) 7.72 (d, J=2.23 Hz, 1H).

Example 71

5-Chloro-N-[7-({[(2R)-1-ethylpyrrolidin-2-yl]methyl}amino)-1-benzofuran-5-yl]-1,3-dimethyl-1H-pyrazole-4-sulfonamide hydrochloride The title compound was prepared according to the procedure of Example 41 using N$^7$-{[(2R)-1-ethylpyrrolidin-2-yl]methyl}-1-benzofuran-5,7-diamine. Yield: 12 mg (12%), HPLC purity=98%, m/z=452 (M+H)$^+$, $^1$H NMR (270 MHz, methanol-d$_4$) δ ppm 1.33 (t, J=7.30 Hz, 3H) 1.87-2.41 (m, 4H) 2.17-2.20 (m, 3H) 3.07-3.28 (m, 2H) 3.44-3.65 (m, 3H) 3.66-3.82 (m, 2H) 3.70-3.73 (m, 3H) 6.53 (d, J=1.98 Hz, 1H) 6.64 (d, J=1.98 Hz, 1H) 6.70 (d, J=1.98 Hz, 1H) 7.70 (d, J=2.23 Hz, 1H).

Example 72

N-(7-{[3-(2-Methylpiperidin-1-yl)propyl]amino}-1-benzofuran-5-yl)benzenesulfonamide hydrochloride The title compound was prepared according to the procedure described for Example 58 using N$^7$-[3-(2-methyl-piperidin-1-yl)-propyl]-benzofuran-5,7-diamine.* Yield: 9%, HPLC purity=97%, m/z=428 (M+H)$^+$, $^1$H NMR (270 MHz, methanol-d$_4$) δ ppm 1.29 (d, J=6.43 Hz, 0.3H, rotamers) 1.32 (d, J=6.43 Hz, 3H) 1.45-2.17 (m, 8H) 2.91-3.07 (m, 1H) 3.13-3.27 (m, 3H) 3.35 (t, J=6.43 Hz, 2H) 3.39-3.56 (m, 1H) 6.43-6.49 (m, 2H) 6.61 (d, J=2.23 Hz, 1H) 7.40-7.58 (m, 3H) 7.63 (d, J=1.98 Hz, 1H) 7.68-7.74 (m, 2H).
*Prepared in two steps starting from 3-(2-methyl-piperidin-1-yl)-propylamine: i) Pd-catalysed amination of 7-iodo-5-nitro-benzofuran according to the procedure of Intermediate 31 to provide [3-(2-methyl-piperidin-1-yl)-propyl]-(5-nitro-benzofuran-7-yl)-amine, and ii) reduction of the nitro group of (3-morpholin-4-yl-propyl)-(5-nitro-benzofuran-7-yl)-amine to provide N$^7$-[3-(2-methyl-piperidin-1-yl)-propyl]-benzofuran-5,7-diamine according to the procedure of Example 48 (Step 1).

Example 73

2-Methoxy-5-methyl-N-(7-{[3-(2-methylpiperidin-1-yl)propyl]amino}-1-benzofuran-5-yl)benzenesulfonamide hydrochloride The title compound was prepared according to the procedure described for Example 58 using N$^7$-[3-(2-methyl-piperidin-1-yl)-propyl]-benzofuran-5,7-diamine. Yield: 7%, HPLC purity=98%, m/z=472 (M+H)$^+$, $^1$H NMR (270 MHz, methanol-d$_4$) δ ppm 1.29 (d, J=6.43 Hz, 0.3H, rotamers) 1.31 (d, J=6.43 Hz, 3H) 1.48-2.16 (m, 8H) 2.18-2.22 (m, 3H) 2.88-3.05 (m, 1H) 3.11-3.27 (m, 3H) 3.31-3.39 (m, 2H) 3.38-3.55 (m, 1H) 3.94-3.98 (m, 3H) 6.46-6.49 (m, 1H) 6.58 (d, J=1.98 Hz, 1H) 6.61 (d, J=1.98 Hz, 1H) 6.99-7.05 (m, 1H) 7.27-7.34 (m, 1H) 7.48-7.52 (m, 1H) 7.60 (d, J=1.98 Hz, 1H).

Example 74

N-(7-{[3-(2-Methylpiperidin-1-yl)propyl]amino}-1-benzofuran-5-yl)-2-(trifluoromethyl)benzenesulfonamide hydrochloride The title compound was prepared according to the procedure described for Example 58 using N$^7$-[3-(2-methyl-piperidin-1-yl)-propyl]-benzofuran-5,7-diamine. Yield: 1%, HPLC purity=97%, m/z=496 (M+H)$^+$, $^1$H NMR (270 MHz, methanol-d$_4$) δ ppm 1.29 (d, J=6.43 Hz, 0.3H, rotamers) 1.33 (d, J=6.43 Hz, 3H) 1.45-2.20 (m, 8H) 2.94-3.08 (m, 1H) 3.12-3.28 (m, 3H) 3.32-3.39 (m, 2H) 3.44-3.59 (m, 1H) 6.46-6.49 (m, 1H) 6.53 (d, J=1.98 Hz, 1H) 6.63 (d, J=2.23 Hz, 1H) 7.60-7.76 (m, 3H) 7.88-7.94 (m, 1H) 7.99-8.06 (m, 1H).

Example 75

5-Chloro-1,3-dimethyl-N-(7-{[3-(2-methylpiperidin-1-yl)propyl]amino}-1-benzofuran-5-yl)-1H-pyrazole-4-sulfonamide hydrochloride The title compound was prepared according to the procedure described for Example 58 using N$^7$-[3-(2-methyl-piperidin-1-yl)-propyl]-benzofuran-5,7-diamine. Yield: 10%, HPLC purity=97%, m/z=480 (M+H)$^+$, $^1$H NMR (270 MHz, methanol-d$_4$) δ ppm 1.30 (d, J=6.43 Hz, 0.4H, rotamers) 1.35 (d, J=6.43 Hz, 3H) 1.50-2.16 (m, 8H) 2.17-2.21 (m, 3H) 2.93-3.08 (m, 1H) 3.15-3.27 (m, 3H) 3.38 (t, J=6.43 Hz, 2H) 3.41-3.58 (m, 1H) 3.70-3.73 (m, 3H) 6.46-6.49 (m, 1H) 6.56 (d, J=1.73 Hz, 1H) 6.66 (d, J=1.98 Hz, 1H) 7.66 (d, J=1.98 Hz, 1H).

Intermediate 39

5-(5-Nitro-benzofuran-7-yl)-pyridin-2-ylamine

7-Iodo-5-nitrobenzofuran (289 mg, 1.0 mmol), pinacolborane (192 mg, 1.5 mmol) and PdCl$_2$(dppf)-DCM were added to a test tube together with dioxane (4 mL). Triethylamine (304 mg, 3.0 mmol) was added carefully to the solution, and the mixture was heated in a StemBlock at 70° C. overnight to form 5-nitro-7-(4,4,5,5-tetramethyl-1,3,2-dioxaborolan-2-yl)-1-benzofuran in situ. Then 2-amino-5-iodopyridine (220 mg, 1.0 mmol) and aqueous barium hydroxide (1 mL; 2 M) were added. The resulting mixture was stirred at 70° C. overnight and then filtered through Celite and evaporated. The residue was extracted with chloroform/water and evaporated to give the title product. Yield: 82%, HPLC purity=82%, m/z=256 (M+H)$^+$.

Intermediate 40

5-(5-Amino-1-benzofuran-7-yl)pyridin-2-amine

The title compound was prepared from 5-(5-nitro-benzofuran-7-yl)-pyridin-2-ylamine (Intermediate 39) according to the procedure of Intermediate 28. The product was used directly in the subsequent reaction.

Example 76

N-[7-(6-Aminopyridin-3-yl)-1-benzofuran-5-yl]-2-methoxy-5-methylbenzenesulfonamide The title compound was prepared from 5-(5-amino-1-benzofuran-7-yl)pyridin-2-amine (Intermediate 40) according to the procedure of Example 41, except the purification step where flash chromatography (eluent: 30% EtOAc in hexane) was employed. Yield: 7%, HPLC purity=93%, m/z=410 (M+H)$^+$, $^1$H NMR (270 MHz, methanol-d$_4$) δ ppm 2.20 (s, 3H) 3.96 (s, 3H) 6.84 (d, J=2.23 Hz, 1H) 6.99-7.05 (m, J=8.41 Hz, 1H) 7.10-7.17 (m, J=9.90 Hz, 1H) 7.27-7.36 (m, 3H) 7.51-7.55 (m, 1H) 7.82 (d, J=2.23 Hz, 1H) 8.27-8.34 (m, 2H).

Intermediate 41

2-Methoxy-5-methyl-N-(7-piperazin-1-yl-1-benzofuran-5-yl)benzenesulfonamide tert-Butyl 4-(5-{[(2-methoxy-5-methylphenyl)sulfonyl]amino}-1-benzofuran-7-yl)piperazine-1-carboxylate* (1.5 g, 2.99 mmol) was reacted according to the procedure of Intermediate 20 and the product was used in the next step without further purification. Yield: 1.2 g (100%). HPLC purity 99%, R$_T$=1.60 min (System A; 10-97% MeCN over 3 min).

*Prepared from tert-butyl 4-(5-amino-1-benzofuran-7-yl)piperazine-1-carboxylate (Intermediate 10) according to the procedure of Intermediate 19.

Example 77

N-{7-[4-(Cyclopropylmethyl)piperazin-1-yl]-1 benzofuran-5-yl}-2-methoxy-5-methylbenzenesulfonamide hydrochloride Cyclopropanecarbaldehyde (0.087 g, 1.25 mmol) was added to a solution of 2-methoxy-5-methyl-N-(7-piperazin-1-yl-1-benzofuran-5-yl)benzenesulfonamide (0.1 g, 0.25 mmol; Intermediate 41) in methanol. After being stirred at room temperature for 5 min, sodium cyanoborohydride (0.156 g, 2.5 mmol) was added and the resulting mixture was stirred at room temperature for 5 days. Precipitation from the reaction mixture was collected by filtration giving the free base of the title compound (0.063 g; 55%). The free base was dissolved in MeOH and treated with HCl/ether 1 M to give the title compound. Yield: 0.029 g (43%). HPLC 100%, R$_T$=1.82 min (System A; 10-97% MeCN over 3 min). $^1$H NMR (400 MHz, DMSO-d$_6$) δ ppm 0.37-0.48 (m, 2H) 0.59-0.72 (m, 2H) 1.09-1.22 (m, 1H) 2.20 (s, 3H) 3.03 (dd, J=6.7, 5.4 Hz, 2H) 3.12-3.26 (m, 4H) 3.59-3.75 (m, 4H) 3.87 (s, 3H) 6.59 (d, J=1.8 Hz, 1H) 6.85 (d, J=2.0 Hz, 1H) 6.95 (d, J=1.8 Hz, 1H) 7.03 (d, J=8.5 Hz, 1H) 7.32 (dd, J=8.4, 2.1 Hz, 1H) 7.51 (d, J=2.0 Hz, 1H) 7.89 (d, J=2.3 Hz, 1H) 9.74 (s, 1H). MS (ESI+) for C$_{24}$H$_{29}$N$_3$O$_4$S m/z 456.2 (M+H)$^+$.

Example 78

2-Methoxy-5-methyl-N-{7-[4-(3,3,3-trifluoropropyl)piperazin-1-yl]-1-benzofuran-5-yl}benzenesulfonamide hydrochloride The title compound was prepared from 2-methoxy-5-methyl-N-(7-piperazin-1-yl-1-benzofuran-5-yl)benzenesulfonamide (0.1 g, 0.25 mmol; Intermediate 41) and 3,3,3-trifluoropropanal according to the procedure of Example 77. Precipitation from the reaction mixture was collected by filtration giving the free base of the title compound (0.075 g; 60%). The free base was dissolved in MeOH and treated with HCl/ether 1 M to give the title compound. Yield: 0.078 g (96%). HPLC 98%, R$_T$=1.84 min (System A; 10-97% MeCN over 3 min). $^1$H NMR (400 MHz, DMSO-d$_6$) δ ppm 2.20 (s, 3H) 2.93-3.10 (m, 2H) 3.15 (s, 2H) 3.16-3.30 (m, 4H) 3.36-3.50 (m, 2H) 3.60-3.77 (m, 3H) 3.87 (s, 3H) 6.58 (d, J=1.8 Hz, 1H) 6.85 (d, J=2.3 Hz, 1H) 6.95 (d, J=1.8 Hz, 1H) 7.03 (d, J=8.5 Hz, 1H) 7.25 (s, 2H) 7.31 (dd, J=8.5, 2.3 Hz, 1H) 7.38 (s, 2H) 7.51 (s, 3H) 7.89 (d, J=2.3 Hz, 1H) 9.74 (s, 1H). MS (ESI+) for C$_{23}$H$_{26}$F$_3$N$_3$O$_4$S m/z 498.2 (M+H)$^+$.

Intermediate 42

3,3-Dibromo-1,1,1-trifluoroacetone*

1,1,1-Trifluoropropanone (50.0 g, 446.2 mmol) was dissolved in concentrated sulphuric acid (250 g). Br$_2$ (81.69 g, 510.1 mmol) was added dropwise, at room temperature, during 2 h and the mixture was stirred overnight. After this time, additional Br$_2$ (40.85 g, 255.6 mmol) was added and the mixture stirred overnight. Separated the two phases formed when allowed to stand and distilled the bottom layer to yield 3,3-dibromo-1,1,1-trifluoroacetone as a yellow oil (10.37 g, 8.6%). $^1$H NMR (270 MHz, CDCl$_3$) δ ppm 6.23 (s, 1H).

*Previously described in Rec. Trav. Chim. Pays-Bas 1995, 114, 97-102.

Intermediate 43

3,3,3-Trifluoro-2-oxopropanal*

3,3-Dibromo-1,1,1-trifluoroacetone (10.37 g, 38.43 mmol; Intermediate 42) was dissolved in water (51.85 g). NaOAc (12.61 g, 153.72 mmol) was added and the resulting mixture was stirred at 100° C. overnight. Extracted the mixture with EtOAc (50 mL) and evaporated the solvents from the organic phase. The residue was redissolved in EtOAc (20 mL) and filtration yielded 3,3,3-trifluoro-2-oxopropanal (1.35 g, 24%).

*Previously described in Rec. Trav. Chim. Pays-Bas 1995, 114, 97-102.

Intermediate 44

1-Benzyl-3-(trifluoromethyl)piperazine*

A solution of 3,3,3-trifluoro-2-oxopropanal (0.31 g, 2.3 mmol; Intermediate 43) in DMF (10 mL) was cooled to 0° C. and a solution of N-benzylethane-1,2-diamine (0.37 g, 2.72 mmol) in DMF (10 mL) was added. After being stirred at room temperature overnight, the mixture was concentrated in vacuo. The residue was redissolved in THF (5 mL) and citrate buffer (5.3 mL; 0.4 M), followed by NaBH$_3$CN (0.31 g, 4.9 mmol), were added. The resulting mixture was stirred at room temperature overnight. The mixture was made basic (pH 8) with aqueous NaOH (8 mL; 1 M) and the aqueous layer was extracted twice with DCM (15 mL). The combined organic layers were dried (Na$_2$SO$_4$) and concentrated. The residue was purified by LC-MS prep to give 1-benzyl-3-(trifluoromethyl)piperazine (66 mg, 12%). HPLC 94%, RT=1.25 min (System A; 10-97% MeCN over 3 min). $^1$H NMR (270 MHz, CDCl$_3$) δ ppm 2.77 (s, 2H) 3.17-3.31 (m, 1H) 3.32-3.64 (m, 3H) 3.83-4.02 (m, 1H) 4.13-4.31 (m, 2H) 6.68 (s, 1H) 7.30-7.55 (m, 5H). MS (ESI+) m/z 245.

*Previously described in Rec. Trav. Chim. Pays-Bas 1995, 114, 97-102.

Intermediate 45

2-(Trifluoromethyl)piperazine*

1-Benzyl-3-(trifluoromethyl)piperazine (0.74 g, 3.0 mmol; Intermediate 44) was dissolved in acetic acid (70 mL) and water (5 mL). Pd, 5% on carbon, (0.074 g) was added and =hydrogenation was performed at 3 bar and 70° C. overnight. The reaction mixture was filtered through Celite and the pad was rinsed with water (5 mL). Solvents were removed in vacuo, toluene (20 mL) added to the residue, followed by re-concentration in vacuo to remove residual water. The desired product sublimated on the evaporator and 0.15 g (32%) was collected as a white powder. $^1$H NMR (270 MHz, methanol-$d_4$) δ ppm 2.67-2.87 (m, 3H) 2.91-3.05 (m, 2H) 3.12-3.21 (m, 1H). MS (ESI+) m/z 155.

*Previously described in Rec. Trav. Chim. Pays-Bas 1995, 114, 97-102.

Intermediate 46

1-(5-Nitro-1-benzofuran-7-yl)-3-(trifluoromethyl) piperazine

To 7-iodo-5-nitro-1-benzofuran (231.4 mg, 0.08 mmol) the following was added: Xantphos (92.6 mg, 0.16 mmol), $Pd_2 dba_3$ (36.6 mg, 0.04 mmol), sodium tert-butoxide (215.4 mg, 2.24 mmol), 2-(trifluoromethyl)piperazine (148.1 mg, 0.96 mmol; Intermediate 45) and xylene (23 mL). The resulting mixture was stirred at 100° C. for 3 days. Filtration through Celite and purification by flash chromatography, using EtOAc:heptane (1:1) as eluent, furnished 1-(5-nitro-1-benzofuran-7-yl)-3-(trifluoromethyl)piperazine (112 mg, 44% yield). HPLC 90%, $R_T$=1.648 min (System A; 10-97% MeCN over 3 min), MS (ESI+) m/z 316 (M+H)$^+$.

Intermediate 47

7-[3-(Trifluoromethyl)piperazin-1-yl]-1-benzofuran-5-amine 1-(5-Nitro-1-benzofuran-7-yl)-3-(trifluoromethyl)piperazine (96.6 mg, 0.31 mmol; Intermediate 46) was dissolved in THF (6 mL) and EtOH (25 mL). Raney nickel (slurry in ethanol; 1 mL) and $H_2NNH_2$ (61.4 mg, 1.23 mmol) were added and the mixture was stirred at room temperature overnight. Filtration through Celite and concentration gave 7-[3-(trifluoromethyl)piperazin-1-yl]-1-benzofuran-5-amine (55 mg, 63%). This material was used in the next reaction step without further purification.

Example 79

2-Methoxy-5-methyl-N-{7-[3-(trifluoromethyl)piperazin-1-yl]-1-benzofuran-5-yl}benzenesulfonamide hydrochloride A mixture of 7-[3-(trifluoromethyl)piperazin-1-yl]-1-benzofuran-5-amine (59 mg, 0.19 mmol; Intermediate 47), pyridine (155 μL, 1.93 mmol) and 6-methoxy-m-toluene-sulfonyl chloride (42.6 mg, 0.19 mmol) in DCM (2 mL) was stirred at room temperature overnight. Volatiles were removed in vacuo. The residue was redissolved in MeOH (1.5 mL) and the solution was filtered. Addition of MeOH (100 μL), HCl in ether (500 μL) and ether (500 μL), followed by removal of solvents in vacuo furnished 2-methoxy-5-methyl-N-{7-[3-(trifluoromethyl)piperazin-1-yl]-1-benzofuran-5-yl}benzenesulfonamide hydrochloride as a brown oil (44.1 mg, 47%). HPLC 100%, $R_T$=1.861 min (System A; 10-97% MeCN over 3 min). $^1$H NMR (270 MHz, methanol-$d_4$) δ ppm 2.23 (s, 3H) 2.28 (s, 1H) 2.98-3.24 (m, 1H) 3.46-3.71 (m, 2H) 3.85 (s, 1H) 3.96 (s, 3H) 4.09-4.19 (m, 1H) 4.56-4.70 (m, 1H) 6.75 (d, J=1.98 Hz, 2H) 6.98 (d, J=1.73 Hz, 1H) 7.02 (s, 1H) 7.05 (s, 1H) 7.33 (dd, J=8.04, 2.60 Hz, 1H) 7.52 (d, J=1.73 Hz, 1H) 7.73 (d, J=2.23 Hz, 1H) 8.10-8.19 (m, 1H) 8.64-8.74 (m, 1H) 8.90 (d, J=5.20 Hz, 1H). MS (ESI+) m/z 470 (M+H)$^+$.

Intermediate 48 tert-Butyl[1-(5-nitro-1-benzofuran-7-yl)piperidin-4-yl]carbamate

Xylene (200 mL) was added to 7-iodo-5-nitro-1-benzofuran (2.78 g, 9.61 mmol), tert-butyl piperidin-4-ylcarbamate (2.31 g, 12.0 mmol), $Pd_2(dba)_3$ (0.22 g, 0.24 mmol), Xantphos (0.56 g, 0.96 mmol) and sodium tert-butoxide (1.29 g, 13.0 mmol). The mixture was heated at 120° C. with stirring for 16 h. The reaction mixture was allowed to reach room temperature, filtered through a pad of Celite, and concentrated in vacuo. The crude product was purified by flash chromatography, using DCM as eluent, to afford 1.03 g (84%) of the title product. HPLC 94%, $R_T$: 2.770 (System B; 10-97% MeCN over 3 min). $^1$H NMR (270 MHz, methanol-$d_4$) δ ppm 1.45 (s, 9H) 1.62-1.72 (m, 2H) 1.75-2.03 (m, 2H) 2.94-3.02 (m, 2H) 3.55-3.57 (m, 1H) 3.88-3.93 (m, 2H) 7.01 (d, J=2.23 Hz, 1H) 7.64 (d, J=2.23 Hz, 1H) 7.93 (d, J=2.23 Hz, 1H) 8.13 (d, J=2.23 Hz, 1H). LC-MS 362 (M+H)$^+$.

Intermediate 49 tert-Butyl[1-(5-amino-1-benzofuran-7-yl)piperidin-4-yl]carbamate

Hydrazine (1.038 mL, 28 mmol) and raney-nickel (slurry in ethanol; 10 mL) were added to tert-butyl[1-(5-nitro-1-benzofuran-7-yl)piperidine-4-yl]carbamate (1.03 g, 2.85 mmol; Intermediate 48) in a mixture of THF (50 mL) and ethanol (150 mL). The mixture was stirred at room temperature for 16 h, filtered through a pad of Celite and concentrated in vacuo to afford 1.02 g (quantitative) of the title product. HPLC 95%, $R_T$: 1.746 (System A; 10-97% MeCN over 3 min). $^1$H NMR (270 MHz, methanol-$d_4$) δ ppm 1.45 (s, 9H) 1.65-1.69 (m, 2H) 1.72-1.96 (m, 2H) 2.76-2.85 (m, 2H) 3.50-3.54 (m, 1H) 3.76 (d, J=12.62 Hz, 2H) 6.33 (d, J=1.98 Hz, 1H) 6.54 (d, J=1.98 Hz, 1H) 6.60 (d, J=2.23 Hz, 1H) 7.59 (d, J=1.98 Hz, 1H). LC-MS 332 (M+H)$^+$.

Example 80

N-[7-(Aminopiperidin-1-yl)-1-benzofuran-5-yl]-2-(trifluoromethyl)-benzenesulfonamide hydrochloride 2-(Trifluoromethyl)benzenesulfonyl chloride (89.0 mg, 0.36 mmol) and pyridine (219 mL) were added to tert-butyl [1-(5-amino-1-benzofuran-7-yl)piperidin-4-yl]carbamate (100.0 mg, 0.30 mmol; Intermediate 49) in DCM (1 mL). The mixture was shaken at room temperature for 1 h, solvent removed in vacuo and the residue was purified by preparative HPLC using acetonitrile-water gradients containing 0.1% trifluoroacetic acid. N-deprotection and conversion into the hydrochloride salt was performed by treatment with 2 M HCl in ether. This furnished 76.1 mg (57%) of the title product. HPLC 100%, $R_T$: 1.834 (System A; 10-97% MeCN over 3 min). $^1$H NMR (500 MHz, DMSO-$d_6$) δ ppm 1.70-1.72 (m, 2H) 2.00-2.02 (m, 2H) 2.78 (t, J=11.30 Hz, 2H) 3.21 (s, 1H) 3.71 (d, J=12.56 Hz, 2H) 6.60 (d, J=1.88 Hz, 1H) 6.83 (d, J=2.20 Hz, 1H) 6.85-6.91 (m, J=1.88 Hz, 1H) 7.80-7.81 (m, 2H) 7.88-7.89 (m, 1H) 7.96-7.98 (m, 1H) 8.08-8.10 (m, 4H) 10.40 (s, 1H). LC-MS 440 (M+H)$^+$.

Example 81

N-[7-(Aminopiperidin-1-yl)-1-benzofuran-5-yl]-benzenesulfonamide hydrochloride

Benzenesulfonyl chloride (64.0 mg, 0.36 mmol) and pyridine (219 µL) were added to tert-butyl[1-(5-amino-1-benzofuran-7-yl)piperidin-4-yl]carbamate (100.0 mg, 0.30 mmol; Intermediate 49) in DCM (1 mL). The mixture was shaken at room temperature for 1 h, solvent was removed in vacuo and the residue was purified by preparative HPLC using acetonitrile-water gradients containing 0.1% trifluoroacetic acid. N-deprotection and conversion into the hydrochloride salt was performed by treatment with 2 M HCl in ether. This furnished 31.3 mg (28%) of the title product. HPLC 100%, $R_T$: 1.612 (System A; 10-97% MeCN over 3 min). $^1$H NMR (500 MHz, DMSO-$d_6$) δ ppm 1.69-1.70 (m, 2H) 2.00-2.01 (m, 2H) 2.76 (t, J=11.30 Hz, 2H) 3.18-3.26 (m, 1H) 6.54 (d, J=1.88 Hz, 1H) 6.82 (d, J=2.20 Hz, 1H) 6.86 (d, J=1.88 Hz, 1H) 7.52 (t, J=7.54 Hz, 2H) 7.57-7.68 (m, 1H) 7.71-7.72 (m, 2H) 7.88 (d, J=2.20 Hz, 1H) 8.14 (s, 3H) 10.03 (s, 1H). LC-MS 372 (M+H)$^+$.

Example 82

N-[7-(Aminopiperidin-1-yl)-1-benzofuran-5-yl]-2-chlorobenzenesulfonamide hydrochloride 2-Chlorobenzenesulfonyl chloride (76.0 mg, 0.36 mmol) and pyridine (219 mL) were added to tert-butyl[1-(5-amino-1-benzofuran-7-yl)piperidin-4-yl]carbamate (100.0 mg, 0.30 mmol; Intermediate 49) in DCM (1 mL). The mixture was shaken at room temperature for 1 h, solvent was removed in vacuo and the residue was purified by preparative HPLC using acetonitrile-water gradients containing 0.1% trifluoroacetic acid. N-deprotection and conversion into the hydrochloride salt was performed by treatment with 2 M HCl in ether. This furnished to 60.6 mg (50%) of the title product. HPLC 100%, $R_T$: 1.702 (System A; 10-97% MeCN over 3 min). $^1$H NMR (500 MHz, DMSO-$d_6$) δ ppm 1.69-1.72 (m, 2H) 2.01-2.02 (m, 2H) 2.76 (t, J=11.62 Hz, 2H) 3.21 (s, 1H) 3.68 (d, J=12.56 Hz, 2H) 6.58 (s, 1H) 6.82 (d, J=2.20 Hz, 1H) 6.88 (s, 1H) 7.47 (t, J=7.54 Hz, 1H) 7.62-7.63 (m, 2H) 7.87 (d, J=1.88 Hz, 1H) 7.99 (d, J=7.54 Hz, 1H) 8.23 (s, 3H) 10.33 (s, 1H). LC-MS 406 (M+H)$^+$.

Example 83

N-[7-(Aminopiperidin-1-yl)-1-benzofuran-5-yl]-2-methoxy-5-methylbenzenesulfonamide hydrochloride 2-Methoxy-5-methylbenzenesulfonyl chloride (80.0 mg, 0.36 mmol) and pyridine (219 mL) were added to tert-butyl [1-(5-amino-1-benzofuran-7-yl)piperidin-4-yl]carbamate (100.0 mg, 0.30 mmol; Intermediate 49) in DCM (1 mL). The mixture was shaken at room temperature for 1 h, solvent was removed in vacuo and the residue was purified by preparative HPLC using acetonitrile-water gradients containing 0.1% trifluoroacetic acid. N-deprotection and conversion into the hydrochloride salt was performed by treatment with 2 M HCl in ether. This furnished 59.0 mg (47%) of the title product. HPLC 100%, $R_T$: 1.731 (System A; 10-97% MeCN over 3 min). $^1$H NMR (500 MHz, DMSO-$d_6$) δ ppm 1.70-1.76 (m, 2H) 2.05 (d, J=10.05 Hz, 2H) 2.20 (s, 3H) 2.76 (t, J=11.46 Hz, 2H) 3.19-3.21 (m, 1H) 3.65 (d, J=12.56 Hz, 2H) 3.87 (s, 3H) 6.58 (d, J=1.88 Hz, 1H) 6.81 (d, J=2.20 Hz, 1H) 6.89 (d, J=1.88 Hz, 1H) 7.04 (d, J=8.48 Hz, 1H) 7.32 (dd, J=8.48, 2.20 Hz, 1H) 7.51 (d, J=2.20 Hz, 1H) 7.86 (d, J=1.88 Hz, 1H) 8.35 (d, J=3.45 Hz, 3H) 9.65 (s, 1H). LC-MS 416 (M+H)$^+$.

Intermediate 50 tert-Butyl cis-3-fluoro-4-[(5-nitro-1-benzofuran-7-yl)oxy]piperidine-1-carboxylate and Intermediate 51 tert-Butyl trans-3-fluoro-4-[(5-nitro-1-benzofuran-7-yl)oxy]piperidine-1-carboxylate 7-Iodo-5-nitrobenzofuran (2.0 g, 6.9 mmol), tert-butyl 3-fluoro-4-hydroxypiperidine-1-carboxylate* (3.8 g, 17.3 mmol; mixture of cis/trans isomers), 1,10-phenanthroline (0.50 g, 2.8 mmol), CuI (0.26 g, 1.4 mmol) and Cs$_2$CO$_3$ (4.5 g, 13.8 mmol) were heated in toluene (20 mL) at 120° C. for 72 h. The reaction mixture was filtered through Celite and evaporated. The resulting diastereomers were separated by flash chromatography using heptane/EtOAc [(4:1)→(2:1)] to yield 255 mg of the cis-isomer and 919 mg of the trans-isomer.
*Prepared according to the procedure described in WO2001085728.

cis-isomer (Intermediate 50): Yield: 10%, HPLC purity=70%, m/z=381 (M+H)$^+$.

trans-isomer (Intermediate 51): Yield: 35%, HPLC purity=94%, m/z=381 (M+H)$^+$.

Intermediate 52 tert-Butyl cis-4-[(5-amino-1-benzofuran-7-yl)oxy]-3-fluoropiperidine-1-carboxylate To a solution of tert-butyl cis-3-fluoro-4-[(5-nitro-1-benzofuran-7-yl)oxy]piperidine-1-carboxylate (200 mg, 0.526 mmol; Intermediate 50) dissolved in THF (10 mL) and ethanol (40 mL), was added Raney-nickel (as a slurry in ethanol) and hydrazine hydrate (0.2 mL). The mixture was stirred at room temperature for 30 min and then filtered through Celite and evaporated. The residue was re-dissolved in toluene and evaporated again. This material was used directly in the subsequent experiment.

Intermediate 53 tert-Butyl trans-4-[(5-amino-1-benzofuran-7-yl)oxy]-3-fluoropiperidine-1-carboxylate The title compound was prepared from Intermediate 51 according to the procedure of Intermediate 52 and was used directly in the subsequent experiment.

Example 84

N-(7-{[cis-3-Fluoropiperidin-4-yl]oxy}-1-benzofuran-5-yl)-2-methoxy-5-methylbenzenesulfonamide hydrochloride To a solution of tert-butyl cis-4-[(5-amino-1-benzofuran-7-yl)oxy]-3-fluoropiperidine-1-carboxylate (92 mg, 0.263 mmol; Intermediate 52) in dichloromethane (3 mL) was added 6-methoxy-m-toluenesulfonyl chloride (70 mg, 0.315 mmol) and triethylamine (73 μl, 0.525 mmol). The mixture was shaken at room temperature for 1 h and then evaporated. Purified by preparative HPLC (gradient 50-85% MeCN in TFA/water). The residue was dissolved in methanol (0.5 mL) and HCl/ether (2 mL). After the solution had been stirred for 2 h, the solvent was evaporated to furnish the title compound. Yield: 25 mg (20%), HPLC purity=95%, m/z=435 (M+H)$^+$, $^1$H NMR (270 MHz, methanol-d$_4$) δ ppm 1.90-2.37 (m, 2H) 2.16-2.26 (m, 3H) 3.14-3.46 (m, 2H) 3.48-3.74 (m, 2H) 3.92-3.98 (m, 3H) 4.73-4.88 (m, 1H) 4.89-5.12 (m, 1H) 6.72 (d, J=2.23 Hz, 0.2H, rotamers) 6.75 (d, J=1.98 Hz, 1H) 6.80 (d, J=1.98 Hz, 0.2H, rotamers) 6.87 (d, J=1.98 Hz, 1H) 6.95 (d, J=1.98 Hz, 0.2H, rotamers) 6.98-7.05 (m, 2H) 7.27-7.35 (m, 1H) 7.50-7.53 (m, 1H) 7.72 (d, J=2.23 Hz, 1H).

Example 85

N-(7-{[trans-3-Fluoropiperidin-4-yl]oxy}-1-benzofuran-5-yl)-2-methoxy-5-methylbenzenesulfonamide hydrochloride The title compound was prepared according to the same procedure as Example 84 starting from tert-butyl trans-4-[(5-amino-1-benzofuran-7-yl)oxy]-3-fluoropiperidine-1-carboxylate (Intermediate 53) and 6-methoxy-m-toluenesulfonyl chloride. Yield: 8 mg (5%), HPLC purity=92%, m/z=435 (M+H)$^+$, $^1$H NMR (270 MHz, methanol-d$_4$) δ ppm 2.12-2.30 (m, 2H) 2.21 (s, 3H) 3.14-3.34 (m, 2H) 3.37-3.53 (m, 1H) 3.63-3.79 (m, 1H) 3.95 (s, 3H) 4.72-4.83 (m, 1H) 4.95-5.20 (m, 1H) 6.73 (d, J=2.23 Hz, 1H) 6.84 (d, J=1.73 Hz, 1H) 6.99 (d, J=1.98 Hz, 1H) 7.00-7.05 (m, 1H) 7.28-7.35 (m, 1H) 7.50 (d, J=1.98 Hz, 1H) 7.70 (d, J=1.98 Hz, 1H).

Example 86

N-(7-{[cis-3-Fluoropiperidin-4-yl]oxy}-1-benzofuran-5-yl)-2-(trifluoromethyl)benzenesulfonamide hydrochloride The title compound was prepared according to the procedure described for Example 84 using 2-(trifluoromethyl)benzenesulfonyl chloride. Yield: 27 mg (21%), HPLC purity=100%, m/z=459 (M+H)$^+$, $^1$H NMR (270 MHz, methanol-d$_4$) δ ppm 1.94-2.37 (m, 2H) 3.14-3.49 (m, 3H) 3.53-3.70 (m, 1H) 4.78-5.16 (m, 2H) 6.74 (d, J=2.23 Hz, 0.3H, rotamers) 6.77 (d, J=2.23 Hz, 1H) 6.79 (d, J=1.98 Hz, 0.3H, rotamers) 6.87 (d, J=1.98 Hz, 1H) 6.95 (d, J=1.98 Hz, 0.3H, rotamers) 7.02 (d, J=1.98 Hz, 1H) 7.61-7.74 (m, 3H) 7.75 (d, J=2.23 Hz, 1H) 7.88-7.95 (m, 1H) 7.98-8.06 (m, 1H).

Example 87

N-(7-{[trans-3-Fluoropiperidin-4-yl]oxy}-1-benzofuran-5-yl)-2-(trifluoromethyl)benzenesulfonamide hydrochloride The title compound was prepared according to the procedure described for Example 84 starting from tert-butyl trans-4-[(5-amino-1-benzofuran-7-yl)oxy]-3-fluoropiperidine-1-carboxylate (Intermediate 53) and 2-(trifluoromethyl)benzenesulfonyl chloride. Yield: 49 mg (25%), HPLC purity=100%, m/z=459 (M+H)$^+$, $^1$H NMR (270 MHz, methanol-d$_4$) δ ppm 2.13-2.31 (m, 2H) 3.15-3.56 (m, 3H) 3.64-3.79 (m, 1H) 4.77-4.97 (m, 1H) 5.00-5.24 (m, 1H) 6.75 (d, J=1.98 Hz, 1H) 6.81-6.84 (m, 1H) 6.99 (d, J=1.73 Hz, 1H) 7.60-7.77 (m, 3H) 7.87-7.95 (m, 1H) 7.98-8.05 (m, 1H).

Example 88

2-Chloro-N-(7-{[trans-3-fluoropiperidin-4-yl]oxy}-1-benzofuran-5-yl)benzenesulfonamide hydrochloride The title compound was prepared according to the procedure described for Example 84 starting from tert-butyl trans-4-[(5-amino-1-benzofuran-7-yl)oxy]-3-fluoropiperidine-1-carboxylate (Intermediate 53) and 2-chlorobenzenesulfonyl chloride. Yield: 40 mg (22%), HPLC purity=100%, m/z=425 (M+H)$^+$, $^1$H NMR (270 MHz, methanol-d$_4$) δ ppm 2.09-2.35 (m, 2H) 3.10-3.57 (m, 3H) 3.62-3.79 (m, 1H) 4.73-4.96 (m, 1H) 4.97-5.23 (m, 1H) 6.74 (d, J=2.23 Hz, 1H) 6.85 (d, J=1.98 Hz, 1H) 7.05 (d, J=1.73 Hz, 1H) 7.31-7.40 (m, 1H) 7.45-7.58 (m, 2H) 7.71 (d, J=2.23 Hz, 1H) 7.96 (dd, J=7.79, 1.61 Hz, 1H).

Example 89

N-(7-{[trans-3-Fluoropiperidin-4-yl]oxy}-1-benzofuran-5-yl)-3-methylbenzenesulfonamide hydrochloride The title compound was prepared according to the procedure described for Example 84 starting from tert-butyl trans-4-[(5-amino-1-benzofuran-7-yl)oxy]-3-fluoropiperidine-1-carboxylate (Intermediate 53) and 3-methylbenzenesulfonyl chloride. Yield: 47 mg (27%), HPLC purity=100%, m/z=405 (M+H)$^+$, $^1$H NMR (270 MHz, methanol-d$_4$) δ ppm 2.12-2.34 (m, 2H) 2.28-2.34 (m, 3H) 3.15-3.57 (m, 3H) 3.64-3.78 (m, 1H) 4.73-4.97 (m, 1H) 4.98-5.21 (m, 1H) 6.71-6.79 (m, 2H) 7.25-7.57 (m, 4H) 7.70-7.74 (m, 1H).

Example 90

3,6-Dichloro-N-(7-{[trans-3-fluoropiperidin-4-yl]oxy}-1-benzofuran-5-yl)-2-methylbenzenesulfonamide hydrochloride The title compound was prepared according to the procedure described for Example 84 starting from tert-butyl trans-4-[(5-amino-1-benzofuran-7-yl)oxy]-3-fluoropiperidine-1-carboxylate (Intermediate 53) and 3,6-dichloro-2-methylbenzenesulfonyl chloride. Yield: 39 mg (19%), HPLC purity=98%, m/z=473 (M+H)$^+$, $^1$H NMR (270 MHz, methanol-d$_4$) δ ppm 2.11-2.34 (m, 2H) 2.47-2.54 (m, 3H) 3.14-3.56 (m, 3H) 3.63-3.79 (m, 1H) 4.76-4.97 (m, 1H) 4.97-5.22 (m, 1H) 6.77 (d, J=1.98 Hz, 1H) 6.83 (d, J=1.73 Hz, 1H) 7.06 (d, J=1.98 Hz, 1H) 7.26 (d, J=1.98 Hz, 1H) 7.50 (d, J=1.98 Hz, 1H) 7.74 (d, J=2.23 Hz, 1H).

Example 91

2-Chloro-5-fluoro-N-(7-{[trans-3-fluoropiperidin-4-yl]oxy}-1-benzofuran-5-yl)benzenesulfonamide hydrochloride The title compound was prepared according to the procedure described for Example 84 starting from tert-butyl trans-4-[(5-amino-1-benzofuran-7-yl)oxy]-3-fluoropiperidine-1-carboxylate (Intermediate 53) and 2-chloro-5-fluorobenzenesulfonyl chloride. Yield: 34 mg (18%), HPLC purity=100%, m/z=443 (M+H)$^+$, $^1$H NMR (270 MHz, methanol-d$_4$) δ ppm 2.11-2.36 (m, 2H) 3.15-3.58 (m, 3H) 3.63-3.81 (m, 1H) 4.77-4.98 (m, 1H) 5.00-5.24 (m, 1H) 6.75 (d, J=2.23 Hz, 1H) 6.85 (d, J=1.98 Hz, 1H) 7.05 (d, J=1.98 Hz, 1H) 7.09-7.20 (m, 1H) 7.42 (dd, J=8.66, 2.47 Hz, 1H) 7.72 (d, J=2.23 Hz, 1H) 7.97-8.06 (m, 1H).

Intermediate 54

2,3-Dihydro-benzofuran-5-sulfonyl chloride

Chlorosulphonic acid (43.4 g, 0.366 mol) in DCM (10 mL) was added to a cold solution (5° C.) of 2,3-dihydrobenzofuran (20 g, 0.166 mol) in DCM (200 mL). After the addition the reaction was left with stirring at room temperature overnight. The reaction mixture was quenched with water (150 mL) keeping the temperature below 10° C. The organic phase was separated and washed with an aqueous solution of NaHCO$_3$ (13.9 g dissolved in 150 mL of water). The organic solvents were evaporated to yield the title compound as a solid residue 3.3 g (23%). $^1$H NMR 270 MHz (CDCl$_3$) δ ppm 3.32 (t, J=8.91 Hz, 2H) 4.75 (t, J=8.91 Hz, 2H) 6.90 (d, J=9.15 Hz, 1H) 7.78-7.90 (m, 2H)

Intermediate 55

7-Iodo-2,3-dihydro-benzofuran-5-sulfonyl chloride

A solution of ICl (7.7 g, 47 mmol) in DCM (100 mL) was added dropwise to a solution of 2,3-dihydro-benzofuran-5-sulfonyl chloride (5 g, 23 mmol; Intermediate 54) in DCM (100 mL) at reflux temperature under nitrogen atmosphere. The reaction was heated at reflux overnight. The reaction mixture was cooled at room temperature and acetonitrile (50 mL) was added. The resultant mixture was washed with a saturated solution of NaHCO$_3$ and the organic phase was separated followed by elimination of the volatiles under vacuum to give 8 g of brown oil which was used to the next step without further purification. $^1$H NMR 270 MHz (CDCl$_3$) δ ppm 3.45 (t, J=8.91 Hz, 2H) 4.82 (t, J=8.91 Hz, 2H) 7.79 (d, J=1.48 Hz, 1H) 8.16 (d, J=1.98 Hz, 1H).

Intermediate 56

7-Iodo-benzofuran-5-sulfonyl chloride

AIBN (270 mg, 1.3 mmol) and NBS (2.5 g, 14 mmol) were added to 7-iodo-2,3-dihydro-benzofuran-5-sulfonyl chloride (4.4 g, 13 mmol; Intermediate 55) in chlorobenzene (30 mL) at 70° C. The heating was turned off one hour after the addition. Acetonitrile (30 mL) was added and the organic phase was washed with sodium sulphite in water. The organic phase was separated and the volatiles were evaporated to give 4 g (90%) of the title compound as yellow crystals. $^1$H NMR 270 MHz (CDCl$_3$) δ ppm 7.07 (d, J=2.23 Hz, 1H) 7.90 (d, J=2.23 Hz, 1H) 8.29-8.37 (m, 1H).

Intermediate 57

7-Iodo-N-(2-methoxy-5-methylphenyl)-1-benzofuran-5-sulfonamide

To a solution of 7-iodo-1-benzofuran-5-sulfonyl chloride (10.75 g, 31 mmol; Intermediate 56) in dichloromethane (200 mL) was added 5-methyl-2-methoxyaniline (4.25 g, 31 mmol) and pyridine (7.4 mL, 93 mmol) and allowed to stir at ambient temperature overnight. The dark red solution was washed with water, separated, dried and filtered through a plug of silica to remove most of the red impurity, and finally concentrated. Yield: 13.51 g (99%) red solid. HPLC 90% R$_T$=2.58 min (System A; 30-80% MeCN over 3 min), 1.75 min (System C; 2-95% MeCN over 2 min). $^1$H NMR (400 MHz, CDCl$_3$) δ ppm 2.23 (m, 3H) 3.52 (s, 3H) 6.54 (d, J=8.30 Hz, 1H) 6.79 (dd, J=8.42, 1.59 Hz, 1H) 6.86 (d, J=2.20 Hz, 1H) 6.96 (s, 1H) 7.31 (d, J=1.71 Hz, 1H) 7.71 (d, J=2.20 Hz, 1H) 7.95 (d, J=1.71 Hz, 1H) 8.04 (d, J=1.71 Hz, 1H). MS (ESI) for C$_{16}$H$_{14}$INO$_4$S m/z 444 (M+H).

Example 92

N-(2-Methoxy-5-methylphenyl)-7-[(3-methylpiperazin-1-yl)methyl]-1-benzofuran-5-sulfonamide hydrochloride Step 1. 7-(3-Methyl-piperazin-1-carbonyl)-benzofuran-5-sulfonic acid (2-methoxy-5-methyl-phenyl)-amide To 7-iodo-N-(2-methoxy-5-methylphenyl)-1-benzofuran-5-sulfonamide (100 mg, 0.23 mmol; Intermediate 57) was added 2-methylpiperazine (45 mg, 0.46 mmol), Herrmann's catalyst (25 mg, 0.02 mmol), Mo(CO)$_6$ (30 mg, 0.12 mmol) and K$_2$CO$_3$ (112 mg, 0.81 mmol) in diglyme (3 mL) and warmed in the StemBlock at 120° C. After 20 minutes, the mixture was filtered, diluted with ethyl acetate and washed with water. After concentration, the crude mixture was purified by preparative HPLC (Gilson; gradient 30-70% MeCN) to give, after making basic with NaOH and washing with water, the title amide product. Yield: 36 mg (36%). HPLC 88% R$_T$=1.09 (System C; 2-95% MeCN over 2 min). MS (ESI) for C$_{22}$H$_{25}$N$_3$O$_5$S m/z 444 (M+H).

Step 2. N-(2-Methoxy-5-methylphenyl)-7-[(3-methylpiperazin-1-yl)methyl]-1-benzofuran-5-sulfonamide hydrochloride To the obtained 7-(3-methyl-piperazin-1-carbonyl)-benzofuran-5-sulfonic acid (2-methoxy-5-methyl-phenyl)-amide (30 mg, 0.07 mmol; Step 1) was added LiAlH$_4$ (9.0 mg, 0.24 mmol) in dry THF (4 mL) and the mixture was warmed to reflux. After 1 h, HPLC analysis showed 15% product and the remaining impurities. Added mixture to 2 M HCl, concentrated and purified by preparative HPLC (Gilson; gradient of 30-70% MeCN). The pure fractions were stripped, HCl/ether added and concentrated to give the title compound as a colourless solid. Yield: 1.3 mg (5%). HPLC 90% R$_T$=1.17 min (System A; 30-80% MeCN over 3 min), 1.13 min (System C; 2-95% MeCN over 2 min). $^1$H NMR (400 MHz, methanol-d$_4$) δ ppm 1.29 (d, J=7.0 Hz, 2H) 2.21 (s, 3H) 2.72 (m, 1H) 2.86 (m, 1H) 3.38 (s, 4H) 3.43-3.64 (m, 4H) 4.30 (d, J=6.59 Hz, 2H) 6.62 (d, J=8.30 Hz, 1H) 6.81-6.88 (m, 1H) 6.99 (d, J=2.44 Hz, 1H) 7.25 (d, J=1.95 Hz, 1H) 7.76 (br s, 1H) 7.94 (d, J=2.20 Hz, 1H) 8.08 (d, J=1.71 Hz, 1H). MS (ESI) for C$_{22}$H$_{27}$N$_3$O$_4$S m/z 430 (M+H).

Intermediate 58

7-Iodo-N-(2-methylphenyl)-1-benzofuran-5-sulfonamide

7-Iodo-1-benzofuran-5-sulfonyl chloride (10 g, 29.2 mmol; Intermediate 56) and 2-methyl aniline (3.43 mL, 32.1 mmol) were dissolved in dichloromethane (150 mL) and pyridine (3.53 mL, 43.8 mmol) was added. The solution was stirred overnight and washed with 1 M HCl (2×100 mL), dried over sodium sulfate and evaporated to give the crude solid product that was recrystallized from methanol. Yield: 5.32 g (44%) of a beige solid.

¹H NMR (400 MHz, CDCl₃) δ ppm 2.05 (s, 3H) 6.36 (s, 1H) 6.95 (d, J=2.3 Hz, 1H) 7.11-7.19 (m, 3H) 7.28 (d, J=7.5 Hz, 1H) 7.81 (d, J=2.3 Hz, 1H) 7.99 (d, J=1.8 Hz, 1H) 8.08 (d, J=1.8 Hz, 1H).

Intermediate 59

N-(2-Methylphenyl)-7-vinyl-1-benzofuran-5-sulfonamide

7-Iodo-N-(2-methylphenyl)-1-benzofuran-5-sulfonamide (0.41 g, 1 mmol; Intermediate 58), tributylvinyltin (0.32 mL, 1.1 mmol), bis(triphenylphosphine)palladium diacetate (10 mg) and acetonitrile (3 mL) were heated under microwave irradiation to 180° C. for 5 min. The mixture was cooled, filtered and evaporated. The resulting oil was washed with hexane (2×50 mL), dissolved in diethyl ether (50 mL), filtered and evaporated to give the crude product which was crystallized from ethanol:water (3:1). Yield 0.19 g (61%) of an off white solid. ¹H NMR (400 MHz, DMSO-d₆) δ ppm 1.93 (s, 3H) 5.57 (dd, J=11.3, 1.0 Hz, 1H) 6.12 (dd, J=17.8, 1.0 Hz, 1H) 6.84-7.07 (m, 6H) 7.62 (d, J=1.8 Hz, 1H) 7.84 (d, J=1.8 Hz, 1H) 8.14 (d, J=2.3 Hz, 1H) 9.43 (s, 1H).

Intermediate 60

7-Formyl-N-(2-methylphenyl)-1-benzofuran-5-sulfonamide

N-(2-Methylphenyl)-7-vinyl-1-benzofuran-5-sulfonamide (1.03 g, 3.3 mmol; Intermediate 59) was dissolved in dioxane (30 mL) and 2,6-lutidine (0.8 mL). Osmium tetroxide (84 mg, 0.33 mmol) was added with stirring followed by a solution of sodium periodate (2.82 g, 13.2 mmol) in water (10 mL). After stirring for 90 minutes, 1 M HCl (40 mL) was added followed by water (200 mL). The precipitated product was collected by filtration, washed with water and dried under vacuo. Yield: 0.95 g (91%) of an off white solid.
¹H NMR (400 MHz, CDCl₃) δ ppm 2.05 (s, 3H) 6.38 (s, 1H) 6.95 (d, J=2.3 Hz, 1H) 7.11 (dd, J=5.1, 1.1 Hz, 2H) 7.13-7.19 (m, 2H) 7.91 (d, J=2.3 Hz, 1H) 8.25 (dd, J=15.8, 1.8 Hz, 2H) 10.42 (s, 1H).

Example 93

N-(2-Methylphenyl)-7-(piperazin-1-ylmethyl)-1-benzofuran-5-sulfonamide, trifluoroacetate 7-Formyl-N-(2-methylphenyl)-1-benzofuran-5-sulfonamide (20 mg, 0.06 mmol; Intermediate 60), N-(tert-butoxycarbonyl)piperazine (13 mg, 0.07 mmol), acetic acid (36 µL, 0.63 mmol), sodium triacetoxyborohydride (27 mg, 0.13 mmol) were combined with dry THF (3 mL) and heated under microwave irradiation to 130° C. for 5 min. The solution was cooled, filtered and evaporated. The residue was dissolved in methanol (3 mL) and treated with concentrated hydrochloric acid (0.3 mL). This solution was heated under microwave irradiation to 100° C. for 5 min. The solvent was evaporated to give the crude product which was purified by preparative HPLC (Gilson system equipped with an ACE 5 C8 column (30×150 mm), Flow: 35 mL/min. Eluent: gradient 15-40% MeCN in 0.1% TFA in MilliQ water. Yield: 16 mg (50%). Analytical HPLC were performed on Agilent 1100, column: ACE 3 C8 (system A) or column: YMC-Pack (system B), eluents: MilliQ/0.1% TFA and MeCN. HPLC 99% $R_T$=1.48 (System A; 10-97% MeCN over 3 min) 99% $R_T$=1.31 (System B; 10-90% MeCN over 3 min). MS (ESI+) for C₂₀H₂₃N₃O₃S m/z 386 (M+1). ¹H NMR (400 MHz, methanol-d₄) δ ppm 1.89 (s, 3H) 2.65-2.72 (m, 4H) 3.10-3.17 (m, 4H) 3.95 (s, 2H) 6.92 (d, J=2.3 Hz, 1H) 6.96-6.99 (m, 2H) 6.99-7.02 (m, J=3.2, 1.8, 1.8 Hz, 2H) 7.51 (d, J=1.8 Hz, 1H) 7.87 (d, J=2.3 Hz, 1H) 7.96 (d, J=1.8 Hz, 1H).

Example 94

7-[(3,5-Dimethylpiperazin-1-yl)methyl]-N-(2-methylphenyl)-1-benzofuran-5-sulfonamide, trifluoroacetate The title compound was prepared according to the procedure described for Example 93, using 7-formyl-N-(2-methylphenyl)-1-benzofuran-5-sulfonamide (40 mg, 0.12 mmol; Intermediate 60) and 3,5-dimethylpiperazine (16 mg, 0.14 mmol) [Note: no HCl deprotection step]. Yield: 21.5 mg (40%). HPLC 97% $R_T$=1.57 (System A; 10-97% MeCN over 3 min) 99% $R_T$=1.39 (System B; 10-90% MeCN over 3 min). MS (ESI+) for C₂₂H₂₇N₃O₃S m/z 414 (M+1). ¹H NMR (400 MHz, methanol-d₄) δ ppm 1.19 (d, J=6.8 Hz, 6H) 1.91 (s, 3H) 2.11 (dd, J=12.7, 11.4 Hz, 2H) 2.96 (dd, J=12.9, 2.4 Hz, 2H) 3.27 (ddd, J=11.1, 6.7, 3.3 Hz, 2H) 3.91 (s, 2H) 6.90 (d, J=2.3 Hz, 1H) 6.95-7.03 (m, 4H) 7.57 (d, J=1.5 Hz, 1H) 7.86 (d, J=2.3 Hz, 1H) 7.91 (d, J=1.8 Hz, 1H).

Example 95

N-(2-Methylphenyl)-7-[(3-methylpiperazin-1-yl)methyl]-1-benzofuran-5-sulfonamide, trifluoroacetate The title compound was prepared according to the procedure described for Example 93, using 7-formyl-N-(2-methylphenyl)-1-benzofuran-5-sulfonamide (40 mg, 0.12 mmol; Intermediate 60) and 2-methylpiperazine (14 mg, 0.14 mmol). [Note: no HCl deprotection step]. Yield: 31.6 mg (59%). HPLC 99% $R_T$=1.50 (System A; 10-97% MeCN over 3 min) 99% $R_T$=1.33 (System B; 10-90% MeCN over 3 min). MS (ESI+) for C₂₁H₂₅N₃O₃S m/z 400 (M+1). ¹H NMR (400 MHz, methanol-d₄) δ ppm 1.20 (d, J=6.8 Hz, 3H) 1.90 (s, 3H) 2.33 (dd, J=12.7, 10.7 Hz, 1H) 2.47 (td, J=12.4, 3.1 Hz, 1H) 2.87-2.94 (m, J=12.8 Hz, 1H) 3.00-3.09 (m, 2H) 3.26-3.34 (m, J=10.0, 6.8, 6.8, 3.0 Hz, 2H) 3.94-4.04 (m, 2H) 6.92 (d, J=2.3 Hz, 1H) 6.97 (dt, J=5.0, 2.2 Hz, 2H) 7.01 (td, J=3.6, 2.0 Hz, 2H) 7.55 (d, J=1.8 Hz, 1H) 7.87 (d, J=2.0 Hz, 1H) 7.95 (d, J=1.8 Hz, 1H).

Example 96

7-(1,4-Diazepan-1-ylmethyl)-N-(2-methylphenyl)-1-benzofuran-5-sulfonamide, trifluoroacetate The title compound was prepared according to the procedure described for Example 93, using 7-formyl-N-(2-methylphenyl)-1-benzofuran-5-sulfonamide (40 mg, 0.12 mmol; Intermediate 60) and N-(tert-butoxycarbonyl)homopiperazine (28 mg, 0.14 mmol). Yield: 21.0 mg (31%). HPLC 99% $R_T$=1.34 (System A; 10-97% MeCN over 3 min) 99% $R_T$=1.18 (System B; 10-90% MeCN over 3 min). MS (ESI+) for C₂₁H₂₅N₃O₃S m/z 400 (M+1). ¹H NMR (400 MHz, methanol-d₄) δ ppm 1.94 (s, 3H) 2.10-2.17 (m, 2H) 3.28-3.35

(m, 4H) 3.49-3.59 (m, 4H) 4.60 (s, 2H) 6.92-7.04 (m, 5H) 7.72 (d, J=1.8 Hz, 1H) 7.94 (d, J=2.3 Hz, 1H) 8.09 (d, J=1.8 Hz, 1H).

Example 97

7-{(trans-2,5-Dimethylpiperazin-1-yl)methyl}-N-(2-methylphenyl)-1-benzofuran-5-sulfonamide, trifluoroacetate The title compound was prepared according to the procedure described for Example 93, using 7-formyl-N-(2-methylphenyl)-1-benzofuran-5-sulfonamide (80 mg, 0.24 mmol; Intermediate 60) and trans-2,5-dimethylpiperazine (58 mg, 0.48 mmol). [Note: no HCl deprotection step]. Yield: 32.2 mg (30%). HPLC 99% $R_T$=1.58 (System A; 10-97% MeCN over 3 min) 99% $R_T$=1.40 (System B; 10-90% MeCN over 3 min). MS (ESI+) for $C_{22}H_{27}N_3O_3S$ m/z 414 (M+1). $^1$H NMR (400 MHz, methanol-$d_4$) δ ppm 1.12 (d, J=6.5 Hz, 3H) 1.22 (d, J=5.8 Hz, 3H) 1.91 (s, 3H) 2.23 (dd, J=13.1, 11.3 Hz, 1H) 2.75-2.86 (m, 3H) 3.14-3.21 (m, 1H) 3.27 (dd, J=12.2, 2.4 Hz, 1H) 3.72 (d, J=14.3 Hz, 1H) 4.37 (d, J=14.3 Hz, 1H) 6.91 (d, J=2.3 Hz, 1H) 6.97-7.03 (m, 4H) 7.58 (d, J=1.8 Hz, 1H) 7.86 (d, J=2.3 Hz, 1H) 7.91 (d, J=1.8 Hz, 1H).

Example 98

N-(2-Methylphenyl)-7-{[(2R)-2-methylpiperazin-1-yl]methyl}-1-benzofuran-5-sulfonamide, trifluoroacetate The title compound was prepared according to the procedure described for Example 93, using 7-formyl-N-(2-methylphenyl)-1-benzofuran-5-sulfonamide (40 mg, 0.12 mmol; Intermediate 60) and (3R)-3-methyl-1-tritylpiperazine (48 mg, 0.14 mmol). Yield: 22.8 mg (35%). HPLC 96% $R_T$=1.49 (System A; 10-97% MeCN over 3 min) 96% $R_T$=1.31 (System B; 10-90% MeCN over 3 min). MS (ESI+) for $C_{21}H_{25}N_3O_3S$ m/z 400 (M+1).

$^1$H NMR (400 MHz, methanol-$d_4$) δ ppm 1.32 (d, J=6.3 Hz, 3H) 1.90 (s, 3H) 2.58-2.66 (m, 1H) 2.87-2.97 (m, 2H) 2.99-3.08 (m, 2H) 3.24-3.27 (m, 1H) 3.33 (dt, J=11.9, 1.8 Hz, 1H) 3.91 (d, J=14.1 Hz, 1H) 4.50 (d, J=14.1 Hz, 1H) 6.94 (d, J=2.3 Hz, 1H) 6.96-6.99 (m, 2H) 7.01 (dd, J=4.0, 2.8 Hz, 2H) 7.56 (d, J=1.8 Hz, 1H) 7.88 (d, J=2.0 Hz, 1H) 7.99 (d, J=1.8 Hz, 1H).

Intermediate 61

N-(2-Methoxy-5-methylphenyl)-7-vinyl-1-benzofuran-5-sulfonamide

Five batches each consisting of a mixture of N-(2-methoxy-5-methylphenyl)-7-iodo-1-benzofuran-5-sulfonamide (443 mg, 1.0 mmol; Intermediate 57), tributyl(vinyl)tin (350 mg, 1.1 mmol) and bis(triphenylphosphine)palladium diacetate (15 mg, 0.02 mmol) in acetonitrile (3 mL) was heated in a Smith Creator microwave oven to 180° C. for 5 min. The combined reaction mixtures were filtered and concentrated to give 2.0 g of crystalline crude material that was put through a $SiO_2$ column using EtOAc/hexane (gradient 5:95→25:75) as eluent giving 1.3 g (75%) of off-white crystalline product. $^1$H NMR (400 MHz, CDCl$_3$) δ 2.26 (s, 3H), 3.53 (s, 3H), 5.56 (dd, 1H), 6.16 (dd, 1H), 6.57 (d, 1H), 6.79-6.98 (m, 4H), 7.38 (d, 1H), 7.71-7.74 (m, 2H), 7.94 (d, 1H); MS (ESI+) for $C_{18}H_{17}NO_4S$ m/z 344 (M+H)$^+$.

Intermediate 62

7-Formyl-N-(2-methoxy-5-methylphenyl)-1-benzofuran-5-sulfonamide

Osmium tetroxide (84 mg, 0.33 mmol) was added to a solution of N-(2-methoxy-5-methylphenyl)-7-vinyl-1-benzofuran-5-sulfonamide (1.25 g, 3.3 mmol; Intermediate 61) and lutidine (0.71 g, 6.6 mmol) in dioxane (30 mL). A solution of sodium periodate (2.82 g, 13.2 mmol) in water (10 mL) was added under stirring. After 90 min, aqueous HCl (2 M; 40 mL) was added to give a clear solution. Addition of water (200 mL) gave a precipitate that was collected by filtration. This material was washed with water and dried to give 1.12 g (88%) of the title product. $^1$H NMR (400 MHz, CDCl$_3$) δ 2.27 (s, 3H), 3.55 (s, 3H), 6.57 (d, 1H), 6.80-6.85 (m, 1H), 6.92 (d, 1H), 7.02 (br s, 1H), 7.38 (d, 1H), 7.85 (d, 1H), 8.22 (d, 1H), 8.28 (d, 1H), 10.38 (s, 1H).

Example 99

N-(2-Methoxy-5-methylphenyl)-7-[(3-methylpiperazin-1-yl)methyl]-1-benzofuran-5-sulfonamide, trifluoroacetate A mixture of 7-formyl-N-(2-methoxy-5-methylphenyl)-1-benzofuran-5-sulfonamide (100 mg, 0.29 mmol; Intermediate 62), 2-methylpiperazine (32 mg, 0.32 mmol) and sodium triacetoxyborohydride (245 mg, 1.16 mmol) in 1,2-dichloroethane (3 mL) was stirred overnight. Filtration and concentration provided 100 mg of crude material that was purified by preparative HPLC to after concentration give 30 mg (19%) of the title product. $^1$H NMR (400 MHz, methanol-$d_4$) δ 1.27 (d, 3H), 2.24 (s, 3H), 2.33-2.40 (m, 1H), 2.46-2.55 (m, 1H), 2.91-2.98 (m, 1H), 3.05-3.17 (m, 2H), 3.32-3.38 (m, 1H), 3.39 (s, 3H), 3.96-4.08 (m, 2H), 6.64 (d, 1H), 6.87 (dd, 1H), 6.97 (d, 1H), 7.28 (d, 1H), 7.66 (d, 1H), 7.91 (d, 1H), 8.04 (d, 1H); MS (ESI+) for $C_{22}H_{27}N_3O_4S$ m/z 430 (M+H)$^+$; HPLC 99%, $R_T$=1.66 in (System A; 10-97% MeCN over 3 min), 99% $R_T$=1.46 (System B; 10-97% MeCN over 3 min).

Example 100

7-(1,4-Diazepan-1-ylmethyl)-N-(2-methoxy-5-methylphenyl)-1-benzofuran-5-sulfonamide, trifluoroacetate The title product was prepared according to the procedure of Example 99. Yield: 55 mg (69%). $^1$H NMR (400 MHz, methanol-$d_4$) δ 2.16-2.23 (m, 2H), 2.23 (s, 3H), 3.35-3.42 (m, 4H), 3.39 (s, 3H), 3.58-3.67 (m, 4H), 4.66 (s, 2H), 6.64 (d, 1H), 6.88 (dd, 1H), 7.05 (d, 1H), 7.28 (d, 1H), 7.84 (d, 1H), 7.98 (d, 1H), 8.18 (d, 1H); MS (ESI+) for $C_{22}H_{27}N_3O_4S$ m/z 430 (M+H)$^+$; HPLC 99%, $R_T$=1.50 in (System A; 10-97% MeCN over 3 min), 99% $R_T$=1.33 (System B; 10-97% MeCN over 3 min).

Example 101

N-(2-Methoxy-5-methylphenyl)-7-(piperazin-1-ylmethyl)-1-benzofuran-5-sulfonamide, trifluoroacetate The title product was prepared according to the procedure of Example 99. Yield:

26 mg (34%). $^1$H NMR (400 MHz, methanol-$d_4$) δ 2.24 (s, 3H), 2.91-2.96 (m, 4H), 3.26-3.32 (m, 4H), 3.38 (s, 3H), 4.17

(s, 2H), 6.63 (d, 1H), 6.87 (dd, 1H), 6.99 (d, 1H), 7.28 (d, 1H), 7.68 (d, 1H), 7.92 (d, 1H), 8.08 (d, 1H); MS (ESI+) for $C_{21}H_{25}N_3O_4S$ m/z 416 (M+H)$^+$; HPLC 99%, $R_T$=1.58 in (System A; 10-97% MeCN over 3 min), 99% $R_T$=1.39 (System B; 10-97% MeCN over 3 min).

Example 102

7-{(cis-3,5-Dimethylpiperazin-1-yl)methyl}-N-(2-methoxy-5-methylphenyl)-1-benzofuran-5-sulfonamide, trifluoroacetate The title product was prepared according to the procedure of Example 99. Yield: 39 mg (48%). $^1$H NMR (400 MHz, methanol-d$_4$) δ 1.26 (d, 6H), 2.20-2.28 (m, 2H), 2.23 (s, 3H), 3.03-3.08 (m, 2H), 3.32-3.39 (m, 2H), 3.41 (s, 3H), 4.01 (s, 2H), 6.65 (d, 1H), 6.86 (dd, 1H), 6.96 (d, 1H), 7.27 (d, 1H), 7.69 (d, 1H), 7.90 (d, 1H), 8.02 (d, 1H); MS (ESI+) for $C_{23}H_{29}N_3O_4S$ m/z 444 (M+H)$^+$; HPLC 99%, $R_T$=1.70 in (System A; 10-97% MeCN over 3 min), 99% $R_T$=1.50 (System B; 10-97% MeCN over 3 min).

Example 103

7-{[trans-2,5-Dimethylpiperazin-1-yl]methyl}-N-(2-methoxy-5-methylphenyl)-1-benzofuran-5-sulfonamide, trifluoroacetate The title product was prepared according to the procedure of Example 99. Yield: 11 mg (13%). $^1$H NMR (400 MHz, methanol-d$_4$) δ 1.17 (d, 3H), 1.26 (d, 3H), 2.16-2.24 (m, 1H), 2.24 (s, 3H), 2.72-2.78 (m, 1H), 2.82-2.91 (m, 2H), 3.19-3.25 (m, 1H), 3.30-3.35 (m, 1H), 3.41 (s, 3H), 3.71 (d, 1H), 4.36 (d, 1H), 6.66 (d, 1H), 6.87 (dd, 1H), 6.97 (d, 1H), 7.29 (d, 1H), 7.67 (d, 1H), 7.91 (d, 1H), 8.02 (d, 1H); MS (ESI+) for $C_{23}H_{29}N_3O_4S$ m/z 444 (M+H)$^+$; HPLC 99%, $R_T$=1.70 in (System A; 10-97% MeCN over 3 min), 99% $R_T$=1.49 (System B; 10-97% MeCN over 3 min).

Example 104

7-(2,5-Diazabicyclo[2.2.1]hept-2-ylmethyl)-N-(2-methoxy-5-methylphenyl)-1-benzofuran-5-sulfonamide, trifluoroacetate The title product was prepared according to the procedure of Example 99. Yield: 46 mg (73%). $^1$H NMR (400 MHz, CD$_3$OD) δ 2.20 (d, 1H), 2.23 (s, 3H), 2.54 (d, 1H), 3.38 (s, 3H), 3.44-3.50 (m, 2H), 3.56 (dd, 1H), 3.78 (dd, 1H), 4.28 (br s, 1H), 4.54 (br s, 1H), 4.61 (d, 1H), 4.71 (d, 1H), 6.64 (d, 1H), 6.88 (dd, 1H), 7.04 (d, 1H), 7.28 (d, 1H), 7.83 (d, 1H), 7.97 (d, 1H), 8.16 (d, 1H); MS (ESI+) for $C_{22}H_{25}N_3O_4S$ m/z 428 (M+H)$^+$; HPLC 99%, $R_T$=1.50 in (System A; 10-97% MeCN over 3 min), 99% $R_T$=1.32 (System B; 10-97% MeCN over 3 min).

Example 105

N-(2-Methoxy-5-methylphenyl)-7-[(2-methylpiperazin-1-yl)methyl]-1-benzofuran-5-sulfonamide, trifluoroacetate The title product was prepared according to the procedure of Example 99. Yield: 31 mg (49%). $^1$H NMR (400 MHz, methanol-d$_4$) δ 1.35 (d, 3H), 2.24 (s, 3H), 2.56-2.65 (m, 1H), 2.87-3.11 (overlapping m, 4H), 3.25-3.28 (m, 1H), 3.33-3.37 (m, 1H), 3.38 (s, 3H), 3.88 (d, 1H), 3.48 (d, 1H), 6.64 (d, 1H), 6.87 (dd, 1H), 6.98 (d, 1H), 7.29 (d, 1H), 7.66 (d, 1H), 7.92 (d, 1H), 8.07 (d, 1H); MS (ESI+) for $C_{22}H_{27}N_3O_4S$ m/z 430 (M+H)$^+$; HPLC 99%, $R_T$=1.58 in (System A; 10-97% MeCN over 3 min), 99% $R_T$=1.40 (System B; 10-97% MeCN over 3 min).

Intermediate 63

7-Methyl-5-nitro-1-benzofuran

7-Iodo-5-nitro-benzofuran (6.5 g, 22.1 mmol), Pd(OAc)$_2$ (1 g, 3.9 mmol), P(o-tolyl)$_3$, Me$_4$Sn, Et$_3$N were dissolved in DMF (40 mL) and portioned out in 13 tubes and heated at 100° C. for 10 min each using controlled microwave energy. The reaction mixtures were combined and filtered and the solvent was evaporated. The crude material was purified using flash chromatography (using a gradient of isohexane—10% EtOAc in isohexane). Yield: 2.82 g (70%) of 7-methyl-5-nitro-1-benzofuran. $^1$H NMR (400 MHz, CDCl$_3$) δ ppm 2.51-2.64 (m, 3H) 6.90 (d, J=2.3 Hz, 1H) 7.77 (d, J=2.3 Hz, 1H) 8.04 (d, J=1.3 Hz, 1H) 8.37 (d, J=2.3 Hz, 1H); HPLC 96% Rt=2.31 min (System A; 10-97% in 3 min ACE column). MS (ESI+) for $C_9H_7NO_3$ m/z 178 (M+H)$^+$.

Intermediate 64

7-(Bromomethyl)-5-nitro-benzofuran

7-Methyl-5-nitro-1-benzofuran (2.1 g, 12 mmol; Intermediate 63) was dissolved in CCl$_4$ and heated to 80° C. Benzoyl peroxide (0.43 g, 1.6 mmol) was added followed by NBS (2.1 g, 12 mmol) that was added in small portions. The reaction mixture was heated at reflux overnight with stirring. Additional benzoyl peroxide (0.08 mmol) and NBS (0.2 mmol) were added and the reaction mixture was stirred for one additional night. After this time, the mixture was filtered and concentrated. The crude was redissolved in DCM and washed with water. The organic solvent was dried (MgSO$_4$) and evaporated. The residue was purified using preparative HPLC with a gradient of 45-70% MeCN. This afforded 0.7 g (22%) of 7-(bromomethyl)-5-nitro-benzofuran as a solid. $^1$H NMR (400 MHz, CDCl$_3$) δ ppm 4.78 (s, 2H) 6.96 (d, J=2.3 Hz, 1H) 7.84 (d, J=2.3 Hz, 1H) 8.28 (d, J=2.3 Hz, 1H) 8.49 (d, J=2.3 Hz, 1H). HPLC Rt=1.9 min (System A; 30-80% MeCN over 3 min ACE column).

Example 106

2-Chloro-N-[7-(piperazin-1-ylmethyl)-1-benzofuran-5-yl]benzenesulfonamide dihydrochloride Step 1: tert-Butyl 4-[(5-nitro-1-benzofuran-7-yl)methyl]piperazine-1-carboxylate 7-(Bromomethyl)-5-nitro-benzofuran (145 mg, 70 mol % pure, 0.44 mmol; Intermediate 64), K$_2$CO$_3$ (181 mg, 1.31 mmol) and 1-boc-piperazine (98 mg, 0.53 mmol) were mixed in dry MeCN (5 mL) and heated to 80° C. while stirring for 2 h using a StemBlock. The solvent was evaporated under reduced pressure and the residue was partitioned between water and DCM (×2). The organic layers were combined, dried (Na$_2$SO$_4$) and purified using flashtube (10% MeOH in DCM). This afforded the title product (123 mg, 78%) as a light yellow solid. HPLC 98%, $R_T$=1.70 min (System A; 10-97% MeCN over 3 min), 99%, $R_T$=1.55 min (System B; 10-97% MeCN over 3 min). MS (ESI+) for $C_{18}H_{23}N_3O_5$ m/z 362 (M+H)$^+$.

Step 2: 4-(5-Amino-benzofuran-7-ylmethyl)-piperazine-1-carboxylic acid tert-butyl ester Raney nickel (slurry in ethanol) and hydrazine hydrate (66 µL, 1.36 mmol) were added to tert-butyl 4-[(5-nitro-1-benzofuran-7-yl)methyl]piperazine-1-carboxylate (123 mg, 0.34 mmol; obtained in Step 1) in ethanol:THF (4:1; 10 mL). The mixture was stirred at room temperature for 1 h. Unreacted starting material was still present and additional Raney nickel and hydrazine hydrate (33 µL, 0.68 mmol) were added with continuos stirring for 1 h. The mixture was filtered through a pad of Celite, which was rinsed several times with ethanol. Evaporation of the solvent gave 119 mg (quantitative) of the title amine as a green sticky oil which was used directly in the next step.

Step 3: 2-Chloro-N-[7-(piperazin-1-ylmethyl)-1-benzofuran-5-yl]benzenesulfonamide dihydrochloride Dry pyridine (20 µL, 0.24 mmol) and 2-chlorobenzenesulfonyl chloride (25 µL, 0.18 mmol) were added to a solution of 4-(5-amino-benzofuran-7-ylmethyl)-piperazine-1-carboxylic acid tert-butyl ester (40 mg, 0.12 mmol; obtained in Step 2) in a mixture of dry DCM:THF (2:1; 3 mL). The resulting mixture was stirred for 3 h and volatiles were then evaporated. The product was purified using flashtube (15% MeOH in DCM). The residue was dissolved in TFA:water (9:1; 2 mL) and the mixture was stirred at room temperature for 30 min to accomplish removal of the N-t-BOC group. The reaction mixture was made basic by addition of saturated aqueous $Na_2CO_3$ (pH 8-9) and extracted with DCM (×2). The organic layers were combined, dried ($Na_2SO_4$) and concentrated. The crude product was purified with preparative HPLC (System A; 10-40% MeCN). Pure fractions were combined and concentrated. The obtained TFA salt was dissolved in MeOH and 1 M HCl in ether was added, followed by concentration to give the title compound (10 mg, 18%) as a light yellow solid. HPLC 100%, $R_T$=1.38 min (System A; 10-97% MeCN over 3 min), 100%, $R_T$=1.23 min (System B; 10-97% MeCN over 3 min). $^1$H NMR (400 MHz, methanol-$d_4$) δ ppm 2.86-2.92 (m, 4H) 3.25-3.28 (m, 4H) 4.04-4.08 (m, 2H) 6.73 (d, J=2.26 Hz, 1H) 7.15 (d, J=2.01 Hz, 1H) 7.26-7.31 (m, 1H) 7.32 (d, J=2.26 Hz, 1H) 7.42-7.47 (m, 1H) 7.47-7.52 (m, 1H) 7.70 (d, J=2.26 Hz, 1H) 7.90 (dd, J=8.03, 1.51 Hz, 1H). MS (ESI+) for $C_{19}H_{20}ClN_3O_3S$ m/z 406 (M+H).

Example 107

2-Methyl-N-[7-(piperazin-1-ylmethyl)-1-benzo furan-5-yl]benzenesulfonamide, dihydrochloride The title compound was prepared according to the procedure of Example 106, Step 3, starting from 4-(5-amino-benzofuran-7-ylmethyl)-piperazine-1-carboxylic acid tert-butyl ester (40 mg, 0.12 mmol; obtained in Example 106, Step 2) and 2-methylbenzenesulfonyl chloride (26 µL, 0.18 mmol). The crude product was purified with preparative HPLC (System B; 10-40% MeCN). The title compound (10 mg, 19%) was obtained as a colorless solid. HPLC 99%, $R_T$=1.41 min (System A; 10-97% MeCN over 3 min), 99%, $R_T$=1.26 min (System B; 10-97% MeCN over 3 min). $^1$H NMR (400 MHz, methanol-$d_4$) δ ppm 2.66 (s, 3H) 3.50-3.65 (m, 8H) 4.67 (s, 2H) 6.86 (d, J=2.01 Hz, 1H) 7.22-7.29 (m, 1H) 7.30-7.37 (m, 2H) 7.40-7.48 (m, 2H) 7.81-7.90 (m, 2H). MS (ESI+) for $C_{20}H_{23}N_3O_3S$ m/z 386 (M+H)$^+$.

Example 108

N-[7-(piperazin-1-ylmethyl)-1-benzofuran-5-yl]thiophene-2-sulfonamide, dihydrochloride The title compound was prepared according to the procedure of Example 106, Step 3, starting from 4-(5-amino-benzofuran-7-ylmethyl)-piperazine-1-carboxylic acid tert-butyl ester (40 mg, 0.12 mmol; obtained in Example 106, Step 2) and 2-thiophenesulfonyl chloride (33 mg, 0.18 mmol). Additional 2-thiophenesulfonyl chloride (10 mg, 0.05 mmol) was added with continued stirring for 1 h. The crude product was purified with preparative HPLC (System B; 10-40% MeCN). The title compound (3 mg, 6%) was obtained as a colorless solid. HPLC 95%, $R_T$=1.25 min (System A; 10-97% MeCN over 3 min), 95%, $R_T$=1.11 min (System B; 10-97% MeCN over 3 min). $^1$H NMR (400 MHz, methanol-$d_4$) δ ppm 3.43-3.49 (m, 4H) 3.50-3.57 (m, 4H) 4.59 (s, 2H) 6.90 (d, J=2.26 Hz, 1H) 7.05 (dd, J=5.02, 3.76 Hz, 1H) 7.35 (d, J=2.26 Hz, 1H) 7.45-7.50 (m, 2H) 7.70 (dd, J=5.02, 1.51 Hz, 1H) 7.88 (d, J=2.26 Hz, 1H). MS (ESI+) for $C_{17}H_{19}N_3O_3S_2$ m/z 378 (M+H)$^+$.

Example 109

2-Chloro-N-[7-(1,4-diazepan-1-ylmethyl)-1-benzofuran-5-yl]benzenesulfonamide dihydrochloride Step 1: tert-Butyl 4-[(5-nitro-1-benzofuran-7-yl)methyl]-1,4-diazepane-1-carboxylate The title product, obtained as a light yellow solid, was prepared according to the procedure of Example 106, Step 1, starting from 1-boc-homopiperazine (103 µL, 0.53 mmol). Yield: 109 mg (66%). HPLC 98%, $R_T$=1.73 min (System A; 10-97% MeCN over 3 min), 100%, $R_T$=1.57 min (System B; 10-97% MeCN over 3 min). MS (ESI+) for $C_{19}H_{25}N_3O_5$ m/z 376 (M+H)$^+$.

Step 2: 4-(5-Amino-benzofuran-7-ylmethyl)-1,4-diazepane-1-carboxylic acid tert-butyl ester The title compound was prepared according to the procedure of Example 106, Step 2, starting from tert-butyl 4-[(5-nitro-1-benzofuran-7-yl)methyl]-1,4-diazepane-1-carboxylate (obtained in Step 1).

Step 3: 2-Chloro-N-[7-(1,4-diazepan-1-ylmethyl)-1-benzofuran-5-yl]benzenesulfonamide dihydrochloride The title compound was prepared according to the procedure of Example 106, Step 3, starting from 4-(5-amino-benzofuran-7-ylmethyl)-1,4-diazepane-1-carboxylic acid tert-butyl ester (36 mg, 0.10 mmol; obtained in Step 2) and 2-chlorobenzenesulfonyl chloride (21 µL, 0.16 mmol). The crude material was purified with preparative HPLC (System B; 10-40% MeCN). The title compound (16 mg, 33%) was obtained as a colorless solid. HPLC 95%, $R_T$=1.31 min (System A; 10-97% MeCN over 3 min), 96%, $R_T$=1.17 min (System B; 10-97% MeCN over 3 min). $^1$H NMR (400 MHz, methanol-$d_4$) δ ppm 2.25-2.37 (m, 2H) 3.41-3.48 (m, 2H) 3.48-3.59 (m, J=4.52 Hz, 2H) 3.69-3.75 (m, J=3.51 Hz, 2H) 3.74-3.83 (m, 2H) 4.70 (s, 2H) 6.86 (d, J=2.26 Hz, 1H) 7.36-7.41 (m, 1H) 7.42 (d, J=2.01 Hz, 1H) 7.51-7.59 (m, 3H) 7.85 (d, J=2.01 Hz, 1H) 8.00-8.04 (m, J=7.91, 1.13 Hz, 1H). MS (ESI+) for $C_{20}H_{22}ClN_3O_3S$ m/z 420 (M+H)$^+$.

Example 110

N-[7-(1,4-Diazepan-1-ylmethyl)-1-benzofuran-5-yl]-2-methylbenzenesulfonamide, dihydrochloride The title compound was prepared according to the procedure of Example 106, Step 3, starting from 4-(5-amino-benzofuran-7-ylmethyl)-1,4-diazepane-1-carboxylic acid tert-butyl ester (36 mg, 0.10 mmol; obtained in Example 109, Step 2) and 2-methylbenzenesulfonyl chloride (23 µL, 0.16 mmol). The title compound (13 mg, 28%) was obtained as a colorless solid. HPLC 99%, $R_T$=1.35 min (System A; 10-97% MeCN over 3 min), 100%, $R_T$=1.22 min (System B; 10-97%

MeCN over 3 min). ¹H NMR (400 MHz, methanol-$d_4$) δ ppm 2.26-2.32 (m, 2H) 2.66 (s, 3H) 3.40-3.60 (m, 4H) 3.69-3.83 (m, 4H) 4.69 (s, 2H) 6.86 (d, J=2.26 Hz, 1H) 7.23-7.29 (m, 1H) 7.32-7.38 (m, 2H) 7.41-7.46 (m, 1H) 7.47 (d, J=2.26 Hz, 1H) 7.84-7.90 (m, 2H). MS (ESI+) for $C_{21}H_{25}N_3O_3S$ m/z 400 (M+H)⁺.

Example 111

N-[7-(1,4-Diazepan-1-ylmethyl)-1-benzofuran-5-yl]thiophene-2-sulfonamide dihydrochloride The title compound was prepared according to the procedure of Example 106, Step 3, starting from 4-(5-amino-benzofuran-7-ylmethyl)-1,4-diazepane-1-carboxylic acid tert-butyl ester (36 mg, 0.10 mmol; obtained in Example 109, Step 2) and 2-thiophenesulfonyl chloride (29 mg, 0.16 mmol). Additional 2-thiophenesulfonyl chloride (10 mg, 0.06 mmol) was added with continuous stirring for 1 h. The title compound (10 mg, 22%) was obtained as a colorless solid. HPLC 100%, $R_T$=1.20 min (System A; 10-97% MeCN over 3 min), 100%, $R_T$=1.06 min (System B; 10-97% MeCN over 3 min). ¹H NMR (400 MHz, methanol-$d_4$) δ ppm 2.20-2.29 (m, 2H) 3.34-3.41 (m, 2H) 3.41-3.55 (m, 2H) 3.63-3.69 (m, 2H) 3.69-3.77 (m, 2H) 4.66 (s, 2H) 6.84 (d, J=2.26 Hz, 1H) 6.98 (dd, J=5.02, 3.76 Hz, 1H) 7.32 (d, J=2.01 Hz, 1H) 7.42 (dd, J=3.76, 1.25 Hz, 1H) 7.47 (d, J=2.26 Hz, 1H) 7.63 (dd, J=5.02, 1.25 Hz, 1H) 7.82 (d, J=2.26 Hz, 1H). MS (ESI+) for $C_{18}H_{21}N_3O_3S_2$ m/z 392 (M+H)⁺.

Example 112

2-Methoxy-5-methyl-N-{7-[(2-methylpiperazin-1-yl)methyl]-1-benzofuran-5-yl}benzenesulfonamide, dihydrochloride Step 1: tert-Butyl 3-methyl-4-[(5-nitro-1-benzofuran-7-yl)methyl]piperazine-1-carboxylate A mixture of 7-(bromomethyl)-5-nitro-1-benzofuran (120 mg, 70 mol %, 0.39 mmol; Intermediate 64), $K_2CO_3$ (162 mg, 1.17 mmol) and tert-butyl 3-methylpiperazine-1-carboxylate (94 mg, 0.47 mmol) in dry MeCN (5 mL) was heated at 80° C. while stirring for 1 h 45 min using a StemBlock. The solvent was evaporated under reduced pressure and the residue was partitioned between water and DCM (×2). The organic layers were combined, dried ($Na_2SO_4$) and purified using flashtube (10% MeOH in DCM). This afforded the title product (115 mg, 78%) as a light yellow sticky oil. HPLC 99%, $R_T$=2.47 min (System A; 5-60% MeCN over 3 min), 99%, $R_T$=2.27 min (System B; 5-60% MeCN over 3 min). MS (ESI+) for $C_{19}H_{25}N_3O_5$ m/z 376 (M+H)⁺.

Step 2: tert-Butyl 4-[(5-amino-1-benzofuran-7-yl)methyl]-3-methylpiperazine-1-carboxylate Raney nickel (slurry in ethanol) and hydrazine hydrate (97 μL, 2.0 mmol) were added to tert-butyl 3-methyl-4-[(5-nitro-1-benzofuran-7-yl)methyl]piperazine-1-carboxylate (115 mg, 0.31 mmol; obtained in Step 1) in ethanol:THF (4:1; 5 mL). The resulting mixture was stirred at room temperature for 1.5 h, followed by filtration through Celite. The Celite pad was rinsed several times with ethanol. The solvent was evaporated to give the crude product (136 mg) as a light green solid. This material was used in the next step without further purification. HPLC 98%, $R_T$=1.77 min (System A; 5-60% MeCN over 3 min), 100%, $R_T$=1.50 min (System B; 5-60% MeCN over 3 min). MS (ESI+) for $C_{19}H_{27}N_3O_3$ m/z 346 (M+H)⁺.

Step 3: 2-Methoxy-5-methyl-N-{7-[(2-methylpiperazin-1-yl)methyl]-1-benzofuran-5-yl}benzenesulfonamide, dihydrochloride Pyridine (17 μL, 0.20 mmol) and 6-methoxy-m-toluenesulfonyl chloride (34 mg, 0.15 mmol) were added to a solution of tert-butyl 4-[(5-amino-1-benzofuran-7-yl)methyl]-3-methylpiperazine-1-carboxylate (45 mg crude material, 0.10 mmol; obtained in Step 2) in dry DCM:THF (2:1; 3 mL). The reaction mixture was stirred at room temperature for 2 h and the solvent was evaporated under reduced pressure followed by purification by flashtube (15% MeOH in DCM). The residue was dissolved in TFA:water (9:1; 4.5 mL) and the mixture was stirred at room temperature for 1 h to accomplish removal of the N-t-BOC group. The reaction mixture was diluted with DCM (10 mL) and saturated aqueous $Na_2CO_3$ was added to reach pH 8-9 (~15 mL). The phases were separated using "phase separator" filters and the organic phase was concentrated. The crude product was purified by preparative HPLC (System B; 10-40% MeCN). Pure fractions were combined and concentrated to give the product as the free base, which was dissolved in MeOH and 1 M HCl in ether (200 μL, 0.2 mmol) was added. The solvent was evaporated to give the title compound (19 mg, 38%) as an off-white solid. HPLC 99%, $R_T$=1.46 min (System A; 10-97% MeCN over 3 min), 100%, $R_T$=1.29 min (System B; 10-97% MeCN over 3 min). ¹H NMR (400 MHz, methanol-$d_4$) δ ppm 1.72 (d, J=6.53 Hz, 3H) 2.20 (s, 3H) 3.39-3.62 (m, 5H) 3.67-3.74 (m, 1H) 3.87-3.96 (m, 1H) 3.98 (s, 3H) 4.60 (d, J=13.55 Hz, 1H) 4.93 (d, J=13.80 Hz, 1H) 6.87 (d, J=2.26 Hz, 1H) 7.04 (d, J=8.53 Hz, 1H) 7.28-7.37 (m, 2H) 7.52 (d, J=2.26 Hz, 1H) 7.54 (d, J=2.01 Hz, 1H) 7.85 (d, J=2.01 Hz, 1H). MS (ESI+) for $C_{22}H_{27}N_3O_4S$ m/z 430 (M+H)⁺.

Example 113

2-Methyl-N-{7-[(2-methylpiperazin-1-yl)methyl]-1-benzofuran-5-yl}benzenesulfonamide dihydrochloride The title product was prepared according to the procedure of Example 112, Step 3, starting from tert-butyl 4-[(5-amino-1-benzofuran-7-yl)methyl]-3-methylpiperazine-1-carboxylate (45 mg crude material, 0.10 mmol; obtained in Example 112, Step 2) and o-toluenesulfonyl chloride (22 μL, 0.15 mmol). The title compound (17 mg, 35%) was obtained as an off-white solid. HPLC 99%, $R_T$=1.42 min (System A; 10-97% MeCN over 3 min), 100%, $R_T$=1.26 min (System B; 10-97% MeCN over 3 min). ¹H NMR (400 MHz, methanol-$d_4$) δ ppm 1.69-1.74 (m, 3H) 2.67 (s, 3H) 3.37-3.62 (m, 5H) 3.67-3.75 (m, 1H) 3.84-3.95 (m, 1H) 4.57-4.65 (m, 1H) 4.90-4.97 (m, J=13.55 Hz, 1H) 6.86 (d, J=2.26 Hz, 1H) 7.23-7.29 (m, J=7.65, 7.65 Hz, 1H) 7.31 (d, J=2.01 Hz, 1H) 7.32-7.36 (m, 1H) 7.40-7.46 (m, 1H) 7.50 (d, J=2.01 Hz, 1H) 7.85-7.90 (m, 2H). MS (ESI+) for $C_{21}H_{25}N_3O_3S$ m/z 400 (M+H)⁺.

Example 114

2,5-Dichloro-N-{7-[(2-methylpiperazin-1-yl)methyl]-1-benzofuran-5-yl}thiophene-3-sulfonamide dihydrochloride The title product was prepared according to the procedure of Example 112, Step 3, starting from tert-butyl 4-[(5-amino-1-benzofuran-7-yl)methyl]-3-methylpiperazine-1-carboxylate (45 mg crude material, 0.10 mmol; obtained in Example 112, Step 2) and 2,5-dichlorothiophene-3-sulphonyl chloride (38 mg, 0.15 mmol). The title compound (23 mg, 43%) was obtained as an off-white solid. HPLC 98%, $R_T$=1.61 min (System A; 10-97% MeCN over 3 min), 100%, $R_T$=1.43 min (System B; 10-100% MeCN over 3 min). ¹H NMR (400 MHz, methanol-$d_4$) δ ppm 1.53 (d, J=6.27 Hz, 3H) 2.87-3.02 (m, 1H) 3.14-3.27 (m, 2H) 3.39-3.47 (m, 1H) 3.47-3.54 (m, 1H) 4.12-4.24 (m, 1H) 4.62-4.71 (m, 1H) 6.89 (d, J=2.26 Hz, 1H) 7.13 (s, 1H) 7.30-7.32 (m, J=1.76 Hz, 1H) 7.45 (d, J=2.26 Hz, 1H) 7.85 (d, J=2.26 Hz, 1H).
*Two hydrogens are not visible in the spectrum. Probably "hidden" behind the H$_2$O— and the MeOH signals. MS (ESI+) for C$_{18}$H$_{19}$Cl$_2$N$_3$O$_3$S$_2$ m/z 460 (M+H)$^+$.

Example 115

2-Methoxy-5-methyl-N-{7-[(3-methylpiperazin-1-yl)methyl]-1-benzofuran-5-yl}benzenesulfonamide, dihydrochloride Step 1: 3-Methyl-1-[(5-nitro-1-benzofuran-7-yl)methyl]piperazine The title compound was prepared according to the procedure of Example 112, Step 1, starting from 7-(bromomethyl)-5-nitro-1-benzofuran (120 mg, 70 mol %, 0.39 mmol; Intermediate 64) and 2-methylpiperazine (196 mg, 1.95 mmol). The crude product was purified by flash chromatography (eluent: 4% MeOH, 1% NEt$_3$ in DCM). The title compound (102 mg, 87%) was obtained as a light yellow sticky oil. HPLC 99%, R$_T$=1.60 min (System A; 5-60% MeCN over 3 min), 100%, R$_T$=1.40 min (System B; 5-60% MeCN over 3 min). MS (ESI+) for C$_{14}$H$_{17}$N$_3$O$_3$ m/z 276 (M+H)$^+$.

Step 2: tert-Butyl 2-methyl-4-[(5-nitro-1-benzofuran-7-yl)methyl]piperazine-1-carboxylate Di-tert-butyl dicarbonate (89 mg, 0.41 mmol) in dry DCM (2 mL) was added, with a syringe, under N$_2$ to 3-methyl-1-[(5-nitro-1-benzofuran-7-yl)methyl]piperazine (102 mg, 0.37 mmol; obtained in Step 1) and NEt$_3$ (77 µL, 0.77 mmol) in dry DCM (5 mL) at 0° C. The resulting mixture was allowed to attain room temperature and stirred for 1.5 h. The reaction mixture was diluted with DCM and saturated aqueous Na$_2$CO$_3$ was added. The organic layer was dried (Na$_2$SO$_4$) and concentrated followed by purification with flash chromatography (eluent: 1.5% MeOH in DCM). This gave the title compound (124 mg, 89%) as a white foam. HPLC 90%, R$_T$=2.53 min (System A; 5-60% MeCN over 3 min), 90%, R$_T$=2.35 min (System B; 5-60% MeCN over 3 min). MS (ESI+) for C$_{19}$H$_{25}$N$_3$O$_5$ m/z 376 (M+H)$^+$.

Step 3: tert-Butyl 4-[(5-amino-1-benzofuran-7-yl)methyl]-2-methylpiperazine-1-carboxylate The title compound was prepared according to the procedure of Example 112, Step 2, using tert-butyl 2-methyl-4-[(5-nitro-1-benzofuran-7-yl)methyl]piperazine-1-carboxylate (124 mg, 0.33 mmol; obtained in Step 2). The crude title compound (124 mg) was obtained as a light green solid. This material was used in the next step without further purification. HPLC 100%, R$_T$=1.82 min (System A; 5-60% MeCN over 3 min), 100%, R$_T$=1.57 min (System B; 5-60% MeCN over 3 min). MS (ESI+) for C$_{19}$H$_{27}$N$_3$O$_3$ m/z 346 (M+H)$^+$.

Step 4: 2-Methoxy-5-methyl-N-{7-[(3-methylpiperazin-1-yl)methyl]-1-benzofuran-5-yl}benzenesulfonamide, dihydrochloride tert-Butyl 4-[(5-amino-1-benzofuran-7-yl)methyl]-2-methylpiperazine-1-carboxylate (41 mg crude starting material, 0.11 mmol; obtained in Step 3) was dissolved in dry DCM: THF (2:1; 3 mL). Pyridine (18 µL, 0.22 mmol) and 6-methoxy-m-toluenesulfonyl chloride (36 mg, 0.17 mmol) were added. The resultant mixture was stirred at room temperature for 2 h and the solvent was evaporated under reduced pressure followed by purification by flashtube (11% MeOH in DCM). The residue was dissolved in TFA:water (9:1; 4.5 mL) and the mixture was stirred at room temperature for 1 h to accomplish removal of the N-t-BOC group. The reaction mixture was diluted with DCM (10 mL) and saturated aqueous Na$_2$CO$_3$ was added to reach pH 8-9 (~15 mL). The phases were separated using "phase separator" filters and the organic phase was concentrated. The crude product was purified by preparative HPLC (System B; 10-40% MeCN). Pure fractions were combined and concentrated to give the product as the free base, which was dissolved in MeOH and 1 M HCl in ether (200 µL, 0.2 mmol) was added. The solvent was evaporated to give the title compound (16 mg, 29%) as an off-white solid. HPLC 99%, R$_T$=1.48 min (System A; 10-97% MeCN over 3 min), 100%, R$_T$=1.30 min (System B; 10-97% MeCN over 3 min). $^1$H NMR (400 MHz, methanol-d$_4$) δ ppm 1.38-1.45 (m, J=6.53 Hz, 3H) 2.20 (s, 3H) 3.34-3.42 (m, J=13.30 Hz, 1H) 3.46-3.78 (m, 5H) 3.79-3.91 (m, 1H) 3.98 (s, 3H) 4.71 (s, 2H) 6.87 (d, J=2.26 Hz, 1H) 7.04 (d, J=8.53 Hz, 1H) 7.29-7.34 (m, J=8.78, 2.01 Hz, 1H) 7.37 (d, J=2.26 Hz, 1H) 7.51-7.53 (m, J=2.01 Hz, 1H) 7.54 (d, J=2.26 Hz, 1H) 7.85 (d, J=2.01 Hz, 1H). MS (ESI+) for C$_{22}$H$_{27}$N$_3$O$_4$S m/z 430 (M+H)$^+$.

Example 116

N-{7-[(3-Methylpiperazin-1-yl)methyl]-1-benzofuran-5-yl}-2-(trifluoromethyl)benzenesulfonamide, dihydrochloride The title compound was prepared according to the procedure of Example 115, Step 4, starting from tert-butyl 4-[(5-amino-1-benzofuran-7-yl)methyl]-2-methylpiperazine-1-carboxylate (41 mg crude starting material, 0.11 mmol; obtained in Example 115, Step 3) and 2-(trifluoromethyl)benzenesulfonyl chloride (25 µL, 0.17 mmol). The title compound (24 mg, 44%) was obtained as an off-white solid. HPLC 98%, R$_T$=1.56 min (System A; 10-97% MeCN over 3 min), 97%, R$_T$=1.37 min (System B; 10-97% MeCN over 3 min). $^1$H NMR (400 MHz, methanol-d$_4$) δ ppm 1.41 (d, J=6.53 Hz, 3H) 3.36-3.44 (m, J=13.30, 12.05 Hz, 1H) 3.47-3.78 (m, 5H) 3.81-3.94 (m, 1H) 4.74 (s, 2H) 6.88 (d, J=2.26 Hz, 1H) 7.41 (d, J=2.01 Hz, 1H) 7.53 (d, J=2.26 Hz, 1H) 7.68-7.76 (m, 2H) 7.88 (d, J=2.01 Hz, 1H) 7.90-7.95 (m, J=6.90, 2.13 Hz, 1H) 8.09-8.13 (m, 1H). MS (ESI+) for C$_{21}$H$_{22}$F$_3$N$_3$O$_3$S m/z 454 (M+H)$^+$.

Example 117

2-Chloro-N-{7-[(3-methylpiperazin-1-yl)methyl]-1-benzofuran-5-yl}benzenesulfonamide, dihydrochloride The title compound was prepared according to the procedure of Example 115, Step 4, starting from tert-butyl 4-[(5-amino-1-benzofuran-7-yl)methyl]-2-methylpiperazine-1-carboxylate (41 mg crude starting material, 0.11 mmol; obtained in Example 115, Step 3) and 2-chlorobenzenesulfonyl chloride (22 µL, 0.17 mmol). The title compound (21 mg, 39%) was obtained as an off-white solid. HPLC 100%, R$_T$=1.42 min (System A; 10-97% MeCN over 3 min), 100%, R$_T$=1.26 min (System B; 10-97% MeCN over 3 min). $^1$H NMR (400 MHz, methanol-d$_4$) δ ppm 1.41 (d, J=6.53 Hz, 3H) 3.32-3.37 (m, 1H) 3.45-3.59 (m, 2H) 3.63-3.76 (m, 3H) 3.78-3.89 (m, 1H) 4.70 (s, 2H) 6.86 (d, J=2.26 Hz, 1H) 7.36-7.41 (m, 1H) 7.42 (d, J=2.01 Hz, 1H) 7.49-7.54 (m, 1H) 7.54-7.58 (m, 2H) 7.86 (d, J=2.01 Hz, 1H) 8.02 (dd, J=7.91, 1.63 Hz, 1H). MS (ESI+) for C$_{20}$H$_{22}$ClN$_3$O$_3$S m/z 420 (M+H)$^+$.

Example 118

N-{7-[(1S,4S)-2,5-Diazabicyclo[2.2.1]hept-2-ylmethyl]-1-benzofuran-5-yl}-2-methoxy-5-methylbenzenesulfonamide, dihydrochloride Step 1: tert-Butyl (1S,4S)-5-[(5-nitro-1-benzofuran-7-yl)methyl]-2,5-diazabicyclo[2.2.1]heptane-2-carboxylate The title compound was prepared according to the procedure of Example 112, Step 1, starting from 7-(bromomethyl)-

5-nitro-1-benzofuran (120 mg, 70 mol %, 0.39 mmol; Intermediate 64) and tert-butyl (1S,4S)-(–)-2,5-diazabicyclo-(2.2.1)heptane-2-carboxylate (93 mg, 0.47 mmol). The title compound (115 mg, 79%) was obtained as a light yellow sticky oil. HPLC 99%, $R_T$=2.34 min (System A; 5-60% MeCN over 3 min), 99%, $R_T$=2.15 min (System B; 5-60% MeCN over 3 min). MS (ESI+) for $C_{19}H_{23}N_3O_5$ m/z 374 (M+H)$^+$.

Step 2: tert-Butyl (1S,4S)-5-[(5-amino-1-benzofuran-7-yl)methyl]-2,5-diazabicyclo[2.2.1]heptane-2-carboxylate The title compound was prepared according to the procedure of Example 112, Step 2, using tert-butyl (1S,4S)-5-[(5-nitro-1-benzofuran-7-yl)methyl]-2,5-diazabicyclo[2.2.1]heptane-2-carboxylate (116 mg, 0.31 mmol; obtained in Step 1). The title compound (133 mg) was obtained as a light green solid. This material was used in the next step without further purification. HPLC 99%, $R_T$=1.69 min (System A; 5-60% MeCN over 3 min), 100%, $R_T$=1.45 min (System B; 5-60% MeCN over 3 min). MS (ESI+) for $C_{19}H_{25}N_3O_3$ m/z 344 (M+H)$^+$.

Step 3: N-{7-[(1S,4S)-2,5-Diazabicyclo[2.2.1]hept-2-ylmethyl]-1-benzofuran-5-yl}-2-methoxy-5-methylbenzenesulfonamide, dihydrochloride The title compound was prepared according to the procedure of Example 112, Step 3, starting from tert-butyl (1S,4S)-5-[(5-amino-1-benzofuran-7-yl)methyl]-2,5-diazabicyclo[2.2.1]heptane-2-carboxylate (44 mg crude starting material, 0.10 mmol; obtained in Step 2) and 6-methoxy-m-toluenesulfonyl chloride (34 mg, 0.15 mmol). The title compound (11 mg, 20%) was obtained as an off-white solid. HPLC 100%, $R_T$=1.39 min (System A; 10-97% MeCN over 3 min), 100%, $R_T$=1.24 min (System B; 10-97% MeCN over 3 min). $^1$H NMR (400 MHz, methanol-$d_4$) δ ppm 2.20 (s, 3H) 2.28-2.34 (m, J=12.80 Hz, 1H) 2.61-2.70 (m, 1H) 3.52-3.58 (m, J=13.80, 2.76 Hz, 1H) 3.64-3.72 (m, J=13.30, 2.51 Hz, 1H) 3.85-3.93 (m, 1H) 3.98 (s, 3H) 4.48 (s, 1H) 4.65 (s, 1H) 4.70-4.76 (m, 1H) 4.77-4.82 (m, 1H) 6.87 (d, J=2.01 Hz, 1H) 7.04 (d, J=8.53 Hz, 1H) 7.30-7.34 (m, J=8.53, 2.26 Hz, 1H) 7.41 (d, J=2.26 Hz, 1H) 7.50 (d, J=2.01 Hz, 1H) 7.51-7.53 (m, J=2.26 Hz, 1H) 7.85 (d, J=2.26 Hz, 1H). MS (ESI+) for $C_{22}H_{25}N_3O_4S$ m/z 428 (M+H)$^+$.

Example 119

N-{7-[(1S,4S)-2,5-Diazabicyclo[2.2.1]hept-2-ylmethyl]-1-benzofuran-5-yl}-2-(trifluoromethyl)benzenesulfonamide, dihydrochloride The title compound was prepared according to the procedure of Example 112, Step 3, starting from tert-butyl (1S,4S)-5-[(5-amino-1-benzofuran-7-yl)methyl]-2,5-diazabicyclo[2.2.1]heptane-2-carboxylate (44 mg crude starting material, 0.10 mmol; obtained in Example 118, Step 2) and 2-(trifluoromethyl)benzenesulfonyl chloride (24 μL, 0.15 mmol). The title compound (18 mg, 34%) was obtained as an off-white solid. HPLC 99%, $R_T$=1.46 min (System A; 10-97% MeCN over 3 min), 100%, $R_T$=1.29 min (System B; 10-97% MeCN over 3 min). $^1$H NMR (400 MHz, methanol-$d_4$) δ ppm 2.31-2.37 (m, J=13.05 Hz, 1H) 2.65-2.78 (m, J=6.27 Hz, 1H) 3.53-3.60 (m, J=13.43, 2.89 Hz, 1H) 3.67-3.76 (m, 1H) 3.88-3.96 (m, J=12.80 Hz, 1H) 4.51 (s, 1H) 4.66 (s, 1H) 4.72-4.79 (m, 1H) 4.84 (d, 2H) 6.88 (d, J=2.01 Hz, 1H) 7.46 (d, J=2.01 Hz, 1H) 7.51 (d, J=2.01 Hz, 1H) 7.68-7.75 (m, 2H) 7.88 (d, J=2.26 Hz, 1H) 7.89-7.94 (m, 1H) 8.09-8.13 (m, 1H). MS (ESI+) for $C_{21}H_{20}F_3N_3O_3S$ m/z 452 (M+H)$^+$.

Example 120

N-{7-[(1S,4S)-2,5-Diazabicyclo[2.2.1]hept-2-ylmethyl]-1-benzofuran-5-yl}-2-methylbenzenesulfonamide, dihydrochloride The title compound was prepared according to the procedure of Example 112, Step 3, starting from tert-butyl (1S,4S)-5-[(5-amino-1-benzofuran-7-yl)methyl]-2,5-diazabicyclo[2.2.1]heptane-2-carboxylate (44 mg crude starting material, 0.10 mmol; obtained in Example 118, Step 2) and o-toluenesulfonyl chloride (22 μL, 0.15 mmol). The title compound (15 mg, 31%) was obtained as an off-white solid. HPLC 98%, $R_T$=1.37 min (System A; 10-97% MeCN over 3 min), 97%, $R_T$=1.21 min (System B; 10-97% MeCN over 3 min). $^1$H NMR (400 MHz, methanol-$d_4$) δ ppm 2.28-2.34 (m, 1H) 2.66 (s, 3H) 2.67-2.72 (m, 1H) 3.52-3.59 (m, J=13.68, 2.64 Hz, 1H) 3.63-3.76 (m, 1H) 3.85-3.93 (m, J=12.80 Hz, 1H) 4.45-4.51 (m, 1H) 4.65 (s, 1H) 4.69-4.78 (m, 1H) 4.78-4.83 (m, 2H) 6.86 (d, J=2.26 Hz, 1H) 7.23-7.29 (m, 1H) 7.31-7.36 (m, J=7.53 Hz, 1H) 7.37-7.46 (m, 2H) 7.48 (d, J=2.26 Hz, 1H) 7.84-7.88 (m, 2H). MS (ESI+) for $C_{21}H_{23}N_3O_3S$ m/z 398 (M+H)$^+$.

Example 121

2-Methoxy-5-methyl-N-{7-[(trans-2,5-dimethylpiperazin-1-yl)methyl]-1-benzofuran-5-yl}benzenesulfonamide, bis(trifluoroacetate)

Step 1: trans-2,5-Dimethyl-1-[(5-nitro-1-benzofuran-7-yl)methyl]piperazine

The title compound was prepared according to the procedure of Example 112, Step 1, starting from 7-(bromomethyl)-5-nitro-1-benzofuran (0.16 g, 0.6 mmol) and trans-2,5-dimethylpiperazine (0.36 g, 3.1 mmol). This afforded the title product (0.11 g, 60%) as a light yellow solid. HPLC 98% $R_T$=1.26 min (System A; 10-97% MeCN over 3 min). $^1$H NMR (400 MHz, CDCl$_3$) δ ppm 0.93 (d, J=6.3 Hz, 3H) 1.17 (d, J=6.0 Hz, 3H) 1.48 (br s, 1H) 1.79 (dd, J=11.0, 10.3 Hz, 1H) 2.29-2.41 (m, 1H) 2.63-2.75 (m, 2H) 2.80-2.89 (m, 1H) 2.93 (dd, J=12.0, 3.3 Hz, 1H) 3.61 (d, J=14.6 Hz, 1H) 4.28 (d, J=14.3 Hz, 1H) 6.91 (d, J=2.3 Hz, 1H) 7.76 (d, J=2.3 Hz, 1H) 8.29 (d, J=2.3 Hz, 1H) 8.41 (d, J=2.3 Hz, 1H). MS (ESI+) m/z 290.1 (M+H)$^+$.

Step 2: tert-Butyl trans-2,5-dimethyl-4-[(5-nitro-1-benzofuran-7-yl)methyl]piperazine-1-carboxylate trans-2,5-Dimethyl-1-[(5-nitro-1-benzofuran-7-yl)methyl]piperazine (0.11 g, 0.4 mmol; obtained in Step 1) was dissolved in MeOH. Boc-anhydride (0.114 g, 0.5 mmol) was added and the reaction was stirred at ambient temperature overnight. The solvent was evaporated and the residue was dissolved in DCM and washed with citric acid. The organic layer was dried (MgSO$_4$) and evaporated to give 0.135 g (91%) of the title product. HPLC 96% Rt=1.79 min (System A; 10-97% MeCN over 3 min). $^1$H NMR (400 MHz, CDCl$_3$) δ ppm 1.07 (d, J=6.5 Hz, 3H) 1.27 (d, J=6.8 Hz, 3H) 1.46 (s, 9H) 2.18-2.27 (m, 1H) 2.82 (dd, J=11.5, 4.3 Hz, 1H) 2.98-3.06 (m, 1H) 3.37 (dd, J=13.1, 3.5 Hz, 1H) 3.65-3.75 (d, J=13.1 Hz, 1H) 3.83-3.95 (m, 2H) 4.16-4.27 (m, 1H) 6.91 (d, J=2.3 Hz, 1H) 7.76 (d, J=2.3 Hz, 1H) 8.25-8.55 (m, 2H). MS (ESI+) m/z 390.2 (M+H)$^+$.

Step 3: tert-Butyl trans-4-[(5-amino-1-benzofuran-7-yl)methyl]-2,5-dimethylpiperazine-1-carboxylate tert-Butyl trans-2,5-dimethyl-4-[(5-nitro-1-benzofuran-7-yl)methyl]piperazine-1-carboxylate (0.14 g, 0.35 mmol; obtained in Step 2) was dissolved in THF/EtOH (4:1; 5 mL).

Excess Raney-Ni (slurry in EtOH) was added followed by hydrazine hydrate (0.07 g, 1.39 mmol). The reaction mixture was stirred overnight at ambient temperature. After filtration and evaporation of solvent, a crude oil (0.11 g, 87%) was obtained that was used in the next step without further purification. HPLC 86% $R_T$=1.15 min (System B; 10-97% MeCN over 3 min). MS (ESI+) m/z 360.2 (M+H)$^+$.

Step 4: tert-Butyl trans-4-[(5-{[(2-methoxy-5-methylphenyl)sulfonyl]amino}-1-benzofuran-7-yl)methyl]-2,5-dimethylpiperazine-1-carboxylate tert-Butyl trans-4-[(5-amino-1-benzofuran-7-yl)methyl]-2,5-dimethylpiperazine-1-carboxylate (0.037 g, 0.1 mmol; obtained in Step 3) was dissolved in DCM and reacted with 2-methoxy-5-methylbenzenesulfonyl chloride (0.045 g, 0.2 mmol) and pyridine (0.024 g, 0.3 mmol) overnight. The mixture was washed with 1 M HCl and the organic layer was dried (MgSO$_4$) and evaporated. The crude was purified using flash-tube (10% MeOH in DCM) and afforded the title product (0.026 g, 48%). HPLC 93% $R_T$=2.01 min (System A; 10-97% MeCN over 3 min), 93% $R_T$=1.85 min (System B; 10-97% MeCN over 3 min). MS (ESI+) m/z 544.2 (M+H)$^+$.

Step 5: 2-Methoxy-5-methyl-N-{7-[(trans-2,5-dimethylpiperazin-1-yl)methyl]-1-benzofuran-5-yl}benzenesulfonamide, bis(trifluoroacetate)

A solution of tert-butyl trans-4-[(5-{[(2-methoxy-5-methylphenyl)sulfonyl]amino}-1-benzofuran-7-yl)methyl]-2,5-dimethylpiperazine-1-carboxylate (0.026 g, 0.047 mmol; obtained in Step 4) in TFA:water (9:1) was stirred at ambient temperature for 1 h. The solvent was evaporated and the residue was purified by preparative HPLC (System A; 20-40% MeCN). Pure fractions were combined and concentrated to give the title compound as a colorless TFA-salt (0.020 mg, 63%). HPLC 100%, $R_T$=1.52 min (System A; 10-97% MeCN over 3 min), 100%, $R_T$=1.25 min (System B; 10-97% MeCN over 3 min). $^1$H NMR (400 MHz, methanol-d$_4$) δ ppm 1.24 (d, J=6.53 Hz, 3H) 1.48 (d, J=6.27 Hz, 3H) 2.20 (s, 3H) 2.61 (dd, J=13.30, 11.54 Hz, 1H) 3.05-3.23 (m, 3H) 3.39-3.47 (m, 1H) 3.50 (dd, J=12.92, 2.64 Hz, 1H) 3.97 (s, 3H) 4.07 (d, J=113.80 Hz, 1H) 4.60 (d, J=13.80 Hz, 1H) 6.80 (d, J=2.26 Hz, 1H) 7.03 (d, J=8.53 Hz, 1H) 7.24 (d, J=2.01 Hz, 1H) 7.29-7.33 (m, J=8.78, 2.01 Hz, 1H) 7.35 (d, J=2.01 Hz, 1H) 7.48-7.51 (m, J=1.51 Hz, 1H) 7.76 (d, J=2.01 Hz, 1H). MS (ESI+) for C$_{23}$H$_{29}$N$_3$O$_4$S m/z 444 (M+H)$^+$.

Example 122

2-Methyl-N-{7-[(trans-2,5-dimethylpiperazin-1-yl)methyl]-1-benzofuran-5-yl}benzenesulfonamide, bis(trifluoroacetate)

Step 1: tert-Butyl trans-2,5-dimethyl-4-[(5-{[(2-methylphenyl)sulfonyl]amino}-1-benzofuran-7-yl)methyl]piperazine-1-carboxylate The title product was prepared according to the procedure of Example 121, Step 4, starting from tert-butyl trans-4-[(5-amino-1-benzofuran-7-yl)methyl]-2,5-dimethylpiperazine-1-carboxylate (obtained in Example 121, Step 3) and 2-methylbenzenesulfonyl chloride (0.039 g, 0.2 mmol). Yield: 0.022 g (43%). HPLC 95% $R_T$=1.99 min (System A; 10-97% MeCN over 3 min), 93% $R_T$=1.85 min (System B; 10-97% MeCN over 3 min). MS (ESI+) m/z 514.2 (M+H)$^+$.

Step 2: 2-Methyl-N-{7-[(trans-2,5-dimethylpiperazin-1-yl)methyl]-1-benzofuran-5-yl}benzenesulfonamide, bis(trifluoroacetate)

The title product was prepared according to the procedure of Example 121, Step 5, starting from tert-butyl trans-2,5-dimethyl-4-[(5-{[(2-methylphenyl)sulfonyl]amino}-1-benzofuran-7-yl)methyl]piperazine-1-carboxylate (0.022 g, 0.043 mmol; obtained in Step 1). Yield: 0.017 g (62%). HPLC 100%, $R_T$=1.49 min (System A; 10-97% MeCN over 3 min), 100%, $R_T$=1.22 min (System B; 10-97% MeCN over 3 min). $^1$H NMR (400 MHz, methanol-d$_4$) δ ppm 1.20-1.27 (m, 3H) 1.43-1.51 (m, 3H) 2.51-2.65 (m, 1H) 2.63 (s, 3H) 3.02-3.25 (m, 3H) 3.38-3.45 (m, 1H) 3.45-3.53 (m, 1H) 4.00-4.11 (m, 1H) 4.53-4.64 (m, 1H) 6.79 (d, J=2.26 Hz, 1H) 7.15-7.35 (m, 4H) 7.40-7.46 (m, 1H) 7.75-7.80 (m, 1H) 7.82-7.87 (m, J=8.03, 1.25 Hz, 1H). MS (ESI+) for C$_{22}$H$_{27}$N$_3$O$_3$S m/z 414 (M+H)$^+$.

Example 123

2-Chloro-N-{7-[(trans-2,5-dimethylpiperazin-1-yl)methyl]-1-benzofuran-5-yl}benzenesulfonamide, bis(trifluoroacetate)

Step 1: tert-Butyl trans-4-[(5-{[(2-chlorophenyl)sulfonyl]amino}-1-benzofuran-7-yl)methyl]-2,5-dimethylpiperazine-1-carboxylate The title product was prepared according to the procedure of Example 121, Step 4, starting from tert-butyl trans-4-[(5-amino-1-benzofuran-7-yl)methyl]-2,5-dimethylpiperazine-1-carboxylate (obtained in Example 121, Step 3) and 2-chlorobenzenesulfonyl chloride (0.043 g, 0.2 mmol). Yield: 0.017 g (26%). HPLC 94% $R_T$=2.01 min (System A; 10-97% MeCN over 3 min), 98% $R_T$=1.85 min (System B; 10-97% MeCN over 3 min). MS (ESI+) m/z 534.2 (M+H)$^+$.

Step 2: 2-Chloro-N-{7-[(trans-2,5-dimethylpiperazin-1-yl)methyl]-1-benzofuran-5-yl}benzenesulfonamide, bis(trifluoroacetate)

The title compound was prepared according to the procedure of Example 121, Step 5, starting from tert-butyl trans-4-[(5-{[(2-chlorophenyl)sulfonyl]amino}-1-benzofuran-7-yl)methyl]-2,5-dimethylpiperazine-1-carboxylate (0.017 g, 0.032 mmol; obtained in Step 1). Yield: 0.016 g (76%). HPLC 99%, $R_T$=1.47 min (System A; 10-97% MeCN over 3 min), 100%, $R_T$=1.20 min (System B; 10-97% MeCN over 3 min). $^1$H NMR (400 MHz, methanol-d$_4$) δ ppm 1.23 (d, J=6.53 Hz, 3H) 1.43 (d, J=5.77 Hz, 3H) 2.48 (dd, J=13.18, 11.42 Hz, 1H) 3.00-3.06 (m, 2H) 3.10 (dd, J=13.30, 3.26 Hz, 1H) 3.34-3.42 (m, 1H) 3.42-3.47 (m, 1H) 3.96 (d, J=14.05 Hz, 1H) 4.51 (d, J=14.05 Hz, 1H) 6.79 (d, J=2.01 Hz, 1H) 7.24 (d, J=2.01 Hz, 1H) 7.33-7.39 (m, 2H) 7.47-7.53 (m, 1H) 7.53-7.57 (m, 1H) 7.76 (d, J=2.26 Hz, 1H) 7.94-7.99 (m, J=7.78, 1.51 Hz, 1H). MS (ESI+) for C$_{21}$H$_{24}$ClN$_3$O$_3$S m/z 434 (M+H)$^+$.

Intermediate 65

Methyl 2,3-dihydro-1-benzofuran-7-carboxylate 2,3-Dihydrobenzofuran-7-carboxylic acid (8 g, 48.7 mmol) was dissolved in methanol (39.6 mL, 975 mmol) and concentrated sulfuric acid (2.6 mL, 48.7 mmol) was slowly added. The mixture was refluxed at 80° C. for 17 h. The solvent was evaporated and the residue was dissolved in ethyl acetate and washed with brine. The organic layer was evaporated to give the title compound as a beige solid. Yield: 8.6 g (99%). HPLC purity 93%, $R_T$=1.72 min (System A; 10-97% MeCN over 3 min); 96%, $R_T$=1.67 min (System B; 10-97% MeCN over 3 min). MS (ESI+) for C$_{10}$H$_{10}$O$_3$ m/z 179 (M+H)$^+$.

Intermediate 66

Methyl 5-[(2-methoxy-5-methylphenyl)sulfonyl]-2,3-dihydro-1-benzofuran-7-carboxylate To methyl 2,3-dihydro-1-benzofuran-7-carboxylate (1 g, 5.6 mmol; Intermediate 65) were 2-methoxy-5-methylbenzenesulfonic acid (1.13 g, 5.6 mmol) and phosphorus pentoxide-methanesulfonic acid solution (1:10; 13.5 mL) added. The mixture was stirred at room temperature for 48 h. Additional 2-methoxy-5-methylbenzenesulfonic acid (0.56 g, 2.8 mmol) was added and the reaction mixture was stirred at 50° C. for 15 h. The mixture was poured onto water/ice and the formed precipitate was filtrated off, dissolved in DCM and evaporated. The crude product was purified using flash chromatography (eluent: isohexane:EtOAc 1:1) yielding the title compound. Yield: 1.07 g (53%). MS (ESI+) for $C_{18}H_{18}O_6S$ m/z 363 (M+H)$^+$.

Intermediate 67

Methyl 5-[(2-methoxy-5-methylphenyl)sulfonyl]-1-benzofuran-7-carboxylate

Methyl 5-[(2-methoxy-5-methylphenyl)sulfonyl]-2,3-dihydro-1-benzofuran-7-carboxylate (879 mg, 2.4 mmol; Intermediate 66) was dissolved in chlorobenzene (6 mL). N-bromosuccinimide (432 mg, 2.4 mmol) and benzoyl peroxide (58 mg, 0.24 mmol) were added and the mixture was stirred at 100° C. for 17 h. The mixture was washed with saturated aqueous NaHCO$_3$ and the organic layer was concentrated. Yield: 405 mg (46%) after purification by preparative HPLC (System F; 40-60% MeCN). MS (ESI+) for $C_{18}H_{16}O_6S$ m/z 361 (M+H)$^+$.

Intermediate 68

{5-[(2-Methoxy-5-methylphenyl)sulfonyl]-1-benzofuran-7-yl}methanol

Methyl 5-[(2-methoxy-5-methylphenyl)sulfonyl]-1-benzofuran-7-carboxylate (400 mg, 1.1 mmol; Intermediate 67) was dissolved in dry THF (3 mL) and 1 M lithium aluminumhydride in THF (0.3 mL) was slowly added. The mixture was stirred at room temperature overnight. After this time, water (0.15 mL) was added and stirring was continued for 10 min, followed by the addition of 2 M aqueous NaOH (0.15 mL) and water (0.45 mL). The precipitate formed was filtered off and the solvent was evaporated. The crude product was used in the next step without further purification. MS (ESI+) for $C_{17}H_{16}O_5S$ m/z 333 (M+H)$^+$.

Intermediate 69

7-(Chloromethyl)-5-[(2-methoxy-5-methylphenyl)sulfonyl]-1-benzofuran

Oxalyl chloride (0.1 mL, 1.1 mmol) was dissolved in dry DCM (2 mL) and DMF (0.9 mL, 1.1 mmol) was added (very exothermic reaction). {5-[(2-Methoxy-5-methylphenyl)sulfonyl]-1-benzofuran-7-yl}methanol (370 mg, 1.1 mmol; Intermediate 68) was added and the resultant mixture was stirred at room temperature for 17 h. The mixture was washed with 2 M NaOH (2×) and the organic layer was concentrated yielding the crude product. This material was used in the next step without further purification. MS (ESI+) for $C_{17}H_{15}ClO_4S$ m/z 351 (M+H)$^+$.

Example 124

1-({5-[(2-Methoxy-5-methylphenyl)sulfonyl]-1-benzofuran-7-yl}methyl)piperazine, trifluoroacetate 7-(Chloromethyl)-5-[(2-methoxy-5-methylphenyl)sulfonyl]-1-benzofuran (35 mg, 0.1 mmol; Intermediate 69) was dissolved in ethanol (2 mL) and N-t-Boc-piperazine (28 mg, 0.1 mmol) and sodium bicarbonate (13 mg, 0.1 mmol) were added. The mixture was heated at 80° C. in a StemBlock overnight. The mixture was extracted with chloroform (×2) and the chloroform-layers were evaporated. Purification was done by preparative HPLC/MS (System A; 10-40% MeCN). The obtained N-t-BOC derivative of the title compound was dissolved in DCM (1 mL) and TFA (1 mL) was added. After being stirred at room temperature overnight, the solvent was evaporated to provide the title compound. Yield: 11 mg (27%) after purification by preparative HPLC/MS (System A; 10-40% MeCN). HPLC purity 98%, R$_T$=1.50 min (System A; 10-97% MeCN over 3 min); 99%, R$_T$=1.30 min (System B; 10-90% MeCN over 3 min). $^1$H NMR (400 MHz, CDCl$_3$) δ ppm 2.35 (s, 3H) 3.26-3.46 (m, 8H) 3.70 (s, 3H) 4.34 (s, 2H) 6.78 (d, J=8.53 Hz, 1H) 6.90 (d, J=2.01 Hz, 1H) 7.32 (dd, J=8.41, 1.63 Hz, 1H) 7.75 (d, J=1.25 Hz, 1H) 7.89-7.98 (m, 2H) 8.30 (d, J=1.25 Hz, 1H). MS (ESI+) for $C_{21}H_{24}N_2O_4S$ m/z 401 (M+H)$^+$.

Example 125

1-{[5-(Phenylsulfonyl)-1-benzofuran-7-yl]methyl}piperazine, trifluoroacetate

Step 1: Methyl 5-(phenylsulfonyl)-2,3-dihydro-1-benzofuran-7-carboxylate

The title compound was prepared according to the procedure of Intermediate 66 starting from methyl 2,3-dihydro-1-benzofuran-7-carboxylate (1 g, 5.6 mmol; Intermediate 65) and benzenesulfonic acid (0.89 g, 5.6 mmol). Yield: 882 mg (49%). MS (ESI+) for $C_{16}H_{14}O_5S$ m/z 319 (M+H)$^+$.

Step 2: Methyl 5-(phenylsulfonyl)-1-benzofuran-7-carboxylate

The title compound was prepared according to the procedure of Intermediate 67 starting from methyl 5-(phenylsulfonyl)-2,3-dihydro-1-benzofuran-7-carboxylate (198 mg, 0.6 mmol; obtained in Step 1). Yield: 80 mg (41%) after purification by preparative HPLC (System F; 40-70% MeCN). MS (ESI+) for $C_{16}H_{14}O_5S$ m/z 317 (M+H)$^+$.

Step 3: [5-(Phenylsulfonyl)-1-benzofuran-7-yl]methanol

The title compound was prepared according to the procedure of Intermediate 68 starting from methyl 5-(phenylsulfonyl)-1-benzofuran-7-carboxylate (80 mg, 0.25 mmol; obtained in Step 2). The crude material was used directly in the subsequent reaction. MS (ESI+) for $C_{15}H_{12}O_4S$ m/z 289 (M+H)$^+$.

Step 4: 7-(Chloromethyl)-5-(phenylsulfonyl)-1-benzofuran

The title compound was prepared according to the procedure of Intermediate 69 starting from [5-(phenylsulfonyl)-1-benzofuran-7-yl]methanol (73 mg, 0.3 mmol; obtained in Step 3). The crude material was used directly in the subsequent reaction. MS (ESI+) for $Cl_5H_{11}ClO_3S$ m/z 307 (M+H)$^+$.

Step 5: 1-{[5-(Phenylsulfonyl)-1-benzofuran-7-yl]methyl}piperazine, trifluoroacetate N-t-BOC-piperazine (24 mg, 0.13 mmol) and sodium bicarbonate (11 mg, 0.13 mmol) were added to a solution of 7-(chloromethyl)-5-(phenylsulfonyl)-1-benzofuran (26 mg, 0.08 mmol; obtained in Step 4) in ethanol (2 mL). The mixture was stirred at 80° C. in a STEM-block overnight and the solvent was evaporated. The obtained N-t-BOC derivative of the title compound was dissolved in DCM (1 mL) and TFA (1 mL) was added. After the mixture had been stirred at room temperature for 2 h, the solvent was evaporated to provide the title compound. Yield: 6.1 mg (12%) after purification by preparative HPLC/MS (System A; 10-40% MeCN). HPLC purity 99%, R$_T$=1.39 min (System A; 10-97% MeCN over 3 min); 96%, $R_T$=1.16 min (System B; 10-90% MeCN over 3 min). $^1$H NMR (400 MHz, CDCl$_3$) δ ppm 3.10-3.17 (m, 4H) 3.34-3.39 (m, 4H) 4.20 (s, 2H) 6.87-6.92 (m, 1H) 7.46-7.58 (m, 3H) 7.75 (d, J=2.26 Hz, 1H) 7.92-7.97 (m, 3H) 8.26 (d, J=1.76 Hz, 1H). MS (ESI+) for C$_{19}$H$_{20}$N$_2$O$_3$S m/z 357 (M+H)$^+$.

Example 126

1-({5-[(4-Methylphenyl)sulfonyl]-1-benzofuran-7-yl}methyl)piperazine, trifluoroacetate Step 1: Methyl 5-[(4-methylphenyl)]sulfonyl]-2,3-dihydro-1-benzofuran-7-carboxylate The title compound was prepared according to the procedure of Intermediate 66 starting from methyl 2,3-dihydro-1-benzofuran-7-carboxylate (1 g, 5.6 mmol; Intermediate 65) and 4-methylbenzenesulfonic acid (0.97 g, 5.6 mmol). Yield: 405 mg (22%). MS (ESI+) for C$_{17}$H$_{16}$O$_5$S m/z 333 (M+H)$^+$.

Step 2: Methyl 5-[(4-methylphenyl)sulfonyl]-1-benzofuran-7-carboxylate

The title compound was prepared according to the procedure of Intermediate 67 starting from methyl 5-[(4-methylphenyl)sulfonyl]-2,3-dihydro-1-benzofuran-7-carboxylate (117 mg, 0.4 mmol; obtained in Step 1). Yield: 62 mg (53%) after purification by preparative HPLC (System F; 40-60% MeCN). MS (ESI+) for C$_{17}$H$_{16}$O$_5$S m/z 331 (M+H)$^+$.

Step 3: (5-[(4-Methylphenyl)sulfonyl]-1-benzofuran-7-yl)methanol

The title compound was prepared according to the procedure of Intermediate 68 starting from methyl 5-[(4-methylphenyl)sulfonyl]-1-benzofuran-7-carboxylate (62 mg, 0.19 mmol; obtained in Step 2). MS (ESI+) for C$_{16}$H$_{14}$O$_4$S m/z 303 (M+H)$^+$.

Step 4: 7-(Chloromethyl)-5-[(4-methylphenyl)sulfonyl]-1-benzofuran

The title compound was prepared according to the procedure of Intermediate 69 starting from {5-[(4-methylphenyl)sulfonyl]-1-benzofuran-7-yl}methanol (57 mg, 0.2 mmol; obtained in Step 3). MS (ESI+) for C$_{16}$H$_{13}$ClO$_3$S m/z 321 (M+H)$^+$.

Step 5: 1-({5-[(4-Methylphenyl)sulfonyl]-1-benzofuran-7-yl}methyl)piperazine, trifluoroacetate The title compound was prepared according to the procedure of Example 125, Step 5, starting from 7-(chloromethyl)-5-[(4-methylphenyl)sulfonyl]-1-benzofuran (20 mg, 0.06 mmol; obtained in Step 4). Yield: 5.8 mg (15%) after purification by preparative HPLC/MS (System A; 5-20% MeCN). HPLC purity 99%, $R_T$=1.52 min (System A; 10-97% MeCN over 3 min); 99%, $R_T$=1.28 min (System B; 10-90% MeCN over 3 min). $^1$H NMR (400 MHz, CHLOROFORM-D) δ ppm 2.37 (s, 3H) 3.33-3.37 (m, 4H) 3.44-3.50 (m, 4H) 4.37 (s, 2H) 6.90 (d, J=2.26 Hz, 1H) 7.28 (d, J=8.03 Hz, 2H) 7.75 (d, J=2.26 Hz, 1H) 7.81 (d, J=8.28 Hz, 2H) 7.97 (d, J=1.51 Hz, 1H) 8.26 (d, J=1.76 Hz, 1H). MS (ESI+) for C$_{20}$H$_{22}$N$_2$O$_3$S m/z 371 (M+H)$^+$.

Example 127

1-({5-[(2-Methoxy-5-methylphenyl)sulfonyl]-1-benzofuran-7-yl}methyl)-1,4-diazepane, trifluoroacetate 7-(Chloromethyl)-5-[(2-methoxy-5-methylphenyl)sulfonyl]-1-benzofuran (66 mg, 0.19 mmol; Intermediate 69) was dissolved in ethanol (2 mL) and 1-boc-homopiperazine (57 mg, 0.28 mmol) and sodium bicarbonate (24 mg, 0.28 mmol) were added. The mixture was heated to 80° C. in a StemBlock overnight. The mixture was extracted with chloroform (×2) and the chloroform-layers were evaporated. The obtained N-t-BOC derivative of the title compound was dissolved in DCM (1 mL) and TFA (1 mL) was added. After being stirred at room temperature for 2 h, the solvent evaporated to provide the title compound. Yield: 39 mg (32%) after purification by preparative HPLC/MS (System A; 10-40% MeCN). HPLC purity 99%, $R_T$=1.41 min (System A; 10-97% MeCN over 3 min); 99%, $R_T$=1.19 min (System B; 10-90% MeCN over 3 min). $^1$H NMR (400 MHz, CDCl$_3$) δ ppm 2.16 (bs, 2H) 2.24 (s, 3H) 3.30 (bs, 2H) 3.39 (bs, 2H) 3.54 (bs, 2H) 3.57-3.67 (m, 5H) 4.50 (s, 2H) 6.69 (d, J=8.78 Hz, 1H) 6.81 (d, J=1.76 Hz, 1H) 7.23 (d, J=8.53 Hz, 1H) 7.66 (s, 1H) 7.81 (s, 1H) 7.94 (s, 1H) 8.22 (s, 1H). MS (ESI+) for C$_{22}$H$_{26}$N$_2$O$_4$S m/z 415 (M+H)$^+$.

Example 128

1-{[5-(Phenylsulfonyl)-1-benzofuran-7-yl]methyl}-1,4-diazepane, trifluoroacetate The title compound was prepared according to the procedure of Example 127 starting from 7-(chloromethyl)-5-(phenylsulfonyl)-1-benzofuran (37 mg, 0.12 mmol; obtained in Example 125, Step 4). Yield: 9.4 mg (13%) after purification by preparative HPLC/MS (System A; 10-40% MeCN). HPLC purity 99%, $R_T$=1.29 min (System A; 10-97% MeCN over 3 min); 99%, $R_T$=1.16 min (System B; 10-90% MeCN over 3 min). $^1$H NMR (400 MHz, CDCl$_3$) δ ppm 2.28-2.35 (m, 2H) 3.42-3.52 (m, 4H) 3.65-3.77 (m, 4H) 4.60 (s, 2H) 6.93 (d, J=2.26 Hz, 1H) 7.46-7.53 (m, 2H) 7.53-7.59 (m, 1H) 7.77 (d, J=2.26 Hz, 1H) 7.92-7.97 (m, 2H) 8.09 (d, J=1.76 Hz, 1H) 8.32 (d, J=1.76 Hz, 1H). MS (ESI+) for C$_{20}$H$_{22}$N$_2$O$_3$S m/z 371 (M+H)$^+$.

Example 129

1-({5-[(4-Methylphenyl)sulfonyl]-1-benzofuran-7-yl}methyl)-1,4-diazepane, trifluoroacetate The title compound was prepared according to the procedure of Example 127 starting from 7-(chloromethyl)-5-[(4-methylphenyl)sulfonyl]-1-benzofuran (32 mg, 0.10 mmol; obtained in Example 126, Step 4). Yield: 8.1 mg (13%) after purification by preparative HPLC/MS (System A; 10-40% MeCN). HPLC purity 99%, $R_T$=1.42 min (System A; 10-97% MeCN over 3 min); 99%, $R_T$=2.94 min (System B; 10-90% MeCN over 3 min). $^1$H NMR (400 MHz, CDCl$_3$) δ ppm 2.31 (bs, 2H) 2.37 (s, 3H) 3.41-3.54 (m, 4H) 3.66-3.79 (m, 4H) 4.61 (s, 2H) 6.91 (d, J=2.26 Hz, 1H) 7.26-7.31 (m, 2H) 7.75 (d, J=2.26 Hz, 1H) 7.81 (d, J=8.28 Hz, 2H) 8.07 (d, J=1.51 Hz, 1H) 8.29 (d, J=1.76 Hz, 1H). MS (ESI+) for C$_{21}$H$_{24}$N$_2$O$_3$S m/z 385 (M+H)$^+$.

Example 130

1-({5-[(2-Methoxy-5-methylphenyl)sulfonyl]-1-benzofuran-7-yl}methyl)-2-methylpiperazine, trifluoroacetate 7-(Chloromethyl)-5-[(2-methoxy-5-methylphenyl)sulfonyl]-1-benzofuran (60 mg, 0.17 mmol; Intermediate 69) was dissolved in ethanol (2 mL) and tert-butyl 3-methylpiperazine-1-carboxylate (41 mg, 0.21 mmol) and sodium bicarbonate (22 mg, 0.26 mmol) were added. The resulting mixture was heated at 80° C. in a StemBlock overnight. The mixture was extracted with chloroform (×2) and the chloroform layers were concentrated. The obtained N-t-BOC derivative of the title compound was dissolved in DCM (1 mL) and TFA (1 mL) was added. After the mixture had been stirred at room temperature for 2 h, the solvent was evaporated. Yield: 33 mg (36%) after purification by preparative HPLC/MS (System A; 10-40% MeCN). HPLC purity 99%, $R_T$=1.55 min (System A; 10-97% MeCN over 3 min); 99%, $R_T$=1.37 min (System B; 10-97% MeCN over 3 min). $^1$H NMR (400 MHz, CDCl$_3$) δ ppm 1.65 (d, J=6.27 Hz, 3H) 2.34 (s, 3H) 3.35-3.61 (m, 6H) 3.68 (s, 3H) 3.90-3.99 (m, 1H) 4.46 (d, J=13.55 Hz, 1H) 4.82 (d, J=13.55 Hz, 1H) 6.77 (d, J=8.53 Hz, 1H) 6.92 (d, J=2.26 Hz, 1H) 7.32 (dd, J=8.53, 1.76 Hz, 1H) 7.75 (d, J=2.26 Hz, 1H) 7.87 (d, J=2.01 Hz, 1H) 7.97 (d, J=1.25 Hz, 1H) 8.34 (d, J=1.51 Hz, 1H). MS (ESI+) for C$_{22}$H$_{26}$N$_2$O$_4$S m/z 414 (M+H)$^+$.

Example 131

1-({5-[(2-Methoxy-5-methylphenyl)sulfonyl]-1-benzofuran-7-yl}methyl)-3-methylpiperazine, trifluoroacetate 7-(Chloromethyl)-5-[(2-methoxy-5-methylphenyl)sulfonyl]-1-benzofuran (60 mg, 0.17 mmol; Intermediate 69) was dissolved in ethanol (2 mL) and 2-methylpiperazine (21 mg, 0.21 mmol) and sodium bicarbonate (22 mg, 0.26 mmol) were added. The mixture was heated at 80° C. in a StemBlock overnight. The mixture was extracted with chloroform (×2) and the chloroform layers were evaporated. The obtained N-t-BOC derivative of the title compound was dissolved in DCM (1 mL) and TFA (1 mL) was added. After the mixture had been stirred at room temperature for 2 h, the solvent was evaporated. Yield: 28 mg (31%) after purification by preparative HPLC/MS (System A; 10-40% MeCN). HPLC purity 99%, $R_T$=1.57 min (System A; 10-97% MeCN over 3 min); 99%, $R_T$=1.35 min (System B; 10-97% MeCN over 3 min). $^1$H NMR (400 MHz, CDCl$_3$) δ ppm 0.80-0.90 (m, 2H) 1.30 (d, J=6.27 Hz, 3H) 2.35 (s, 3H) 3.14 (t, J=12.05 Hz, 1H) 3.27-3.45 (m, 4H) 3.70 (s, 3H) 4.40 (s, 2H) 6.78 (d, J=8.53 Hz, 1H) 6.91 (d, J=2.26 Hz, 1H) 7.32 (dd, J=8.41, 1.88 Hz, 1H) 7.76 (d, J=2.01 Hz, 1H) 7.88-7.99 (m, 2H) 8.32 (d, J=1.51 Hz, 1H). MS (ESI+) for C$_{22}$H$_{26}$N$_2$O$_4$S m/z 414 (M+H)$^+$.

Intermediate 70

(5-Bromo-1-benzofuran-7-yl)amine

Step 1: Ethyl 5-bromo-7-nitro-1-benzofuran-3-carboxylate

A mixture of 5-bromo-2-hydroxy-3-nitrobenzaldehyde (8.9 g, 36.2 mmol), diethyl bromomalonate (6.3 mL, 37.3 mmol) and potassium carbonate (4.6 g) in butanone (50 mL) was heated a reflux for 4 h. The mixture was cooled, filtered and evaporated to give the crude product which was recrystallized from ethanol. Yield: 6.6 g (58%) of a pale yellow solid. $^1$H NMR (400 MHz, DMSO-d$_6$) δ ppm 1.29 (t, J=7.0 Hz, 3H) 4.35 (q, J=7.1 Hz, 2H) 7.83 (s, 1H) 8.39 (d, J=2.0 Hz, 1H) 8.43 (d, J=2.0 Hz, 1H).

Step 2: 5-Bromo-7-nitro-1-benzofuran-3-carboxylic acid

Ethyl 5-bromo-7-nitro-1-benzofuran-3-carboxylate (5.5 g, 17.5 mmol; obtained in Step 1) was suspended in ethanol (20 mL). 2 M NaOH (20 mL) was added and the mixture was heated at reflux for 2 h. The ethanol was removed by evaporation and the remaining solution acidified with concentrated HCl (4 mL), diluted with water and the product collected by filtration, washed with water and dried in a vacuum oven. Yield: 4.65 g (93%). $^1$H NMR (400 MHz, DMSO-d$_6$) δ ppm 7.43 (s, 1H) 8.26 (d, J=1.8 Hz, 1H) 8.34 (d, J=2.0 Hz, 1H).

Step 3: 5-Bromo-7-nitro-1-benzofuran

5-Bromo-7-nitro-1-benzofuran-3-carboxylic acid (4.65 g, 16 mmol; obtained in Step 2) was suspended in quinoline (25 mL), 0.1 g CuO was added and the mixture heated to 190° C. for 30 minutes. The warm reaction mixture was diluted with hot toluene (100 mL), filtered and the filter cake washed with hot toluene (total 400 mL). The combined toluene extracts were washed with 1 M HCl (2×100 mL) and brine, evaporated and the solid product washed with hexane, collected by filtration and dried. Yield: 1.9 g (48%). $^1$H NMR (400 MHz, DMSO-d$_6$) δ ppm 7.13 (d, J=2.3 Hz, 1H) 8.20 (d, J=2.0 Hz, 1H) 8.28 (d, J=2.3 Hz, 1H) 8.32 (d, J=2.0 Hz, 1H).

Step 4: (5-Bromo-1-benzofuran-7-yl)amine

A mixture of 5-bromo-7-nitro-1-benzofuran (1.9 g, 7.9 mmol; obtained in Step 3), iron powder (2.3 g) methanol (20 mL), 1,4-dioxane (20 mL) and ammonium chloride (2.3 g dissolved in 10 mL of water), was refluxed overnight. The warm mixture was filtered through wetted Celite, which was further washed with hot methanol and the solvents were evaporated. The crude product was dissolved in hot ethanol/water (100 mL) and then water added so that product began to crystallize out. The product was collected by filtration, washed with water and dried in a vacuum oven. Yield: 1.1 g (65%). $^1$H NMR (400 MHz, DMSO-d$_6$) δ ppm 5.63 (s, 2H) 6.68 (d, J=2.0 Hz, 1H) 6.81 (d, J=2.3 Hz, 1H) 6.96 (d, J=2.0 Hz, 1H) 7.92 (d, J=2.3 Hz, 1H).

Example 132

2-Methoxy-5-methyl-N-[5-(piperazin-1-ylmethyl)-1-benzofuran-7-yl]benzenesulfonamide, bis(trifluoroacetate)

Step 1: N-(5-Bromo-1-benzofuran-7-yl)-2-methoxy-5-methylbenzenesulfonamide

A mixture of (5-bromo-1-benzofuran-7-yl)amine (500 mg, 2.4 mmol; Intermediate 70, Step 4), pyridine (0.38 mL, 4.7 mmol) and 6-methoxy-m-toluenesulfonyl chloride (0.78 g, 3.5 mmol) in dry DCM (20 mL) was stirred at room temperature for 2.5 h. Additional 6-methoxy-m-toluenesulfonyl chloride (0.26 g, 1.2 mmol) was added with continuous stirring over night. The reaction mixture was diluted with DCM and extracted with water. The organic layer was concentrated. The product precipitated from a mixture of DCM/isohexane/MeOH (80:20:20) and was collected by filtration to give the title compound 580 mg (61%) as a light brown solid. HPLC 94%, $R_T$=2.32 min (System A; 30-80% MeCN over 3 min). MS (ESI+) for C$_{16}$H$_{14}$BrNO$_4$S m/z 396 (monoisotop.mass+H)$^+$.

Step 2: 2-Methoxy-5-methyl-N-[5-(piperazin-1-ylmethyl)-1-benzofuran-7-yl]benzenesulfonamide, bis(trifluoroacetate)

Pd(PPh$_3$)$_2$OAc$_2$ (189 mg, 0.25 mmol) and vinyltributyltin (295 µL, 1.01 mmol) were added to N-(5-bromo-1-benzofuran-7-yl)-2-methoxy-5-methylbenzenesulfonamide (200 mg, 0.51 mmol; obtained in Step 1) in dry toluene under argon. The mixture was stirred at 110° C. over weekend (62 h). The reaction mixture was filtered and concentrated. The crude mixture was stirred with isohexane for 10 min. The isohexane was decanted off and the residue was dried under reduced pressure. The alkene intermediate was dissolved in dioxane (6 mL) and lutidine (120 µL, 1.0 mmol). Osmium tetroxide (26 mg, 0.10 mmol) was added and a color change from light brown to dark brown/black was noticed. Sodium periodate (432 mg, 2.02 mmol) in water (1.5 mL, warmed to dissolve) was added while stirring. A light brown precipitation was formed after 1 min. The mixture was stirred for 2 h, and partitioned between 2 M aqueous HCl and DCM. The organic layer was dried ($Na_2SO_4$), filtered and concentrated to give the crude aldehyde as a black solid. Half of the material was suspended in dry THF (4 mL) and N-t-BOC-piperazine (50 mg, 0.27 mmol), acetic acid (140 µL, 2.5 mmol) and sodium triacetoxyborohydride (104 mg, 0.49 mmol) were added. The reaction mixture was irradiated using microwaves, 300 s at 130° C. The mixture was filtered, dissolved in MeOH (2 mL) and concentrated HCl (0.5 mL) and irradiated using microwaves, 300 s 100° C. The solvent was evaporated, the residue dissolved in MeOH and purified by preparative HPLC (System A; 19-40% MeCN). Pure fractions were combined and concentrated to give the title compound (31 mg, 20%) as a brown gum. HPLC 100%, $R_T$=1.35 min (System A; 10-97% MeCN over 3 min), 99%, $R_T$=1.15 min (System B; 10-97% MeCN over 3 min). $^1$H NMR (400 MHz, methanol-$d_4$) δ ppm 2.22 (s, 3H) 3.30-3.36 (m, 4H) 3.43-3.50 (m, 4H) 3.81 (s, 3H) 4.29 (s, 2H) 6.82 (d, J=2.26 Hz, 1H) 6.95 (d, J=8.53 Hz, 1H) 7.28-7.33 (m, J=8.53, 2.26 Hz, 1H) 7.43 (d, J=1.51 Hz, 1H) 7.48 (d, J=1.51 Hz, 1H) 7.56-7.59 (m, J=2.26 Hz, 1H) 7.77 (d, J=2.26 Hz, 1H). MS (ESI+) for $C_{21}H_{25}N_3O_4S$ m/z 416 (M+H)$^+$.

Example 133

2-Methoxy-5-methyl-N-{5-[(3-methylpiperazin-1-yl)methyl]-1-benzofuran-7-yl}benzenesulfonamide, bis(trifluoroacetate)

The title compound was prepared according to the procedure of Example 132, Step 2, using 2-methylpiperazine (27 mg, 0.27 mmol). The title compound (18 mg, 11%) was obtained as a brown gum. HPLC 97%, $R_T$=1.38 min (System A; 10-97% MeCN over 3 min), 98%, $R_T$=1.18 min (System B; 10-97% MeCN over 3 min). $^1$H NMR (400 MHz, methanol-$d_4$) δ ppm 1.33 (d, J=6.53 Hz, 3H) 2.22 (s, 3H) 2.82 (dd, J=13.18, 11.42 Hz, 1H) 2.94-3.04 (m, 1H) 3.31-3.44 (m, 2H) 3.51-3.59 (m, 2H) 3.79-3.87 (m, 1H) 3.81 (s, 3H) 4.18 (s, 2H) 6.81 (d, J=2.01 Hz, 1H) 6.95 (d, J=8.53 Hz, 1H) 7.27-7.32 (m, J=8.53, 2.26 Hz, 1H) 7.41 (d, J=1.76 Hz, 1H) 7.45 (d, J=1.76 Hz, 1H) 7.55-7.58 (m, J=1.51 Hz, 1H) 7.75 (d, J=2.26 Hz, 1H). MS (ESI+) for $C_{22}H_{27}N_3O_4S$ m/z 430 (M+H)$^+$.

Example 134

N-(2-Methylphenyl)-7-{[(3R)-pyrrolidin-3-ylamino]methyl}-1-benzofuran-5-sulfonamide, trifluoroacetate The title compound was prepared according to the procedure of Example 93 starting from 7-formyl-N-(2-methylphenyl)-1-benzofuran-5-sulfonamide (80 mg, 0.24 mmol; Intermediate 60) and (R)-(+)-3-aminopyrrolidine (50 mg, 0.6 mmol). [Note: no HCl deprotection step]. Yield: 17.8 mg (28%). HPLC 97% $R_T$=1.39 (System A; 10-97% MeCN over 3 min) 98% $R_T$=1.22 (System B; 10-90% MeCN over 3 min). MS (ESI+) for $C_{20}H_{23}N_3O_3S$ m/z 386 (M+1). $^1$H NMR (400 MHz, methanol-$d_4$) δ ppm 1.94 (s, 3H) 2.02-2.12 (m, 1H) 2.44-2.54 (m, 1H) 3.24-3.31 (m, 1H) 3.40-3.52 (m, 2H) 3.72 (dd, J=12.8, 8.3 Hz, 1H) 4.04 (tt, J=8.3, 5.5 Hz, 1H) 4.68 (d, J=2.5 Hz, 2H) 6.92-7.03 (m, 5H) 7.73 (d, J=1.5 Hz, 1H) 7.94 (d, J=2.3 Hz, 1H) 8.08 (d, J=1.8 Hz, 1H).

Example 135

N-(2-Methylphenyl)-7-(piperidin-4-ylmethyl)-1-benzofuran-5-sulfonamide, trifluoroacetate 9-Borabicyclo[3.3.1]-nonane (9-BBN; 0.5 M in THF, 2.2 mL, 2.2 mmol) was added to a solution of 1-(4-methylidene-piperidino)ethan-1-one (Maybridge Chemical Company, 140 mg, 1 mmol) in dry THF (2 mL) under a nitrogen atmosphere at 0° C. After stirring for 1 h at 0° C., the solution was allowed to warm to room temperature for 3 h. Next, a microwave reaction tube was charged with 7-iodo-N-(2-methylphenyl)-1-benzofuran-5-sulfonamide (40 mg, 0.1 mmol; Intermediate 58), Herrmann's catalyst (5 mg), dry THF (3 mL), 4 M aqueous NaOH (0.1 mL) and the above solution of in situ generated 1-[4-(9-borabicyclo[3.3.1]non-9-ylmethyl)-piperidin-1-yl]-ethanone (0.75 mL, 0.17 mmol). The mixture was heated under microwave irradiation to 140° C. for 5 minutes. This reaction mixture and three similar mixtures were combined, filtered and evaporated. The residue was dissolved in DCM (20 mL) and washed with 1 M HCl. After evaporation of the solvent, the crude acetylated derivative of the title product was purified by preparative HPLC-MS (Venus 30-60% MeCN 0.1% TFA). The purified material was N-deprotected by dissolving in methanol (3 mL), adding concentrated aqueous HCl (1 mL) and heating under microwave irradiation to 120° C. for 1 hour. The final product was purified by preparative HPLC-MS (System A 30-60% MeCN 0.1% TFA) to give 5.9 mg (3%) of the title compound. HPLC 95% $R_T$=1.75 (System A; 10-97% MeCN over 3 min) 95% $R_T$=1.58 (System B; 10-90% MeCN over 3 min). MS (ESI+) for $C_{21}H_{24}N_2O_3S$ m/z 385 (M+1). $^1$H NMR (400 MHz, methanol-$d_4$) δ ppm 1.26-1.38 (m, 2H) 1.60-1.71 (m, J=14.1 Hz, 2H) 1.87 (s, 2H) 1.89-1.97 (m, 2H) 2.76-2.85 (m, 4H) 3.11-3.19 (m, 1H) 3.26-3.30 (m, 2H) 6.88 (d, J=2.3 Hz, 1H) 6.96-7.03 (m, 4H) 7.27 (d, J=1.5 Hz, 1H) 7.83 (d, J=2.3 Hz, 1H) 7.86 (d, J=1.8 Hz, 1H).

Intermediate 71 tert-Butyl 4-methylenepiperidine-1-carboxylate*

To a solution of methyl triphenylphosphonium bromide (2.69 g, 7.5 mmol) in THF (20 mL) was n-butyllithium (1.8 M; 4.2 mL, 7.5 mmol) in hexane slowly added at −78° C. The mixture was stirred for 1 h. After this time, a solution of tert-butyl 4-oxopiperidine-1-carboxylate (1 g, 5.0 mmol) in THF (10 mL) was added dropwise to the mixture. The resultant mixture was stirred at room temperature overnight. The reaction mixture was quenched with water and extracted with isohexane (×3). The combined isohexane layers were evaporated and filtrated through a silica-plug. The crude product was purified using flash chromatography with DCM as eluent yielding 0.58 g (59%) of the title compound. HPLC purity 91%, $R_T$=2.47 min (System A; 10-97% MeCN over 3 min); 86%, $R_T$=2.43 min (System B; 10-97% MeCN over 3 min). $^1$H NMR (400 MHz, CDCl$_3$) δ ppm 1.46 (s, 9H) 2.12-2.22 (m, 4H) 3.35-3.46 (m, 4H) 4.73 (s, 2H). MS (ESI+) for $C_{11}H_{19}NO_2$ m/z 142 (M-$C_4H_8$)$^+$.

*Previously reported in J. Med. Chem. 2002, 45, 3143-3160.

Intermediate 72 tert-Butyl 3-methylenepyrrolidine-1-carboxylate*

The title compound was prepared according to the procedure of Intermediate 71 starting from tert-butyl 3-oxopyrrolidine-1-carboxylate (0.8 g, 4.3 mmol), triphenylphosphonium bromide (2.31 g, 6.5 mmol) and n-BuLi (1.8 M; 2.4 mL, 6.5 mmol). Yield: 0.23 g (29%) after purification by flash chromatography with DCM as eluent. HPLC purity 99%, $R_T$=2.28 min (System A; 10-97% MeCN over 3 min); 99%, $R_T$=2.21 min (System B; 10-97% MeCN over 3 min). $^1$H NMR (400 MHz, CDCl$_3$) δ ppm 1.23-1.40 (m, 9H) 2.42 (t, J=6.78 Hz, 2H) 3.31 (t, J=7.40 Hz, 2H) 3.71-3.85 (m, 2H) 4.74-4.91 (m, 2H). MS (ESI+) for C$_{10}$H$_{17}$NO$_2$ m/z 128 (M-C$_4$H$_8$)$^+$.

*Previously reported in Tetrahedron 1997, 53, 539-556.

Intermediate 73 tert-Butyl 3-methylenepiperidine-1-carboxylate

The title compound was prepared according to the procedure of Intermediate 71 starting from tert-butyl 3-oxopiperidine-1-carboxylate (1 g, 5.0 mmol), triphenylphosphonium bromide (2.69 g, 7.5 mmol) and n-BuLi (1.8 M; 4.2 mL, 7.5 mmol). Yield: 0.28 g (28%) after purification by flash chromatography with 10% isohexane in DCM as eluent. HPLC purity 95%, $R_T$=2.43 min (System A; 10-97% MeCN over 3 min); 90%, $R_T$=2.38 min (System B; 10-97% MeCN over 3 min). $^1$H NMR (400 MHz, CDCl$_3$) δ ppm 1.41-1.48 (m, 9H) 1.56-1.65 (m, 2H) 2.20-2.30 (m, 2H) 3.38-3.47 (m, 2H) 3.86 (s, 2H) 4.74 (s, 1H) 4.80 (s, 1H). MS (ESI+) for C$_{11}$H$_{19}$NO$_2$ m/z 142 (M-C$_4$H$_8$)$^+$.

*Previously reported in Tetrahedron 2002, 58, 7165-7175.

Example 136

N-(2-Methylphenyl)-7-(pyrrolidin-3-ylmethyl)-1-benzofuran-5-sulfonamide, trifluoroacetate 9 BBN (0.5 M in THF; 1.5 mL, 0.75 mmol) was added to a solution of tert-butyl 3-methylenepyrrolidine-1-carboxylate (110 mg, 0.6 mmol; Intermediate 72) in dry THF (1 mL) under a nitrogen atmosphere at 0° C. After stirring for 1 h at 0° C., the solution was allowed to warn to room temperature for 3 h. A microwave reaction tube was charged with 7-iodo-N-(2-methylphenyl)-1-benzofuran-5-sulfonamide (90 mg, 0.2 mmol; Intermediate 58), Herrmann's catalyst (10 mg), dry THF (2.5 mL), 4 M aqueous NaOH (0.2 mL) and half of the above solution of in situ generated 3-(9-borabicyclo [3.3.1]non-9-ylmethyl)-pyrrolidine-1-carboxylic acid tert-butyl ester (1.1 mL, 0.3 mmol). The mixture was heated under microwave irradiation at 140° C. for 5 min. This reaction mixture and a similar mixture were combined, filtered and evaporated. The residue was dissolved in methanol (3 mL), concentrated HCl (0.5 mL) was added and the mixture heated under microwave irradiation at 100° C. for 5 min to accomplish deprotection of the N-t-BOC group. Purification by preparative HPLC (System F 20-45% MeCN 0.1% TFA) provided 31 mg (13%) of the title compound. HPLC 98% $R_T$=1.69 (System A; 10-97% MeCN over 3 min) 98% $R_T$=1.53 (System B; 10-90% MeCN over 3 min). MS (ESI+) for C$_{20}$H$_{22}$N$_2$O$_3$S m/z 371 (M+1). $^1$H NMR (400 MHz, methanol-d$_4$) δ ppm 1.57 (dq, J=13.3, 8.8 Hz, 1H) 1.87 (s, 3H) 1.88-1.95 (m, 1H) 2.58-2.70 (m, 1H) 2.81 (dd, J=11.4, 8.9 Hz, 1H) 2.96 (ddd, J=118.1, 14.0, 7.5 Hz, 2H) 3.10-3.21 (m, 2H) 3.30 (ddd, J=11.9, 8.2, 4.3 Hz, 1H) 6.89 (d, J=2.3 Hz, 1H) 6.97-7.02 (m, 4H) 7.32 (d, J=1.8 Hz, 1H) 7.85 (d, J=2.0 Hz, 1H) 7.87 (d, J=1.8 Hz, 1H).

Example 137

N-(2-Methylphenyl)-7-(piperidin-3-ylmethyl)-1-benzofuran-5-sulfonamide, trifluoroacetate The title compound was prepared according to the procedure of Example 136 starting from tert-butyl 3-methylenepiperidine-1-carboxylate (120 mg, 0.6 mmol; Intermediate 73) and 7-iodo-N-(2-methylphenyl)-1-benzofuran-5-sulfonamide (180 mg, 0.4 mmol; Intermediate 58). Yield: 40 mg (21%). HPLC 99% $R_T$=1.74 (System A; 10-97% MeCN over 3 min) 100% $R_T$=1.58 (System B; 10-90% MeCN over 3 min). MS (ESI+) for C$_{21}$H$_{24}$N$_2$O$_3$S m/z 385 (M+1). $^1$H NMR (400 MHz, methanol-d$_4$) δ ppm 1.60-1.72 (m, 3H) 1.85-1.95 (m, 2H) 1.99 (s, 3H) 2.15-2.26 (m, J=11.3, 7.6, 7.6, 3.8, 3.8 Hz, 1H) 2.73 (t, J=12.3 Hz, 1H) 2.86-2.97 (m, 3H) 3.24 (dd, J=12.5, 3.5 Hz, 1H) 3.34-3.37 (m, 1H) 6.98 (d, J=2.3 Hz, 1H) 7.05-7.09 (m, 2H) 7.09-7.12 (m, 2H) 7.41 (d, J=1.8 Hz, 1H) 7.94 (d, J=2.3 Hz, 1H) 7.96 (d, J=1.8 Hz, 1H).

Intermediate 74

7-Iodo-1-benzofuran-5-amine

7-Iodo-5-nitro-1-benzofuran (2.5 g, 8.6 mmol) and iron (2.51 g, 45.0 mmol) were added to a round bottom flask. Methanol (25 mL), 1,4-dioxane (25 mL) and ammonium chloride (2.5 g, 46.7 mmol), dissolved in water (50 mL), were added and the mixture was heated at 100° C. for 16 h. The reaction mixture was filtered through Celite and volatiles were evaporated off. The residue was dissolved in a mixture of methanol (10 mL) and DCM (90 mL). This mixture was filtered through a silica plug and the solvent was evaporated yielding 2.22 g (99%) of the title compound as a brown oil. HPLC purity 70%, $R_T$=1.26 min (System A; 10-97% MeCN over 3 min). MS (ESI+) for C$_8$H$_6$INO m/z is 260 (M+H)$^+$.

Intermediate 75

N-(7-Iodo-1-benzofuran-5-yl)-2-methoxy-5-methyl-benzenesulfonamide

To a mixture of 7-iodo-1-benzofuran-5-amine (2.22 g, 8.6 mmol; Intermediate 74) in dry DCM/THF (5:1; 50 mL, starting material partly dissolved), were added pyridine (1.43 mL, 17.1 mmol) and 6-methoxy-m-toluenesulfonyl chloride (2.64 g, 12.8 mmol). The resultant mixture was stirred at ambient temperature overnight for 21 h. The solvent was evaporated under reduced pressure and the crude product was purified using flash chromatography (eluent: 20% isohexane in DCM). Pure fractions were combined and concentrated to give the product (1.62 g, 42%) as a light brown fluffy solid. HPLC 81%, $R_T$=2.26 min (System A; 30-80% MeCN over 3 min), 86%, $R_T$=2.27 min (System B; 10-97% MeCN over 3 min). $^1$H NMR (400 MHz, CDCl$_3$) δ ppm 2.22 (s, 3H) 4.04 (s, 3H) 6.77 (d, J=2.01 Hz, 1H) 6.92 (d, J=8.28 Hz, 1H) 7.25-7.29 (m, 1H) 7.32 (d, J=2.01 Hz, 1H) 7.36 (d, J=2.01 Hz, 1H) 7.53-7.55 (m, J=2.26 Hz, 1H) 7.62 (d, J=2.26 Hz, 1H). MS (ESI+) for C$_{16}$H$_{14}$INO$_4$ m/z 444 (M+H)$^+$.

Example 138

2-Methoxy-5-methyl-N-[7-(piperidin-4-ylmethyl)-1-benzofuran-5-yl]benzenesulfonamide, trifluoroacetate The title compound was prepared according to the procedure of Example 136 starting from tert-butyl 4-methylenepiperidine-1-carboxylate (120 mg, 0.6 mmol; Intermediate 71) and N-(7-iodo-1-benzofuran-5-yl)-2-methoxy-5-methylbenzenesulfonamide (180 mg, 0.42 mmol; Intermediate 75). Yield: 69 mg (33%). HPLC 96% $R_T$=1.75 (System A; 10-97% MeCN over 3 min) 99% $R_T$=1.58 (System B; 10-90% MeCN over 3 min). MS (ESI+) for C$_{22}$H$_{26}$N$_2$O$_4$S m/z 415 (M+1). $^1$H NMR (400 MHz, methanol-d$_4$) δ ppm 1.22-1.34 (m, 2H) 1.61 (d, J=13.6 Hz, 2H) 1.80-1.91 (m, J=1.3, 7.6, 7.6, 3.6, 3.6 Hz, 1H) 2.10 (s, 3H) 2.69 (d, J=7.3 Hz, 2H) 2.78 (td, J=12.9, 2.6 Hz, 2H) 3.24 (d, J=2.0 Hz, 2H) 3.87 (s, 3H) 6.62 (d, J=2.3 Hz, 1H) 6.79 (d, J=2.0 Hz, 1H) 6.93 (d, J=8.5 Hz, 1H) 7.10 (d, J=2.0 Hz, 1H) 7.21 (dd, 1H) 7.38 (d, J=2.0 Hz, 1H) 7.58 (d, J=2.3 Hz, 1H).

Intermediate 76

2-(2,6-Dibromophenoxy)ethyl bromide*

A mixture of 2,6-dibromophenol (10.2 g, 40 mmol), 1,2-dibromoethane (7.6 g, 40 mmol) and NaOH (1.76 g, 44 mmol) in water was heated at reflux overnight under stirring. The mixture was cooled, extracted with diethyl ether (2×100 mL), the extract washed with aqueous NaOH, brine, dried (MgSO$_4$) and concentrated to give the product as a pale yellow oil. Yield: 10.0 g (70%). $^1$H NMR (400 MHz, CDCl$_3$) δ 3.73 (t, 2H), 4.31 (t, 2H), 6.88 (t, 1H), 7.50 (d, 2H).
*Previously reported in Tetrahedron Lett. 1998, 39, 2219-2222.

Intermediate 77

7-Bromo-2,3-dihydrobenzofuran*

A solution of 2-(2,6-dibromophenoxy)ethyl bromide (1.08 g, 3 mmol; Intermediate 76) in a mixture of THF (12 mL) and hexane (3 mL) was cooled in a ethanol/dry ice bath for 30 min. n-BuLi in hexane (2 mL of 1.5 M solution) was added dropwise over 15 min. The reaction mixture was stirred at −78° C. for another 30 min after which time the bath was allowed to slowly warm to 0° C. The mixture was poured onto water and extracted with diethyl ether (2×100 mL). The combined extract was dried and concentrated to give a pale brown oil (0.5 g) containing the product contaminated with approximately 25% 2,3-dihydrobenzofuran. This material was used as such for further synthesis but could if necessary be purified by flash chromatography [eluent: hexane→EtOAc/hexane (5:95)]. $^1$H NMR (400 MHz, CDCl$_3$) δ 3.30 (t, 2H), 4.65 (t, 2H), 6.71 (t, 1H), 7.11 (dd, 1H), 7.25 (dd, 1H).
*Previously reported in Tetrahedron Lett. 1998, 39, 2219-2222.

Intermediate 78

7-Bromo-5-[(4-methylphenyl)sulfonyl]-2,3-dihydro-1-benzofuran

7-Bromo-1,2-dihydrobenzofuran (64 mg, 0.3 mmol; Intermediate 77) and para-toluenesulfonic acid monohydrate (62 mg, 0.3 mmol) were mixed and then a 1:10 mixture (by weight) of methanesulfonic and phosphorous pentoxide (1 mL) was added. The resultant mixture was stirred over night at room temperature and was then poured onto ice/water. The obtained crystalline material was filtered and dried to give 120 mg of the title product. $^1$H NMR (400 MHz, CDCl$_3$) δ 2.40 (s, 3H), 3.33 (t, 2H), 4.73 (t, 2H), 7.29 (d, 2H), 7.65 (d, 1H), 7.79 (d, 2H), 7.89 (d, 1H); GC-MS (EI+) for C$_{15}$H$_{13}$BrSO$_3$ m/z 354 (M+H)$^+$.

Intermediate 79

7-Bromo-5-[(4-methylphenyl)sulfonyl]-1-benzofuran

A mixture of 7-bromo-5-[(4-methylphenyl)sulfonyl]-2,3-dihydro-1-benzofuran (353 mg, 1 mmol; Intermediate 78), NBS (178 mg, 1 mmol) and dibenzoylperoxide (24 mg, 0.1 mmol) in carbon tetrachloride (20 mL) was heated to 80° C. for 2 h. TEA (2 mL) was added and the mixture was heated for another 2 h. Flash chromatography using EtOAc/hexane 10:90→25:75 as eluent gave the title product as a white crystalline material. Yield: 130 mg (37%). $^1$H NMR (400 MHz, CDCl$_3$) δ 2.39 (s, 3H), 6.93 (d, 1H), 7.30 (d, 2H), 7.78 (d, 1H), 7.84 (d, 2H), 8.02 (d, 1H), 8.19 (d, 1H).

Example 139

3-({5-[(4-Methylphenyl)sulfonyl]-1-benzofuran-7-yl}methyl)pyrrolidine, trifluoroacetate The title compound was prepared according to the procedure of Example 136 starting from tert-butyl 3-methylenepiperidine-1-carboxylate (60 mg, 0.3 mmol; Intermediate 73) and 7-bromo-5-[(4-methylphenyl)sulfonyl]-1-benzofuran (70 mg, 0.21 mmol; Intermediate 79).

Yield: 3 mg (3%). HPLC 97% R$_T$=1.79 (System A; 10-97% MeCN over 3 min) 97% R$_T$=1.61 (System B; 10-90% MeCN over 3 min). MS (ESI+) for C$_{21}$H$_{23}$NO$_3$S m/z 356 (M+1).

Example 140

2-Methoxy-5-methyl-N-[5-(piperidin-4-ylmethyl)-1-benzofuran-7-yl]benzenesulfonamide, trifluoroacetate The title compound was prepared according to the procedure of Example 136 starting from tert-butyl 4-methylenepiperidine-1-carboxylate (120 mg, 0.6 mmol; Intermediate 71) and N-(5-bromo-1-benzofuran-7-yl)-2-methoxy-5-methyl-benzenesulfonamide (150 mg, 0.42 mmol; obtained in Example 132, Step 1). Yield: 27 mg (12%). HPLC 97% R$_T$=1.68 (System A; 10-97% MeCN over 3 min) 97% R$_T$=1.52 (System B; 10-90% MeCN over 3 min). MS (ESI+) for C$_{22}$H$_{26}$N$_2$O$_4$S m/z 415 (M+1). $^1$H NMR (400 MHz, methanol-d$_4$) δ ppm 1.22-1.33 (m, 2H) 1.62-1.73 (m, 3H) 2.13 (s, 3H) 2.51 (d, J=7.0 Hz, 2H) 2.80 (td, J=12.7, 2.4 Hz, 2H) 3.24-3.28 (m, 2H) 3.77 (s, 3H) 6.63 (d, J=2.0 Hz, 1H) 6.87 (d, J=8.5 Hz, 1H) 6.98 (d, J=1.5 Hz, 1H) 7.05 (d, J=1.5 Hz, 1H) 7.21 (dd, J=8.2, 1.9 Hz, 1H) 7.46 (d, J=2.3 Hz, 1H) 7.59 (d, J=2.3 Hz, 1H).

Biological Tests

The ability of a compound according to the invention to bind to the human 5-HT$_6$ receptor, and to be pharmaceutically useful, can be determined using in vivo and in vitro assays known in the art.

(a) 5-HT$_6$ Binding Assay

Binding affinity experiment for the 5-HT$_6$ receptor are performed in HEK293 cells transfected with the human 5-HT$_6$ receptor using [$^3$H]-LSD as labeled ligand according to the general method as described by Boess F. G et al. Neuropharmacology 36(4/5) 713-720, 1997.

Materials

Cell Culture

The HEK-293 cell line transfected with the human 5-HT$_6$ receptor was cultured in Dulbeccos Modified Eagles Medium containing 5% dialyzed foetal bovine serum, (Gibco BRL 10106-169), 0.5 mM sodium pyruvate and 400 μg/mL Geneticin (G-418) (Gibco BRL10131-019). The cells were passaged 1:10, twice a week.

Chemicals

The radioligand [$^3$H] LSD 60-240 Ci/mmol, obtained from Amersham Pharmacia Biotech, (Buckinghamshire, England)

was in ethanol and stored at −20° C. The compounds were dissolved in 100% DMSO and diluted with binding buffer.

Disposable

Compounds were diluted in Costar 96 well V-bottom polypropylene plates (Corning Inc. Costar, N.Y., USA). Samples were incubated in Packard Optiplate (Packard Instruments B.V., Groningen, The Netherlands). The total amount of added radioligand was measured in Packard 24-well Barex plates (Packard Instruments B.V., Groningen, The Netherlands) in the presence of Microscint 20 scintillation fluid (Packard Bioscience, Meriden, Conn., USA).

Buffer

The binding buffer consisted of 20 mM HEPES, 150 mM NaCl, 10 mM $MgCl_2$, and 1 mM, EDTA, pH 7.4.

Methods

Membrane Preparation

Cells were grown to approximately 90% confluence on 24.5×24.5 mm culture dishes. The medium was aspirated, and after rinsing with ice-cold PBS, the cells were scraped off using 25 mL Tris buffer (50 mM Tris-HCl, 1 mM EDTA, 1 mM EGTA, pH 7.4) and a window scraper. The cells were then broken with a Polytron homogeniser, and remaining particulate matter was removed by low-speed centrifugation, 1000×g for 5 min. Finally, the membranes were collected by high-speed centrifugation (20 000×g), suspended in binding buffer, and frozen in aliquots at −70° C.

Radioligand Binding

Frozen cell membranes were thawed, immediately rehomogenized with a Polytron homogenizer, and coupled to SPA wheat germ agglutinin beads (Amersham Life Sciences, Cardiff, England) for 30 min under continuous shaking of the tubes. After coupling, the beads were centrifuged for 10 minutes at 1000 g, and subsequently suspended in 20 mL of binding buffer per 96-well plate The binding reaction was then initiated by adding radioligand and test compounds to the bead-membrane suspension. Following incubation at room temperature, the assay plates were subjected to scintillation counting.

The original SPA method was followed except for that membranes were prepared from HEK293 cells expressing the human $5\text{-}HT_6$ receptor instead of from HeLa cells (Dinh D M, Zaworski P G, Gill G S, Schlachter S K, Lawson C F, Smith M W. Validation of human $5\text{-}HT_6$ receptors expressed in HeLa cell membranes: saturation binding studies, pharmacological profiles of standard CNS agents and SPA development. (The Upjohn Company Technical Report 7295-95-064 1995; 27 December). The specific binding of [$^3$H]-LSD was saturable, while the non-specific binding increased linearly with the concentration of added radioligand. [$^3$H]-LSD bound with high affinity to $5\text{-}HT_6$ receptors. The $K_d$ value was estimated to 2.6±0.2 nM based on four separate experiments.

The total binding at 3 nM of [$^3$H]-LSD, the radioligand concentration used in the competition experiments, was typically 6000 dpm, and the specific binding more than 70%. 5-HT caused a concentration dependent inhibition of [$^3$H]-LSD binding with an over all average Ki value of 236 nM when tested against two different membrane preparations. The inter assay variability over three experiments showed a CV of 10% with an average $K_i$ values of 173 nM (SD 30) and a Hill coefficient of 0.94 (SD 0.09). The intra assay variation was 3% (n=4). All unlabelled ligands displaced the specific binding of [$^3$H]-LSD in a concentration-dependent manner, albeit at different potencies. The rank order of affinity for the $5\text{-}HT_6$ receptor of reference compounds was methiothepin (Ki 2 nM)>mianserin (190 nM)≈5-HT (236 nM)>methysergide (482 nM)>mesulergine (1970 nM).

Protein Determination

Protein concentrations were determined with BioRad Protein Assay (Bradford M M. A rapid and sensitive method for the quantitation of microgram quantities of protein utilizing the principle of protein-dye binding. Anal. Biochem. 1976; 72:248-54). Bovine serum albumin was used as standard.

Scintillation Counting

The radioactivity was determined in a Packard Top-Count™ scintillation counter (Packard Instruments, Meriden, Conn., USA) at a counting efficiency of approximately 20%. The counting efficiency was determined in separate sets of experiments.

Saturation Experiments

At least 6 concentrations in duplicates of radioligand (0.1-20 nM of [$^3$H]-LSD) were used in saturation experiments. The specific binding was calculated as the difference between total binding and non-specific binding, which was determined as the binding of radioligand in the presence of 5 µM lisuride. $B_{max}$ and the dissociation constant, $K_d$, were determined from the non-linear regression analysis using equation 1. $L_u$ is the unbound concentration of radioligand, and is y is the amount bound.

$$y = \frac{B_{max} \cdot Lu}{Lu + Kd} \quad \text{(equation 1)}$$

Competition Experiments

Total- and non-specific binding of radioligand was defined in eight replicates of each. Samples containing test compound were run in duplicate at 11 concentrations. Incubations were carried out at room temperature for 3 hours. The $IC_{50}$ value, i.e. the concentration of test compound that inhibited 50% of the specific binding of radioligand, was determined with non linear regression analysis and the $K_i$ value was calculated using equation 2 [Cheng Y. C. Biochem. Pharmacol. 22, 3099-3108, 1973].

$$Ki = \frac{IC_{50}}{1 + \frac{L}{K_d}} \quad \text{(equation 2)}$$

L=concentration of radioligand
$K_d$=Affinity of radioligand (b) $5\text{-}HT_6$ Intrinsic Activity Assay Antagonists to the $5\text{-}HT_6$ receptor were characterized by measuring inhibition of 5-HT induced increase in cAMP in HEK 293 cells expressing the human $5\text{-}HT_6$ receptor (see Boess et al. (1997) Neuropharmacology 36: 713-720). Briefly, HEK293/$5\text{-}HT_6$ cells were seeded in polylysine coated 96-well plates at a density of 25,000/well and grown in DMEM (Dulbecco's Modified Eagle Medium) (without phenol-red) containing 5% dialyzed Foetal Bovine Serum for 48 h at 37° C. in a 5% $CO_2$ incubator. The medium was then aspirated and replaced by 0.1 mL assay medium (Hanks Balance Salt Solution containing 20 mM HEPES, 1.5 mM isobutylmethylxanthine and 1 mg/mL bovine serum albumin). After addition of test substances, 50 µl dissolved in assay medium, the cells were incubated for 10 min at 37° C. in a 5% $CO_2$ incubator. The medium was again aspirated and the cAMP content was determined using a radioactive cAMP kit (Amersham Pharmacia Biotech, BIOTRAK RPA559). The potency of antagonists was quantified by determining the concentration that caused 50% inhibition of 5-HT (at [5-HT]=8 times $EC_{50}$) evoked increase in cAMP, using the formula $fKi=IC_{50}/(1+[5HT]/EC_{50})$.

The compounds in accordance with the invention have a selective affinity to $5\text{-}HT_6$ receptors with $K_i$ and $IC_{50,corr}$ values between 0.5 nM and 5 µM or display a % inhibition of [$^3$H]-LSD≧20% at 50 nM and are antagonists, agonists or partial agonists at 5-HT$_6$. The compounds show good selectivity over 5-HT$_{1a}$, 5-HT$_{1b}$, 5-HT$_{2a}$, 5-HT$_{2b}$, 5-HT$_{2c}$.

(c) In Vivo Assay of Reduction of Food Intake

For a review on serotonin and food intake, see Blundell, J. E. and Halford, J. C. G. (1998) Serotonin and Appetite Regulation. Implications for the Pharmacological Treatment of Obesity. CNS Drugs 9:473-495.

Obese (ob/ob) mouse is selected as the primary animal model for screening as this mutant mouse consumes high amounts of food resulting in a high signal to noise ratio. To further substantiate and compare efficacy data, the effect of the compounds on food consumption is also studied in wild type (C57BL/6J) mice. The amount of food consumed during 15 hours of infusion of compounds is recorded.

Male mice (obese C57BL/6JBom-Lep$^{ob}$ and lean wild-type C57BL/6JBom; Bomholtsgaard, Denmark) 8-9 weeks with an average body weight of 50 g (obese) and 25 g (lean) are used in all the studies. The animals are housed singly in cages at 23±1° C., 40-60% humidity and have free access to water and standard laboratory chow. The 12/12-h light/dark cycle is set to lights off at 5 p.m. The animals are conditioned for at least one week before start of study.

The test compounds are dissolved in solvents suitable for each specific compound such as cyclodextrin, cyclodextrin/methane sulphonic acid, polyethylene glycol/methane sulphonic acid, saline. Fresh solutions are made for each study. Doses of 30, 50 and 100 mg kg$^{-1}$ day$^{-1}$ are used. The purity of the test compounds is of analytical grade.

The animals are weighed at the start of the study and randomized based on body weight. Alzet osmotic minipumps (Model 2001D; infusion rate 8 μl/h) are used and loaded essentially as recommended by the Alzet technical information manual (Alza Scientific Products, 1997; Theeuwes, F. and Yam, S. I. Ann. Biomed. Eng. 4(4). 343-353, 1976). Continuous subcutaneous infusion with 24 hours duration is used. The minipumps are either filled with different concentrations of test compounds dissolved in vehicle or with only vehicle solution and maintained in vehicle pre-warmed to 37° C. (approx. 1 h). The minipumps are implanted subcutaneously in the neck/back region under short acting anesthesia (metofane/enflurane). This surgical procedure lasts approximately 5 min.

The weight of the food pellets are measured at 5 p.m. and at 8 p.m. for two days before (baseline) and one day after the implantation of the osmotic minipumps. The weigh-in is performed with a computer assisted Mettler Toledo PR 5002 balance. Occasional spillage is corrected for. At the end of the study the animals are killed by neck dislocation and trunk blood sampled for later analysis of plasma drug concentrations.

The plasma sample proteins are precipitated with methanol, centrifuged and the supernatant is transferred to HPLC vials and injected into the liquid chromatography/mass spectrometric system. The mass spectrometer is set for electrospray positive ion mode and Multiple Reaction Monitoring. A linear regression analysis of the standards forced through the origin is used to calculate the concentrations of the unknown samples.

Food consumption for 15 hours is measured for the three consecutive days and the percentage of basal level values is derived for each animal from the day before and after treatment. The values are expressed as mean±SD and ±SEM from eight animals per dose group. Statistical evaluation is performed by Kruskal-Wallis one-way ANOVA using the percent basal values. If statistical significance is reached at the level of p<0.05, Mann-Whitney U-test for statistical comparison between control and treatment groups is performed.

The compounds according to the invention show an effect (i.e., reduction of food intake) in the range of 5-200 mg/kg/d.

Table 4. Functional in vitro data at the h-5-HT receptor (fKi). Data are expressed as fKi$_i$=IC$_{50}$/(1+[5HT]/EC$_{50}$). The potency of antagonists was quantified by determining the concentration that caused 50% inhibition of 5-HT (at [5-HT]=8 times EC$_{50}$) evoked increase in cAMP, using the formula fKi=IC$_{50}$/(1+[5HT]/EC$_{50}$).

TABLE 4

| EXAMPLE | fKi (nM) |
| --- | --- |
| 1 | 87 |
| 12 | 87 |
| 28 | 66 |
| 32 | 54 |
| 33 | 20 |

Table 5. Competitive binding in vitro data at the h-5-HT receptor (Ki). The IC$_{50}$ value, i.e. the concentration of test compound that inhibited 50% of the specific binding of radioligand ([$^3$H]-LSD), was determined with non linear regression analysis and the K$_i$ value was calculated using the equation $$Ki = \frac{IC_{50}}{1 + \frac{L}{K_d}}$$

TABLE 5

| Example | Ki (nM) |
| --- | --- |
| 92 | 5.56 |
| 36 | 20 |
| 67 | 13 |
| 84 | 7.5 |
| 85 | 7 |
| 86 | 7 |
| 87 | 5.3 |
| 89 | 14 |
| 91 | 56 |
| 54 | 17.4 |

A number of embodiments of the invention have been described. Nevertheless, it will be understood that various modifications may be made without departing from the spirit and scope of the invention. Accordingly, other embodiments are in the claims claims.

What is claimed is:

1. A compound of the Formula (I):

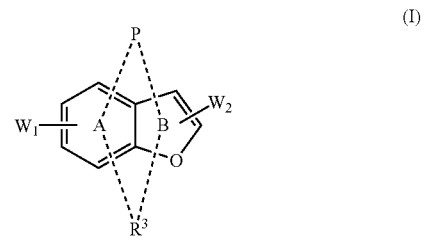

wherein:

P is a substituent selected from Formulae (II)-(V) and (VII) below:

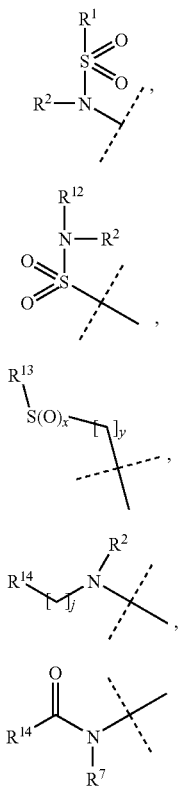

wherein:

x, y and j are each independently selected from 0, 1, and 2;

wherein the dashed bonds in Formula (I) denote that P and $R^3$, respectively, may be attached to either the A or B ring at any carbon atom that allows the substitution, provided that P and $R^3$ are not both simultaneously attached to ring B;

$R^1$ is selected from:
(a) $C_{1-6}$-alkyl,
(b) $C_{1-6}$-alkoxy-$C_{1-6}$-alkyl,
(c) $C_{3-6}$-alkenyl,
(d) hydroxy-$C_{1-6}$-alkyl,
(e) halo-$C_{1-6}$-alkyl,
(f) aryl,
(g) arylcarbonylmethyl,
(h) aryl-$C_{3-6}$-alkenyl,
(i) aryl-$C_{1-6}$-alkyl,
(j) $C_{3-7}$-cycloalkyl,
(k) heteroaryl,
(l) 4-piperidinyl,
(m) N-substituted 4-piperidinyl, wherein the substituents are selected from $C_{1-6}$-alkyl and aryl-$C_{1-6}$-alkyl, and
(o) heteroaryl-$C_{1-6}$-alkyl, wherein any heteroaryl or aryl residue, alone or as part of another group in $R^1$, may be substituted, independently, in one or more positions with a substituent selected from:
(a) hydrogen,
(b) halogen,
(c) $C_{1-6}$-alkyl,
(d) hydroxy,
(e) $C_{1-6}$-alkoxy,
(f) $C_{2-6}$-alkenyl,
(g) $C_{2-3}$-alkynyl,
(h) phenyl,
(i) phenoxy,
(j) benzyloxy,
(k) benzoyl,
(l) benzyl,
(m) —$OCF_3$,
(n) —CN,
(o) hydroxy-$C_{1-6}$-alkyl,
(p) $C_{1-6}$-alkoxy-$C_{1-6}$-alkyl,
(q) halo-$C_{1-6}$-alkyl,
(r) —$NR^9R^9$,
(s) —$NO_2$,
(t) —$CONR^9R^9$,
(u) —$NR^7COR^{10}$,
(v) —$C(=O)R^{10}$,
(x) $C_{1-6}$-alkoxycarbonyl,
(y) $C_{1-6}$-alkylthio,
(z) —$SCF_3$,
(ab) methylsulfonyl, and
(ac) —COOH with the proviso that when the substituent on the said aryl or heteroaryl residue is selected from phenyl, phenoxy, benzyloxy, benzoyl and benzyl, the phenyl ring of the substituent may itself be optionally substituted by one or more of halogen, $C_{1-4}$-alkyl, $C_{1-4}$-alkylthio, $C_{1-4}$-alkoxy, cyano, and trifluoromethyl;

$R^2$ is selected from:
(a) hydrogen,
(b) $C_{1-6}$-alkyl,
(c) $C_{1-6}$-alkoxy-$C_{2-6}$ alkyl,
(d) hydroxy-$C_{2-6}$-alkyl,
(e) —$(CH_2)_m$—$CH_2$—F, wherein m is 2-4,
(f) 3,3,3-trifluoropropyl, and
(g) $C_{1-4}$-alkylsulfonyl, provided that P is a substituent of formula (V);

$W_1$ is attached to ring A;
$W_2$ is attached to ring B;
$W_1$ and $W_2$ are each independently selected from:
(a) hydrogen,
(b) halogen,
(c) $C_{1-6}$-alkyl,
(d) hydroxy,
(e) $C_{1-6}$-alkoxy,
(f) $C_{1-6}$-alkylthio,
(g) $C_{2-6}$-alkenyl,
(h) phenyl,
(i) phenoxy,
(j) benzyloxy,
(k) benzoyl,
(l) benzyl,
(m) —$OCF_3$,
(n) —CN,
(o) hydroxy-$C_{1-6}$-alkyl,
(p) $C_{1-6}$-alkoxy-$C_{1-6}$-alkyl,
(q) halo-$C_{1-6}$-alkyl,
(r) —$CONR^9R^9$,
(s) —$C(=O)R^{10}$,
(t) $C_{1-6}$-alkoxycarbonyl, and
(u) —$SCF_3$, with the proviso that when $W_1$ and $W_2$ are selected from phenyl, phenoxy, benzoyl, benzyloxy and benzyl, the phenyl ring thereof may be optionally substituted by one or more of halogen, $C_{1-4}$-alkyl, $C_{1-4}$-alkoxy, cyano, and trifluoromethyl, and with the further proviso that, when $W_1$ and $W_2$ are not selected from methoxy, methyl and halogen, at least one of $W_1$ and $W_2$ is hydrogen;

$R^3$ is a group selected from the following groups:

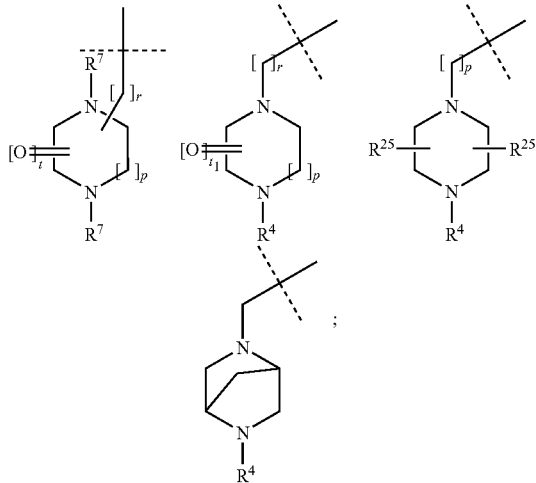

wherein:
r is 1,
p is 1, and
t=0 or 1,
$t_1$=1 or 2, wherein $R^4$ is a group selected from:
(a) hydrogen,
(b) $C_{1-6}$-alkyl,
(c) 2-cyanoethyl,
(d) hydroxy-$C_{2-4}$-alkyl,
(e) $C_{3-6}$-alkenyl,
(f) $C_{3-6}$-alkynyl,
(g) $C_{3-7}$-cycloalkyl,
(h) $C_{3-7}$-cycloalkyl-$C_{1-4}$-alkyl,
(i) $C_{1-6}$-alkoxy-$C_{2-6}$-alkyl
(j) —C(=NH)—N—$R^{11}R^{11}$,
(k) —C(=O)—N—$R^{11}R^{11}$,
(l) —CH$_2$—CO—N—$R^{11}R^{11}$, and
(m) 3,3,3-trifluoropropyl;

each $R^7$ is independently selected from:
(a) hydrogen, provided that $R^7$ is not hydrogen when present simultaneously with r and said r is 1,
(b) $C_{1-4}$-alkyl,
(c) hydroxy-$C_{2-4}$-alkyl, and
(d) methoxy-$C_{2-4}$-alkyl;

each $R^9$ is independently selected from:
(a) hydrogen,
(b) $C_{1-6}$-alkyl, and
(c) $C_{3-7}$-cycloalkyl, or
wherein the two $R^9$ groups together with the nitrogen to which they are attached form a heterocyclic ring; and provided that when the two $R^9$ groups form a piperazine ring, the nitrogen of the said piperazine ring that allows the substitution is optionally substituted with $C_{1-4}$-alkyl, and further provided that when the two $R^9$ groups form a piperidine ring, any ring carbon atom in the said piperidine ring may be optionally substituted with methyl;

$R^{10}$ is selected from:
(a) $C_{1-6}$-alkyl,
(c) aryl, and
(d) heteroaryl, wherein heteroaryl or aryl may be substituted in one or more positions with substituents selected from halogen, $C_{1-4}$-alkyl, $C_{1-4}$-alkoxy, cyano, trifluoromethyl;

each $R^{11}$ is independently selected from:
(a) hydrogen,
(b) methyl, and
(c) ethyl, provided that $R^{11}$ is present in a group $R^4$ selected from —CH$_2$—CO—N—$R^{11}R^{11}$;

$R^{12}$ is selected from:
(a) hydrogen,
(b) $C_{1-6}$-alkyl,
(c) aryl,
(d) aryl-$C_{1-6}$-alkyl,
(e) $C_{3-7}$-cycloalkyl,
(f) $C_{3-7}$-cycloalkyl-$C_{1-4}$-alkyl,
(g) heteroaryl, and
(h) heteroaryl-$C_{1-6}$-alkyl, wherein any heteroaryl or aryl residue, alone or as part of another group, is optionally substituted, independently, in one or more positions with substituents selected from:
(a) hydrogen,
(b) halogen,
(c) $C_{1-6}$-alkyl,
(d) hydroxy,
(e) $C_{1-6}$-alkoxy,
(f) $C_{2-6}$-alkenyl,
(g) $C_{2-6}$-alkynyl,
(h) phenyl,
(i) phenoxy,
(j) benzyloxy,
(k) benzoyl,
(l) benzyl,
(m) —OCF$_3$,
(n) —CN,
(o) hydroxy-$C_{1-6}$-alkyl,
(p) $C_{1-6}$-alkyl,
(q) halo-$C_{1-6}$-alkyl,
(r) —NR$^9$R$^9$,
(s) —NO$_2$,
(t) —CONR$^9$R$^9$,
(u) —NR$^7$COR$^{10}$,
(v) —C(=O)R$^{10}$,
(x) $C_{1-6}$-alkoxycarbonyl,
(y) $C_{1-6}$-alkylthio,
(z) —SCF$_3$,
(ab) methylsulfonyl, and
(ac) —COOH with the proviso that when the substituent on the said aryl or heteroaryl residue is selected from phenyl, phenoxy, benzyloxy, benzoyl, and benzyl, the phenyl ring of the substituent may itself be optionally substituted by one or more of halogen, $C_{1-4}$-alkyl, $C_{1-4}$-alkoxy, cyano, and trifluoromethyl;

$R^{13}$ is selected from:
(a) $C_{1-6}$-alkyl,
(b) $C_{3-6}$-cycloalkyl,
(c) aryl,
(d) heteroaryl,
(e) aryl-$C_{1-2}$-alkyl, and
(f) heteroaryl-$C_{1-2}$-alkyl, wherein any heteroaryl or aryl residue may be substituted in one or more positions with substituents selected from halogen, $C_{1-4}$-alkyl, $C_{1-4}$-alkoxy, cyano, trifluoromethyl, and acetyl;

$R^{14}$ is selected from:
  (a) aryl,
  (b) heteroaryl,
  (c) aryl-$C_{1-3}$-alkyl, and
  (d) heteroaryl-$C_{1-3}$-alkyl;
    wherein any heteroaryl or aryl residue may be substituted in one or more positions with substituents selected from halogen, $C_{1-4}$-alkyl, $C_{1-4}$-alkoxy, cyano, and trifluoromethyl;
each $R^{25}$ is independently selected from
  (a) hydrogen,
  (b) $C_{1-4}$-alkyl,
  (c) hydroxy-$C_{1-4}$-alkyl,
  (d) $C_{1-4}$-alkoxy-$C_{1-4}$-alkyl, and
  (e) fluoromethyl,
    with the proviso that when both $R^{25}$ simultaneously are selected from $C_{1-4}$-alkyls, wherein said $C_{1-4}$-alkyls may be attached to the same or different carbon atoms and with the further proviso that when one $R^{25}$ is selected from hydroxy-$C_{1-4}$-alkyl, $C_{1-4}$-alkoxy-$C_{1-4}$-alkyl, and fluoromethyl, the other $R^{25}$ represents hydrogen; and
with the proviso that $R^2$ and $R^{12}$ in Formula (III) are not simultaneously hydrogen; and with the further proviso that the said $R^2$ and $R^{12}$ together may form a heterocyclic ring selected from piperidine, pyrrolidine, morpholine, piperazine thiomorpholine, and provided that when $R^2$ and $R^{12}$ together form a piperazine ring, the distal piperazine nitrogen is optionally substituted by $C_{1-4}$ alkyl or aryl, and wherein said aryl may be substituted in one or more positions with substituents selected from halogen, $C_{1-4}$-alkyl, $C_{1-4}$-alkoxy, cyano, trifluoromethyl; or $R^2$ and $R^{12}$ together form a heteroaromatic ring of Formula (VIII):

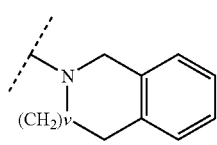

(VIII)

wherein v is 0, 1 or 2; and
or a geometrical isomer, tautomer, or optical isomer thereof;
or a pharmaceutically acceptable salt of such a compound.

2. The compound according to claim 1 of the formula (1b)

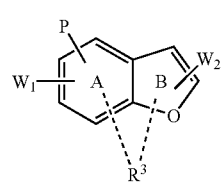

wherein:
P is a substituent selected from Formulae (II)-(V) and (VII) below:

(II)

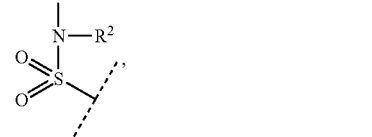
(III)

(IV)

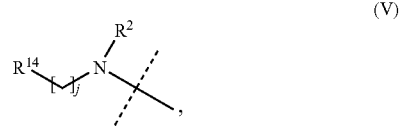
(V)

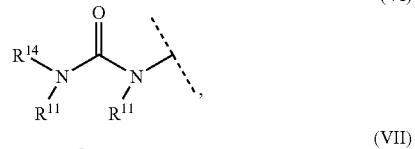
(VI)

(VII)

wherein:
x, y and j are each independently selected from 0, 1, and 2;
wherein the dashed bonds denote that $R^3$ may be attached to either the A or B ring at any carbon atom that allows the substitution;
$R^1$ is selected from:
  (a) $C_{1-6}$-alkyl,
  (b) $C_{1-6}$-alkoxy-$C_{2-6}$-alkyl,
  (c) $C_{3-6}$-alkenyl,
  (d) hydroxy-$C_{2-6}$-alkyl,
  (e) halo-$C_{1-6}$-alkyl,
  (f) aryl,
  (g) arylcarbonylmethyl,
  (h) aryl-$C_{3-6}$-alkenyl,
  (i) aryl-$C_{1-6}$-alkyl,
  (j) $C_{3-7}$-cycloalkyl,
  (k) heteroaryl, and
  (o) heteroaryl-$C_{1-6}$-alkyl,
    wherein any heteroaryl or aryl residue, alone or as part of another group may be optionally substituted, independently, in one or more positions with a substituent selected from:
      (b) halogen,
      (c) $C_{1-6}$-alkyl,
      (d) hydroxy,
      (e) $C_{1-6}$-alkoxy,
      (f) $C_{2-6}$-alkenyl, (g) $C_{2-3}$-alkynyl,
(h) phenyl,
(i) phenoxy,
(j) benzyloxy,
(k) benzoyl,
(l) benzyl,
(m) —$OCF_3$,
(n) —CN,
(o) hydroxy-$C_{1-6}$-alkyl,
(p) $C_{1-6}$-alkoxy-$C_{1-6}$-alkyl,
(q) halo-$C_{1-6}$-alkyl,
(r) —$NR^9R^9$,
(s) —$NO_2$,
(t) —$CONR^9R^9$,
(u) —$NR^7COR^{10}$,
(v) —$C(=O)R^{10}$,
(x) $C_{1-6}$-alkoxycarbonyl,
(y) $C_{1-6}$-alkylthio,
(z) —$SCF_3$,
(ab) methylsulfonyl, and
(ac) —COOH, with the proviso that when the substituent on the said aryl or heteroaryl residue is selected from phenyl, phenoxy, benzyloxy, benzoyl and benzyl, the phenyl ring of the substituent may itself be optionally substituted by one or more of halogen, $C_{1-4}$-alkyl, $C_{1-4}$-alkylthio, $C_{1-4}$-alkoxy, cyano, and trifluoromethyl;

$R^2$ is selected from:
(a) hydrogen,
(b) $C_{1-6}$-alkyl,
(c) $C_{1-6}$-alkoxy-$C_{2-6}$ alkyl,
(d) hydroxy-$C_{2-6}$-alkyl,
(e) —$(CH_2)_m$—$CH_2$—F, wherein m is 2-4, and
(g) $C_{1-4}$-alkylsulfonyl, provided that P is selected from a substituent of formula (V);

$W_1$ and $W_2$ are each independently selected from:
(a) hydrogen,
(b) halogen,
(c) $C_{1-6}$-alkyl,
(d) hydroxy,
(e) $C_{1-6}$-alkoxy,
(f) $C_{1-6}$-alkylthio,
(g) $C_{2-6}$-alkenyl,
(m) —$OCF_3$,
(n) —CN,
(o) hydroxy-$C_{1-6}$-alkyl,
(p) $C_{1-6}$-alkoxy-$C_{1-6}$-alkyl,
(q) halo-$C_{1-6}$-alkyl,
(r) —$CONR^9R^9$,
(s) —$C(=O)R^{10}$,
(t) $C_{1-6}$-alkoxycarbonyl, and
(u) —$SCF_3$, with the proviso that when $W_1$ and $W_2$ are not selected from methoxy, methyl and halogen, at least one of $W_1$ and $W_2$ is hydrogen;

$R^3$ is a group selected from the following groups:

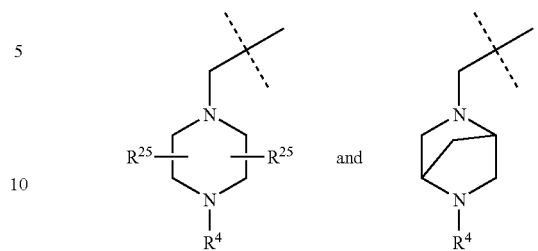

and wherein
$R^4$ is selected from:
(a) hydrogen,
(b) $C_{1-6}$-alkyl,
(c) 2-cyanoethyl,
(d) hydroxy-$C_{2-6}$-alkyl,
(e) $C_{3-6}$-alkenyl,
(f) $C_{3-6}$-alkynyl,
(g) $C_{3-7}$-cycloalkyl,
(h) $C_{3-7}$-cycloalkyl-$C_{1-4}$-alkyl
(i) $C_{1-6}$-alkoxy-$C_{2-6}$-alkyl
(l) —$CH_2$—CO—N—$R^{11}R^{11}$, and
(m) 3,3,3-trifluoropropyl;

each $R^7$ is independently selected from:
(a) hydrogen,
(b) $C_{1-4}$-alkyl,
(c) hydroxy-$C_{2-4}$-alkyl, and
(d) methoxy-$C_{2-4}$-alkyl;

each $R^9$ is independently selected from:
(a) hydrogen,
(b) $C_{1-6}$-alkyl, and
(c) $C_{3-7}$-cycloalkyl, or the two $R^9$ groups together with the nitrogen to which they are attached form a heterocyclic ring; and provided that when the two $R^9$ groups form a piperazine ring, the nitrogen of the said piperazine ring that allows the substitution may be optionally substituted with $C_{1-4}$-alkyl; and further provided that when the two $R^9$ groups form a piperidine ring, any ring carbon atom in the said piperidine ring may be optionally substituted with methyl;

$R^{10}$ is selected from:
(a) $C_{1-6}$-alkyl,
(c) aryl, and
(d) heteroaryl,
wherein heteroaryl or aryl may be optionally substituted in one or more positions with substituents selected from halogen, $C_{1-4}$-alkyl, $C_{1-4}$-alkoxy, cyano, and trifluoromethyl;

each $R^{11}$ is independently selected from:
(a) hydrogen,
(b) methyl, and
(c) ethyl, provided that $R^{11}$ is present in a group $R^4$ selected from —$CH_2$—CO—N—$R^{11}R^{11}$;

$R^{12}$ is selected from:
(a) hydrogen,
(b) $C_{1-6}$-alkyl,
(c) aryl,
(d) aryl-$C_{1-6}$-alkyl,
(e) $C_{3-7}$-cycloalkyl,
(f) $C_{3-7}$-cycloalkyl-$C_{1-4}$-alkyl
(g) heteroaryl, and
(h) heteroaryl-$C_{1-6}$-alkyl, wherein any heteroaryl or aryl residue, alone or as part of another group, may be optionally substituted, independently, in one or more positions with substituents selected from:
(b) halogen,
(c) $C_{1-6}$-alkyl,
(d) hydroxy,
(e) $C_{1-6}$-alkoxy,
(f) $C_{2-6}$-alkenyl,
(g) $C_{2-3}$-alkynyl,
(h) phenyl,
(i) phenoxy,
(j) benzyloxy,
(k) benzoyl,
(l) benzyl,
(m) —OCF$_3$,
(n) —CN,
(o) hydroxy-$C_{1-6}$-alkyl,
(p) $C_{1-6}$-alkoxy-$C_{1-6}$-alkyl,
(q) halo-$C_{1-6}$-alkyl,
(r) —NR$^9$R$^9$,
(s) —NO$_2$,
(t) —CONR$^9$R$^9$,
(u) —NR$^7$COR$^{10}$,
(v) —C(=O)R$^{10}$,
(x) $C_{1-6}$-alkoxycarbonyl,
(y) $C_{1-6}$-alkylthio,
(z) —SCF$_3$,
(ab) methylsulfonyl, and
(ac) —COOH,
with the proviso that when the substituent on the said aryl or heteroaryl residue is selected from phenyl, phenoxy, benzyloxy, benzoyl, and benzyl, the phenyl ring of the substituent may itself be optionally substituted by one or more of halogen, $C_{1-4}$-alkyl, $C_{1-4}$-alkoxy, cyano, and trifluoromethyl;
R$^{13}$ is selected from:
(a) $C_{1-6}$-alkyl,
(b) $C_{3-6}$-cycloalkyl,
(c) aryl,
(d) heteroaryl,
(e) aryl-$C_{1-2}$-alkyl, and
(f) heteroaryl-$C_{1-2}$-alkyl,
wherein any heteroaryl or aryl residue may be optionally substituted in one or more positions with substituents selected from halogen, $C_{1-4}$-alkyl, $C_{1-4}$-alkoxy, cyano, trifluoromethyl, and acetyl;
R$^{14}$ is selected from:
(a) aryl,
(b) heteroaryl,
(c) aryl-$C_{1-3}$-alkyl, and
(d) heteroaryl-$C_{1-3}$-alkyl,
wherein any heteroaryl or aryl residue may be substituted in one or more positions with substituents selected from halogen, $C_{1-4}$-alkyl, $C_{1-4}$-alkoxy, cyano, and trifluoromethyl;
each R$^{25}$ is independently selected from
(a) hydrogen,
(b) $C_{1-4}$-alkyl,
(c) hydroxy-$C_{1-4}$-alkyl,
(d) $C_{1-4}$-alkoxy-$C_{1-4}$-alkyl, and
(e) fluoromethyl,
with the proviso that when both R$^{25}$ simultaneously are selected from $C_{1-4}$-alkyl, said $C_{1-4}$-alkyl may be attached to the same or different carbon atoms, and with the further proviso that when one R$^{25}$ is selected from hydroxy-$C_{1-4}$-alkyl, $C_{1-4}$-alkoxy-$C_{1-4}$-alkyl, and fluoromethyl, the other R$^{25}$ represents hydrogen; and with the proviso that R$^2$ and R$^{12}$ in Formula (III) are not simultaneously hydrogen; and with the further proviso that the said R$^2$ and R$^{12}$ together may form a heterocyclic ring selected from piperidine, pyrrolidine, morpholine, piperazine thiomorpholine, and provided that when R$^2$ and R$^{12}$ together form a piperazine ring, the distal piperazine nitrogen may be optionally substituted by $C_{1-4}$ alkyl or aryl, and wherein said aryl may be optionally substituted in one or more positions with substituents selected from halogen, $C_{1-4}$-alkyl, $C_{1-4}$-alkoxy, cyano, trifluoromethyl; or R$^2$ and R$^{12}$ together form a heteroaromatic ring of Formula (VIII):

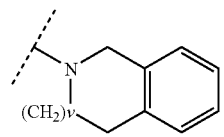

(VIII)

wherein v is 0 or 1;

or a pharmaceutically acceptable salt of such a compound.

3. The compound according to claim 1, or a pharmaceutically acceptable salt thereof, wherein P is a substituent selected from Formulae (II)-(V) below:

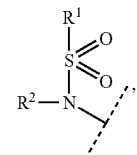

(II)

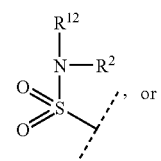

(III)

, or

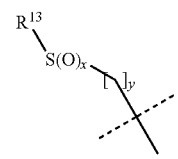

(IV)

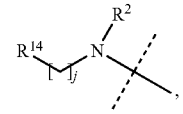

(V)

wherein x is 2, y is 0 and j is 1;

R$^1$ is selected from
(f) aryl,
(i) aryl-$C_{1-3}$-alkyl,
(k) heteroaryl, and
(o) heteroaryl-$C_{1-3}$-alkyl, wherein any heteroaryl or aryl residue, alone or as part of another group may be optionally substituted, independently, in one or more positions with a substituent selected from:
(b) halogen,
(c) $C_{1-4}$-alkyl,
(d) hydroxy,
(e) $C_{1-4}$-alkoxy,
(m) —$OCF_3$,
(n) —CN,
(o) hydroxy-$C_{1-4}$-alkyl,
(p) $C_{1-2}$-alkoxy-$C_{1-2}$-alkyl,
(q) halo-$C_{1-3}$-alkyl,
(r) —$NR^9R^9$,
(t) —$CONR^9R^9$,
(u) —$NR^7COR^{10}$,
(v) —$C(=O)R^{10}$,
(x) $C_{1-3}$-alkoxycarbonyl,
(y) $C_{1-3}$-alkylthio, and
(ab) methylsulfonyl, $R^2$ is selected from:
(a) hydrogen, and
(b) $C_{1-4}$-alkyl, $W_1$ and $W_2$ are each independently selected from:
(a) hydrogen,
(b) halogen,
(c) $C_{1-4}$-alkyl,
(d) hydroxy,
(e) $C_{1-4}$-alkoxy,
(f) $C_{1-4}$-alkylthio,
(m) —$OCF_3$,
(n) —CN,
(o) hydroxy-$C_{1-2}$-alkyl,
(p) $C_{1-2}$-alkoxy-$C_{1-2}$-alkyl,
(q) —$CF_3$,
(r) —$CONR^9R^9$,
(s) acetyl, and
(t) $C_{1-4}$-alkoxycarbonyl,
  with the proviso that when $W_1$ and $W_2$ are not selected from methoxy, methyl and halogen, at least one of $W_1$ and $W_2$ is hydrogen;

$R^3$ is a group selected from the following groups:

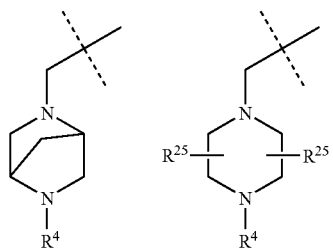

$R^4$ is selected from:
(a) hydrogen,
(b) $C_{1-4}$-alkyl,
(d) hydroxy-$C_{2-4}$-alkyl,
(g) $C_{3-6}$-cycloalkyl,
(h) $C_{3-6}$-cycloalkyl-$C_{1-4}$-alkyl,
(i) $C_{1-4}$-alkoxy-$C_{2-4}$-alkyl, and
(m) 3,3,3-trifluoropropyl;

each $R^7$ is independently selected from:
(a) hydrogen,
(b) $C_{1-4}$-alkyl,
(c) hydroxy-$C_{2-4}$-alkyl, and
(d) methoxy-$C_{2-4}$-alkyl;

each $R^9$ is independently selected from:
(a) hydrogen, and
(b) $C_{1-6}$-alkyl, or
the two $R^9$ groups together with the nitrogen to which they are attached form a heterocyclic ring; and provided that when the two $R^9$ groups form a piperazine ring, the nitrogen of the said piperazine ring that allows the substitution is optionally substituted with $C_{1-4}$-alkyl;

$R^{10}$ is selected from:
(a) $C_{1-6}$-alkyl,
(c) aryl, and
(d) heteroaryl,
  wherein heteroaryl or aryl may be substituted in one or more positions with substituents selected from halogen, $C_{1-4}$-alkyl, $C_{1-4}$-alkoxy, cyano, trifluoromethyl;

$R^{12}$ is selected from:
(a) hydrogen,
(c) aryl,
(d) aryl-$C_{1-3}$-alkyl,
(g) heteroaryl, and
(h) heteroaryl-$C_{1-3}$-alkyl,
  wherein any heteroaryl or aryl residue, alone or as part of another group, may be optionally substituted, independently, in one or more positions with substituents selected from
(b) halogen,
(c) $C_{1-4}$-alkyl,
(d) hydroxy,
(e) $C_{1-4}$-alkoxy,
(m) —$OCF_3$,
(n) —CN,
(o) hydroxy-$C_{1-3}$-alkyl,
(p) $C_{1-3}$-alkoxy-$C_{1-3}$-alkyl,
(q) halo-$C_{1-4}$-alkyl,
(r) —$NR^9R^9$,
(t) —$CONR^9R^9$,
(u) —$NR^7COR^{10}$,
(v) —$C(=O)R^{10}$,
(x) $C_{1-3}$-alkylthio, and
(ab) methylsulfonyl;

$R^{13}$ is selected from
(c) aryl,
(d) heteroaryl,
(e) aryl-$C_{1-2}$-alkyl, and
(f) heteroaryl-$C_{1-2}$-alkyl,
  wherein any heteroaryl or aryl residue may be optionally substituted in one or more positions with substituents selected from halogen, $C_{1-4}$-alkyl, $C_{1-4}$-alkoxy, cyano, trifluoromethyl and acetyl;

$R^{14}$ is selected from:
(a) aryl,
(b) heteroaryl,
(c) aryl-$C_{1-3}$-alkyl, and
(d) heteroaryl-$C_{1-3}$-alkyl;
  wherein any heteroaryl or aryl residue may be optionally substituted in one or more positions with substituents selected from halogen, $C_{1-4}$-alkyl, $C_{1-4}$-alkoxy, cyano, and trifluoromethyl;

each $R^{25}$ is independently selected from:
(a) hydrogen,
(b) $C_{1-4}$-alkyl,
(c) hydroxy-$C_{1-4}$-alkyl,
(d) $C_{1-4}$-alkoxy-$C_{1-4}$-alkyl, and
(e) fluoromethyl;
  with the proviso that when both $R^{25}$ simultaneously are selected from $C_{1-4}$-alkyl, said $C_{1-4}$-alkyl may be attached to the same or different carbon atoms, and with the further proviso that when one $R^{25}$ is selected from hydroxy-$C_{1-4}$-alkyl, $C_{1-4}$-alkoxy-$C_{1-4}$-alkyl, and fluoromethyl; the other $R^{25}$ represents hydrogen; with the proviso that $R^2$ and $R^{12}$ in Formula (III) are not simultaneously hydrogen; and with the further proviso that the said $R^2$ and $R^{12}$ together may form a heterocyclic ring selected from piperidine, pyrrolidine, morpholine, piperazine thiomorpholine, and provided that when $R^2$ and $R^{12}$ together form a piperazine ring, the distal piperazine nitrogen may be optionally substituted by $C_{1-4}$ alkyl or aryl, and wherein said aryl may be substituted in one or more positions with substituents selected from halogen, $C_{1-4}$-alkyl, $C_{1-4}$-alkoxy, cyano, trifluoromethyl; or $R^2$ and $R^{12}$ together form a heteroaromatic ring of Formula (VIII):

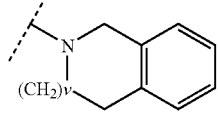
(VIII)

wherein v is 0 or 1.

4. The compound according to claim 1, which has the Formula (XII):

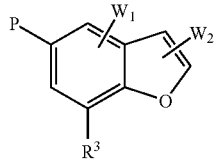
(XII)

wherein P, $R^3$, $W_1$ and $W_2$ are as defined in claim 1; or a pharmaceutically acceptable salt of such a compound.

5. The compound according to claim 4, or a pharmaceutically acceptable salt thereof, wherein
P is a substituent selected from Formulae (II)-(IV) below:

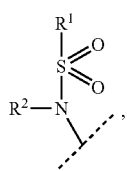
(II)

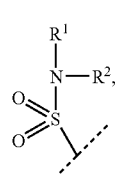
(III)

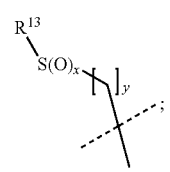
(IV)

x is 2 and y is 0;
$R^1$ is selected from aryl and heteroaryl, wherein any heteroaryl or aryl residue may be optionally substituted, independently, in one or more positions with a substituent selected from halogen, $C_{1-4}$-alkyl $C_{1-4}$-alkoxy and trifluoromethyl;
$R^2$ is hydrogen;
$W_1$ and $W_2$ are hydrogen;
$R^3$ is a group selected from the following groups:

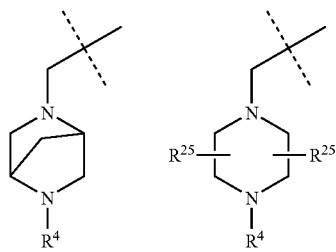

$R^4$ is selected from:
(a) hydrogen, and
(b) $C_{1-4}$-alkyl;
$R^{12}$ and $R^{13}$ are each independently selected from aryl and heteroaryl,
wherein any heteroaryl or aryl residue may be optionally substituted, independently, in one or more positions with a substituent selected from halogen, $C_{1-4}$-alkyl, $C_{1-4}$-alkoxy, and $CF_3$;
each $R^{25}$ is independently selected from:
(a) hydrogen, and
(b) $C_{1-4}$-alkyl.

6. The compound according to claim 5, or a pharmaceutically acceptable salt thereof, wherein
$R^1$, $R^{12}$ and $R^{13}$ are each independently selected from phenyl or substituted phenyl selected from 2-methoxy-5-methylphenyl, 2-methylphenyl, 4-methylphenyl, 4-fluorophenyl, 3,4-dimethoxyphenyl, 2-chlorophenyl, 2-trifluoromethylphenyl, 2,6-dichlorophenyl, 3-chloro-4-methylphenyl, 3-methylphenyl, 3,6-dichloro-2-methylphenyl, and 2-chloro-5-fluorophenyl; and heteroaryl or substituted heteroaryl selected from 2-thienyl, 5-chloro-2-thienyl, and 5-chloro-1,3-dimethyl-1H-pyrazol-4-yl; and
$R^2$ is hydrogen.

7. The compound according to claim 5, or a pharmaceutically acceptable salt thereof, wherein $R^3$ is a group selected from the following groups:

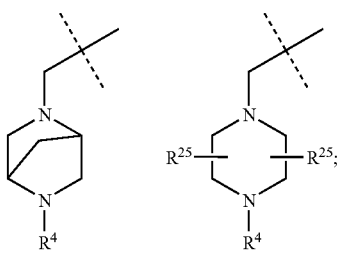

wherein
$R^4$ is selected from:
(a) hydrogen, and
(b) methyl, and
each $R^{25}$ is independently selected from:
(a) hydrogen, and
(b) methyl.

8. The compound according to claim 5, or a pharmaceutically acceptable salt thereof, wherein $R^4$ is selected from:
(a) hydrogen,
(b) methyl, and
(c) ethyl.

9. The compound according to claim 5, or a pharmaceutically acceptable salt thereof, wherein $R^4$ is hydrogen.

10. The compound according to claim 1, which has the Formula (XIII):

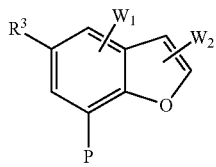

(XIII)

wherein P, $R^3$, $W_1$ and $W_2$ are as defined as in claim 1;
or a pharmaceutically acceptable salt of such a compound.

11. The compound according to claim 10, or a pharmaceutically acceptable salt thereof, wherein
P is a substituent selected from Formulae (II)-(IV) below:

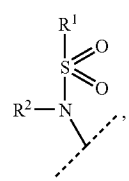

(II)

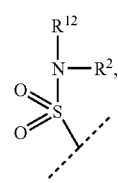

(III)

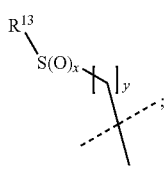

(IV)

x is 2 and y is 0;
$R^1$ is selected from aryl and heteroaryl, wherein any heteroaryl or aryl residue may be optionally substituted, independently, in one or more positions with a substituent selected from halogen, $C_{1-4}$-alkyl, trifluoromethoxy, and $C_{1-4}$-alkoxy;
$R^2$ is hydrogen;
$W_1$ and $W_2$ are hydrogen;
$R^3$ is:

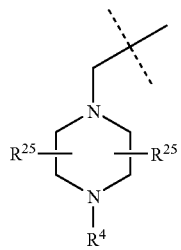

wherein
$R^4$ is selected from:
(a) hydrogen, and
(b) $C_{1-4}$-alkyl;

each $R^{25}$ is independently selected from:
(a) hydrogen, and
(b) $C_{1-4}$-alkyl, with the proviso that when both $R^{25}$ represent $C_{1-4}$-alkyl, said $C_{1-4}$-alkyl may be attached to the same or different carbon atoms;
$R^{12}$ and $R^{13}$ are each independently selected from aryl and heteroaryl, wherein any heteroaryl or aryl residue may be optionally substituted, independently, in one or more positions with a substituent selected from halogen, $C_{1-4}$-alkyl, trifluoromethyl, and $C_{1-4}$-alkoxy.

12. The compound according to claim 11, or a pharmaceutically acceptable salt thereof, wherein
P is a substituent of Formula (II)

(II)

$R^1$ is 2-methoxy-5-methylphenyl;
$R^2$ is hydrogen;
$W_1$ and $W_2$ are hydrogen;
$R^3$ is:

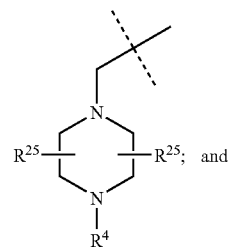

and $R^4$ is selected from
a) hydrogen, and
b) methyl;
each $R^{25}$ is independently selected from
a) hydrogen, and
b) methyl.

13. The compound selected from the following compounds and pharmaceutically acceptable salts thereof:
2-Methoxy-5-methyl-N-[7-(piperazin-1-ylcarbonyl)-1-benzofuran-5-yl]benzenesulfonamide,
2-Methoxy-5-methyl-N-[7-(piperazin-1-ylmethyl)-1-benzofuran-5-yl]benzenesulfonamide,
N-(2-Methoxy-5-methylphenyl)-7-[(3-methylpiperazin-1-yl)methyl]-1-benzofuran-5-sulfonamide,
N-(2-Methylphenyl)-7-(piperazin-1-ylmethyl)-1-benzofuran-5-sulfonamide,
7-[(3,5-Dimethylpiperazin-1-yl)methyl]-N-(2-methylphenyl)-1-benzofuran-5-sulfonamide,
N-(2-Methylphenyl)-7-[(3-methylpiperazin-1-yl)methyl]-1-benzofuran-5-sulfonamide,
7-{(trans-2,5-Dimethylpiperazin-1-yl)methyl}-N-(2-methylphenyl)-1-benzofuran-5-sulfonamide,
N-(2-Methylphenyl)-7-{[(2R)-2-methylpiperazin-1-yl]methyl}-1-benzofuran-5-sulfonamide,
N-(2-Methoxy-5-methylphenyl)-7-(piperazin-1-ylmethyl)-1-benzofuran-5-sulfonamide, 7-{(cis-3,5-Dimethylpiperazin-1-yl)methyl}-N-(2-methoxy-5-methylphenyl)-1-benzofuran-5-sulfonamide, 7-{[trans-2,5-Dimethylpiperazin-1-yl]methyl}-N-(2-methoxy-5-methylphenyl)-1-benzofuran-5-sulfonamide, 7-[(1S,4S)-2,5-Diazabicyclo[2.2.1]hept-2-ylmethyl]-N-(2-methoxy-5-methylphenyl)-1-benzo furan-5-sulfonamide, N-(2-Methoxy-5-methylphenyl)-7-[(2-methylpiperazin-1-yl)methyl]-1-benzofuran-5-sulfonamide, 2-Chloro-N-[7-(piperazin-1-ylmethyl)-1-benzofuran-5-yl]benzenesulfonamide, 2-Methyl-N-[7-(piperazin-1-ylmethyl)-1-benzofuran-5-yl]benzenesulfonamide, N-[7-(piperazin-1-ylmethyl)-1-benzofuran-5-yl]thiophene-2-sulfonamide, 2-Methoxy-5-methyl-N-{7-[(2-methylpiperazin-1-yl)methyl]-1-benzofuran-5-yl}benzenesulfonamide, 2-Methyl-N-{7-[(2-methylpiperazin-1-yl)methyl]-1-benzofuran-5-yl}benzenesulfonamide, 2,5-Dichloro-N-{7-[(2-methylpiperazin-1-yl)methyl]-1-benzofuran-5-yl}thiophene-3-sulfonamide, 2-Methoxy-5-methyl-N-{7-[(3-methylpiperazin-1-yl)methyl]-1-benzofuran-5-yl}benzenesulfonamide, N-{7-[(3-Methylpiperazin-1-yl)methyl]-1-benzofuran-5-yl}-2-(trifluoromethyl)benzenesulfonamide, 2-Chloro-N-{7-[(3-methylpiperazin-1-yl)methyl]-1-benzofuran-5-yl}benzenesulfonamide, N-{7-[(1S,4S)-2,5-Diazabicyclo[2.2.1]hept-2-ylmethyl]-1-benzofuran-5-yl}-2-methoxy-5-methylbenzenesulfonamide, N-{7-[(1S,4S)-2,5-Diazabicyclo[2.2.1]hept-2-ylmethyl]-1-benzofuran-5-yl}-2-(trifluoromethyl)benzenesulfonamide, N-{7-[(1S,4S)-2,5-Diazabicyclo[2.2.1]hept-2-ylmethyl]-1-benzofuran-5-yl}-2-methylbenzenesulfonamide, 2-Methoxy-5-methyl-N-{7-[(trans-2,5-dimethylpiperazin-1-yl)methyl]-1-benzofuran-5-yl}benzenesulfonamide, 2-Methyl-N-{7-[(trans-2,5-dimethylpiperazin-1-yl)methyl]-1-benzofuran-5-yl}benzenesulfonamide, 2-Chloro-N-{7-[(trans-2,5-dimethylpiperazin-1-yl)methyl]-1-benzofuran-5-yl}benzenesulfonamide, 1-({5-[(2-Methoxy-5-methylphenyl)sulfonyl]-1-benzofuran-7-yl}methyl)piperazine, 1-{[5-(Phenylsulfonyl)-1-benzofuran-7-yl}methyl)piperazine, 1-({5-[(4-Methylphenyl)sulfonyl]-1-benzofuran-7-yl}methyl)piperazine, 1-({5-[(2-Methoxy-5-methylphenyl)sulfonyl]-1-benzofuran-7-yl}methyl)-2-methylpiperazine, 1-({5-[(2-Methoxy-5-methylphenyl)sulfonyl]-1-benzofuran-7-yl}methyl)-3-methylpiperazine, and 2-Methoxy-5-methyl-N-{5-[(3-methylpiperazin-1-yl)methyl]-1-benzofuran-7-yl}benzenesulfonamide.

14. A pharmaceutical formulation comprising a compound according to claim 1, or a pharmaceutically acceptable salt thereof, as active ingredient, in combination with a pharmaceutically acceptable diluent or carrier.

15. A method of treating obesity comprising administering to a subject in need of such treatment an effective amount of a compound according to claim 1, or a pharmaceutically acceptable salt thereof.

16. A method of treating type II diabetes comprising administering to a subject in need of such treatment an effective amount of a compound according to claim 1, or a pharmaceutically acceptable salt thereof.

17. A method of achieving reduction of body weight or reduced body weight gain, the method comprising administering to a subject in need thereof an effective amount of a compound according to claim 1, or a pharmaceutically acceptable salt thereof.

18. A method for reducing food intake comprising administering to a subject in need thereof an effective amount of a compound according to claim 1, or a pharmaceutically acceptable salt thereof.

19. A method for treating a disorder of the central nervous system, wherein the disorder is selected from the group consisting of anxiety, depression, panic attacks, memory disorders, cognitive disorders, epilepsy, sleep disorders, migraine, anorexia, bulimia, binge eating disorders, obsessive compulsive disorders, psychoses, Alzheimer's disease, Parkinson's disease, Huntington's chorea, schizophrenia, attention deficit hyperactive disorder and pain, comprising administering to a subject in need thereof an effective amount of a compound according to claim 1, or a pharmaceutically acceptable salt thereof.

20. A method according to claim 19 wherein the disorder is anxiety.

21. A method according to claim 19 wherein the disorder is depression.

22. A method according to claim 19 wherein the disorder is panic attacks.

23. A method according to claim 19 wherein the disorder is a memory disorder.

24. A method according to claim 19 wherein the disorder is a cognitive disorder.

25. A method according to claim 19 wherein the disorder is epilepsy.

26. A method according to claim 19 wherein the disorder is sleep disorder.

27. A method according to claim 19 wherein the disorder is selected from the group consisting of anorexia, bulimia and binge eating disorders.

28. A method according to claim 19 wherein the disorder is an obsessive compulsive disorder.

29. A method according to claim 19 wherein the disorder is a psychosis.

30. A method according to claim 19 wherein the disorder is Alzheimer's disease.

31. A method according to claim 19 wherein the disorder is Parkinson's disease.

32. A method according to claim 19 wherein the disorder is Huntington's chorea.

33. A method according to claim 19 wherein the disorder is schizophrenia.

34. A method according to claim 19 wherein the disorder is attention deficit hyperactive disorder.

35. A method according to claim 19 wherein the disorder is pain.

* * * * *

UNITED STATES PATENT AND TRADEMARK OFFICE
CERTIFICATE OF CORRECTION

PATENT NO. : 7,820,675 B2
APPLICATION NO. : 11/018019
DATED : October 26, 2010
INVENTOR(S) : Gary Johansson, Peter Brandt and Bjorn M. Nilsson It is certified that error appears in the above-identified patent and that said Letters Patent is hereby corrected as shown below:

Col. 181, Line 35 (claim 1), delete "(d) hydroxy-$C_{2-4}$-alkyl," and insert --(d) hydroxy-$C_{2-6}$-alkyl,--.

Col. 181, Line 40 (claim 1), after "(i) $C_{1-6}$-alkoxy-$C_{2-6}$-alkyl" insert --,--.

Col. 182, Line 38 (claim 1), delete "(p) $C_{1-6}$-alkyl," and insert --(p) $C_{1-6}$-alkoxy-$C_{1-6}$-alkyl,--.

Col. 183, Line 12 (claim 1), after "from" insert --:--.

Col. 184, Line 29-33 (claim 2), delete "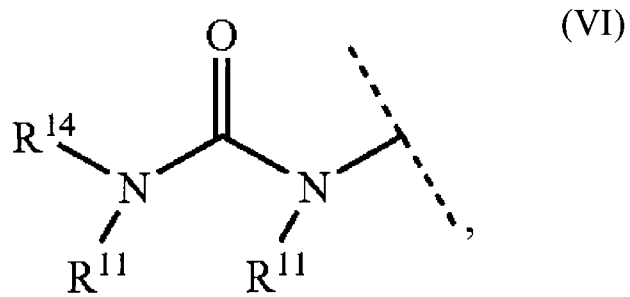".

Col. 186, Line 24 (claim 2), after "(h) $C_{3-7}$-cycloalkyl-$C_{1-4}$-alkyl" insert --,--.

Col. 186, Line 25 (claim 2), after "(i) $C_{1-6}$-alkoxy-$C_{2-6}$-alkyl" insert --,--.

Col. 186, Line 65 (claim 2), after "(f) $C_{3-7}$-cycloalkyl-$C_{1-4}$-alkyl" insert --,--.

Signed and Sealed this
Twenty-ninth Day of March, 2011

David J. Kappos
*Director of the United States Patent and Trademark Office*

Col. 188, Line 41-2 (claim 3), replace:

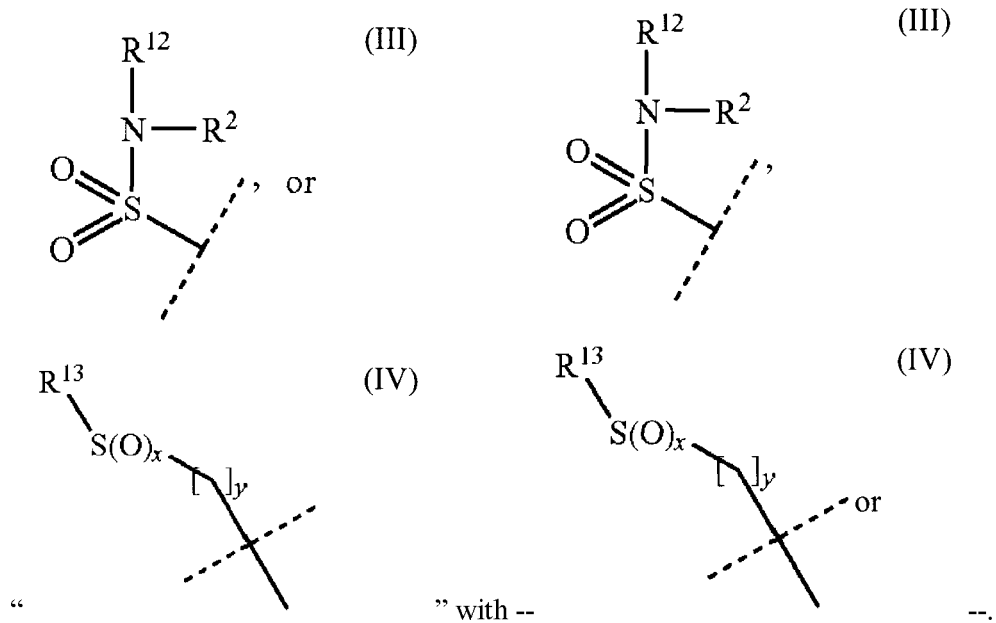

Col. 191, Line 50-2 (claim 5), replace:

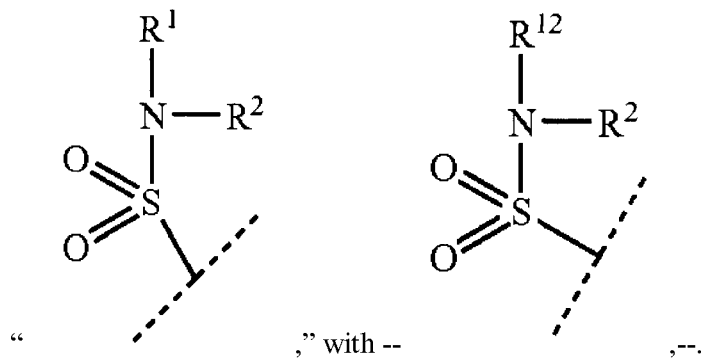

Col. 192, Line 2 (claim 5), replace "$C_{1-4}$-alkyl $C_{1-4}$-alkoxy" with --$C_{1-4}$-alkyl, $C_{1-4}$-alkoxy--.

Col. 195, Lines 6-9 (claim 13), replace
"7-[(1S,4S)-2,5-Diazabicyclo[2.2.1]hept-2-ylmethyl]-N-(2-methoxy-5-methylphenyl)-1-benzo furan-5-sulfonamide," with
--7-[(1S,4S)-2,5-Diazabicyclo[2.2.1]hept-2-ylmethyl]-N-(2-methoxy-5-methylphenyl)-1-benzofuran-5-sulfonamide,--.

Col. 195, Lines 49-50 (claim 13), replace
"1-{[5-(Phenylsulfonyl)-1-benzofuran-7-yl}methyl)piperazine," with
--1-{[5-(Phenylsulfonyl)-1-benzofuran-7-yl]methyl}piperazine,--